US010751402B2

(12) United States Patent
Anderson et al.

(10) Patent No.: US 10,751,402 B2
(45) Date of Patent: *Aug. 25, 2020

(54) IMMUNOGENIC COMPOSITIONS AND USES THEREOF

(71) Applicant: Pfizer Inc., New York, NY (US)

(72) Inventors: Annaliesa Sybil Anderson, Upper Saddle River, NJ (US); Leena Shriram Bagle, Edgewater, NJ (US); Amardeep Singh Bhupender Bhalla, Montvale, NJ (US); Miguel Angel Garcia, Midland Park, NJ (US); Lei Hu, New City, NY (US); Lakshmi Khandke, Nanuet, NY (US); Avvari Krishna Prasad, Chapel Hill, NC (US); Cindy Xudong Yang, Tappan, NY (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/800,373

(22) Filed: Nov. 1, 2017

(65) Prior Publication Data

US 2018/0125958 A1 May 10, 2018

Related U.S. Application Data

(60) Provisional application No. 62/419,704, filed on Nov. 9, 2016.

(51) Int. Cl.
*A61K 39/00* (2006.01)
*A61K 39/02* (2006.01)
*A61K 39/09* (2006.01)
*A61K 39/39* (2006.01)

(52) U.S. Cl.
CPC ............ *A61K 39/092* (2013.01); *A61K 39/39* (2013.01); *A61K 2039/545* (2013.01); *A61K 2039/55* (2013.01); *A61K 2039/55505* (2013.01); *A61K 2039/6031* (2013.01); *A61K 2039/6037* (2013.01); *A61K 2039/6068* (2013.01); *A61K 2039/70* (2013.01)

(58) Field of Classification Search
CPC ......... A61K 39/00; A61K 39/02; A61K 39/09
USPC ....... 424/93.44, 184.1, 193.1, 197.11, 234.1, 424/244.1
See application file for complete search history.

(56) References Cited

U.S. PATENT DOCUMENTS

| 5,057,540 | A | 10/1991 | Kensil et al. |
| 5,078,996 | A | 1/1992 | Conlon, III et al. |
| 5,254,339 | A | 10/1993 | Morein |
| 5,360,897 | A | 11/1994 | Anderson et al. |
| 5,614,382 | A | 3/1997 | Metcalf |
| 5,723,127 | A | 3/1998 | Scott et al. |
| 6,149,919 | A | 11/2000 | Domenighini et al. |
| 6,207,646 | B1 | 3/2001 | Krieg et al. |
| 7,115,730 | B1 | 10/2006 | Pizza et al. |
| 7,285,281 | B2 | 10/2007 | Green et al. |
| 7,291,588 | B2 | 11/2007 | Pizza et al. |
| 7,332,174 | B2 | 2/2008 | Green et al. |
| 7,361,355 | B2 | 4/2008 | Green et al. |
| 7,384,640 | B1 | 6/2008 | Holmes et al. |
| 8,652,480 | B2 | 2/2014 | Yuan et al. |
| 10,226,525 | B2 * | 3/2019 | Anderson .......... C07K 16/1275 |
| 2006/0228380 | A1 | 10/2006 | Hausdorff et al. |
| 2006/0228381 | A1 | 10/2006 | Bahler et al. |
| 2007/0184071 | A1 | 8/2007 | Hausdorff et al. |
| 2007/0184072 | A1 | 8/2007 | Hausdorff et al. |
| 2007/0231340 | A1 | 10/2007 | Hausdorff et al. |
| 2008/0102498 | A1 | 5/2008 | Bahler et al. |

FOREIGN PATENT DOCUMENTS

| WO | WO 93/15760 | 8/1993 |
| WO | WO 95/08348 | 3/1995 |
| WO | WO 96/29094 | 9/1996 |
| WO | WO 98/42721 | 10/1998 |
| WO | WO 2000/56357 | 9/2000 |
| WO | WO 01/093905 | 12/2001 |
| WO | WO 02/032451 | 4/2002 |
| WO | WO 2004/011027 | 2/2004 |
| WO | WO 2004/083251 | 9/2004 |
| WO | WO 2005/033148 | 4/2005 |
| WO | WO 2006/082527 | 8/2006 |
| WO | WO 2006/082530 | 8/2006 |
| WO | WO 2008/118752 | 10/2008 |
| WO | WO 2012/035519 | 3/2012 |

(Continued)

OTHER PUBLICATIONS

Heath, P.T., et al. Expert Rev. Vaccines, vol. 4, No. 2, pp. 207-218, 2005.* Paoletti, L.C., et al. Infection and Immunity, vol. 62, No. 8, pp. 3236-3243, Aug. 1994.*
Paoletti, L.C., The Journal of Infectious Diseases, vol. 186, pp. 123-126, 2002.*
Baker, C.J., "The Spectrum of Perinatal Group B Streptococcal Disease", Vaccine, 31(Suppl. 4):D3-D6 (2013).
Baker, C.J., "Safety and Immunogenicity of a Bivalent Group B Streptococccal Conjugate Vaccine for Serotypes II and III", Journal of Infectious Diseases, 2003, 188:66-73.

(Continued)

Primary Examiner — Rodney P Swartz
(74) Attorney, Agent, or Firm — Keith D. Hutchinson; Matthew J. Pugmire

(57) ABSTRACT

The invention relates to immunogenic compositions comprising a capsular polysaccharide (CP) from *Streptococcus agalactiae*, commonly referred to as group B streptococcus (GBS), conjugated to a carrier protein, and optionally including an aluminum-based adjuvant. The invention further relates to methods for inducing an immune response in subjects against GBS and/or for reducing or preventing invasive GBS disease in subjects using the compositions disclosed herein. The resulting antibodies can be used to treat or prevent GBS infection via passive immunotherapy.

24 Claims, 49 Drawing Sheets

(56) References Cited

FOREIGN PATENT DOCUMENTS

| WO | 2014/097099 | 6/2014 |
| WO | 2014/053612 | 10/2014 |

OTHER PUBLICATIONS

Baker, C.J., et al., "Dose—response to type V group B streptococcal polysaccharide—tetanus toxoid conjugate vaccine in healthy adults", Vaccine, 25(1):55-63 (2007).
Baker, C.J., et al., "Immune Response of Healthy Women to 2 Different Group B Streptococcal Type V Capsular", Journal of Infectious Diseases, 2004, 189:1103-12.
Black, W.J., et al., "ADP-Ribosyltransferase Activity of Pertussis Toxin and Immunomodulation by Bordetella Pertussis", Science, 240(4852):656-659 (1988).
Bekker, V., et al., "Incidence of Invasive group B streptococcal disease and pathogen genotype distribution in newborn babies in the Netherlands over 25 years: a nationwide surveillance study", The Lancet Infectious Diseases, 14(11):1083-1089 (2014).
Bergmann, C., et al.,"An Endogenously Synthesized Decamer Peptide Efficiently Primes Cytotoxic T Cells Specific for the HIV-1 Envelope Glycoprotein", Eur. J. Immunol., 23(11):2777-2781(1993).
Bergmann, C.C., et al., "Flanking Residues Alter Antigenicity and Immunogenicity of Multi-Unit CTL Epitopes", J. Immunol., 157(8):3242-3249 (1996).
Berti, F., et al., "Structure of the Type IX Group B Streptococcus Capsular Polysaccharide and Its Evolutionary Relationship with Types V and VII", The Journal of Biological Chemistry, 289(34):23437-2348 (2014).
Brigtsen, A.K., et al., "Induction of Cross-Reactive Antibodies by Immunization of Healthy Adults with Types Ia and Ib Group B Streptococcal Polysaccharide—Tetanus Toxoid Conjugate Vaccines Journal of Infectious Diseases", 185(9):1277-1284 (2002).
Hunolstein, C., et al., "Immunochemistry of Capsular Type Polysaccharide and Virulence Properties of Type VI Streptococcus agalactiae (Group B Streptococci)", Infection and Immunity, 6194):1272-1280 (1993).
Chaffin, D.O., et al., "Sialylation of Group B Streptococcal Capsular Polysaccharide Is Mediated by cpsK and Is Required for Optimal Capsule Polymerization and Expression", J Bacteriol 187(13):4615-4626 (2005).
Diedrick, M.J., et al., "Clonal Analysis of Colonizing Group B Streptococcus, Serotype IV, an Emerging Pathogen in the United States", J. Clin. Microbiol., 48(9):3100-3104 (2010).
Dillon, H.C., et al., "Group B streptococcal carriage and disease: a 6-year prospective study", J Pediatr., 110(1):31-36 (1987).
Doe, B., et al., "Induction of HIV-1 Envelope (gp12)-specific Cytotoxic T Lymphocyte Responses in Mice by Recombinant CHO Cell-Derived gp120 is Enhanced by Enzymatic Removal of N-linked Glycans", Eur. J. Immunol. 24(10):2369-2376 (1994).
Edmond, K.M, et al., "Group B Streptococcal Disease in Infants Aged Younger Than 3 Months: Systematic Review and Meta-Analysis" Lancet, 379(9815):547-556 (2012).
Egan, P.M., et al., Vaccine, 27:3175-3180 (2009.
Bethell, G., et al., "A Novel Method of Activation of Cross-linked Agaroses with 1,1'-Carbonyldiimidazole which gives a Matrix for Affinity Chromatography Devoid of Additonal Charged Groups," Communication, 1979, pp. 2572-2574, vol. 254, No. 8.
Erickson A.L., et al., "Hepatitis C Virus-Specific CTL Responses in the Liver of Chimpanzees With Acute and Chronic Hepatitis C", J. Immunol., 151(8):4189-4199 (1993).
Ferrieri, P., et al., "Serotype IV and Invasive Group B Streptococcus Disease in Neonates, Minnesota, USA, 2000-2010", Emerg. Infect. Dis. [Internet], 19(4): 551-558 (2013), available at http://wwwnc.cdc.gov/eid/article/19/4/12-1572_article.

Florindo, C., et al., Euro Surveillance: Bulletin European sur les Maladies Transmissibles (European Communicable Disease Bulletin), 19(23), (2014).
Geysen, H.M., et al., "A priori delineation of a peptide which mimics a discontinuous antigenic determinant", Molec. Immunol., 23(7):709-715 (1986).
Geysen, H.M., et al., "Use of Peptide Synthesis to Probe Viral Antigens for Epitopes to a Resolution of a Single Amino Acid", Proc. Natl. Acad. Sci. USA, 81:3998-4002 (1984).
Heath, P.T., et al., "Neonatal Infections: group B streptococcus", BMJ Clinical Evidence, 323 (2014).
Hestrin, S., "The Reaction of Acetylcholine and Other Carboxylic Acid Derivatives With Hydroxylamine, and Its Analytical Application", J. Biol. Chem., 180:249-261 (1949).
Jones, C., et al., "Use and Validation of NMR Assays for the Identity and O-acetyl Content of Capsular Polysaccharides from Neisseria meningitidis Used in Vaccine Manufacture", Journal of Pharmaceutical and Biomedical Analysis, 30:1233-1247 (2002).
Kessous, R., et al., "Bacteruria With Group-B Streptococcus: Is It a Risk Factor for Adverse Pregnancy Outcomes?", J. Matern. Fetal Neonatal Med., 25(10):1983-1986 (2012).
Lachenauer, C.S., et al., "Serotypes VI and VIII Predominate among Group B Streptococci Isolated from Pregnant Japanese Women", JID, 179(4):1030-1033 (1999).
Lamagni, T.L., et al., "Emerging Trends in the Epidemiology of Invasive Group B Streptococcal Disease in England and Wales, 1991-2010", Clin. Infect. Dis., 57(5):682-688 (2013).
Lemercinier, X., et al., "Full 1H NMR Assignment and Detailed O-acetylation Patterns of Capsular Polysaccharides from Neisseria meningitidis Used in Vaccine Production", Carbohydrate Research, 296:83-96 (1996).
Libster, R., et al., "Long-term Outcomes of Group B Streptococcal Meningitis", Pediatrics, 130(1):e8-e15 (2012).
Madzivhandila, M., et al., "Serotype Distribution and Invasive Potential of Group B Streptococcus Isolates Causing Disease in Infants and Colonizing Maternal-Newborn Dyads", PloS One, 6(3):e17861 (2011).
Matson, M.A., et al, ICAAC, Abstract 1-306 (Washington, DC, Sep. 5-9, 2014).
Mcdonald, H.M., et al., "Intrauterine Infection and Spontaneous Midgestation Abortion: Is the Spectrum of Microorganisms Similar to That in Preterm Labor?", Infectious Diseases in Obstetrics and Gynecology, 8:220-227 (2000).
Meehan, M. et al., "Molecular epidemiology of group B streptococci in Ireland reveals a diverse population with evidence of capsular switching", European Journal of Clinical Microbiology & Infectious Diseases, 33(7):1155-1162 (2014).
Palmiero, J.K, et al., "Phenotypic and Genotypic Characterization of Group B Streptococcal Isolates in Southern Brazil", Journal of Clinical Microbiology, 48(12):4397-4403 (2010).
Pappenheimer, A.M., et al., Immunochem., 9(9):891-906 (1972).
Randis, T.M., et al., "Group B Streptococcus β-hemolysin/ Cytolysin Breaches Maternal-Fetal Barriers to Cause Preterm Birth and Intrauterine Fetal Demise in Vivo", The Journal of Infectious Diseases, 210(2):265-273 (2014).
Suhrbier, A., "Multi-epitope DNA vaccines", Immunol. and Cell Biol., 75(4):402-408 (1997).
Teatero, S., et al., "Characterization of Invasive Group B Streptococcus Strains from the Greater Toronto Area, Canada", Journal of Clinical Microbiology, 52(5):1441-1447 (2014).
Thigpen, M.C., et al., "Bacterial Meningitis in the United States, 1998-2007", New England Journal of Medicine, 364 (21):2016-2025 (2011).
Verani, J.R., et al., "Prevention of Perinatal Group B Streptococcal Disease Revised Guidelines from CDC, 2010", Morbidity and Mortality Weekly Report, 59(RR10):1-32 (2010).
Vuocitelli, a., et al., "Group B Streptococcus vaccine: state of the art", Therapeutic Advances in Vaccines, 2015, Dgs 76-90, vol. 3. nternational Search Report, PCT/162017/056830, Feb. 11, 2017.

\* cited by examiner

IMMUNOGENIC COMPOSITIONS AND USES THEREOF

CROSS REFERENCE TO RELATED APPLICATIONS

This application claims the benefit under 35 USC § 119(e) of U.S. Provisional Application Ser. No. 62/419,704, filed Nov. 9, 2016, which is incorporated by reference in its entirety.

FIELD OF THE INVENTION

The invention relates to immunogenic compositions comprising a capsular polysaccharide (CP) from *Streptococcus agalactiae*, commonly referred to as group B streptococcus (GBS), conjugated to a carrier protein and optionally including an aluminum-based adjuvant. The invention further relates to methods for inducing an immune response in subjects against GBS and/or for reducing or preventing invasive GBS disease in subjects using the compositions disclosed herein. The resulting antibodies can be used to treat or prevent GBS infection via passive immunotherapy.

BACKGROUND OF THE INVENTION

*Streptococcus agalactiae* are Gram positive polysaccharide encapsulated organisms that are also known as group B streptococcus (GBS). They are a common commensal of the human gastrointestinal and genital tract and also a cause of serious disease in infants and older adults (Baker, C. J., Vaccine, 31(Suppl. 4):D3-D6 (2013)). The main risk factor for GBS infection in infants is maternal colonization (Dillon, H. C., et al., J. Pediatr., 110(1):31-36 (1987)). As many as one in four women carry GBS recto-vaginally, which can infect the amniotic fluid or baby before or during delivery causing sepsis, pneumonia, and meningitis (Baker 2013; Heath, P. T., et al., BMJ Clin. Evid. (Online), pii:0323 (2014)). Twenty five percent of infants who survive GBS meningitis suffer from neurologic impairment with 19% experiencing cognitive delay, cerebral palsy, blindness, and hearing loss (Libster, R., et al., Pediatrics, 130(1):e8-152012 (2012)). GBS can also cause miscarriages and preterm deliveries and is linked to stillbirths (McDonald, H. M., et al., Infect. Dis. Obstetr. Gynecol., 8(5-6):220-227 (2000); Randis, T. M., et al., J. Infect. Dis., 210(2):265-273 (2014): Kessous, R., et al., J. Matern. Fetal Neonatal Med., 25(10): 1983-1986 (2012)). Very low birth weight infants are at much higher risk of infection, with up to 3% infected and mortality rates of up to 30%, even with immediate antibiotic treatment (Heath 2014).

The introduction in the late 1990's of GBS screening and intrapartum antibiotic prophylaxis (IAP) in the U.S. demonstrated reduced rates of neonatal disease occurring within the first week of life (early onset disease [EOD]), but has had no measurable impact on rates of late onset disease (LOD) appearing thereafter within the first 3 months of life. U.S. rates of EOD and LOD cases are currently 0.25 and 0.27 per 1,000 births respectively (Centers for Disease Control and Prevention (CDC), Active Bacterial Core (ABC) Surveillance Report (2013) available at http://www.cdc.gov/abcs/reports-findings/survreports/gbs13.pdf). Following introduction of pneumococcal conjugate vaccines for prevention of invasive pneumococcal disease, including bacteremia and meningitis, and in spite of IAP for prevention of GBS disease, GBS has become the single most common cause of neonatal sepsis (EOD) and meningitis (<2 mo) in infants in the U.S. (Verani, J. R., et al., MMWR, 59(RR10):1-32 (2010); Thigpen, M. C., et al., N. Engl. J. Med., 364(21): 2016-2025 (2011)). Unlike in the U.S., the introduction of prevention guidelines for invasive GBS disease and IAP has not reduced the incidence of EOD in the Netherlands or the U.K. (Bekker, V., et al., The Lancet Infectious Dis., 14(11): 1083-1089 (2014); Lamagni, T. L., et al., Clin. Infect. Dis., 57(5):682-688 (2013)). This lack of effect may be due to the lack of universal screening and restricting IAP to mothers in the highest risk groups (e.g., fever, prolonged ruptured membranes). Rates of EOD are significantly higher in countries that do not use IAP, with a mean incidence reported of 0.75 per 1,000 live births (95% CI 0.58-0.89) (Edmond, K. M, et al., Lancet, 379(9815):547-556 (2012)).

Another population at risk for GBS disease is the elderly. Risk factors include chronic medical problems such as diabetes mellitus, cancer, heart failure, neurologic, and urologic conditions. According to CDC ABC surveillance data, the annual U.S. incidence of invasive GBS in 2013 was 0.28/1,000 adults or 12,400 cases/year in adults ≥65 years of age. This rate approaches the incidence of invasive pneumococcal disease in the elderly (vs. 0.30/1,000 for >65). These rates are expected to continue to increase in both the U.S. and in Europe (CDC 2013; Lamagni 2013).

One approach to prevent GBS disease among infants and the elderly is the use of a polysaccharide-based vaccine. The implementation of a maternal GBS prophylactic vaccine has the potential to prevent GBS disease among infants in the U.S., regardless of whether IAP is used. Although polysaccharides can be immunogenic on their own, conjugation of polysaccharides to protein carriers has been used to improve immunogenicity, particularly in infants and the elderly. Polysaccharide-protein conjugate vaccines are made using polysaccharides, generally from the surface coat of bacteria, linked to protein carriers. The polysaccharide-protein conjugate-induces an immune response against bacteria displaying the polysaccharide contained within the vaccine on their surface, thus preventing disease. Accordingly, vaccination using polysaccharide conjugates from pathogenic bacteria is a potential strategy for boosting host immunity.

The polysaccharides that cover bacteria vary greatly, even within a single species of bacteria. For example, in GBS there are ten different serotypes due to variation in the bacterial polysaccharide capsule. Therefore, it is desirable for polysaccharide-based vaccines to consist of a panel of polysaccharides to ensure breadth of coverage against different circulating serotypes.

The carrier protein can be either a related protein antigen from the target pathogen, boosting the specific immune response to that pathogen, or a generally immunogenic protein that serves more as an adjuvant or general immune response stimulant.

Individual monovalent polysaccharide-protein conjugates of GBS serotypes Ia, Ib, II, III, and V have been evaluated in phase 1 and 2 clinical trials in non-pregnant adults (Brigtsen, A. K., et al., J. Infect. Dis., 185(9):1277-1284 (2002); Baker, C. J., et al., J. Infect. Dis., 188(1):66-73 (2003); Baker, C. J., et al., J. Infect. Dis., 189(6):1103-1112 (2004); Baker, C. J., et al., Vaccine, 25(1):55-63 (2007)). Bivalent II-TT and III-TT glycoconjugate vaccines and a trivalent vaccine comprising Ia-CRM$_{197}$, Ib-CRM$_{197}$ and III-CRM$_{197}$ glycoconjugates have also been studied (Baker 2003; clinicaltrials.gov NCT01193920, NCT01412801, and NCT01446289). However, GBS vaccines have yet to be approved.

Moreover, while the tri-valent vaccine covers >90% of invasive strains causing neonatal disease in South Africa (Madzivhandila, M., et al., PloS One, 6(3):e17861 (2011)), these same serotypes represent only 62% and 66% of invasive isolates in North America and Europe, respectively, based on surveillance of recent neonatal isolates from a global collection of 901 samples collected between 2004-2013 from the Tigecycline Evaluation and Surveillance Trial (T.E.S.T., http://www.testsurveillance.com/).

Analysis of the strains obtained from the T.E.S.T. samples showed that 95% of the strains collected belonged to one of the five documented major serotypes (Ia, Ib, II, III, and V) and a further 3% were serotype IV. A series of publications have also confirmed the appearance of serotype IV over the last decade in the Americas and in Europe (Diedrick, M. J., et al., J. Clin. Microbiol., 48(9):3100-3104 (2010); Teatero (2014); Meehan, M. et al., Eur. J. Clin. Microbiol. Infect. Dis., 33(7):1155-1162 (2014); Florindo, C., et al., Euro Surveillance: Bulletin European sur les Maladies Transmissibles (European Communicable Disease Bulletin), 19(23) (2014); Palmiero, J. K., et al., J. Clin. Microbiol., 48(12): 4397-4403 (2010)). A study surveying recto/vaginal carriage in adults, which is a risk factor for transmission of GBS to the infant, also found 97% of isolates belonging to one of these six serotypes, with serotype IV representing a frequency of ~4%. The study was designed to monitor carriage of beta-hemolytic streptococci (which includes GBS), *Clostridium difficile*, and *Staphylococcus aureus* in healthy U.S. adults (see Matson, M. A., et al, ICAAC, Abstract 1-306 (Washington, D.C., Sep. 5-9, 2014)).

Similarly, analysis of T.E.S.T. samples showed 98% of U.S. blood isolates from older adults ≥65 years of age belong to the same six predominant serogroups. The most noticeable difference between the elderly isolates and the other populations is the serogroup distribution. For the isolates from elderly patients, serotype V strains constitute the largest group (34% vs. 18% for neonatal or 18% for adult carriage strains).

Other studies have found that there is a geographic variance of serotype prevalence. For instance, serotype VI and VIII isolates have been shown to be predominant colonizers of healthy pregnant women in Japan (Lachenauer, C. S., et al., J. Infect. Dis., 179(4):1030-1033 (1999).

Accordingly, a need exists for polysaccharide-protein conjugate vaccines or monoclonal antibodies to confer passive immunity as a means to prevent or treat GBS diseases, including those caused by emerging serotype IV, among broad populations worldwide. In addition, there is a need for such vaccines or immunogenic compositions to be stable and easily resuspendable in any container known in the art.

SUMMARY OF THE INVENTION

The present invention relates to novel immunogenic compositions comprising GBS polysaccharide-protein conjugates and optionally including an adjuvant. The following clauses describe some aspects and embodiments of the invention.

In one aspect, the invention relates to an immunogenic composition comprising a capsular polysaccharide from a group B streptococcus (GBS) conjugated to a carrier protein and optionally an aluminum-based adjuvant. In one embodiment, the aluminum-based adjuvant is selected from the group consisting of aluminum phosphate, aluminum hydroxyl phosphate, and aluminum hydroxide. In one such embodiment, the aluminum-based adjuvant is in a concentration of about 0.25 mg/ml to about 0.75 mg/ml.

In another embodiment, the capsular polysaccharide is selected from the group consisting of serotypes Ia, Ib, II, III, IV, V, VI, VII, VIII, and IX. In another embodiment, the immunogenic composition is a hexavalent GBS conjugate composition. In one such embodiment, the immunogenic composition comprises the capsular polysaccharides from GBS serotypes Ia, Ib, II, III, IV, and V.

In yet another embodiment, the invention relates to an immunogenic composition comprising polysaccharide-protein conjugates, wherein the conjugates comprise capsular polysaccharides from group B streptococcus (GBS) and are selected from the group consisting of serotypes Ia, Ib, II, III, IV, V, VI, VII, VIII, and IX; and the composition further comprises one or more of a pharmaceutically acceptable excipient, buffer, stabilizer, adjuvant, a cryoprotectant, a salt, a divalent cation, a non-ionic detergent, an inhibitor of free radical oxidation, a carrier, or a mixture thereof.

In still another embodiment, the invention relates to an immunogenic composition as described herein, wherein the capsular polysaccharides are individually conjugated to the same carrier protein.

In another aspect of the invention, the immunogenic composition is filled in a syringe. In one embodiment, the syringe is glass. In another embodiment, the immunogenic composition is filled in the syringe with a headspace of about 1 mm to about 15 mm.

In a further aspect of the invention, the immunogenic composition is resuspended in about 50 or fewer shakes.

In one embodiment, the immunogenic composition further comprises phosphate. In one such embodiment, the phosphate is in a concentration of about 15 mM to about 25 mM.

In another embodiment, the immunogenic composition further comprises sodium chloride. In one such embodiment, the sodium chloride is in a concentration of about 10 mM to about 350 mM.

In a further embodiment, the immunogenic composition comprises a total conjugate dose of about 60 mcg/ml to about 360 mcg/ml.

In an additional embodiment, the immunogenic composition has a pH of about 6.5 to about 7.5.

In one aspect of the invention, the immunogenic composition comprises about 0.25 mg/ml to about 0.75 mg/ml of aluminum phosphate, about 15 mM to about 25 mM of phosphate, about 225 mM to about 265 mM of sodium chloride, and a total conjugate dose of about 60 mcg/ml to about 360 mcg/ml, wherein the immunogenic composition has a pH of about 6.5 to about 7.5.

In another aspect of the invention, the immunogenic composition comprises about 0.25 mg/ml to about 0.75 mg/ml of aluminum hydroxide, about 15 mM to about 25 mM of phosphate, about 120 mM to about 170 mM of sodium chloride, and a total conjugate dose of about 60 mcg/ml to about 360 mcg/ml, wherein the immunogenic composition has a pH of about 6.5 to about 7.5.

Another aspect of the invention relates to a method of inducing an immune response against GBS comprising administering to a subject an effective amount of the immunogenic composition as described herein. In one embodiment, the invention relates to a method of preventing or reducing a disease or condition associated with GBS in a subject comprising administering to a subject an effective amount of the immunogenic composition described herein. In a particular embodiment, the subject is a female planning to become pregnant or a pregnant female. In one such embodiment, the pregnant female is in her second half of pregnancy, such as at least at 20 weeks or at least 27 weeks gestation. In a preferred embodiment, the pregnant female is at 27 weeks to 36 weeks gestation. In another embodiment, the subject is an older adult, such as an adult 50 years of age or older, 65 years of age or older, and 85 years of age or older. In a further embodiment, the subject is immunocompromised. In one aspect, the subject may have a medical condition selected from the group consisting of obesity, diabetes, HIV infection, cancer, cardiovascular disease, or liver disease. In a preferred embodiment, the group B streptococcus is *Streptococcus agalactiae*.

An additional aspect of the invention relates to antibodies that bind to a capsular polysaccharide in the immunogenic composition of the present invention. In some embodiments, the antibodies are generated upon administration of the immunogenic composition to a subject. In another aspect relates to a composition comprising the antibodies of the present invention A further aspect of the invention relates to a method of conferring passive immunity to a subject comprising the steps of (a) generating an antibody preparation using the immunogenic composition described herein; and (b) administering the antibody preparation to the subject to confer passive immunity.

DETAILED DESCRIPTION OF THE INVENTION

Figure 1:
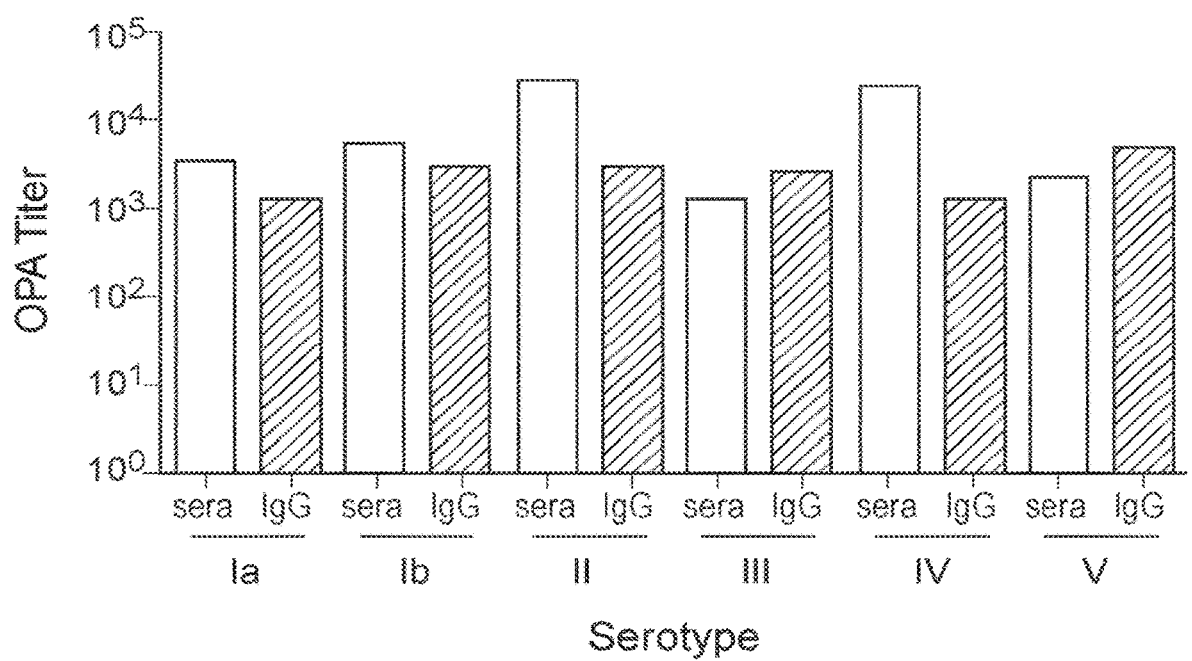
FIG. 1: Comparison of opsonic activity of sera and isolated IgG from mice immunized with GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$ monovalent vaccines.
Figure 2:
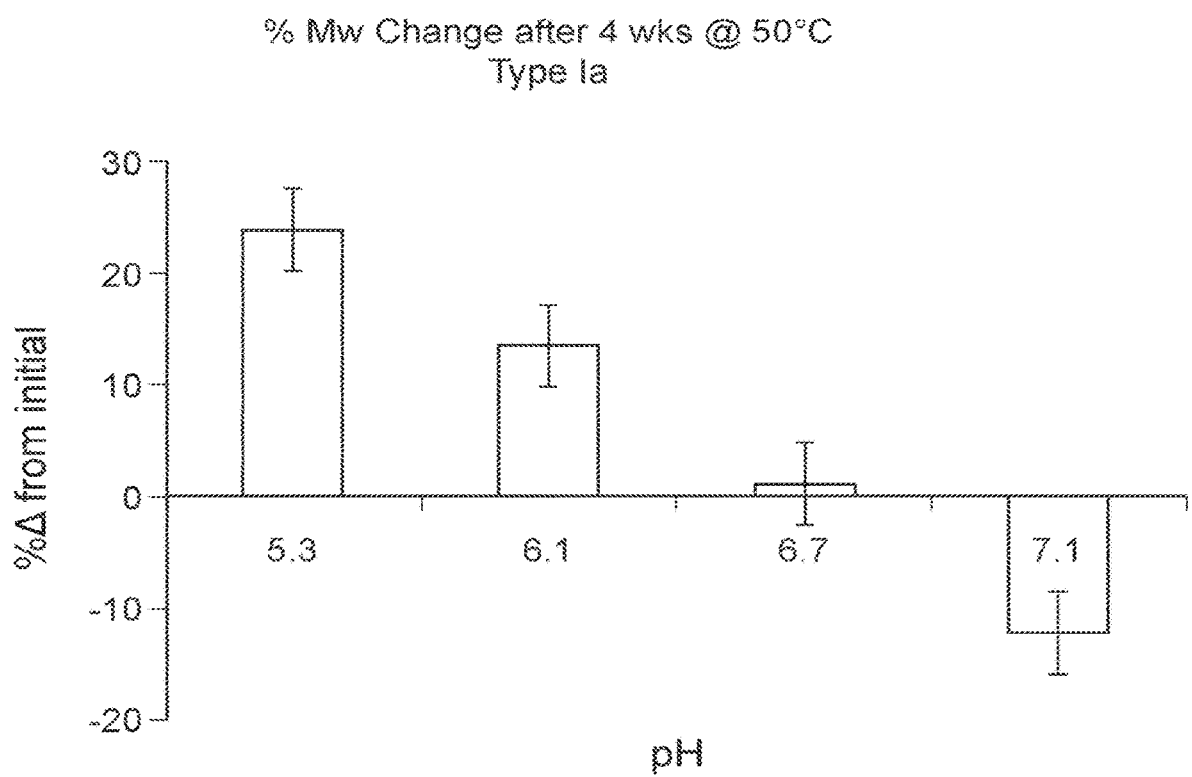
FIG. 2: Stability of GBS Ia-CRM$_{197}$ (as shown by % change in molecular weight using SEC MALLS) following accelerated storage (4 weeks) at 50° C.
Figure 3:
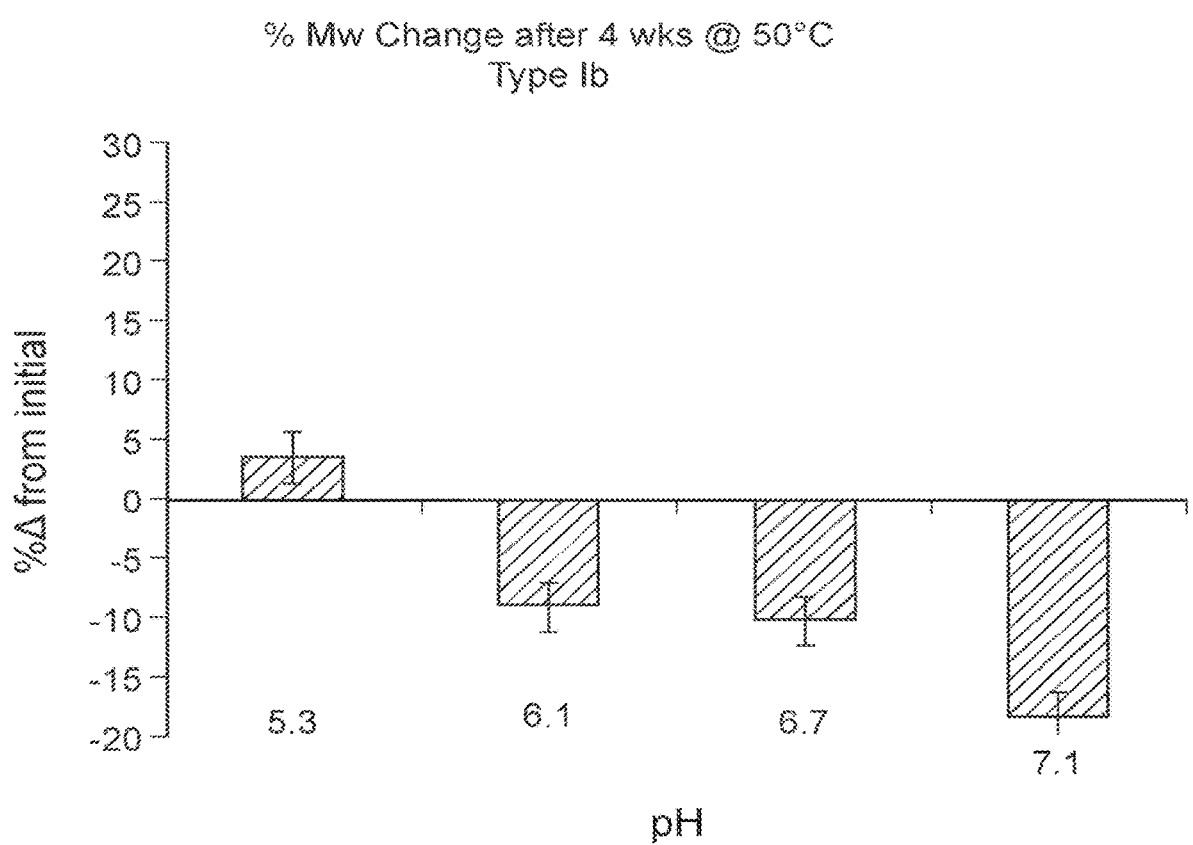
FIG. 3: Stability of GBS Ib-CRM$_{197}$ (as shown by % change in molecular weight using SEC MALLS) following accelerated storage (4 weeks) at 50° C.
Figure 4:
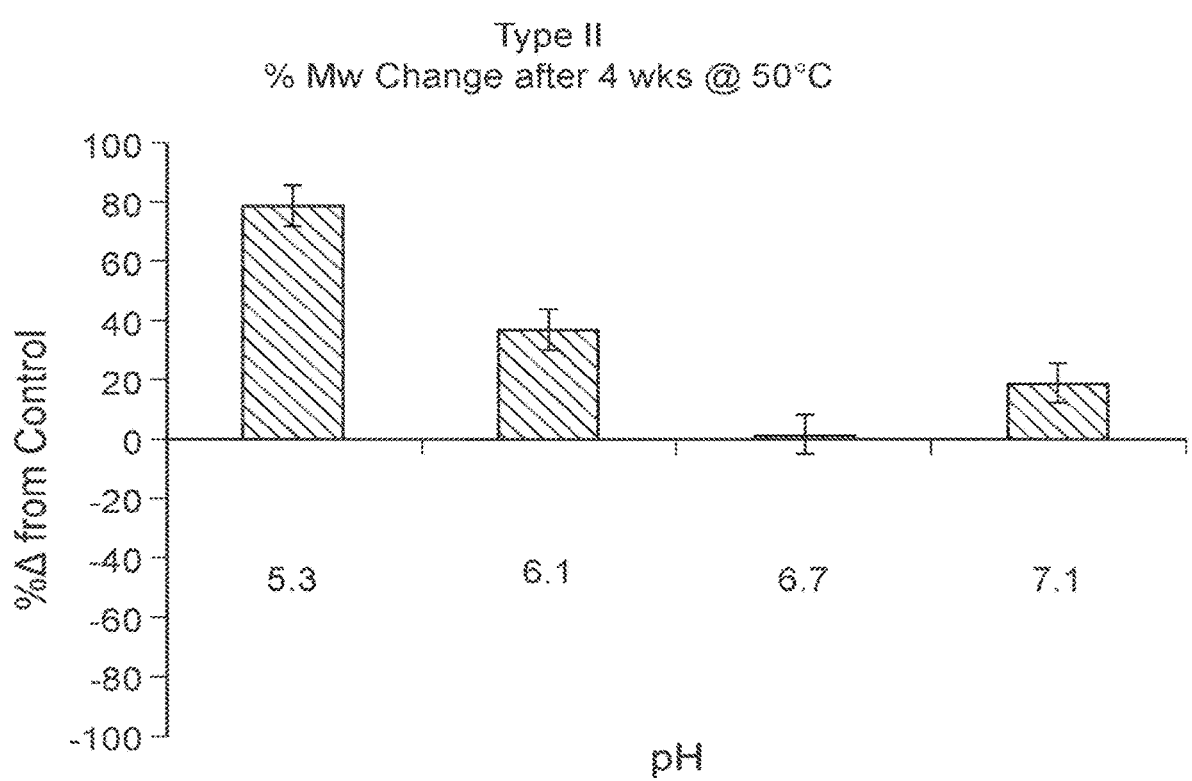
FIG. 4: Stability of GBS II-CRM$_{197}$ (as shown by % change in molecular weight using SEC MALLS) following accelerated storage (4 weeks) at 50° C.
Figure 5:
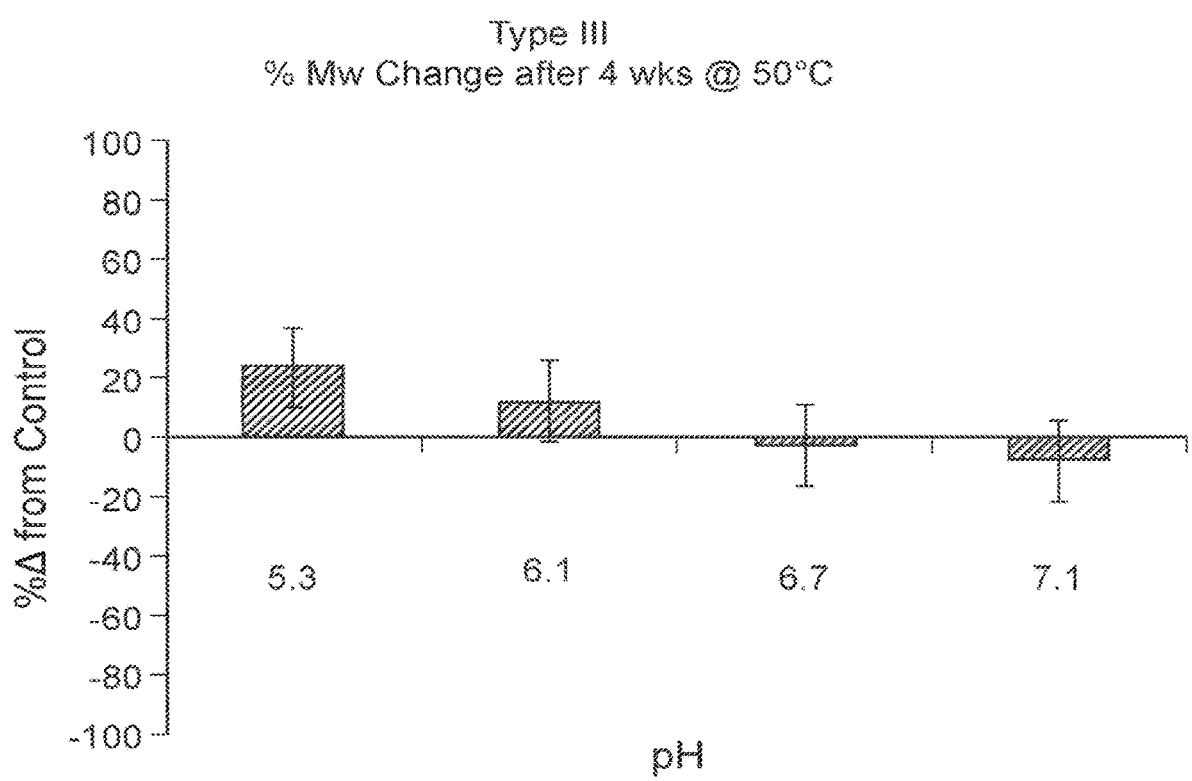
FIG. 5: Stability of GBS III-CRM$_{197}$ (as shown by % change in molecular weight using SEC MALLS) following accelerated storage (4 weeks) at 50° C.
Figure 6:
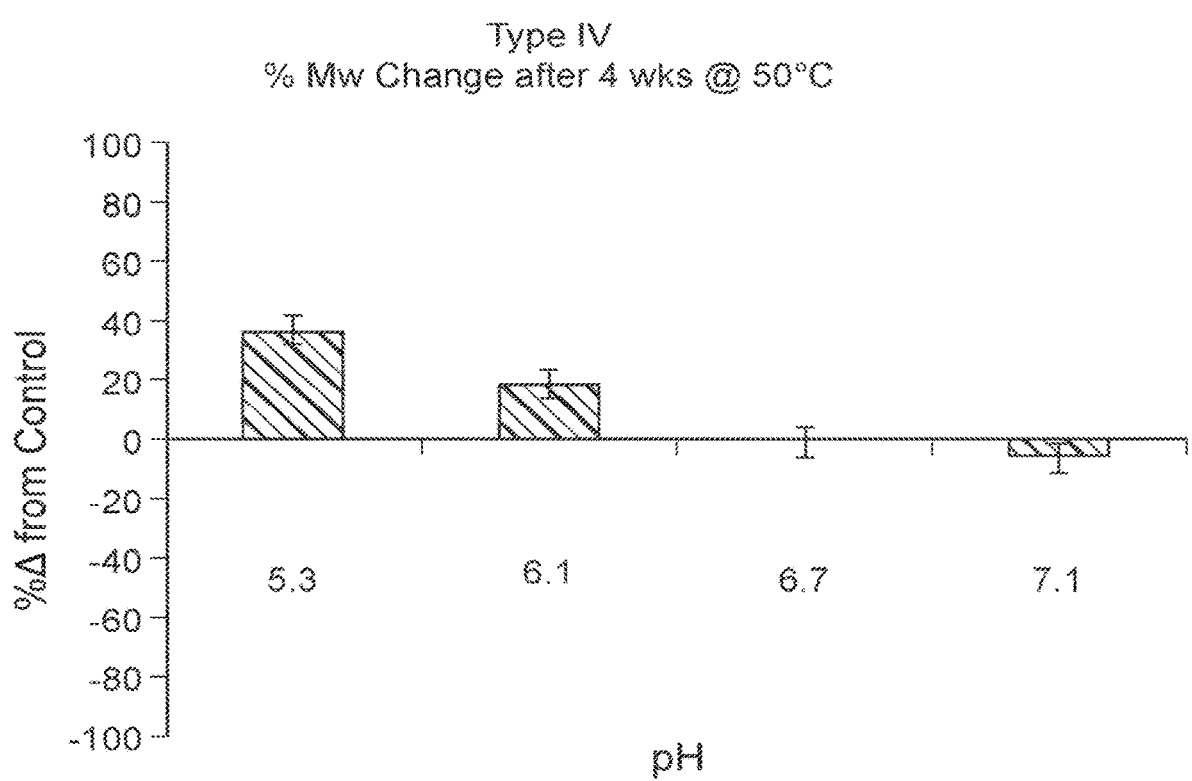
FIG. 6: Stability of GBS IV-CRM$_{197}$ (as shown by % change in molecular weight using SEC MALLS) following accelerated storage (4 weeks) at 50° C.
Figure 7:
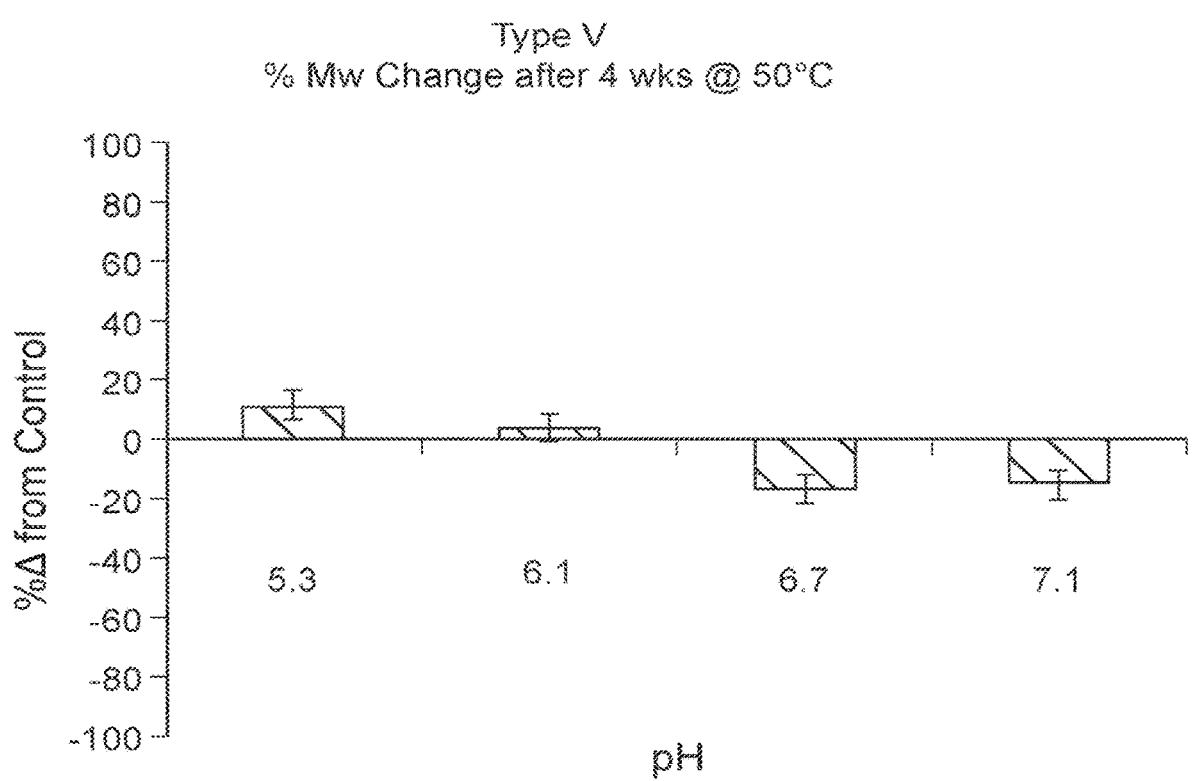
FIG. 7: Stability of GBS V-CRM$_{197}$ (as shown by % change in molecular weight using SEC MALLS) following accelerated storage (4 weeks) at 50° C.

It is to be understood that this invention is not limited to particular methods, and experimental conditions described, as such methods and conditions may vary. It is also to be understood that the terminology used herein is for purposes of describing particular embodiments only, and is not intended to be limiting.

Although any methods and materials similar or equivalent to those described herein can be used in the practice or testing of the invention, the preferred methods and materials are now described. All publications mentioned herein are incorporated by reference in their entirety.

The terms used herein have the meanings recognized and known to those of skill in the art, however, for convenience and completeness, particular terms and their meanings are set forth below and throughout the specification.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

The term "about" or "approximately" means within a statistically meaningful range of a value. Such a range can be within an order of magnitude, typically within 20%, more typically still within 10%, and even more typically within 5% of a given value or range. The allowable variation encompassed by the term "about" or "approximately" depends on the particular system under study, and can be readily appreciated by one of ordinary skill in the art. Whenever a range is recited within this application, every whole number integer within the range is also contemplated as an embodiment of the invention.

In this disclosure, terms such as "comprises", "comprised", "comprising", "contains", "containing" and the like can have the meaning attributed to them in U.S. patent law; e.g., they can mean "includes", "included", "including" and the like. Such terms refer to the inclusion of a particular ingredients or set of ingredients without excluding any other ingredients. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are close-ended. Accordingly, these terms refer to the inclusion of a particular ingredient or set of ingredients and the exclusion of all other ingredients.

The term "antigen" generally refers to a biological molecule, usually a protein, peptide, polysaccharide, lipid or conjugate which contains at least one epitope to which a cognate antibody can selectively bind; or in some instances, to an immunogenic substance that can stimulate the production of antibodies or T-cell responses, or both, in an animal, including compositions that are injected or absorbed into an animal. The immune response may be generated to the whole molecule, or to one or more various portions of the molecule (e.g., an epitope or hapten). The term may be used to refer to an individual molecule or to a homogeneous or heterogeneous population of antigenic molecules. An antigen is recognized by antibodies, T cell receptors or other elements of specific humoral and/or cellular immunity. The term "antigen" includes all related antigenic epitopes. Epitopes of a given antigen can be identified using any number of epitope mapping techniques, well known in the art (see, e.g., Epitope Mapping Protocols in Methods in Molecular Biology, Vol. 66 (Glenn E. Morris, Ed., 1996) Humana Press, Totowa, N.J.). For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen, H. M., et al., Proc. Natl. Acad. Sci. USA, 81:3998-4002 (1984); Geysen, H. M., et al., Molec. Immunol., 23(7):709-715 (1986), all incorporated herein by reference in their entireties. Similarly, conformational epitopes may be identified by determining spatial conformation of amino acids such as by, e.g., x-ray crystallography and 2-dimensional nuclear magnetic resonance (see, e.g., Epitope Mapping Protocols, supra). Furthermore, for purposes of the present invention, an "antigen" may also be used to refer to a protein that includes modifications, such as deletions, additions and substitutions (generally conservative in nature, but they may be non-conservative), to the native sequence, as long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived, obtained, or isolated from a microbe, e.g., a bacterium, or can be a whole organism. Similarly, an oligonucleotide or polynucleotide, which expresses an antigen, such as in nucleic acid immunization applications, is also included in the definition. Synthetic antigens are also included, for example, polyepitopes, flanking epitopes, and other recombinant or synthetically derived antigens (Bergmann, C., et al., Eur. J. Immunol., 23(11):2777-2781(1993); Bergmann, C. C., et al., J. Immunol., 157(8):3242-3249 (1996); Suhrbier, A., Immunol. and Cell Biol., 75(4):402-408 (1997)).

The terms "vaccine" or "vaccine composition", which are used interchangeably, refer to pharmaceutical compositions comprising at least one immunogenic composition that induces an immune response in an animal.

Capsular Polysaccharides

As used herein, the term "saccharide" refers to a single sugar moiety or monosaccharide unit as well as combinations of two or more single sugar moieties or monosaccharide units covalently linked to form disaccharides, oligosaccharides, and polysaccharides. The term "saccharide" may be used interchangeably with the term "carbohydrate." The polysaccharide may be linear or branched.

A "monosaccharide" as used herein refers to a single sugar residue in an oligosaccharide. The term "disaccharide" as used herein refers to a polysaccharide composed of two monosaccharide units or moieties linked together by a glycosidic bond.

In one embodiment, the polysaccharide is an oligosaccharide (OS). An "oligosaccharide" as used herein refers to a compound containing two or more monosaccharide units or moieties. Within the context of an oligosaccharide, an individual monomer unit or moiety is a monosaccharide which is, or can be, bound through a hydroxyl group to another monosaccharide unit or moiety. Oligosaccharides can be prepared by either chemical synthesis from protected single residue sugars or by chemical degradation of biologically produced polysaccharides. Alternatively, oligosaccharides may be prepared by in vitro enzymatic methods.

In a preferred embodiment, the polysaccharide PS refers to a linear or branched polymer of at least 5 monosaccharide units or moieties. For clarity, larger number of repeating units, wherein n is greater than about 5, such as greater than about 10, will be referred to herein as a polysaccharide.

In one embodiment, the polysaccharide is a cell surface polysaccharide. A cell surface polysaccharide refers to a polysaccharide having at least a portion located on the outermost bacterial cell membrane or bacterial cell surface, including the peptidoglycan layer, cell wall, and capsule. Typically, a cell surface polysaccharide is associated with inducing an immune response in vivo. A cell surface polysaccharide may be a "cell wall polysaccharide" or a "capsular polysaccharide." A cell wall polysaccharide typically forms a discontinuous layer on the bacterial surface.

In one embodiment, the polysaccharide is a capsular polysaccharide. A capsular polysaccharide refers to a glycopolymer that includes repeating units of one or more monosaccharides joined by glycosidic linkages. A capsular polysaccharide typically forms a capsule-like layer around a bacterial cell. "Capsular polysaccharide" or "capsule polysaccharide" refers to the polysaccharide capsule that is external to the cell wall of most isolates of streptococci. For example, all GBS capsular polysaccharides have a branched repeat structure with a terminal α2-3-linked sialic acid that is required for bacterial virulence. Capsule-associated sialic acid (quantified by HPLC assay) has been detected in >94% of invasive neonatal isolates from T.E.S.T. cultured in vitro.

The present inventors have discovered that the sialic acid level of GBS capsular polysaccharides is an important characteristic for producing an immune response. Prior disclosures have only provided conflicting information regarding sialic acid levels for serotype V, finding that desialylated serotype V was preferred (Int'l Patent Appl. Pub. No. WO 2012/035519) and that sialic acid content >50% for serotype V could be used (Int'l Patent Appl. Pub. No. WO 2014/053612). However, nothing in these references describe the importance of sialic acid levels for at least a majority of GBS polysaccharides on immunogenicity. The present inventors have surprisingly found that GBS capsular polysaccharides require about 60% or more sialic acid prior to conjugation to provide an immune response comparable to those polysaccharides having native sialic acid levels (i.e. 100% or greater than about 95%). Sialic acid levels of even 58%, which is within the prior range disclosed for serotype V, negatively impacted immunogenicity.

Accordingly, in one embodiment of the invention, the capsular polysaccharides comprise their natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), and up to about 5% (sialylation level greater than about 95%).

It should be noted that 100% sialic acid level corresponds to about 1.0 mM sialic acid per mM of polysaccharide. Therefore, the capsular polysaccharides may have about 1.0 mM sialic acid per mM of polysaccharide, such as at least about 0.95 mM sialic acid per mM of polysaccharide. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide.

The terminal sialic residues of some capsular polysaccharide (CP) serotypes are partially O-acetylated (OAc) (Lewis, A. L., et al., Proceedings of the National Academy of Sciences USA, 101(30):11123-8 (2004)). Serotypes Ib, III, IV, V, VI, and IX are partially O-acetylated (up to ~40%), whereas serotypes Ia, II, and VII have little or no O-acetylation (less than about 5%) (Lewis 2004). In one embodiment of the invention, the capsular polysaccharides comprise their natural O-acetylation level (about 0% to about 40%). In another embodiment, the capsular polysaccharides may be de-O-acetylated (less than about 5%). The degree of O-acetylation of the polysaccharide or oligosaccharide can be determined by any method known in the art, for example, by proton NMR (Lemercinier, X., et al., Carbohydrate Research, 296:83-96 (1996); Jones, C., et al., Journal of Pharmaceutical and Biomedical Analysis, 30:1233-1247 (2002); Int'l Patent Appl. Pub. Nos. WO 2005/033148 and WO 00/56357). Another commonly used method is described by Hestrin, S., J. Biol. Chem., 180:249-261 (1949).

Also, 100% O-acetate corresponds to about 1.0 mM O-acetate per mM of saccharide repeating unit. Accordingly, partially O-acetylated polysaccharides comprise at least about 0.1, 0.2, 0.3, 0.35 or about 0.4 mM O-acetate per mM saccharide repeating unit. A de-O-acetylated polysaccharide comprises less than about 0.01, 0.02, 0.03, 0.04, or 0.05 mM O-acetate per mM saccharide repeating unit.

Streptococcal microorganisms capable of causing invasive disease generally also are capable of producing a CP that encapsulates the bacterium and enhances its resistance to clearance by host innate immune system. The CP serves to cloak the bacterial cell in a protective capsule that renders the bacteria resistant to phagocytosis and intracellular killing. Bacteria lacking a capsule are more susceptible to phagocytosis. Capsular polysaccharides are frequently an important virulence factor for many bacterial pathogens, including *Haemophilus influenzae, Streptococcus pneumoniae, Neisseria meningitidis,* and *Staphylococcus aureus.*

The capsule polysaccharide can be used to serotype a particular species of bacteria. Typing is usually accomplished by reaction with a specific antiserum or monoclonal antibody generated to a specific structure or unique epitope characteristic of the capsule polysaccharide. There are ten GBS serotypes: Ia, Ib, and II-IX (Ferrieri, P., et al., Emerg. Infect. Dis. [Internet], 19(4) (2013), available at http://wwwnc.cdc.gov/eid/article/19/4/12-1572_article.

In one embodiment of the invention, the polysaccharide is isolated from *Streptococcus agalactiae*. The polysaccharide may be isolated from any encapsulated strain of *S. agalactiae*, such as 090, A909 (ATCC Accession No. BAA-1138), 515 (ATCC Accession No. BAA-1177), B523, CJB524, MB 4052 (ATCC Accession No. 31574), H36B (ATCC Accession No. 12401), S40, S42, MB 4053 (ATCC Accession No. 31575), M709, 133, 7357, PFEGBST0267, MB 4055 (ATCC Accession No. 31576), 18RS21 (ATCC Accession No. BAA-1175), S16, S20, V8 (ATCC Accession No. 12973), DK21, DK23, UAB, 5401, PFEGBST0708, MB 4082 (ATCC Accession No. 31577), M132, 110, M781 (ATCC Accession No. BAA-22), D136C(3) (ATCC Accession No. 12403), M782, S23, 120, MB 4316 (M-732; ATCC Accession No. 31475), M132, K79, COH1 (ATCC Accession No. BAA-1176), PFEGBST0563, 3139 (ATCC Accession No. 49446), CZ-NI-016, PFEGBST0961, 1169-NT1, CJB111 (ATCC Accession No. BAA-23), CJB112, 2603 V/R (ATCC Accession No. BAA-611), NCTC 10/81, CJ11, PFEGBST0837, 118754, 114852, 114862, 114866, 118775, B 4589, B 4645, SS1214, CZ-PW-119, 7271, CZ-PW-045, JM9130013, JM9130672, IT-NI-016, IT-PW-62, and IT-PW-64.

The polysaccharides described herein may be isolated by methods known in the art, including, for example, methods described herein. As used herein, "isolated" refers to being obtained from and separated from a particular source. The term "isolated" further refers to not being in its respective naturally occurring form, state, and/or environment. For example, "isolated from streptococcus" refers to a matter that was obtained from and separated from a streptococcus cell. The isolated polysaccharide is not naturally occurring. The term "isolated" means that the material is removed from its original environment (e.g., the natural environment if it is naturally occurring or from its host organism if it is a recombinant entity, or taken from one environment to a different environment). For example, an "isolated" capsule polysaccharide, protein or peptide is substantially free of cellular material or other contaminating proteins from the cell or tissue source from which the protein is derived, or substantially free of chemical precursors or other chemicals when chemically synthesized, or otherwise present in a mixture as part of a chemical reaction. In the present invention, the proteins or polysaccharides may be isolated from the bacterial cell or from cellular debris, so that they are provided in a form useful in the manufacture of an immunogenic composition. The term "isolated" or "isolating" may include purifying, or purification, including methods for purifying an isolated polysaccharide known in the art and/or methods described herein. The language "substantially free of cellular material" includes preparations of a polypeptide/protein in which the polypeptide/protein is separated from cellular components of the cells from which it is isolated or recombinantly produced. Thus, a capsule polysaccharide, protein or peptide that is substantially free of cellular material includes preparations of the capsule polysaccharide, protein or peptide having less than about 30%, 20%, 10%, 5%, 2.5% or 1% (by dry weight) of contaminating protein or polysaccharide or other cellular material. When the polypeptide/protein is recombinantly produced, it is also preferably substantially free of culture medium, i.e., culture medium represents less than about 20%, 10%, or 5% of the volume of the protein preparation. When polypeptide/protein or polysaccharide is produced by chemical synthesis, it is preferably substantially free of chemical precursors or other chemicals, i.e., it is separated from chemical precursors or other chemicals which are involved in the synthesis of the protein or polysaccharide. Accordingly, such preparations of the polypeptide/protein or polysaccharide have less than about 30%, 20%, 10%, 5% (by dry weight) of chemical precursors or compounds other than polypeptide/protein or polysaccharide fragment of interest.

In one embodiment of the invention, the polysaccharide is isolated from a bacterium. In another embodiment of the invention, the polysaccharide is produced recombinantly. In further embodiment, the polysaccharide is synthetic or chemically synthesized according to conventional methods. In yet another embodiment of the invention, the polysaccharide is prepared by expression in a surrogate host after cloning and expressing a biosynthetic pathway to produce the polysaccharide. In one embodiment, the polysaccharide is immunogenic. For example, the inventors discovered that each polysaccharide described herein is capable of inducing or eliciting an immune response. The term "immunogenic" refers to an ability to initiate, trigger, cause, enhance, improve, and/or augment a humoral and/or cell-mediated immune response in a mammal. In one embodiment, the mammal is a human, primate, rabbit, pig, mouse, etc.

The molecular weight of the capsular polysaccharide is a consideration for use in immunogenic compositions. High molecular weight capsular polysaccharides are able to induce certain antibody immune responses due to a higher valence of the epitopes present on the antigenic surface. The isolation and purification of high molecular weight capsular polysaccharides is contemplated for use in the conjugates, compositions and methods of the present invention.

However, in one embodiment, the polysaccharide may be sized to a molecular weight (MW) range that is lower than the molecular weight of the native capsular polysaccharide prior to conjugation to a carrier protein. The size of the purified capsular polysaccharide is reduced in order to generate conjugates with advantageous filterability characteristics and/or yields.

In one such embodiment, the size of the purified capsular polysaccharide is reduced by high pressure homogenization.

positive coccus, preferably against a *Streptococcus* species, more preferably against at least one strain of *S. agalactiae*.

In yet another embodiment, the polysaccharide described herein is capable of inducing a bactericidal immune response. In one embodiment, the bactericidal activity is against a Gram positive coccus, preferably against a *Streptococcus* species, more preferably against at least one strain of *S. agalactiae*.

Methods for measuring opsonization, phagocytosis, and/or bactericidal activity are known in the art, such as, for example, by measuring reduction in bacterial load in vivo (e.g., by measuring bacteremia levels in mammals challenged with a *Streptococcus* species) and/or by measuring bacterial cell killing in vitro (e.g., an in vitro opsonophagocytic assay). In one embodiment, the polysaccharide is capable of inducing opsonic, phagocytic, and/or bactericidal activity as compared to an appropriate control, such as, for example, as compared to antisera raised against a heat-killed Gram positive coccus.

Serotype Ia

One embodiment includes a serotype Ia GBS capsular polysaccharide. The structure of serotype Ia can be depicted as follows:

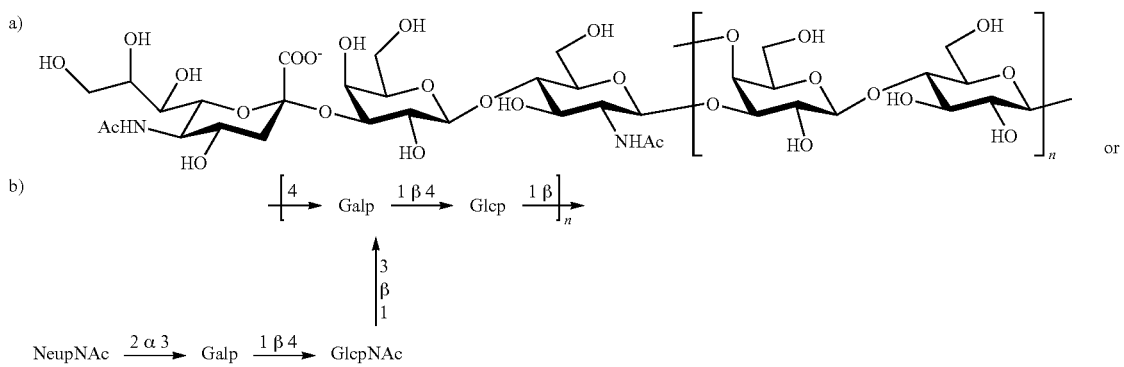

High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

In one embodiment, the polysaccharide described herein is capable of inducing opsonic activity. In another embodiment, the polysaccharide described herein is capable of inducing opsonic and phagocytic activity (e.g., opsonophagocytic activity).

Opsonic activity or opsonization refers to a process by which an opsonin (for example, an antibody or a complement factor) binds to an antigen (e.g., an isolated polysaccharide described herein), which facilitates attachment of the antigen to a phagocyte or phagocytic cell (e.g., a macrophage, dendritic cell, and polymorphonuclear leukocyte (PMNL). Some bacteria, such as, for example, encapsulated bacteria that are not typically phagocytosed due to the presence of the capsule, become more likely to be recognized by phagocytes when coated with an opsonic antibody. In one embodiment, the polysaccharide induces an immune response, such as, e.g., an antibody, that is opsonic. In one embodiment, the opsonic activity is against a Gram The molecular weight of serotype Ia capsular polysaccharides prior to conjugation are between about 5 kDa and about 1,000 kDa, such as between about 25 kDa and about 750 kDa, between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 250 kDa, between about 25 kDa and about 200 kDa, between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. In one preferred embodiment, the molecular weight of the capsular polysaccharide prior to conjugation is between about 25 kDa and about 200 kDa. In another preferred embodiment, the molecular weight of the capsular polysaccharide prior to conjugation is between about 100 kDa and about 400 kDa. Any whole number integer within any of the above ranges is contemplated as an embodiment of the disclosure.

In a particular embodiment, a high pressure homogenization process is used to reduce the size of native GBS capsular polysaccharide serotype Ia while preserving the structural features, such as sialic acid, of the polysaccharide.

In one embodiment of the invention, the serotype Ia capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype Ia capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype Ia capsular polysaccharides are less than about 5% O-acetylated. Some exemplary strains of serotype Ia capsular polysaccharides of the invention include 090, A909 (ATCC Accession No. BAA-1138), 515 (ATCC Accession No. BAA-1177), B523, CJB524, and MB 4052 (ATCC Accession No. 31574).

Serotype Ib

One embodiment includes a serotype Ib GBS capsular polysaccharide. The structure of serotype Ib can be depicted as follows:

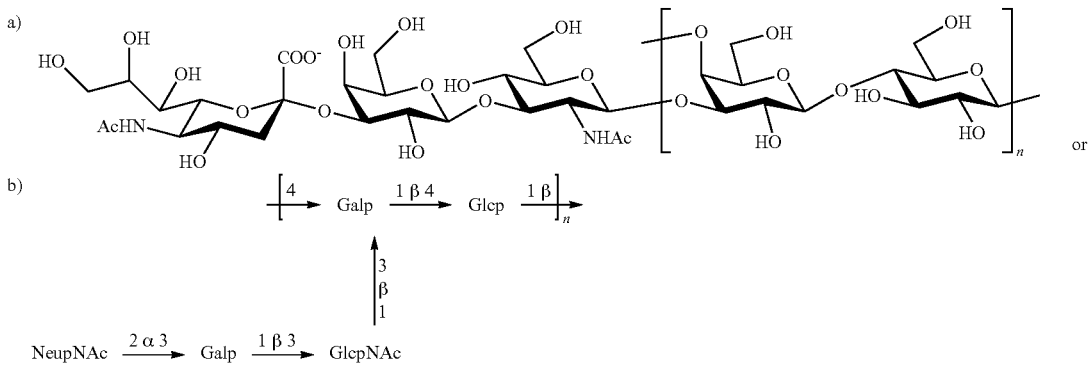

The molecular weight of serotype Ib capsular polysaccharides prior to conjugation are between about 5 kDa and about 1,000 kDa, such as between about 25 kDa and about 750 kDa, between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 250 kDa, between about 25 kDa and about 200 kDa, between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and about 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. In one preferred embodiment, the molecular weight of the capsular polysaccharide prior to conjugation is between about 25 kDa and about 400 kDa. Any whole number integer within any of the above ranges is contemplated as an embodiment of the disclosure.

In one embodiment of the invention, the serotype Ib capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype Ib capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype Ib capsular polysaccharides are between about 0% and about 40% O-acetylated. In one embodiment of the invention, the polysaccharide is de-O-acetylated (i.e., less than about 5% O-acetylated). Some exemplary strains of serotype Ib capsular polysaccharides of the invention include H36B (ATCC Accession No. 12401), S40, S42, MB 4053 (ATCC Accession No. 31575), M709, 133, 7357, and PFEGBST0267.

Serotype II

One embodiment includes a serotype II GBS capsular polysaccharide. The structure of serotype II can be depicted as follows:

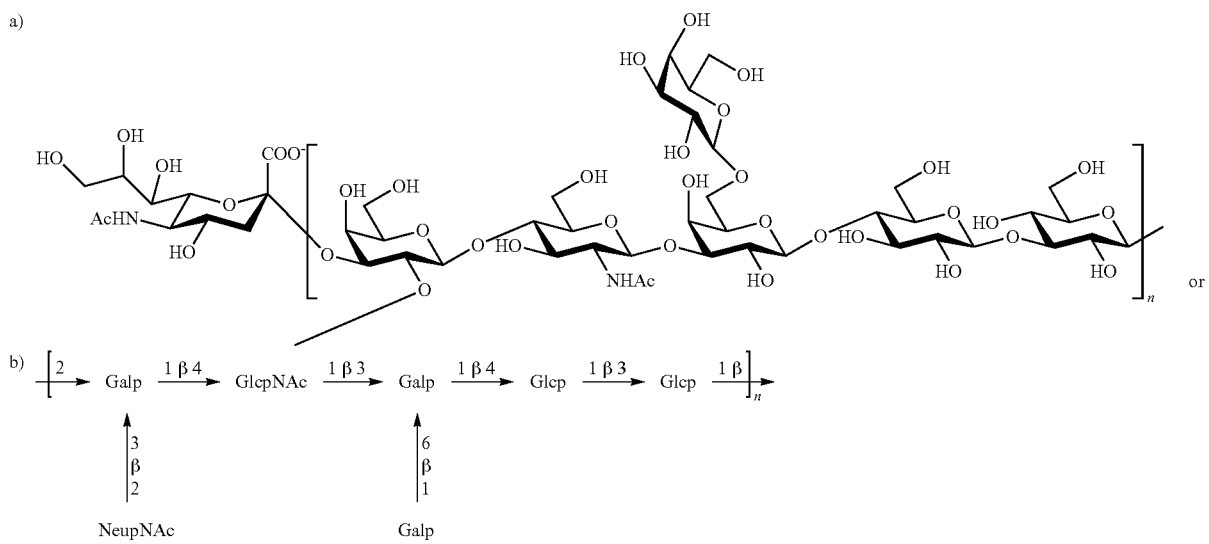

The molecular weight of serotype II capsular polysaccharides prior to conjugation are between about 5 kDa and about 1,000 kDa, such as between about 25 kDa and about 750 kDa, between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 250 kDa, between about 25 kDa and about 200 kDa, between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype II capsular polysaccharides are less than about 5% O-acetylated. Some exemplary strains of serotype II capsular polysaccharides of the invention include MB 4055 (ATCC Accession No. 31576), 18RS21 (ATCC Accession No. BAA-1175), S16, S20, V8 (ATCC Accession No. 12973), DK21, DK23, UAB, 5401, and PFEGBST0708.

Serotype III

One embodiment includes a serotype III GBS capsular polysaccharide. The structure of serotype III can be depicted as follows:

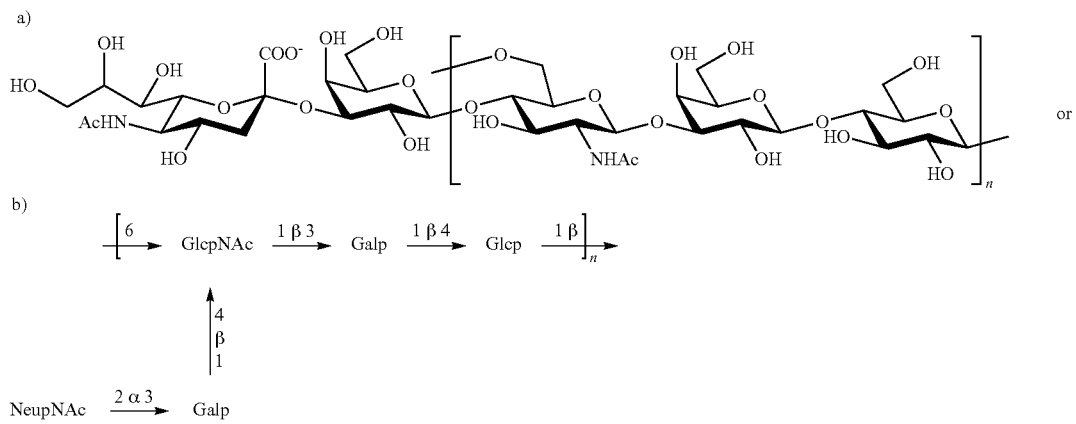

between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. In one preferred embodiment, the molecular weight of the capsular polysaccharide prior to conjugation is between about 25 kDa and about 400 kDa. Any whole number integer within any of the above ranges is contemplated as an embodiment of the disclosure.

In one embodiment of the invention, the serotype II capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype II capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, The molecular weight of serotype III capsular polysaccharides prior to conjugation are between about 5 kDa and about 1,000 kDa, such as between about 25 kDa and about 750 kDa, between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 250 kDa, between about 25 kDa and about 200 kDa, between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. In one preferred embodiment, the molecular weight of the capsular polysaccharide prior to conjugation is between about 25 kDa and about 200 kDa. In another preferred embodiment, the molecular weight of the capsular polysaccharide prior to conjugation is between about 100 kDa and about 400 kDa. Any whole number integer within any of the above ranges is contemplated as an embodiment of the disclosure.

In a particular embodiment, a high pressure homogenization process is used to reduce the size of native GBS capsular polysaccharide serotype III while preserving the structural features, such as sialic acid, of the polysaccharide.

In one embodiment of the invention, the serotype III capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype III capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype III capsular polysaccharides are between about 0% and about 40% O-acetylated. In one embodiment of the invention, the polysaccharide is de-O-acetylated (i.e., less than about 5% O-acetylated). Some exemplary strains of serotype III capsular polysaccharides of the invention include MB 4082 (ATCC Accession No. 31577), M132, 110, M781 (ATCC Accession No. BAA-22), D136C(3) (ATCC Accession No. 12403), M782, S23, 120, MB 4316 (M-732; ATCC Accession No. 31475), M132, K79, COH1 (ATCC Accession No. BAA-1176), and PFEGBST0563.

Serotype IV

One embodiment includes a serotype IV GBS capsular polysaccharide. The structure of serotype IV can be depicted as follows:

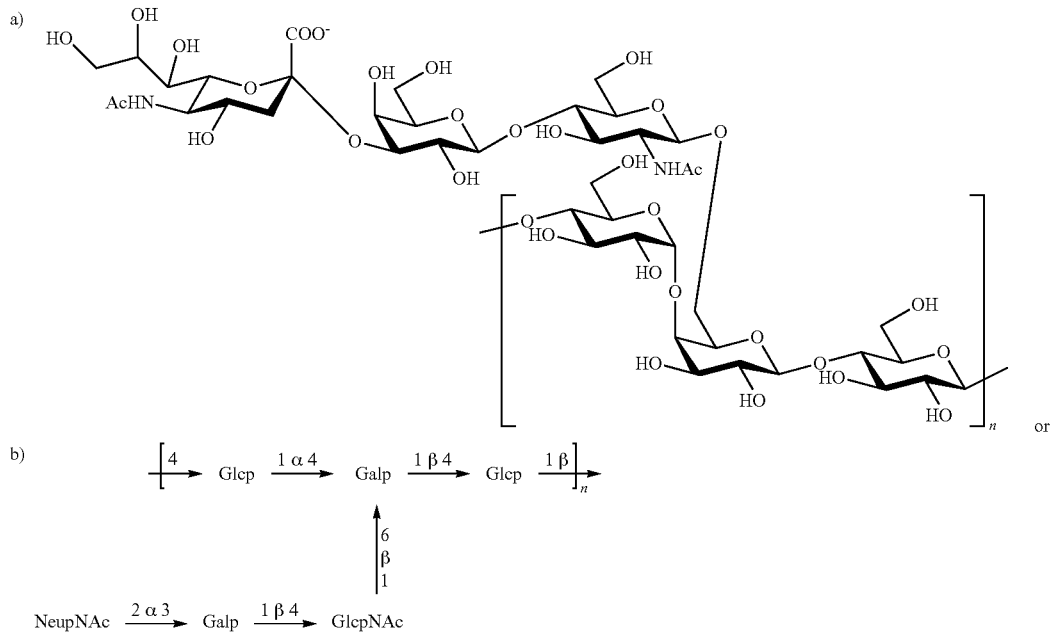

The molecular weight of serotype IV capsular polysaccharides prior to conjugation are between about 5 kDa and about 1,000 kDa, such as between about 25 kDa and about 750 kDa, between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 250 kDa, between about 25 kDa and about 200 kDa, between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. In one preferred embodiment, the molecular weight of the capsular polysaccharide prior to conjugation is between about 25 kDa and about 400 kDa. Any whole number integer within any of the above ranges is contemplated as an embodiment of the disclosure.

In one embodiment of the invention, the serotype IV capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype IV capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype IV capsular polysaccharides are between about 0% and about 40% O-acetylated. In one embodiment of the invention, the polysaccharide is de-O-acetylated (i.e., less than about 5% O-acetylated). Some exemplary strains of serotype IV capsular polysaccharides of the invention include 3139 (ATCC Accession No. 49446), CZ-NI-016, and PFEGBST0961.

Serotype V

One embodiment includes a serotype V GBS capsular polysaccharide. The structure of serotype V can be depicted as follows:

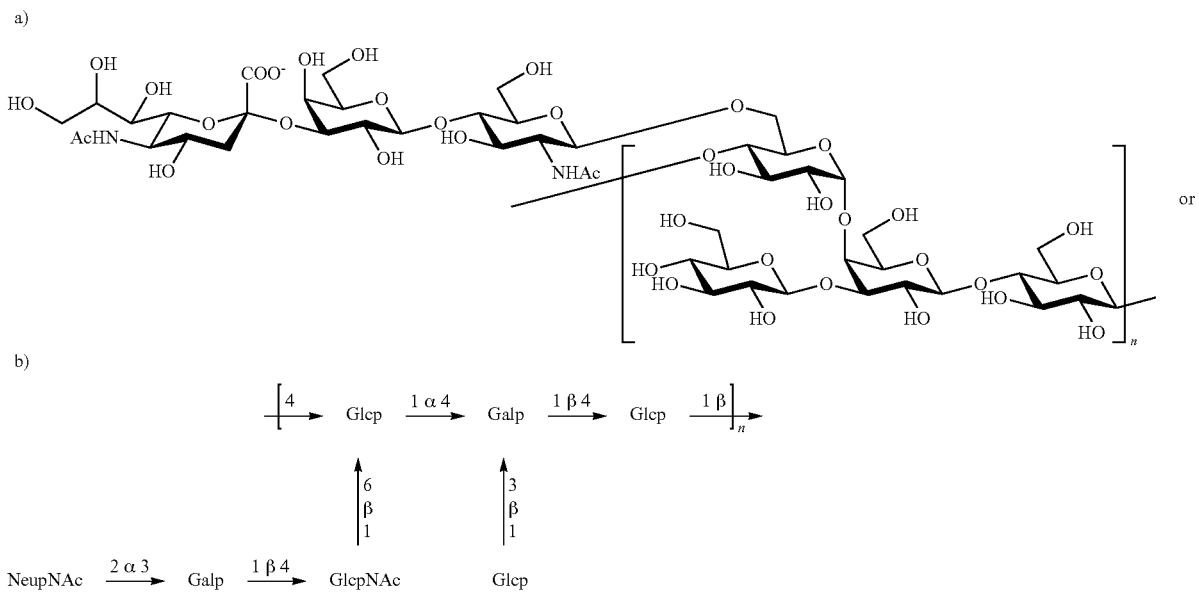

The molecular weight of serotype V capsular polysaccharides prior to conjugation are between about 5 kDa and about 1,000 kDa, such as between about 25 kDa and about 750 kDa, between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 250 kDa, between about 25 kDa and about 200 kDa, between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. In one preferred embodiment, the molecular weight of the capsular polysaccharide prior to conjugation is between about 25 kDa and about 400 kDa. Any whole number integer within any of the above ranges is contemplated as an embodiment of the disclosure.

In one embodiment of the invention, the serotype V capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype V capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype V capsular polysaccharides are between about 0% and about 40% O-acetylated. In one embodiment of the invention, the polysaccharide is de-O-acetylated (i.e., less than about 5% O-acetylated). Some exemplary strains of serotype V capsular polysaccharides of the invention include 1169-NT1, CJB111 (ATCC Accession No. BAA-23), CJB112, 2603 V/R (ATCC Accession No. BAA-611), NCTC 10/81, CJ11, and PFEGBST0837.

Serotype VI

GBS Serotype VI capsular polysaccharides are described by von Hunolstein, C., et al., Infection and Immunity, 6194):1272-1280 (1993), the disclosures of which are hereby incorporated by reference in their entirety. The structure of serotype VI can be depicted as follows:

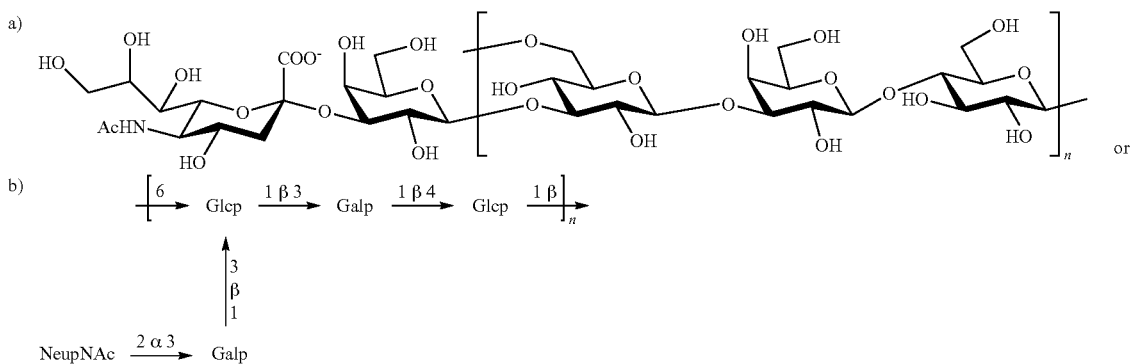

The molecular weight of serotype VI capsular polysaccharides prior to conjugation are between about 5 kDa and about 1,000 kDa, such as between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. Any whole number integer within any of the above ranges is contemplated as an embodiment of the disclosure.

In one embodiment of the invention, the serotype VI capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95 poly %) prior to conjugation.

In another embodiment, the serotype VI capsular polysaccharide has about 1.0 mM sialic acid per mM of saccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype VI capsular polysaccharides are between about 0% and about 40% O-acetylated. In one embodiment of the invention, the polysaccharide is de-O-acetylated (i.e., less than about 5% O-acetylated). Some exemplary strains of serotype IIII capsular polysaccharides of the invention include 118754, 114852, 114862, 114866, 118775, B 4589, B 4645, SS1214, and CZ-PW-119.

Serotype VII

GBS Serotype VII capsular polysaccharides are described by Kogan, G., et al., Carbohydrate Research, 277(1):1-9 (1995), the disclosures of which are hereby incorporated by reference in their entirety. The repeating unit of serotype VII is as follows:

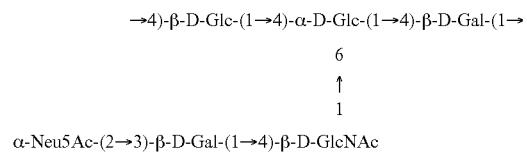

The molecular weight of serotype VII capsular polysaccharides prior to conjugation are between about 5 kDa and about 1,000 kDa, such as between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. Any whole number integer within any of the above ranges is contemplated as an embodiment of the disclosure.

In one embodiment of the invention, the serotype VII capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype VII capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype VII capsular polysaccharides are less than about 5% O-acetylated. Some exemplary strains of serotype VII capsular polysaccharides of the invention include 7271 and CZ-PW-045.

Serotype VIII

GBS Serotype VIII capsular polysaccharides are described by Kogan, G., et al., The Journal of Biological Chemistry, 271(15):8786-8790 (1996), the disclosures of which are hereby incorporated by reference in their entirety. The repeating unit of serotype VIII is as follows:

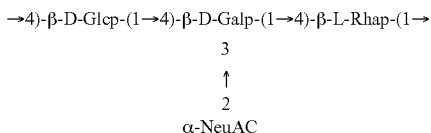

The molecular weight of serotype VIII capsular polysaccharides prior to conjugation are between about 5 kDa and about 1,000 kDa, such as between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and about 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. Any whole number integer within any of the above ranges is contemplated as an embodiment of the disclosure.

In one embodiment of the invention, the serotype VIII capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype VIII capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype VIII capsular polysaccharides are between about 0% and about 40% O-acetylated. In one embodiment of the invention, the polysaccharide is de-O-acetylated (i.e., less than about 5% O-acetylated). Some exemplary strains of serotype VIII capsular polysaccharides of the invention include JM9130013 and JM9130672.

Serotype IX

GBS Serotype IX capsular polysaccharides are described by Berti, F., et al., The Journal of Biological Chemistry, 289(34):23437-2348 (2014), the disclosures of which are hereby incorporated by reference in their entirety. The structure of serotype IX can be depicted as follows:

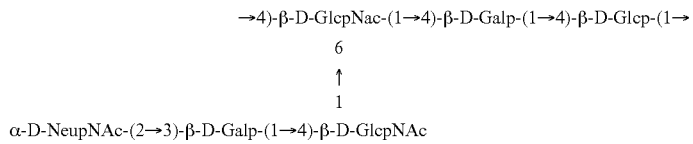

The molecular weight of serotype IX capsular polysaccharides prior to conjugation are between about 5 kDa and about 1,000 kDa, such as between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and about 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. Any whole number integer within any of the above ranges is contemplated as an embodiment of the disclosure.

In one embodiment of the invention, the serotype IX capsular polysaccharide comprises its natural sialic acid level, such as about 100% or greater than about 95%. In another embodiment, the capsular polysaccharides may be desialylated up to about 40% (sialylation level greater than about 60%), such as up to about 35% (sialylation level greater than about 65%), up to about 30% (sialylation level greater than about 70%), up to about 25% (sialylation level greater than about 75%), up to about 20% (sialylation level greater than about 80%), up to about 15% (sialylation level greater than about 85%), up to about 10% (sialylation level greater than about 90%), or up to about 5% (sialylation level greater than about 95%) prior to conjugation.

In another embodiment, the serotype IX capsular polysaccharide has about 1.0 mM sialic acid per mM of polysaccharide, such as at least about 0.95 mM sialic acid per mM of polysaccharide prior to conjugation. In a further embodiment, the capsular polysaccharide may have at least about 0.6 mM sialic acid per mM of polysaccharide, such as at least about 0.65 mM sialic acid per mM of polysaccharide, at least about 0.7 mM sialic acid per mM of polysaccharide, at least about 0.75 mM sialic acid per mM of polysaccharide, at least about 0.8 mM sialic acid per mM of polysaccharide, at least about 0.85 mM sialic acid per mM of polysaccharide, at least about 0.9 mM sialic acid per mM of polysaccharide, or at least about 0.95 mM sialic acid per mM of polysaccharide prior to conjugation.

Serotype IX capsular polysaccharides are between about 0% and about 40% O-acetylated. In one embodiment of the invention, the polysaccharide is de-O-acetylated (i.e., less than about 5% O-acetylated). Some exemplary strains of serotype IX capsular polysaccharides of the invention include IT-NI-016, IT-PW-62, and IT-PW-64.

Polysaccharide-Protein Conjugates

As used herein, "conjugates" comprise a capsule polysaccharide usually of a desired range of molecular weight and a carrier protein, wherein the capsule polysaccharide is conjugated to the carrier protein. Conjugates may or may not contain some amount of free capsule polysaccharide. As used herein, "free capsule polysaccharide" refers to capsule polysaccharide that is non-covalently associated with (i.e., non-covalently bound to, adsorbed to or entrapped in or with) the conjugated capsular polysaccharide-carrier protein. The terms "free capsule polysaccharide," "free polysaccharide" and "free saccharide" may be used interchangeably and are intended to convey the same meaning. Regardless of the nature of the carrier molecule, it can be conjugated to the capsular polysaccharide either directly or through a linker. As used herein, "to conjugate", "conjugated" and "conjugating" refers to a process whereby a bacterial capsular polysaccharide is covalently attached to the carrier molecule. Conjugation enhances the immunogenicity of the bacterial capsular polysaccharide. The conjugation can be performed according to the methods described below or by processes known in the art.

A "conjugate immunogenic composition," as used herein, refers to an immunogenic composition wherein the immunogenic material includes an antigenic polysaccharide that is covalently linked to a carrier protein to produce a polysaccharide-protein conjugate. In one embodiment, a polysaccharide-protein conjugate of the invention may be formulated as a multivalent immunogenic composition.

As used herein, the term "molecular weight" of polysaccharide or of carrier protein-polysaccharide conjugate refers to molecular weight calculated by size exclusion chromatography (SEC) combined with multiangle laser light scattering detector (MALLS).

As used herein, a "polysaccharide-protein conjugate" refers to a polysaccharide molecule conjugated to a protein carrier molecule through one or more covalent bonds. It may be desirable to conjugate the polysaccharide to a protein from another species known to be immunogenic in the target host. Accordingly, in one embodiment, the carrier molecule is a carrier protein. As defined herein, such a foreign protein is referred to as a "carrier protein." Carrier proteins serve to enhance the antigenicity and immunogenicity of the polysaccharide. As used herein, the term "carrier effect" refers to the process where the antigenicity and immunogenicity of a weakly immunogenic or non-immunogenic molecule is enhanced, by being attached to a more immunogenic molecule as carrier (e.g., a heterologous protein). In this case, the polysaccharide in the combined polysaccharide-protein conjugate becomes more immunogenic than if it were presented alone. Carrier proteins contain T cell epitopes for stimulating T-cell help for producing antibody responses.

"Carrier protein" or "protein carrier" as used herein, refers to any protein molecule that may be conjugated to an antigen (such as the capsular polysaccharides) against which an immune response is desired. Conjugation of an antigen such as a polysaccharide to a carrier protein can render the antigen immunogenic. Carrier proteins are preferably proteins that are non-toxic and non-reactogenic and obtainable in sufficient amount and purity. Examples of carrier proteins are toxins, toxoids or any mutant cross-reactive material (CRM1g1) of the toxin from tetanus, diphtheria, pertussis, *Pseudomonas* species, *E. coli, Staphylococcus species*, and *Streptococcus* species. Carrier proteins should be amenable to standard conjugation procedures. In a particular embodiment of the present invention, CRM197 is used as the carrier protein.

Cross-reacting materials or CRMs are especially useful for some embodiments of the present invention. One may produce genetically altered proteins, which are antigenically similar to the certain bacterial toxins, yet non-toxic. These are called "cross reacting materials", or CRMs. CRM197 (Wyeth/Pfizer Inc., Sanford, N.C.) is noteworthy since it has a single amino acid change from the native diphtheria toxin and is immunologically indistinguishable from it. See Pappenheimer, A M., et al., Immunochem., 9(9):891-906 (1972); U.S. Pat. No. 5,614,382, the disclosures of which are hereby incorporated by reference in their entirety. CRM197 is a non-toxic variant (i.e., toxoid) of diphtheria toxin isolated from cultures of Corynebacterium diphtheriae strain C7 ([3197) grown in casamino acids and yeast extract-based medium. CRM197 is purified through ultra-filtration, ammonium sulfate precipitation, and ion-exchange chromatography. A culture of C. diphtheriae strain C7 ([3197), which produces CRM197 protein, has been deposited with the American Type Culture Collection, Manassas, Va. and has been assigned accession number ATCC 53281. Other diphtheria toxoids are also suitable for use as carrier proteins. CRM3201 is a genetically manipulated variant of pertussis toxin. See Black, W. J., et al., Science, 240(4852): 656-659 (1988), the disclosure of which is hereby incorporated by reference in their entirety.

In addition to a diphtheria toxoid (DT), CRM197, and a pertussis toxoid, further examples of carrier proteins include a tetanus toxoid (TT), a cholera toxoid (e.g., as described in Intl Patent Appl. Pub. No. WO 2004/083251), an E. coli heat labile toxoid (LT), an E. coli heat stable toxoid (ST), pneumolysin from S. pneumonia (wild-type or mutant with reduced toxicity), pneumococcal surface protein A (PspA), pneumococcal adhesin protein A (PsaA), a C5a peptidase from Streptococcus, hemolysin from Staphylococcal aureus, Nontypeable Haemophilus influenzae (NTHi) proteins, Haemophilus influenzae protein D, Clostridium perfringens exotoxins/toxoid, hepatitis B surface antigen, hepatitis B core antigen, rotavirus VP 7 protein, and respiratory syncytial virus F and G protein, ovalbumin, keyhole limpet haemocyanin (KLH), bovine serum albumin (BSA), purified protein derivative of tuberculin (PPD), and a Pseudomonas exotoxin or its derivatives, including a recombinantly-produced non-toxic mutant Pseudomonas aeruginosa Exotoxin A. Bacterial outer membrane proteins such as outer membrane protein complex c (OMPC), porins, transferrin binding proteins, or C. difficile enterotoxin (toxin A) and cytotoxin (toxin B) can also be used. Other proteins, such as ovalbumin, keyhole limpet hemocyanin (KLH), bovine serum albumin (BSA) or purified protein derivative of tuberculin (PPD) can also be used as carrier proteins. In a preferred embodiment, the carrier protein is a diphtheria toxoid. More preferably, the carrier protein is $CRM_{197}$. In another embodiment of the invention, the carrier protein is tetanus toxoid.

For the synthesis of a multivalent conjugate immunogenic composition, polysaccharide-protein conjugates may be produced by conjugating a mixture of polysaccharides purified from bacteria of two different species to a carrier protein. Alternatively, a multivalent conjugate immunogenic composition may be produced by combining polysaccharides purified from bacteria of two or more different serotypes of the same bacteria and conjugating them as a mixture to a carrier protein. Alternatively, polysaccharide-protein conjugates produced by reacting a single type of polysaccharide with carrier protein in separate reactions using different polysaccharides, may be mixed. Thus, a multivalent immunogenic composition may include a carrier protein bearing a homogeneous or a heterogeneous population of linked polysaccharides.

After conjugation of the capsular polysaccharide to the carrier protein, the polysaccharide-protein conjugates are purified (enriched with respect to the amount of polysaccharide-protein conjugate) by a variety of techniques. These techniques include, e.g., concentration/diafiltration operations, precipitation/elution, column chromatography, and depth filtration.

As described above, the present invention relates to conjugates comprising GBS capsular polysaccharides conjugated to carrier proteins. One embodiment of the invention provides conjugates comprising a GBS serotype IV capsular polysaccharide conjugated to a carrier protein and at least one additional conjugate comprising a GBS serotype Ia capsular polysaccharide conjugated to a carrier protein, a GBS serotype Ib capsular polysaccharide conjugated to a carrier protein, a GBS serotype II capsular polysaccharide conjugated to a carrier protein, a GBS serotype IIII capsular polysaccharide conjugated to a carrier protein, a GBS serotype V capsular polysaccharide conjugated to a carrier protein, a GBS serotype VI capsular polysaccharide conjugated to a carrier protein, a GBS serotype VII capsular polysaccharide conjugated to a carrier protein, a GBS serotype VIII capsular polysaccharide conjugated to a carrier protein, or a GBS serotype IX capsular polysaccharide conjugated to a carrier protein. In one aspect of the invention, the polysaccharides have a molecular weight of between about 5 kDa and 1,000 kDa; the conjugates have molecular weights of between about 300 kDa and about 20,000 kDa; and the conjugates comprise less than about 40% free polysaccharide relative to total polysaccharide. In one embodiment, the conjugates comprise less than about 30%, less than about 25%, less than about 20%, less than about 15%, less than about 10%, or less than about 5% free polysaccharide relative to total polysaccharide. In one embodiment, the serotype Ia, Ib, II, III, IV, V, VI, VII, VIII, and/or IX polysaccharide has a molecular weight before conjugation of between about 5 kDa and about 1,000 kDa, such as between about 50 kDa and about 750 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 250 kDa, between about 50 kDa and about 200 kDa, between about 75 kDa and about 750 kDa, between about 75 kDa and about 500 kDa, between about 75 kDa and about 450 kDa, between about 75 kDa and about 400 kDa, between about 75 kDa and about 350 kDa, between about 75 kDa and about 300 kDa, between about 75 kDa and about 250 kDa, between about 75 kDa and about 200 kDa, between about 100 kDa and about 750 kDa, between about 100 kDa and about 700 kDa, between about 100 kDa and about 650 kDa, between about 100 kDa and about 600 kDa, between about 100 kDa and about 550 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 200 kDa and about 750 kDa, between about 200 kDa and about 700 kDa, between about 200 kDa and about 650 kDa, between about 200 kDa and about 600 kDa, between about 200 kDa and about 550 kDa, between about 200 kDa and about 500 kDa, between about 200 kDa and about 450 kDa, between about 200 kDa and about 400 kDa, between about 250 kDa and about 750 kDa, between about 250 kDa and about 700 kDa, between about 250 kDa and about 650 kDa, between about 250 kDa and about 600 kDa, between about 250 kDa and about 550 kDa, between about 250 kDa and about 500 kDa, between about 250 kDa and about 450 kDa, between about 250 kDa and about 400 kDa, between about 300 kDa and 750 kDa, between about 300 kDa and about 700 kDa, between about 300 kDa and about 650 kDa, between about 300 kDa and about 600 kDa, between about 300 kDa and about 550 kDa, or between about 300 kDa and about 500 kDa. Any whole number integer within any of the above ranges is contemplated as an embodiment of the disclosure.

In one embodiment, the conjugate has a molecular weight of between about 300 kDa and about 20,000 kDa, such as between about 300 kDa and about 15,000 kDa, between about 300 kDa and about 10,000 kDa, between about 300 kDa and about 9,000 kDa, between about 300 kDa and about 8,000 kDa, between about 300 kDa and about 7,000 kDa, between about 300 kDa and about 6,000 kDa, between about 300 kDa and about 5,000 kDa, between about 300 kDa and about 4,000 kDa, between about 300 kDa and about 3,000 kDa, between about 300 kDa and about 2,000 kDa, between about 300 kDa and about 1,000 kDa, between about 500 kDa and about 20,000 kDa, between about 500 kDa and about 15,000 kDa, between about 500 kDa and about 10,000 kDa, between about 500 kDa and about 9,000 kDa, between about 500 kDa and about 8,000 kDa, between about 500 kDa and about 7,000 kDa, between about 500 kDa and about 6,000 kDa, between about 500 kDa and about 5,000 kDa, between about 500 kDa and about 4,000 kDa, between about 500 kDa and about 3,000 kDa, between about 500 kDa and about 2,000 kDa, between about 500 kDa and about 1,000 kDa, between about 1,000 kDa and about 20,000 kDa, between about 1,000 kDa and about 15,000 kDa, between about 1,000 kDa and about 10,000 kDa, between about 1,000 kDa and about 9,000 kDa, between about 1,000 kDa and about 8,000 kDa, between about 1,000 kDa and about 7,000 kDa, between about 1,000 kDa and about 6,000 kDa, between about 1,000 kDa and about 5,000 kDa, between about 1,500 kDa and about 20,000 kDa, between about 1,500 kDa and about 15,000 kDa, between about 1,500 kDa and about 10,000 kDa, between about 1,500 kDa and about 9,000 kDa, between about 1,500 kDa and about 8,000 kDa, between about 1,500 kDa and about 7,000 kDa, between about 1,500 kDa and about 6,000 kDa, between about 1,500 kDa and about 5,000 kDa, between about 2,000 kDa and about 20,000 kDa, between about 2,000 kDa and about 15,000 kDa, between about 2,000 kDa and about 10,000 kDa, between about 2,000 kDa and about 9,000 kDa, between about 2,000 kDa and about 8,000 kDa, between about 2,000 kDa and about 7,000 kDa, between about 2,000 kDa and about 6,000 kDa, between about 2,500 kDa and about 20,000 kDa, between about 2,500 kDa and about 15,000 kDa, between about 2,500 kDa and about 10,000 kDa, between about 2,500 kDa and about 9,000 kDa, between about 2,500 kDa and about 8,000 kDa, between about 2,500 kDa and about 7,000 kDa, between about 2,500 kDa and about 6,000 kDa, between about 3,000 kDa and about 20,000 kDa, between about 3,000 kDa and about 15,000 kDa, between about 3,000 kDa and about 10,000 kDa, between about 3,000 kDa and about 9,000 kDa, between about 3,000 kDa and about 8,000 kDa, between about 3,000 kDa and about 7,000 kDa, or between about 3,000 kDa and about 6,000 kDa.

In an embodiment, a GBS serotype IV capsular polysaccharide conjugate has a molecular weight of any of the above ranges.

In an embodiment, a GBS serotype Ia capsular polysaccharide conjugate has a molecular weight of any of the above ranges.

In an embodiment, a GBS serotype Ib capsular polysaccharide conjugate has a molecular weight of any of the above ranges.

In an embodiment, a GBS serotype II capsular polysaccharide conjugate has a molecular weight of any of the above ranges.

In an embodiment, a GBS serotype III capsular polysaccharide conjugate has a molecular weight of any of the above ranges.

In an embodiment, a GBS serotype V capsular polysaccharide conjugate has a molecular weight of any of the above ranges.

In an embodiment, a GBS serotype VI capsular polysaccharide conjugate has a molecular weight of any of the above ranges.

In an embodiment, a GBS serotype VII capsular polysaccharide conjugate has a molecular weight of any of the above ranges.

In an embodiment, a GBS serotype VIII capsular polysaccharide conjugate has a molecular weight of any of the above ranges.

In an embodiment, a GBS serotype IX capsular polysaccharide conjugate has a molecular weight of any of the above ranges.

In one embodiment, the conjugates of the invention have at least about 0.6, 0.65, 0.7, 0.75, 0.8, 0.85, 0.9, 0.95, 0.97 or 0.98 mM sialic acid per mM polysaccharide. In a preferred embodiment, the conjugates have at least about 0.9 or 0.95 mM sialic acid per mM polysaccharide.

In an embodiment, a GBS serotype IV capsular polysaccharide conjugate has a sialic acid content of at least any of the above value.

In an embodiment, a GBS serotype Ia capsular polysaccharide conjugate has a sialic acid content of at least any of the above value.

In an embodiment, a GBS serotype Ib capsular polysaccharide conjugate has a sialic acid content of at least any of the above value.

In an embodiment, a GBS serotype II capsular polysaccharide conjugate has a sialic acid content of at least any of the above value.

In an embodiment, a GBS serotype III capsular polysaccharide conjugate has a sialic acid content of at least any of the above value.

In an embodiment, a GBS serotype V capsular polysaccharide conjugate has a sialic acid content of at least any of the above value.

In an embodiment, a GBS serotype VI capsular polysaccharide conjugate has a sialic acid content of at least any of the above value.

In an embodiment, a GBS serotype VII capsular polysaccharide conjugate has a sialic acid content of at least any of the above value.

In an embodiment, a GBS serotype VIII capsular polysaccharide conjugate has a sialic acid content of at least any of the above value.

In an embodiment GBS, a serotype IX capsular polysaccharide conjugate has a sialic acid content of at least any of the above value.

In an embodiment, the conjugate of the invention comprises less than about 0.01, 0.02, 0.03, 0.04, or 0.05 mM O-acetate per mM saccharide repeating unit. In another embodiment, the conjugate comprises at least about 0.1, 0.2, 0.3, 0.35 or about 0.4 mM O-acetate per mM saccharide repeating unit.

In an embodiment, a GBS serotype IV capsular polysaccharide conjugate has an O-acetate content of any of the above value.

In an embodiment, a GBS serotype Ia capsular polysaccharide conjugate has an O-acetate content of any of the above value.

In an embodiment, a GBS serotype Ib capsular polysaccharide conjugate has an O-acetate content of any of the above value.

In an embodiment, a GBS serotype II capsular polysaccharide conjugate has an O-acetate content of any of the above value.

In an embodiment, a GBS serotype III capsular polysaccharide conjugate has an O-acetate content of any of the above value.

In an embodiment, a GBS serotype V capsular polysaccharide conjugate has an O-acetate content of any of the above value.

In an embodiment, a GBS serotype VI capsular polysaccharide conjugate has an O-acetate content of any of the above value.

In an embodiment, a GBS serotype VII capsular polysaccharide conjugate has an O-acetate content of any of the above value.

In an embodiment, a GBS serotype VIII capsular polysaccharide conjugate has an O-acetate content of any of the above value.

In an embodiment GBS, a serotype IX capsular polysaccharide conjugate has an O-acetate content of any of the above value.

In a further embodiment, the immunogenic conjugate comprises less than about 40%, less than about 35%, less than about 30%, less than about 25%, less than about 20%, less than about 15%, less than about 10%, or less than about 5% of free GBS capsular polysaccharide compared to the total amount of GBS capsular polysaccharide. In a preferred embodiment the immunogenic conjugate comprises less than about 5% of unreacted free saccharide compared to the total amount of GBS capsular polysaccharide.

In yet another embodiment, the ratio (weight by weight) of GBS capsular polysaccharide to carrier protein in the conjugate is between about 0.5 and about 3.0. In one aspect, the ratio of GBS capsular polysaccharide to carrier protein in the conjugate is between about 0.5 and about 2.0, between about 0.5 and about 1.5, between about 0.5 and about 1.0, between about 1.0 and about 1.5, or between about 1.0 and about 2.0. In a preferred embodiment, the ratio of GBS capsular polysaccharide to carrier protein in the conjugate is between about 0.8 and about 1.0.

In another embodiment, the degree of conjugation of the conjugate is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15, or between 10 and 12. In a preferred embodiment, the degree of conjugation of the conjugate is between 2 and 5.

Conjugation

Conjugation may be direct, where the atoms from the polysaccharide are covalently bonded to atoms from the protein surface. Alternatively, conjugation may be through a linker molecule, which reacts with both the polysaccharide and the protein and connects the two, tethering the carbohydrate to the protein.

Where a carrier and one or more antigens such as a polysaccharide are conjugated (i.e., covalently associated), conjugation may be by any chemical method, process or genetic technique known in the art. For example, a carrier polypeptide and one or more antigens selected from a group comprising a carbohydrate, an oligosaccharide, a lipid, a lipooligosaccharide, a polysaccharide, an oligosaccharide-protein conjugate, a polysaccharide-protein conjugate, a peptide-protein conjugate, an oligosaccharide-peptide conjugate, a polysaccharide-peptide conjugate, a protein-protein conjugate, a lipooligosaccharide-protein conjugate, a polysaccharide-protein conjugate, or any combination thereof, may be conjugated by techniques, including, but not limited to: (1) direct coupling via protein functional groups (e.g., thiol-thiol linkage, amine-carboxyl linkage, amine-aldehyde linkage; enzyme direct coupling); (2) homobifunctional coupling of amines (e.g., using bis-aldehydes); (3) homobifunctional coupling of thiols (e.g., using bis-maleimides); (4) homobifunctional coupling via photoactivated reagents (5) heterobifunctional coupling of amines to thiols (e.g., using maleimides); (6) heterobifunctional coupling via photoactivated reagents (e.g., the β-carbonyidiazo family); (7) introducing amine-reactive groups into a poly- or oligosaccharide via cyanogen bromide activation or carboxymethylation; (8) introducing thiol-reactive groups into a poly- or oligosaccharide via a heterobifunctional compound such as maleimido-hydrazide; (9) protein-lipid conjugation via introducing a hydrophobic group into the protein and (10) protein-lipid conjugation via incorporating a reactive group into the lipid. Also, contemplated are heterobifunctional "non-covalent coupling" techniques such the Biotin-Avidin interaction. Other methods well known in the art for effecting conjugation of oligosaccharides and polysaccharides to immunogenic carrier proteins are also within the scope of some embodiments of the invention.

In an embodiment, the GBS capsular polysaccharide-protein conjugates are obtained by activating polysaccharide with 1-cyano-4-dimethylamino pyridinium tetrafluoroborate (CDAP) to form a cyanate ester. The activated polysaccharide may be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide, SIB, SIAB, sulfo-SIAB, SIA, or SBAP).

In one aspect, the cyanate ester (optionally made by CDAP chemistry) is coupled with hexane diamine or adipic acid dihydrazide (ADH) and the amino-derivatised saccharide is conjugated to the carrier protein using carbodiimide (e.g., EDAC or EDC) chemistry via a carboxyl group on the protein carrier. Such conjugates are described for example in Int'l Patent Appl. Pub. Nos. WO 93/15760, WO 95/08348, and WO 96/29094.

Other suitable techniques use carbodiimides, hydrazides, active esters, norborane, p-nitrobenzoic acid, N-hydroxysuccinimide, S-NHS, EDC, and TSTU. Many are described in Int'l Patent Appl. Pub. No. WO 98/42721. Conjugation may involve a carbonyl linker which may be formed by reaction of a free hydroxyl group of the saccharide with 1,1 carbonyldiimidazole (CDI) or 1,1 carboyl di 1,2,4 triazole (CDT) (See Bethell, et al., J. Biol. Chem., 254:2572-2574 (1979); Hearn, et al., J. Chromatogr., 218:509-518 (1981))

followed by reaction with a protein to form a carbamate linkage. This may involve reduction of the anomeric terminus to a primary hydroxyl group, optional protection/deprotection of the primary hydroxyl group, reaction of the primary hydroxyl group with CDI/CDT to form a CDI/CDT carbamate intermediate, and coupling the CDI/CDT carbamate intermediate with an amino group on a protein.

In preferred embodiments, the GBS capsular polysaccharide-protein conjugates of the invention are prepared using reductive amination. Reductive amination involves two steps: (1) oxidation of the polysaccharide to generate aldehyde functionalities from vicinal diols in individual hexasaccharide unit and (2) reduction of the activated polysaccharide and a carrier protein to form a conjugate.

In an embodiment, GBS capsular polysaccharide is activated (oxidized) by a process comprising the steps of:
(a) reacting isolated GBS capsular polysaccharide with an oxidizing agent; and
(b) quenching the oxidation reaction by addition of a quenching agent resulting in an activated GBS capsular polysaccharide.

In an aspect of the invention, the concentration of the isolated capsular polysaccharide is between about 0.1 mg/mL and about 10.0 mg/mL, such as between about 0.5 mg/mL and about 5.0 mg/mL, between about 1.0 mg/mL and about 3.0 mg/mL, or about 2.0 mg/mL.

In a particular embodiment, the oxidizing agent is periodate. The periodate oxidizes vicinal hydroxyl groups to form carbonyl or aldehyde groups and causes cleavage of a C—C bond. The term 'periodate' includes both periodate and periodic acid. This term also includes both metaperiodate ($IO_4^-$) and orthoperiodate ($IO_6^{5-}$). The term 'periodate' also includes the various salts of periodate including sodium periodate and potassium periodate. In a preferred embodiment, the oxidizing agent is sodium periodate. In a preferred embodiment, the periodate used for the oxidation of GBS capsular polysaccharides is metaperiodate. In a preferred embodiment the periodate used for the oxidation of serotype capsular polysaccharide is sodium metaperiodate.

In another embodiment, the polysaccharide is reacted with 0.01 to 10.0, 0.05 to 5.0, 0.1 to 1.0, 0.5 to 1.0, 0.7 to 0.8, 0.05 to 0.5, or 0.1 to 0.3 molar equivalents of oxidizing agent. In a particular embodiment, the polysaccharide is reacted with about 0.05, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, or about 0.95 molar equivalents of oxidizing agent. In a further embodiment, the polysaccharide is reacted with about 0.1 molar equivalents of oxidizing agent. In a further embodiment, the polysaccharide is reacted with about 0.15 molar equivalents of oxidizing agent. In an additional embodiment, the polysaccharide is reacted with about 0.25 molar equivalents of oxidizing agent. In yet another embodiment, the polysaccharide is reacted with about 0.5 molar equivalents of oxidizing agent. In an alternative embodiment, the polysaccharide is reacted with about 0.6 molar equivalents of oxidizing agent. In a further embodiment, the polysaccharide is reacted with about 0.7 molar equivalents of oxidizing agent.

In one aspect of the invention, the duration of the oxidation reaction is between about 1 hour and about 50 hours, between about 10 hours and about 30 hours, between about 15 hours and about 20 hours, between about 15 hours and about 17 hours, or about 16 hours.

In another aspect of the invention, the temperature of the oxidation reaction is maintained between about 2° C. and about 25° C., between about 2° C. and about 8° C., or between about 20° C. and about 25° C. In one preferred embodiment, the temperature of the reaction is maintained at about 23° C. In another preferred embodiment, the temperature of the reaction is maintained at about 5° C.

In a further aspect, the oxidation reaction is carried out in a buffer selected from the group consisting of sodium phosphate, potassium phosphate, 2-(N-morpholino)ethanesulfonic acid (MES), and Bis-Tris. In a preferred embodiment, the buffer is potassium phosphate.

In an additional aspect, the buffer has a concentration of between about 1 mM and about 500 mM, between about 1 mM and about 300 mM, or between about 50 mM and about 200 mM. In a preferred embodiment the buffer has a concentration of about 100 mM.

In one aspect, the oxidation reaction is carried out at a pH between about 4.0 and about 8.0, between about 5.0 and about 7.0, or between about 5.5 and about 6.5. In a preferred embodiment, the pH is about 6.0.

In one embodiment, the activated GBS capsular polysaccharide is obtained by reacting about 0.5 mg/L to about 5.0 mg/mL of isolated capsular polysaccharide with about 0.05 to about 0.3 molar equivalents periodate at a temperature between about 20° C. and 25° C.

In another embodiment, the activated GBS capsular polysaccharide is obtained by reacting about 0.5 mg/L to about 5.0 mg/mL of isolated capsular polysaccharide with about 0.05 to about 0.3 molar equivalents periodate at a temperature between about 2° C. and about 8° C.

In another embodiment, the activated GBS capsular polysaccharide is purified according to methods known to one skilled in the art, such as gel permeation chromatography (GPC), dialysis, or ultrafiltration/diafiltration. For example, the activated capsular polysaccharide is purified by concentration and diafiltration using an ultrafiltration device.

In one embodiment, the degree of oxidation of the activated GBS capsular polysaccharide is between 5 and 25, such as between 5 and 15, between 5 and 10, between 10 and 25, between 10 and 20, between 10 and 15. In a preferred embodiment the degree of oxidation of the activated GBS capsular polysaccharide is between 10 and 20, between 11 and 19, between 12 and 18, between 13 and 17, or between 14 and 16.

In another embodiment, the activated GBS capsular polysaccharide has a molecular weight between about 5 kDa and about 1,000 kDa, such as between about 50 kDa and about 300 kDa, between about 75 kDa and about 400 kDa, between about 75 kDa and about 200 kDa, between about 100 kDa and about 700 kDa, between about 100 kDa and about 500 kDa, between about 100 kDa and about 400 kDa, between about 100 kDa and about 300 kDa, between about 200 kDa and about 400 kDa, an between about 300 kDa and about 700 kDa. In a preferred embodiment, the activated GBS capsular polysaccharide has a molecular weight of between about 75 kDa and about 400 kDa In an embodiment, the activated GBS capsular polysaccharide is lyophilized, optionally in the presence of saccharide. In a preferred embodiment, the saccharide is selected from sucrose, trehalose, raffinose, stachyose, melezitose, dextran, mannitol, lactitol and palatinit. In a preferred embodiment, the saccharide is sucrose. The lyophilized activated capsular polysaccharide can then be compounded with a solution comprising the carrier protein.

In another embodiment, the activated GBS capsular polysaccharide is compounded with the carrier protein and lyophilized, optionally in the presence of a saccharide. In one aspect, the saccharide is selected from sucrose, trehalose, raffinose, stachyose, melezitose, dextran, mannitol, lactitol and palatinit. In a preferred embodiment, the saccharide is sucrose. The co-lyophilized polysaccharide and carrier protein can then be resuspended in solution and reacted with a reducing agent.

The activated GBS capsular polysaccharide can be conjugated to a carrier protein by a process comprising the step of:

(a) compounding the activated GBS capsular polysaccharide with a carrier protein, and (b) reacting the compounded activated GBS capsular polysaccharide and carrier protein with a reducing agent to form a GBS capsular polysaccharide-carrier protein conjugate.

The conjugation of activated GBS capsular polysaccharide with a protein carrier by reductive amination in a polar aprotic solvent is suitable to maintain low levels of the free polysaccharide as compared, for example, to reductive amination in aqueous solution where the level of unreacted (free) polysaccharide is significantly elevated. In a preferred embodiment, step (a) and step (b) are carried out in a polar aprotic solvent.

In one embodiment, step (a) comprises dissolving lyophilized GBS capsular polysaccharide in a solution comprising a carrier protein and a polar aprotic solvent. In another embodiment, step (a) comprises dissolving co-lyophilized GBS capsular polysaccharide and carrier protein in a polar aprotic solvent.

In one embodiment, the polar aprotic solvent is selected from the group consisting of dimethylsulfoxide (DMSO), sulfolane, dimethylformamide (DMF), and hexamethylphosporamide (HMPA). In a preferred embodiment, the polar aprotic solvent is DMSO.

When steps (a) and (b) are carried out in aqueous solution, steps (a) and (b) are carried out in a buffer in an aqueous medium, preferably selected from PBS, MES, HEPES, Bis-tris, ADA, PIPES, MOPSO, BES, MOPS, DIPSO, MOBS, HEPPSO, POPSO, TEA, EPPS, Bicine or HEPB at a pH between about 6.0 and about 8.5, between about 7.0 and about 8.0, or between about 7.0 and about 7.5. In a preferred embodiment the buffer is PBS. In a preferred embodiment the pH is about 7.3.

In one embodiment, the concentration of activated GBS capsular polysaccharide in step (b) is between about 0.1 mg/mL and about 10.0 mg/mL, between about 0.5 mg/mL and about 5.0 mg/mL, or between about 0.5 mg/mL and about 2.0 mg/mL. In a preferred embodiment, the concentration of activated serotype GBS capsular polysaccharide in step (b) is about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2.0 mg/mL, about 2.1 mg/mL, about 2.2, about 2.3 mg/mL, about 2.4 mg/mL, about 2.5 mg/mL, about 2.6 mg/mL, about 2.7 mg/mL, about 2.8 mg/mL, about 2.9 mg/mL, or about 3.0 mg/mL.

In a preferred embodiment the initial ratio (weight by weight) of activated serotype GBS capsular polysaccharide to carrier protein is between 5:1 and 0.1:1, 2:1 and 0.1:1, 2:1 and 1:1, 1.5:1 and 1:1, 0.1:1 and 1:1, 0.3:1 and 1:1, 0.6:1 and 1:1. In a preferred embodiment the initial ratio of activated serotype GBS capsular polysaccharide to carrier protein is about 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1.

In an embodiment, the reducing agent is sodium cyanoborohydride, sodium triacetoxyborohydride, sodium or zinc borohydride in the presence of Bronsted or Lewis acids, amine boranes such as pyridine borane, 2-picoline borane, 2,6-diborane-methanol, dimethylamine-borane, t-BuMe$^i$PrN—BH$_3$, benzylamine-BH$_3$ or 5-ethyl-2-methylpyridine borane (PEMB). In a preferred embodiment, the reducing agent is sodium cyanoborohydride.

In another embodiment, the quantity of reducing agent used in step (b) is between about 0.1 and about 10.0 molar equivalents, between about 0.5 and about 5.0 molar equivalents, or between about 1.0 and about 2.0 molar equivalents. In a preferred embodiment, the quantity of reducing agent used in step (b) is about 1.0, 1.1, 1.2, 1.3, 1.4, 1.5, 1.6, 1.7, 1.8, 1.9, or 2.0 molar equivalents.

In a preferred embodiment, the duration of step (b) is between 1 hour and 60 hours, between 10 hours and 50 hours, between 40 hours and 50 hours, or between 42 hours and 46 hours. In a preferred embodiment, the duration of step (b) is about 44 hours.

In a further embodiment, the temperature of the reaction in step (b) is maintained between 10° C. and 40° C., between 15° C. and 30° C., or between 20° C. and 26° C. In a preferred embodiment, the temperature of the reaction in step (b) is maintained at about 23° C.

In an additional embodiment, the process for the preparation of an immunogenic conjugate comprising GBS capsular polysaccharide covalently linked to a carrier protein further comprises a step (step (c)) of capping unreacted aldehydes (quenching) by addition of a borohydride.

In one embodiment, the capping reagent is a borohydride selected from the group consisting of sodium borohydride (NaBH$_4$), sodium cyanoborohydride, lithium borohydride, potassium borohydride, tetrabutylammonium borohydride, calcium borohydride, and magnesium borohydride. In a preferred embodiment, the capping reagent is sodium borohydride.

In yet another embodiment, the quantity of borohydride used in step (c) is between about 0.1 and about 10.0 molar equivalents, between about 0.5 and about 5.0 molar equivalents, or between about 1.0 and 3.0 molar equivalents. In a preferred embodiment, the quantity of borohydride used in step (c) is about 2.0 molar equivalents.

In one preferred embodiment, the borohydride used in step (c) is NaBH$_4$ in a concentration of about 2.0 molar equivalents.

In one embodiment, the duration of step (c) is between 0.1 hours and 10 hours, between 0.5 hours and 5 hours, between 2 hours and 4 hours. In a preferred embodiment, the duration of step (c) is about 3 hours.

In another embodiment, the temperature of the reaction in step (c) is maintained between about 15° C. and about 45° C., between about 15° C. and about 30° C., or between about 20° C. and about 26° C. In a preferred embodiment, the temperature of the reaction in step (c) is maintained at about 23° C.

After conjugation of the GBS capsular polysaccharide to the carrier protein and capping, the polysaccharide-protein conjugate can be purified (enriched with respect to the amount of polysaccharide-protein conjugate) by a variety of techniques known to the skilled person. These techniques include dialysis, concentration/diafiltration operations, tangential flow filtration, precipitation/elution, column chromatography (DEAE or hydrophobic interaction chromatography), and depth filtration.

In a further embodiment, the immunogenic conjugate comprises less than about 40%, less than about 35%, less than about 30%, less than about 25%, less than about 20%, less than about 15%, less than about 10%, or less than about 5% of free GBS capsular polysaccharide compared to the total amount of GBS capsular polysaccharide. In a preferred embodiment the immunogenic conjugate comprises less than about 5% of unreacted free saccharide compared to the total amount of GBS capsular polysaccharide.

In a preferred embodiment, the GBS polysaccharide-protein conjugate has a molecular weight between about 300 kDa and about 20,000 kDa, such as between about 1,000 kDa and about 15,000 kDa or between about 1,000 kDa and about 10,000 kDa.

In yet another embodiment, the ratio (weight by weight) of GBS capsular polysaccharide to carrier protein in the conjugate is between about 0.5 and about 3.0. In one aspect, the ratio of GBS capsular polysaccharide to carrier protein in the conjugate is between about 0.5 and about 2.0, between about 0.5 and about 1.5, between about 0.5 and about 1.0, between about 1.0 and about 1.5, or between about 1.0 and about 2.0. In a preferred embodiment, the ratio of GBS capsular polysaccharide to carrier protein in the conjugate is between about 0.8 and about 1.0.

In another embodiment, the degree of conjugation of the conjugate is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15, or between 10 and 12. In a preferred embodiment, the degree of conjugation of the conjugate is between 2 and 5.

In one aspect of the invention, GBS capsular polysaccharide-protein conjugates are obtained by reductive amination method described above. For example, in one aspect the present disclosure provides a GBS capsular polysaccharide-protein conjugates comprising a polysaccharide conjugated to a carrier protein that is produced or obtainable by the method comprising the steps of:

(a) reacting isolated GBS capsular polysaccharide with an oxidizing agent;

(b) quenching the oxidation reaction by addition of a quenching agent resulting in an activated GBS capsular polysaccharide;

(c) compounding the activated GBS capsular polysaccharide with a carrier protein, (d) reacting the compounded activated GBS capsular polysaccharide and carrier protein with a reducing agent to form a GBS capsular polysaccharide-carrier protein conjugate, and optionally (e) capping unreacted aldehyde by addition of sodium borohydride ($NaBH_4$).

In a preferred embodiment, steps (c) and (d) are carried out in DMSO.

In another aspect of the invention, the GBS capsular polysaccharide-protein conjugates of the invention are prepared using reductive amination as described above, but with 2,2,6,6-tetramethyl-1-piperidinyloxy (TEMPO) free radical and N-chlorosuccinimide (NCS) as the cooxidant in the activation/oxidization step. See Int'l Patent Appl. Pub. No. WO 2014/097099, which is incorporated herein by reference in its entirety. In such an embodiment, the glycoconjugates from GBS capsular polysaccharides are prepared using TEMPO free radical to oxidize primary alcohols of the saccharide to aldehydes using NCS as the cooxidant (hereinafter "TEMPO/NCS oxidation"), such as described at Example 7 and of Int'l Patent Appl. Pub. No. WO 2014/097099. Therefore in one aspect, conjugates of GBS capsular polysaccharides are obtainable by a method comprising the steps of: a) reacting a GBS capsular polysaccharide with TEMPO and NCS in an solvent to produce an activated saccharide; and b) reacting the activated saccharide with a carrier protein comprising one or more amine groups (hereinafter "TEMPO/NCS-reductive amination"). In one embodiment, the solvent may be an aqueous solvent or DMSO.

In one aspect, GBS capsular polysaccharide-protein conjugates are obtained by said method. For example, in one aspect the present disclosure provides a GBS capsular polysaccharide-protein conjugate comprising a polysaccharide conjugated to a carrier protein that is produced or obtainable by the method comprising the steps of: a) reacting a saccharide with 2,2,6,6-tetramethyl-1-piperidinyloxy (TEMPO) and N-chlorosuccinimide (NCS) in an solvent to produce an activated saccharide; and b) reacting the activated saccharide with a carrier protein comprising one or more amine groups. In one embodiment, the solvent may be an aqueous solvent or DMSO.

Immunogenic Compositions

After the individual conjugates are purified, they may be combined to formulate an immunogenic composition of the present invention, which may be used, for example, in a vaccine. Formulation of the immunogenic composition of the present invention can be accomplished using art-recognized methods.

An "immune response" to an immunogenic composition is the development in a subject of a humoral and/or a cell-mediated immune response to molecules present in the composition of interest (for example, an antigen, such as a protein or polysaccharide). For purposes of the present invention, a "humoral immune response" is an antibody-mediated immune response and involves the generation of antibodies with affinity for the antigens present in the immunogenic compositions of the invention, while a "cell-mediated immune response" is one mediated by T-lymphocytes and/or other white blood cells. A "cell-mediated immune response" is elicited by the presentation of antigenic epitopes in association with Class I or Class II molecules of the major histocompatibility complex (MHC). This activates antigen-specific CD4+ T helper cells or CD8+ cytotoxic T lymphocyte cells (CTLs). CTLs have specificity for peptide or lipid antigens that are presented in association with proteins encoded by the MHC or CD1 and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with classical or nonclassical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson, A. L., et al., J. Immunol., 151(8):4189-4199 (1993); Doe, B., et al., Eur. J. Immunol. 24(10):2369-2376 (1994).

The term "immunogenic" refers to the ability of an antigen or a vaccine to elicit an immune response, either humoral or cell-mediated, or both.

An "immunogenic amount", or an "immunologically effective amount" or "dose", each of which is used interchangeably herein, generally refers to the amount of antigen or immunogenic composition sufficient to elicit an immune response, either a cellular (T cell) or humoral (B cell or antibody) response, or both, as measured by standard assays known to one skilled in the art.

"Immune interference" or "significant immune interference" as used herein refers to a statistically significant decrease in immune response to an individual antigen in a multivalent or multicomponent vaccine compared to the immune response to the same antigen when administered in a monovalent vaccine.

A "protective" immune response refers to the ability of an immunogenic composition to elicit an immune response, either humoral or cell mediated, which serves to protect the subject from an infection. The protection provided need not be absolute, i.e., the infection need not be totally prevented or eradicated, if there is a statistically significant improvement compared with a control population of subjects, e.g., infected animals not administered the vaccine or immunogenic composition. Protection may be limited to mitigating the severity or rapidity of onset of symptoms of the infection. Several assays are known in the art to determine whether an immune response is indicative of a "protective immune response." For instance, an increase in antibody levels may be measured by a binding assay, such as a whole cell ELISA assay described further below. Other assays include measuring functional antibody responses, such as the facilitation of bacterial killing, which can be tested with an opsonophagocytosis assay (OPA) as described below. In particular situations, a "protective immune response" could include the induction of a two-fold increase in antibody levels or a four-fold increase in antibody levels specific for a particular antigen in at least 50% of subjects. In another situation, a "protective immune response" could include a decrease in bacterial count of at least 10%, 25%, 50%, 65%, 75%, 80%, 85%, 90%, 95% or more.

The amount of a particular conjugate in a composition is generally calculated based on total polysaccharide, conjugated and non-conjugated, for that conjugate. For example, a GBS capsular polysaccharide conjugate with 20% free polysaccharide will have about 80 mcg/ml of conjugated GBS capsular polysaccharide and about 20 mcg/ml of non-conjugated GBS capsular polysaccharide in a 100 mcg/ml GBS capsular polysaccharide dose. The protein carrier contribution to the conjugate is usually not considered when calculating the dose of a conjugate. The amount of conjugate can vary depending upon the streptococcal serotype. Generally, each dose will comprise about 0.01 mg/ml to about 100 mcg/ml of each polysaccharide, particularly about 1 mcg/ml to about 70 mcg/ml, and more particularly about 5 mcg/ml to about 50 mcg/ml. The "immunogenic amount" of the different polysaccharide components in the immunogenic composition, may diverge and each may comprise about 0.01 mcg/ml, about 0.1 mcg/ml, about 0.25 mcg/ml, about 0.5 mcg/ml, about 1 mcg/ml, about 2 mcg/ml, about 3 mcg/ml, about 4 mcg/ml, about 5 mcg/ml, about 6 mcg/ml, about 7 mcg/ml, about 8 mcg/ml, about 9 mcg/ml, about 10 mcg/ml, about 15 mcg/ml, about 20 mcg/ml, about 25 mcg/ml, about 30 mcg/ml, about 40 mcg/ml, about 50 mcg/ml, about 60 mcg/ml, about 70 mcg/ml, about 80 mcg/ml, about 90 mcg/ml, or about 100 mcg/ml of any particular polysaccharide antigen. A dose or immunogenic amount of a multivalent immunogenic composition would indicate the dose of each polysaccharide unless indicated otherwise. For example, a 10 mcg/ml dose of a hexavalent immunogenic composition would contain 10 mcg/ml of each of the six polysaccharides for a total antigen or conjugate dose of 60 mcg/ml.

In one aspect of the invention, the total conjugate dose is at least about 60 mcg/ml, such as at least about 120 mcg/ml or at least about 240 mcg/I. In one embodiment, the total conjugate dose is about 60 mcg/ml to about 600 mcg/ml, such as about 60 mcg/ml to about 540 mcg/ml, about 60 mcg/ml to about 480 mcg/ml, about 60 mcg/ml to about 420 mcg/ml, about 60 mcg/ml to about 360 mcg/ml, about 60 mcg/ml to about 300 mcg/ml, about 60 mcg/ml to about 240 mcg/ml, about 60 mcg/ml to about 180 mcg/ml, about 60 mcg/ml to about 120 mcg/ml, about 120 mcg/ml to about 600 mcg/ml, about 120 mcg/ml to about 540 mcg/ml, about 120 mcg/ml to about 480 mcg/ml, about 120 mcg/ml to about 420 mcg/ml, about 120 mcg/ml to about 360 mcg/ml, about 120 mcg/ml to about 300 mcg/ml, about 120 mcg/ml to about 240 mcg/ml, about 120 mcg/ml to about 180 mcg/ml, about 180 mcg/ml to about 600 mcg/ml, about 180 mcg/ml to about 540 mcg/ml, about 180 mcg/ml to about 480 mcg/ml, about 180 mcg/ml to about 420 mcg/ml, about 180 mcg/ml to about 360 mcg/ml, about 180 mcg/ml to about 300 mcg/ml, about 180 mcg/ml to about 240 mcg/ml, about 240 mcg/ml to about 600 mcg/ml, about 240 mcg/ml to about 540 mcg/ml, about 240 mcg/ml to about 480 mcg/ml, about 240 mcg/ml to about 420 mcg/ml, about 240 mcg/ml to about 360 mcg/ml, or about 240 mcg/ml to about 300 mcg/ml. In a preferred embodiment, the total conjugate dose is about 60 mcg/ml to about 360 mcg/ml, and most preferably about 120 mg/ml to about 240 mcg/ml.

The effectiveness of an antigen as an immunogen can be measured by measuring the levels of B cell activity by measuring the levels of circulating antibodies specific for the antigen in serum using immunoassays, immunoprecipitation assays, functional antibody assays, such as in vitro opsonic assay and many other assays known in the art. Another measure of effectiveness of an antigen as a T-cell immunogen can be measured by either by proliferation assays, by cytolytic assays, such as chromium release assays to measure the ability of a T cell to lyse its specific target cell. Furthermore, in the present invention, an "immunogenic amount" may also be defined by measuring the serum levels of antigen specific antibody induced following administration of the antigen or by measuring the ability of the antibodies so induced to enhance the opsonophagocytic ability of particular white blood cells as described herein. The level of protection of the immune response may be measured by challenging the immunized host with the antigen that has been injected. For example, if the antigen to which an immune response is desired is a bacterium, the level of protection induced by the "immunogenic amount" of the antigen can be measured by detecting the percent survival or the percent mortality after challenge of the animals with the bacterial cells. In one embodiment, the amount of protection may be measured by measuring at least one symptom associated with the bacterial infection, for example, a fever associated with the infection. The amount of each of the antigens in the multi-antigen or multi-component vaccine or immunogenic compositions will vary with respect to each of the other components and can be determined by methods known to the skilled artisan. Such methods would include, for example, procedures for measuring immunogenicity and/or in vivo efficacy.

The term "immunogenic composition" relates to any pharmaceutical composition containing an antigen, e.g., a microorganism, or a component thereof, which composition can be used to elicit an immune response in a subject. The immunogenic compositions of the present invention can be used to treat a human susceptible to GBS infection, by means of administering the immunogenic compositions via a systemic transdermal or mucosal route. These administrations can include injection via the intramuscular (i.m.), intraperitoneal (i.p.), intradermal (i.d.) or subcutaneous routes; application by a patch or other transdermal delivery device; or via mucosal administration to the oral/alimentary, respiratory or genitourinary tracts. In one embodiment, the immunogenic composition may be used in the manufacture of a vaccine or in the elicitation of a polyclonal or monoclonal antibodies that could be used to passively protect or treat an animal.

In one aspect, the present invention relates to immunogenic compositions that include an effective amount of at least one polysaccharide, oligosaccharide, polysaccharide-protein conjugate, or biological equivalent thereof, as described herein. For example, in one embodiment, the immunogenic composition includes polysaccharide-protein conjugates, wherein the capsular polysaccharide is selected from the group consisting of group B streptococcus serotypes Ia, Ib, II, III, IV, V, VI, VII, VIII, and IX and wherein the capsular polysaccharide has a sialic acid level of greater than about 60%. In another example, the immunogenic composition includes polysaccharide-protein conjugates, wherein the conjugates comprise capsular polysaccharides from group B streptococcus serotype IV and at least one additional serotype selected from the group consisting of serotypes Ia, Ib, II, III, V, VI, VII, VIII, and IX. In another embodiment, the immunogenic composition comprises polysaccharide-protein conjugates, wherein the conjugates comprise capsular polysaccharides from group B streptococcus serotype IV and at least two additional serotypes selected from the group consisting of serotypes Ia, Ib, II, III, V, VI, VII, VIII, and IX. In yet another embodiment, the immunogenic composition comprises polysaccharide-protein conjugates, wherein the conjugates comprise capsular polysaccharides from group B streptococcus serotype IV and at least three additional serotypes selected from the group consisting of serotypes Ia, Ib, II, III, V, VI, VII, VIII, and IX. In a further embodiment, the immunogenic composition comprises polysaccharide-protein conjugates, wherein the conjugates comprise capsular polysaccharides from group B streptococcus serotype IV and at least four additional serotypes selected from the group consisting of serotypes Ia, Ib, II, III, V, VI, VII, VIII, and IX. In a particular embodiment, the immunogenic composition polysaccharide-protein conjugates, wherein the conjugates comprise capsular polysaccharides from group B streptococcus serotypes Ia, Ib, II, III, and V. In another embodiment, the immunogenic composition polysaccharide-protein conjugates, wherein the conjugates comprise capsular polysaccharides from group B streptococcus serotypes Ia, Ib, II, III, and IV. In yet another embodiment, the immunogenic composition polysaccharide-protein conjugates, wherein the conjugates comprise capsular polysaccharides from group B streptococcus serotype IV and at least five additional serotypes selected from the group consisting of serotypes Ia, Ib, II, III, V, VI, VII, VIII, and IX. In one such embodiment, the immunogenic composition comprises six polysaccharide-protein conjugates, wherein the conjugates comprise a capsular polysaccharide from group B streptococcus serotypes Ia, Ib, II, III, IV and V.

In an embodiment, the immunogenic composition of the invention comprises from 2 to 10 different serotypes of S. agalactiae. Therefore in an embodiment, the immunogenic composition of the invention is a 2, 3, 4, 5, 6, 7, 8, 9 or 10-valent GBS conjugate composition. In one such embodiment, the immunogenic composition is a 5-valent GBS conjugate composition. In another embodiment, the immunogenic composition is a 6-valent GBS conjugate composition. In yet another embodiment, the immunogenic composition is a 7-valent GBS conjugate composition. In a further embodiment, the immunogenic composition is an 8-valent GBS conjugate composition.

Despite prior teachings of using less than six, less than five, or less than four GBS antigens in a composition (see Int'l Patent Appl. Pub. Nos. WO 2006/082527 and WO 2006/082530) and experiences of immune interference, particularly with regard to the use of serotype V in multivalent compositions (see Int'l Patent Appl. Pub. No. WO 2012/035519), the present invention does not show any significant immune interference with the use of four or more GBS antigens nor with the use of serotype V in a multivalent composition. Accordingly, the present invention relates to multivalent immunogenic compositions comprising polysaccharide-protein conjugates comprising at least four GBS capsular polysaccharide serotypes, such as at least five GBS capsular polysaccharide serotypes, at least six GBS capsular polysaccharide serotypes, at least seven GBS capsular polysaccharide serotypes, at least eight GBS capsular polysaccharide serotypes, or at least nine GBS capsular polysaccharide serotypes, wherein the composition does not have significant immune interference. In a particular embodiment, the immunogenic composition comprises GBS capsular polysaccharide serotype V.

The polysaccharide-protein conjugates may comprise the same or different protein carriers. In one embodiment, the conjugates comprise the same protein carrier and the saccharides are conjugated to the same molecule of the protein carrier (carrier molecules having 2 or more different polysaccharides conjugated to it) [see for instance Int'l Patent Appl. Pub. No. WO 2004/083251]. In another embodiment, the polysaccharides are each individually conjugated to different molecules of the protein carrier (each molecule of protein carrier only having one type of polysaccharide conjugated to it). In said embodiment, the capsular saccharides are said to be individually conjugated to the carrier protein.

Optimal amounts of components for a particular immunogenic composition can be ascertained by standard studies involving observation of appropriate immune responses in subjects. Following an initial vaccination, subjects can receive one or several booster immunizations adequately spaced.

The immunogenic compositions of the invention may further comprise one or more preservatives in addition to a plurality of capsular polysaccharide protein conjugates. The FDA requires that biological products in multiple-dose (multi-dose) vials contain a preservative, with only a few exceptions. The present invention contemplates the use of such multi-dose vials. Vaccine products containing preservatives include vaccines containing benzethonium chloride (anthrax), 2-phenoxyethanol (DTaP, HepA, Lyme, Polio (parenteral)), and phenol (Pneumo, Typhoid (parenteral). Preservatives approved for use in injectable drugs include, e.g., chlorobutanol, m cresol, methylparaben, propylparaben, 2-phenoxyethanol, benzethonium chloride, benzalkonium chloride, benzoic acid, benzyl alcohol, phenol, and phenylmercuric nitrate.

In another aspect, the invention relates to a composition including at least one of any polysaccharide described herein and a pharmaceutically acceptable excipient, buffer, stabilizer, adjuvant, a cryoprotectant, a salt, a divalent cation, a non-ionic detergent, an inhibitor of free radical oxidation, a diluent or a carrier, or mixture thereof.

The immunogenic composition optionally can comprise one or more physiologically acceptable buffers selected from, but not limited to HEPES, PIPES, MES, Tris (trimethamine), phosphate, acetate, borate, citrate, glycine, histidine and succinate. In a preferred embodiment, the buffer is histidine or phosphate.

In one embodiment, the immunogenic composition comprises a buffer at a concentration of from about 5 mM to about 50 mM, about 5 mM to about 40 mM, about 5 mM to about 30 mM, about 5 mM to about 20 mM, about 5 mM to about 10 mM, about 10 mM to about 50 mM, about 10 mM to about 40 mM, about 10 mM to about 35 mM, about 10 mM to about 30 mM, about 10 mM to about 25 mM, about 10 mM to about 20 mM, about 10 mM to about 15 mM, about 15 mM to about 50 mM, about 15 mM to about 40 mM, about 15 mM to about 35 mM, about 15 mM to about 30 mM, about 15 mM to about 25 mM, or about 15 mM to about 20 mM. In a preferred embodiment, the immunogenic composition comprises a buffer at a concentration of about 10 mM to about 25 mM, such as about 15 mM to about 25 mM, and most preferably about 20 mM.

In one preferred embodiment, the immunogenic composition comprises histidine at a concentration of about 20 mM. In another preferred embodiment, the immunogenic composition comprises phosphate at a concentration of about 20 mM.

In certain embodiments, the formulation is buffered to within a pH range of about 5.0 to about 7.5, such as 5.3 to about 7.5, about 5.5 to about 7.5, about 6.0 to about 7.5, about 6.5 to about 7.5, about 5.3 to about 7.1, about 5.5 to about 7.0, about 6.0 to about 7.0, about 6.0 to about 6.5, about 6.3 to about 7.0, or about 6.5 to about 7.0. In another embodiment, the formulation is buffered to a pH of about 6.0, 6.1, 6.2, 6.3, 6.4, 6.5, 6.6, 6.7, 6.8, 6.9, 7.0, 7.1, 7.2, 7.3, 7.4, or 7.5. In a preferred embodiment, the formulation is buffered to a pH range of from about 6.0 to about 7.5, such as about 6.5 to about 7.5 and most preferably about 6.5 or about 7.0.

The immunogenic composition optionally can comprise one or more non-ionic surfactants, including but not limited to polyoxyethylene sorbitan fatty acid esters, polysorbate-80 (TWEEN 80), polysorbate-60 (TWEEN 60), polysorbate-40 (TWEEN 40), polysorbate-20 (TWEEN 20), and polyoxyethylene alkyl ethers, including but not limited to BRIJ 58, BRIJ 35, as well as others such as TRITON X-100; TRITON X-114, NP40, SPAN 85 and the PLURONIC series of non-ionic surfactants (e.g., PLURONIC 121). In one embodiment, the immunogenic composition comprises polysorbate-80 or polysorbate-40, preferably polysorbate-80 (PS80).

In one embodiment, the immunogenic composition comprises a surfactant at a concentration of from about 0.001% to about 2% (v/w), about 0.001% to about 1%, about 0.001% to about 0.5%, about 0.001% to about 0.1%, about 0.001% to about 0.05%, about 0.001% to about 0.01%, about 0.001% to 0.005%, about 0.005% to about 2%, about 0.005% to about 1%, about 0.005% to about 0.5%, about 0.005% to about 0.1%, about 0.005% to about 0.05%, about 0.005% to about 0.01%, about 0.01% to about 2%, about 0.01% to about 1%, about 0.01% to about 0.5%, about 0.01% to about 0.1%, about 0.01% to about 0.05%, about 0.01% to about 0.04%, about 0.01% to about 0.03%, about 0.015% to about 2%, about 0.015% to about 1%, about 0.015% to about 0.5%, about 0.015% to about 0.1%, about 0.015% to about 0.05%, about 0.015% to about 0.04%, about 0.015% to about 0.03%, about 0.02% to about 2%, about 0.02% to about 1%, about 0.02% to about 0.5%, about 0.02% to about 0.1%, about 0.02% to about 0.05%, about 0.02% to about 0.04%, about 0.02% to about 0.03%, about 0.05% to about 2%, about 0.05% to about 1%, about 0.05% to about 0.5%, about 0.05% to about 0.1%, about 0.1% to about 2%, about 0.1% to about 1%, about 0.1% to about 0.5% or about 0.1% to about 0.25%. In a preferred embodiment, the immunogenic composition comprises a surfactant at a concentration of about 0.01% to about 0.03%, and most preferably about 0.02%.

In another embodiment, the immunogenic composition comprises polysorbate-80 at a concentration from about 0.001% to about 2% (with up to about 0.25% being preferred) or polysorbate-40 at a concentration from about 0.001% to 1% (with up to about 0.5% being preferred).

In a preferred embodiment, the immunogenic composition comprises PS80 at a concentration of about 0.02%.

Pharmaceutically acceptable carriers are not to be confused with "carrier proteins", which are used in attaching the carbohydrate of the invention to a protein and modify the immune response to that carbohydrate. To avoid confusion with the protein carriers herein described, the term pharmaceutically acceptable diluent will be preferred over pharmaceutically acceptable carriers, but these terms may occasionally be used interchangeably. The term "pharmaceutically acceptable carrier" means a carrier approved by a regulatory agency of a Federal, a state government, or other regulatory agency, or listed in the U.S. Pharmacopeia or other generally recognized pharmacopeia for use in animals, including humans as well as non-human mammals. The term "carrier" refers to a diluent, adjuvant, excipient, or vehicle with which the pharmaceutical composition is administered. Suitable pharmaceutically acceptable diluents include any and all conventional solvents, dispersion media, fillers, solid carriers, aqueous solutions, coatings, antibacterial and antifungal agents, isotonic and absorption delaying agents, and the like. Such pharmaceutically acceptable diluents can be sterile liquids, such as water and oils, including those of petroleum, animal, vegetable or synthetic origin. Water, water for injection (WFI), sterile isotonic saline solutions, phosphate buffered saline, adjuvant suspensions, aqueous dextrose and glycerol solutions, and combination thereof, can be employed as liquid carriers, particularly for injectable solutions. Pharmaceutically acceptable diluents may further comprise minor amounts of auxiliary substances such as wetting or emulsifying agents, preservatives or buffers, which enhance the shelf life or effectiveness in the body. The preparation and use of pharmaceutically acceptable diluents is well known in the art. Examples of suitable pharmaceutical carriers are described in "Remington's Pharmaceutical Sciences" by E. W. Martin. In one embodiment, the diluent is water, water for injection (WFI), an adjuvant suspension, or saline. In a particular embodiment, the diluent is a suspension of any adjuvant described herein. In a preferred embodiment, the diluent is an aluminum-based adjuvant suspension, such as an aluminum phosphate suspension.

Suitable pharmaceutical excipients include starch, glucose, lactose, sucrose, trehalose, raffinose, stachyose, melezitose, dextran, mannitol, lactitol, palatinit, gelatin, malt, rice, flour, chalk, silica gel, sodium stearate, glycerol monostearate, talc, glycine, arginine, lysine, sodium chloride (NaCl), dried skim milk, glycerol, propylene glycol, water, ethanol and the like. In a preferred embodiment, the excipient is NaCl.

In one embodiment, the immunogenic composition comprises an excipient at a concentration of from about 10 mM to about 500 mM, about 10 mM to about 450 mM, about 10 mM to about 400 mM, about 10 mM to about 350 mM, about 10 mM to about 300 mM, about 10 mM to about 250 mM, about 10 mM to about 200 mM, about 10 mM to about 150 mM, about 10 mM to about 100 mM, about 10 mM to about 50 mM, about 10 mM to about 30 mM, about 10 mM to about 20 mM, 20 mM to about 500 mM, about 20 mM to about 450 mM, about 20 mM to about 400 mM, about 20 mM to about 350 mM, about 20 mM to about 300 mM, about 20 mM to about 250 mM, about 20 mM to about 200 mM, about 20 mM to about 150 mM, about 20 mM to about 100 mM, about 20 mM to about 50 mM, about 20 mM to about 30 mM, 50 mM to about 500 mM, about 50 mM to about 450 mM, about 50 mM to about 400 mM, about 50 mM to about 350 mM, about 50 mM to about 300 mM, about 50 mM to about 250 mM, about 50 mM to about 200 mM, about 50 mM to about 150 mM, about 50 mM to about 100 mM, about 100 mM to about 500 mM, about 100 mM to about 450 mM, about 100 mM to about 400 mM, about 100 mM to about 350 mM, about 100 mM to about 300 mM, about 100 mM to about 250 mM, about 100 mM to about 200 mM, about 100 mM to about 150 mM, about 120 mM to about 470 mM, about 120 mM to about 420 mM, about 120 mM to about 370 mM, about 120 mM to about 320 mM, about 120 mM to about 270 mM, about 120 mM to about 220 mM, about 120 mM to about 170 mM, about 150 mM to about 500 mM, about 150 mM to about 450 mM, about 150 mM to about 400 mM, about 150 mM to about 350 mM, about 150 mM to about 300 mM, about 150 mM to about 250 mM, about 150 mM to about 200 mM, about 200 mM to about 500 mM, about 200 mM to about 450 mM, about 200 mM to about 400 mM, about 200 mM to about 350 mM, about 200 mM to about 300 mM, about 200 mM to about 250 mM, about 225 mM to about 465 mM, about 225 mM to about 425 mM, about 225 mM to about 365 mM, about 225 mM to about 325 mM, about 225 mM to about 265 mM, about 250 mM to about 500 mM, about 250 mM to about 450 mM, about 250 mM to about 400 mM, about 250 mM to about 350 mM, about 250 mM to about 300 mM, about 300 mM to about 500 mM, about 300 mM to about 450 mM, about 300 mM to about 400 mM, about 300 mM to about 350 mM, about 350 mM to about 500 mM, about 350 mM to about 450 mM, about 350 mM to about 400 mM, about 400 mM to about 500 mM, about 400 mM to about 450 mM, or about 450 mM to about 500 mM. In a preferred embodiment, the immunogenic composition comprises an excipient at a concentration of from about 10 mM to about 350 mM, such as about 130 mM to about 170 mM and about 225 mM to about 265 mM, and most preferably about 150 mM or about 245 mM.

In one preferred embodiment, the excipient is NaCl at a concentration of about 150 mM. In another preferred embodiment, the excipient is NaCl at a concentration of about 245 mM.

The composition, if desired, can also contain minor amounts of wetting, bulking, emulsifying agents, or pH buffering agents. These compositions can take the form of solutions, suspensions, emulsion, lyophilized powder or cake, and the like. The formulation should suit the mode of administration. Except insofar as any conventional media or agent is incompatible with the active ingredient, use thereof in the immunogenic compositions of the present invention is contemplated.

In an embodiment, the immunogenic composition is lyophilized, optionally in the presence of at least one excipient. In a preferred embodiment, the at least one excipient is selected from the group consisting of starch, glucose, lactose, sucrose, trehalose, raffinose, stachyose, melezitose, dextran, mannitol, lactitol, palatinit, gelatin, malt, rice, flour, chalk, silica gel, sodium stearate, glycerol monostearate, talc, glycine, arginine, lysine, sodium chloride (NaCl), dried skim milk, glycerol, propylene glycol, water, and ethanol. In a preferred embodiment, the at least one excipient is selected from the group consisting of sucrose, mannitol, and glycine. In a particular embodiment, the at least one excipient is sucrose. In another embodiment, the lyophilized composition comprises an additional excipient. In one such embodiment, the additional excipient is mannitol or glycine.

In another embodiment, the lyophilized composition comprises about 1% (w/v) to about 10% (w/v) of at least one saccharide, such as about 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5% or 10.0%. In a preferred embodiment, the lyophilized composition comprises greater than about 5.5% (w/v) of at least one excipient, such as greater than about 7.0% (w/v). In a further embodiment, the lyophilized composition comprises about 1% (w/v) to about 10% (w/v) of an additional excipient, such as about 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5% or 10.0%. In a preferred embodiment, the lyophilized composition comprises about 1% (w/v) to about 10% (w/v) of the at least one excipient and about 1% (w/v) to about 10% (w/v) of the additional excipient.

In yet another embodiment, the lyophilized composition is reconstituted with water, water for injection (WFI), an adjuvant suspension, or saline. In a preferred embodiment, the diluent is an aluminum-based adjuvant suspension, such as an aluminum phosphate suspension.

In one embodiment, the composition includes an isolated polysaccharide described herein and a carrier molecule. Suitable carrier molecules may include proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG.

The immunogenic compositions of the present invention can further comprise one or more additional "immunomodulators", which are agents that perturb or alter the immune system, such that either up-regulation or down-regulation of humoral and/or cell-mediated immunity is observed. In one particular embodiment, up-regulation of the humoral and/or cell-mediated arms of the immune system is preferred. Examples of certain immunomodulators include, for example, an adjuvant or cytokine, or ISCOMATRIX (CSL Limited, Parkville, Australia), described in U.S. Pat. No. 5,254,339, among others. The term "adjuvant" refers to a compound or mixture that enhances the immune response to an antigen as further described herein.

Non-limiting examples of adjuvants that can be used in the composition of the present invention include the RIBI adjuvant system (Ribi Inc., Hamilton, Mont.); mineral gels, such as aluminum hydroxide gel; water-in-oil emulsions, such as Freund's complete and incomplete adjuvants; Block copolymer (CytRx, Atlanta Ga.); SAF-M (Chiron, Emeryville, Calif.); AMPHIGEN® adjuvant; saponin; Quil A or other saponin fraction; monophosphoryl lipid A; and Avridine lipid-amine adjuvant. Non-limiting examples of oil-in-water emulsions useful as an adjuvant in the vaccine of the invention include MF59 (U.S. Pat. No. 6,299,884) (containing 5% Squalene, 0.5% polysorbate 80, and 0.5% Span 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% polysorbate 80, 5% pluronic-blocked polymer L121, and thr-MDP, either microfluidized into a submicron emulsion or vortexed to generate a larger particle size emulsion); modified SEAM62 (containing 5% (v/v) squalene (Sigma), 1% (v/v) SPAN® 85 detergent (ICI Surfactants), 0.7% (v/v) polysorbate 80 detergent (ICI Surfactants), 2.5% (v/v) ethanol, 200 mcg/ml Quil A, 100 mcg/ml cholesterol, and 0.5% (v/v) lecithin); and modified SEAM 1/2 (containing 5% (v/v) squalene, 1% (v/v) SPAN® 85 detergent, 0.7% (v/v) polysorbate 80 detergent, 2.5% (v/v) ethanol, 100 mcg/ml Quil A, and 50 mcg/ml cholesterol).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxy¬tetradecanoyl¬amino] ethyl 2-Deoxy-4-O-phosphono-3-O-[(R)-3-tetra¬decanoyoxy¬tetrade¬canoyl]-2-[(R)-3-tetradecanoyloxy¬tetradecanoyl-amino]-b-D-glucopyranoside, which is also known as 529 (formerly known as RC529). This 529 adjuvant is formulated as an aqueous form (AF) or as a stable emulsion (SE).

Still other adjuvants include a cyclodextrin derivative (U.S. Pat. No. 6,165,995); a polyanionic polymer (U.S. Pat. No. 6,610,310); muramyl peptides, such as N-acetyl-muramyl-L-threonyl-D-isoglutamine (thr-MDP), and N-acetylnormuramyl-L-alanine-2-(1'-2' dipalmitoyl-sn-glycero-3-hydroxy¬phosphoryl¬oxy)-ethylamine (MTP-PE); Amphigen; Avridine; L121/squalene; D-lactide-polylactide/glycoside; pluronic polyols; killed Bordetella; saponins, such as Stimulon™ QS-21 (Antigenics, Framingham, Mass.), described in U.S. Pat. No. 5,057,540; *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296, 713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

Other "immunomodulators" that can be included in the vaccine include, e.g., one or more of the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078, 996 and ATCC Accession Number 39900); macrophage colony stimulating factor (M-CSF); granulocyte colony stimulating factor (G-CSF); or the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as B7-1, B7-2, CD40 and CD40L; growth factors including vascular growth factor, nerve growth factor, fibroblast growth factor, epidermal growth factor, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

It is to be understood that the decision whether to use an immunomodulator and/or adjuvant or the choice of which immunomodulator and/or adjuvant to be used will depend on the subject to which the vaccine or immunogenic composition will be administered, the route of injection, and the number of injections to be given. For instance, if the subject has been exposed to the pathogen naturally, an adjuvant may not be required as the vaccine antigens can effectively induce a memory response. In certain embodiments, the immunogenic composition will include one or more adjuvants. In one embodiment, the immunogenic composition comprises an aluminum-based adjuvant. In one such embodiment, the aluminum adjuvant is aluminum hydroxide, aluminum phosphate, or aluminum hydroxyl phosphate. In a particular embodiment, the adjuvant is aluminum phosphate. In another embodiment of the invention, the immunogenic composition comprises QS-21 as the adjuvant.

In one embodiment, the immunogenic composition comprises an adjuvant at a concentration of from about 0.1 mg/ml to about 1.0 mg/ml, 0.1 mg/ml to about 0.9 mg/ml, 0.1 mg/ml to about 0.8 mg/ml, 0.1 mg/ml to about 0.7 mg/ml, 0.1 mg/ml to about 0.6 mg/ml, 0.1 mg/ml to about 0.5 mg/ml, 0.1 mg/ml to about 0.4 mg/ml, 0.1 mg/ml to about 0.3 mg/ml, 0.1 mg/ml to about 0.2 mg/ml, 0.25 mg/ml to about 0.95 mg/ml, 0.25 mg/ml to about 0.85 mg/ml, 0.25 mg/ml to about 0.75 mg/ml, 0.25 mg/ml to about 0.65 mg/ml, 0.25 mg/ml to about 0.55 mg/ml, 0.25 mg/ml to about 0.45 mg/ml, 0.25 mg/ml to about 0.35 mg/ml, 0.5 mg/ml to about 1.0 mg/ml, 0.5 mg/ml to about 0.9 mg/ml, 0.5 mg/ml to about 0.8 mg/ml, 0.5 mg/ml to about 0.75 mg/ml, 0.5 mg/ml to about 0.7 mg/ml, 0.5 mg/ml to about 0.65 mg/ml, 0.5 mg/ml to about 0.6 mg/ml, 0.75 mg/ml to about 1.0 mg/ml, 0.75 mg/ml to about 0.95 mg/ml, 0.75 mg/ml to about 0.9 mg/ml, and 0.75 mg/ml to about 0.85 mg/ml. In a preferred embodiment, the immunogenic composition comprises an adjuvant at a concentration of from about 0.25 mg/ml to about 0.75 mg/ml, and most preferably about 0.5 mg/ml.

In a preferred embodiment, the adjuvant is an aluminum-based at a concentration of about 0.5 mg/ml. In one such embodiment, the aluminum-based adjuvant is aluminum phosphate or aluminum hydroxyl phosphate. In another embodiment, the aluminum-based adjuvant is aluminum hydroxide.

It should be noted that immunogenic compositions comprising an aluminum-based adjuvant tend to phase separate as a function of time; aluminum particles will separate from the liquid as sediments settle during storage. To ensure successful administration, the immunogenic composition must be visually uniform and resuspended prior to administration. Accordingly, it is important that the composition is easy to uniformly resuspend. In one aspect of the invention, the immunogenic composition is resuspended in about 50 or fewer shakes, such as about 40 or fewer shakes, about 30 or fewer shakes, about 25 or fewer shakes, about 20 or fewer shakes, about 15 or fewer shakes, about 10 or fewer shakes, or about 5 or fewer shakes. In a preferred embodiment, the immunogenic composition is resuspended in about 10 or fewer shakes. In another aspect of the invention, the immunogenic composition is resuspended in about 1 to about 50 shakes, such as about 1 to about 40 shakes, about 1 to about 30 shakes, about 1 to about 25 shakes, about 1 to about 20 shakes, about 1 to about 15 shakes, about 1 to about 10 shakes, or about 1 to about 5 shakes. In a preferred embodiment, the immunogenic composition is resuspended in about 1 to about 10 shakes.

In one aspect of the invention, the immunogenic composition is filled in a container. In one embodiment, the container is selected from the group consisting of a vial, flask, bag, and syringe. In one embodiment, the container is made of glass, metal (such as steel, stainless steel, and aluminum), and polymers (such as thermoplastics, elastomers, thermoplastic-elastomers). In one embodiment, the container is siliconized. In a preferred embodiment, the container is a syringe, and most preferably a glass syringe.

In one particular embodiment, the immunogenic composition is filled in a syringe with a headspace of about 1 mm to about 15 mm, such as about 1 mm to about 11 mm, about 1 mm to about 10 mm, about 1 mm to about 9 mm, about 1 mm to about 8 mm, about 1 mm to about 7 mm, about 1 mm to about 6 mm, about 1 mm to about 5 mm, about 1 mm to about 4 mm, about 1 mm to about 3 mm, about 2 mm to about 15 mm, about 2 mm to about 11 mm, about 2 mm to about 10 mm, about 2 mm to about 9 mm, about 2 mm to about 8 mm, about 2 mm to about 7 mm, about 2 mm to about 6 mm, about 2 mm to about 5 mm, about 2 mm to about 4 mm, about 3 mm to about 15 mm, about 3 mm to about 11 mm, about 3 mm to about 10 mm, about 3 mm to about 9 mm, about 3 mm to about 8 mm, about 3 mm to about 7 mm, about 32 mm to about 6 mm, about 3 mm to about 5 mm, about 4 mm to about 15 mm, about 4 mm to about 11 mm, about 4 mm to about 10 mm, about 4 mm to about 9 mm, about 4 mm to about 8 mm, about 4 mm to about 7 mm, about 4 mm to about 6 mm, about 5 mm to about 15 mm, about 5 mm to about 11 mm, about 5 mm to about 10 mm, about 5 mm to about 9 mm, about 5 mm to about 8 mm, or about 5 mm to about 7 mm. In a preferred embodiment, the headspace is about 2 mm to about 6 mm, and most preferably about 4 mm.

In one embodiment, the immunogenic composition comprises a polysaccharide-protein conjugate as described herein, a buffer, a surfactant, an excipient, and optionally an adjuvant, wherein the composition is buffered to a pH of about 6.0 to about 7.5.

In one such embodiment, the immunogenic composition comprises a GBS polysaccharide-protein conjugate, a buffer, a surfactant, an excipient, and optionally an adjuvant, wherein the composition is buffered to a pH of about 6.0 to about 7.5 and wherein the capsular polysaccharide has a sialic acid level of greater than about 60%.

In one embodiment, the immunogenic composition comprises a GBS polysaccharide-protein conjugate, histidine, polysorbate-80, sodium chloride, and optionally aluminum phosphate, wherein the composition is buffered to a pH of about 6.0 to about 7.0.

In one particular embodiment, the immunogenic composition comprises a GBS polysaccharide-protein conjugate, histidine, polysorbate-80, sodium chloride, and optionally aluminum phosphate, wherein the composition is buffered to a pH of about 6.0 to about 7.0 and wherein the capsular polysaccharide has a sialic acid level of greater than about 60%.

In a preferred embodiment, the immunogenic composition comprises about 5 mcg/ml to about 50 mcg/ml of a GBS polysaccharide-protein conjugate, about 10 mM to about 25 mM of histidine, about 0.01% to about 0.03% (v/w) of polysorbate-80, about 10 mM to about 250 mM of sodium chloride, and optionally about 0.25 mg/ml to about 0.75 mg/ml of aluminum as aluminum phosphate, wherein the capsular polysaccharide has a sialic acid level of greater than about 60%.

In another embodiment, the immunogenic composition comprises a GBS polysaccharide-protein conjugate, phosphate, polysorbate-80, sodium chloride, and aluminum phosphate, wherein the composition is buffered to a pH of about 6.0 to about 7.5.

In an additional embodiment, the immunogenic composition comprises a GBS polysaccharide-protein conjugate, phosphate, polysorbate-80, sodium chloride, and aluminum phosphate, wherein the composition is buffered to a pH of about 6.0 to about 7.5 and wherein the capsular polysaccharide has a sialic acid level of greater than about 60%.

In a preferred embodiment, the immunogenic composition comprises about 5 mcg/ml to about 50 mcg/ml of a GBS polysaccharide-protein conjugate, about 10 mM to about 25 mM of phosphate, about 0.01% to about 0.03% (v/w) of polysorbate-80, about 10 mM to about 350 mM of sodium chloride, and about 0.25 mg/ml to about 0.75 mg/ml of aluminum as aluminum phosphate, wherein the capsular polysaccharide has a sialic acid level of greater than about 60%.

In one such embodiment, the immunogenic composition comprises at least two GBS polysaccharide-protein conjugates, a buffer, a surfactant, an excipient, and optionally an adjuvant, wherein the composition is buffered to a pH of about 6.0 to about 7.5 and wherein the conjugates comprise capsular polysaccharides from group B streptococcus (GBS) serotype IV and at least one additional serotype selected from the group consisting of Ia, Ib, II, III, V, VI, VII, VIII, and IX.

In one particular embodiment, the immunogenic composition comprises at least two GBS polysaccharide-protein conjugates, histidine, polysorbate-80, sodium chloride, and optionally aluminum phosphate, wherein the composition is buffered to a pH of about 6.0 to about 7.0 and wherein the conjugates comprise capsular polysaccharides from group B streptococcus (GBS) serotype IV and at least one additional serotype selected from the group consisting of Ia, Ib, II, III, V, VI, VII, VIII, and IX.

In a preferred embodiment, the immunogenic composition comprises about 5 mcg/ml to about 50 mcg/ml each of at least two GBS polysaccharide-protein conjugates, about 10 mM to about 25 mM of histidine, about 0.01% to about 0.03% (v/w) of polysorbate-80, about 10 mM to about 250 mM of sodium chloride, and optionally about 0.25 mg/ml to about 0.75 mg/ml of aluminum as aluminum phosphate, wherein the conjugates comprise capsular polysaccharides from group B streptococcus (GBS) serotype IV and at least one additional serotype selected from the group consisting of Ia, Ib, II, III, V, VI, VII, VIII, and IX.

In another particular embodiment, the immunogenic composition comprises at least two GBS polysaccharide-protein conjugates, phosphate, polysorbate-80, sodium chloride, and aluminum phosphate, wherein the composition is buffered to a pH of about 6.0 to about 7.5 and wherein the conjugates comprise capsular polysaccharides from group B streptococcus (GBS) serotype IV and at least one additional serotype selected from the group consisting of Ia, Ib, II, III, V, VI, VII, VIII, and IX.

In one preferred embodiment, the immunogenic composition comprises about 5 mcg/ml to about 50 mcg/ml each of at least two GBS polysaccharide-protein conjugates, about 10 mM to about 25 mM of phosphate, about 0.01% to about 0.03% (v/w) of polysorbate-80, about 10 mM to about 350 mM of sodium chloride, and about 0.25 mg/ml to about 0.75 mg/ml of aluminum as aluminum phosphate, wherein the conjugates comprise capsular polysaccharides from group B streptococcus (GBS) serotype IV and at least one additional serotype selected from the group consisting of Ia, Ib, II, III, V, VI, VII, VIII, and IX.

Evaluation of Immunogenic Compositions

Various in vitro tests are used to assess the immunogenicity of the immunogenic compositions of the invention. For example, an in vitro opsonic assay is conducted by incubating together a mixture of streptococcal cells, heat inactivated serum containing specific antibodies to the antigens in question, and an exogenous complement source. Opsonophagocytosis proceeds during incubation of freshly isolated polymorphonuclear cells (PMN's) or differentiated effector cells such as HL60s and the antibody/complement/streptococcal cell mixture. Bacterial cells that are coated with antibody and complement are killed upon opsonophagocytosis. Colony forming units (cfu) of surviving bacteria that are recovered from opsonophagocytosis are determined by plating the assay mixture. Titers are reported as the reciprocal of the highest dilution that gives 50% bacterial killing, as determined by comparison to assay controls.

A whole cell ELISA assay may also be used to assess in vitro immunogenicity and surface exposure of the antigen, wherein the bacterial strain of interest (*S. agalactiae*) is coated onto a plate, such as a 96 well plate, and test sera from an immunized animal is reacted with the bacterial cells. If an antibody, specific for the test antigen, is reactive with a surface exposed epitope of the antigen, it can be detected by standard methods known to one skilled in the art. Alternatively, flow cytometry may be used to measure surface exposure of capsular polysaccharide antigens and specificity of antibodies, including monoclonal antibodies.

An antigen demonstrating the desired in vitro activity may then be tested in an in vivo animal challenge model. In certain embodiments, immunogenic compositions are used in the immunization of an animal (e.g., a mouse) by methods and routes of immunization known to those of skill in the art (e.g., intranasal, parenteral, oral, rectal, vaginal, transdermal, intraperitoneal, intravenous, subcutaneous, etc.). Following immunization of the animal with a GBS immunogenic composition, the animal is challenged with a *Streptococcus agalactiae* strain and assayed for resistance to the streptococcal infection.

In one embodiment, pathogen-free mice are immunized and challenged with *S. agalactiae*. For example, mice are immunized with one or more doses of the desired antigen in an immunogenic composition. Subsequently, the mice are challenged with *S. agalactiae* and survival is monitored over time post challenge.

Methods of Use

"Immunocompromised", as used herein, refers to a subject suffering from a deficiency with respect to the cellular and/or humoral arm(s) of the immune system. Accordingly, the extent of deficiency in immune function varying from slight impairment in the immune process to complete immune suppression is contemplated.

The term "subject" refers to a mammal, bird, fish, reptile, or any other animal. The term "subject" also includes humans. The term "subject" also includes household pets. Non limiting examples of household pets include: dogs, cats, pigs, rabbits, rats, mice, gerbils, hamsters, guinea pigs, ferrets, birds, snakes, lizards, fish, turtles, and frogs. The term "subject" also includes livestock animals. Non limiting examples of livestock animals include: alpaca, bison, camel, cattle, deer, pigs, horses, llamas, mules, donkeys, sheep, goats, rabbits, reindeer, yak, chickens, geese, and turkeys.

As used herein, "treatment" (including variations thereof, for example, "treat" or "treated") refers to any one or more of the following: (i) the prevention of infection or reinfection, as in a traditional vaccine, (ii) the reduction in the severity of or the elimination of symptoms, and (iii) the substantial or complete elimination of the pathogen or disorder in question. Hence, treatment may be effected prophylactically (prior to infection) or therapeutically (following infection). In the present invention, prophylactic or therapeutic treatments can be used. According to a particular embodiment of the present invention, compositions and methods are provided which treat, including prophylactically and/or therapeutically immunize, a host animal against a microbial infection (e.g., a bacterium such as *S. agalactiae*). The methods of the present invention are useful for conferring prophylactic and/or therapeutic immunity to a subject. The methods of the present invention can also be practiced on subjects for biomedical research applications.

In another aspect, the invention relates to a method of inducing an immune response against GBS in a subject by administering to the subject an effective amount of an immunogenic composition described herein. In one embodiment, the invention relates to a method of preventing or reducing a disease or condition associated with group B streptococcus in a subject by administering to the subject an effective amount of an immunogenic composition described herein. In an aspect, the invention relates to the immunogenic composition described herein for use as a medicament. In an aspect, the invention relates to the immunogenic composition described herein for use in a method of inducing an immune response against GBS in a subject. In a particular embodiment, the subject is a female planning to become pregnant or a pregnant female. In one such embodiment, the pregnant female is in her second half of pregnancy, such as at least 20 weeks or at least 27 weeks gestation. In a preferred embodiment, the pregnant female is at 27 weeks to 36 weeks gestation. In another embodiment, the subject is an older adult, such as an adult 50 years of age or older, 65 years of age or older, and 85 years of age or older. In a further embodiment, the subject is immunocompromised. In one aspect, the subject may have a medical condition selected from the group consisting of obesity, diabetes, HIV infection, cancer, cardiovascular disease, or liver disease. In a preferred embodiment, the group B streptococcus is *S. agalactiae*.

In one embodiment, the immunogenic composition comprises a polysaccharide-protein conjugates comprising GBS serotype IV and at least one additional serotype selected from the group consisting of serotypes Ia, Ib, II, III, V, VI, VII, VIII, and IX. In another embodiment, the conjugates comprise GBS serotype IV and at least two additional serotypes selected from the group consisting of serotypes Ia, Ib, II, III, V, VI, VII, VIII, and IX. In an additional embodiment, the conjugates comprise GBS serotype IV and at least three additional serotypes selected from the group consisting of serotypes Ia, Ib, II, III, V, VI, VII, VIII, and IX. In yet another embodiment the conjugates comprise GBS serotype IV and at least four additional serotypes selected from the group consisting of serotypes Ia, Ib, II, III, V, VI, VII, VIII, and IX. In a particular embodiment, the conjugates comprise GBS serotypes Ia, Ib, II, III, and IV. In a further embodiment the conjugates comprise GBS serotype IV and at least five additional serotypes selected from the group consisting of serotypes Ia, Ib, II, III, V, VI, VII, VIII, and IX. In a further embodiment the composition comprises GBS serotype V. In a particular embodiment, the conjugates comprise GBS serotypes Ia, Ib, II, III, and V. In a preferred embodiment the immunogenic composition comprises six polysaccharide-protein conjugates from GBS serotypes Ia, Ib, II, III, IV, and V. One aspect of the invention relates to an immunogenic composition that does not have immune interference.

An immunogenic or effective amount of an immunogenic composition can be determined by doing a dose response study in which subjects are immunized with gradually increasing amounts of the immunogenic composition and the immune response analyzed to determine the optimal dosage. Starting points for the study can be inferred from immunization data in animal models. The dosage amount can vary depending upon specific conditions of the individual. The amount can be determined in routine trials by means known to those skilled in the art.

An immunologically effective amount of the immunogenic composition in an appropriate number of doses is administered to the subject to elicit an immune response. The dosage amount can vary depending upon specific conditions of the individual, such as age and weight. This amount can be determined in routine trials by means known to those skilled in the art.

In one embodiment, patients being administered immunogenic compositions of the invention show a reduction in *S. agalactiae* carriage rates. Such reduction in carriage or a prolonged interval of time spent as a non-carrier following administration of an immunogenic composition is significant from a medical need perspective. For example, reduction in overall *S. agalactiae* carriage in carriers may be assessed following one dose of the immunogenic composition of the invention. For example, 1 day prior to administration of the immunogenic composition, a group of adults aged 18-50 years may be screened for carriage by nasal, throat, axillary, rectal, perineal, and vaginal swabs followed by cultivation to determine their carriage state. Next, the group can be administered an immunogenic composition of the invention with a group receiving a control. Nasal, throat, axillary, rectal, perineal, and vaginal swabs performed weekly over a 12 week period, and monthly up to 6 months post administration of the immunogenic composition are performed and compared to placebo. One primary endpoint is to compare carriage rates in patients after administration of an immunogenic composition versus placebo at 3 month intervals post immunization.

Antibodies

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also engineered antibodies (e.g., chimeric, humanized and/or derivatized to alter effector functions, stability and other biological activities) and fragments thereof (such as Fab, Fab', F(ab')2, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2 in humans. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody.

"Functional activity" of an antibody or "functional antibody" as used herein refers to an antibody that, at a minimum, can bind specifically to an antigen. Additional functions are known in the art and may include additional components of the immune system that effect clearance or killing of the pathogen such as through opsonization, ADCC or complement-mediated cytotoxicity. After antigen binding, any subsequent antibody functions can be mediated through the Fc region of the antibody. The antibody opsonophagocytosis assay (OPA) is an in vitro assay designed to measure in vitro Ig complement-assisted killing of bacteria with effector cells (white blood cells), thus mimicking a biological process. Antibody binding may also directly inhibit the biological function of the antigen it binds. In some embodiments, a "functional antibody" refers to an antibody that is functional as measured by the killing of bacteria in an animal efficacy model or an opsonophagocytic killing assay that demonstrates that the antibodies kill the bacteria.

In one aspect, the invention relates to an isolated antibody or fragment thereof that specifically binds to a polysaccharide described herein. An "isolated" antibody as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In exemplary embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. An isolated antibody includes the antibody in situ within recombinant cells since at least one component of the antibody's natural environment will not be present. Ordinarily, however, an isolated antibody will be prepared by at least one purification step.

An antibody that "specifically binds to" or is "specific for" a particular polysaccharide or an epitope on a particular polysaccharide is one that binds to that particular polysaccharide or epitope on a particular polysaccharide without substantially binding to any other polysaccharide or polysaccharide epitope.

The word "label" when used herein refers to a detectable compound or composition which is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition which is detectable.

The invention further provides antibodies and antibody compositions which bind specifically and selectively to one or more antigens of an immunogenic composition of the present invention. In some embodiments, antibodies are generated upon administration to a subject of an immunogenic composition of the present invention. In some embodiments, the invention provides purified or isolated antibodies directed against one or more of the antigens of an immunogenic composition of the present invention. In some embodiments, the antibodies of the present invention are functional as measured by killing bacteria in either an animal efficacy model or via an opsonophagocytic killing assay. In some embodiments, the antibodies of the invention confer passive immunity to a subject. The present invention further provides polynucleotide molecules encoding an antibody or antibody fragment of the invention, and a cell or cell line (such as hybridoma cells or other engineered cell lines for recombinant production of antibodies) and a transgenic animal that produces an antibody or antibody composition of the invention, using techniques well-known to those of skill in the art.

Antibodies or antibody compositions of the invention may be used in a method of treating or preventing a streptococcal infection, disease or condition associated with *S. agalactiae* in a subject, the method comprising generating a polyclonal or monoclonal antibody preparation, and using said antibody or antibody composition to confer passive immunity to the subject. Antibodies of the invention may also be useful for diagnostic methods, e.g., detecting the presence of or quantifying the levels of one or more antigens of the immunogenic compositions of the present invention.

Antibody responses to repeat structures such as a polysaccharide of the present invention may exhibit some unique features. For example, the regularity of the repeating units may mean that antigen molecules of vastly different molecular weights can bind to antibodies specific for the polysaccharide. Second, the repeat structures of the larger length polysaccharides are capable of inducing T-cell independent antibody responses. Therefore, when using polysaccharides conjugated to protein carriers having T-cell helper epitopes, both T-cell independent and T-cell dependent antibody responses can be stimulated. Therefore, immune response can be modified by appropriate selection of polysaccharide size and whether or not a carrier protein is used.

Polyclonal Antibodies

In certain embodiments, the anti-polysaccharide antibody is a polyclonal antibody. Polyclonal antibodies, as defined herein, refers to a mixture of antibodies having differing specificities derived from a preparation of serum and originating from different B-cell clones. The preparation and characterization of polyclonal antibodies are known in the art.

Polyclonal antibodies are raised in a subject, for example in a mammal, by administering one or more injections of an immunogen or immunogenic composition described herein and, if desired, an adjuvant, buffer, and/or diluent. A range of animal species may be used for the production of specific antisera. Typically an animal used for production of anti-saccharide polyclonal antisera is a nonhuman primate, a goat, a sheep, a rabbit, a mouse, a rat, a hamster or a guinea pig. Typically, the immunogen or immunogenic composition with or without the adjuvant is injected in the mammal by multiple injections. The immunogenic material may include a polysaccharide, oligosaccharide, polysaccharide, polysaccharide-protein conjugate described herein, or a larger assembly of immunogens. Typically, beginning 2-6 weeks after the first immunization, blood is collected from the immunized animal, allowed to clot and serum is harvested. The serum contains the anti-saccharide polyclonal antibodies from the immunized animal and is often referred to as antisera.

Monoclonal Antibodies

An anti-saccharide monoclonal antibody may be prepared through use of known hybridoma techniques. Typically, preparing monoclonal antibodies involves first immunizing a suitable target animal host with a selected immunogen comprising a polysaccharide, oligosaccharide, polysaccharide or polysaccharide-protein conjugate of the present invention. If desired, an adjuvant, buffer, and/or diluents may be included. The immunization is conducted in a manner sufficient to elicit B lymphocytes to produce or express antibodies that specifically bind to the polysaccharide or conjugate thereof. Alternatively, the lymphocytes are immunized in vitro.

The lymphocytes are then fused with an immortalized cell line using a suitable fusing agent, such as polyethylene glycol, to form a hybridoma cell. The source of the lymphocytes determines whether the monoclonal antibodies are of human or animal origin. In general, peripheral blood lymphocytes ("PBLs") are used if antibodies and cells of human origin are desired, and spleen cells or lymph node cells are used if non-human mammalian sources are desired.

Immortalized cell lines are typically transformed mammalian cells, particularly myeloma cells of rodent, bovine and human origin. Usually, rat or mouse myeloma cell lines are employed. The hybridoma cells are cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Immortalized cell lines are chosen for practical considerations such as species of origin, fusion and growth characteristics. For example, suitable immortalized cell lines are those that fuse efficiently, support stable high level expression of antibody by the selected antibody-producing cells, and are sensitive to a medium such as HAT medium. Examples of immortalized cell lines include: murine myeloma lines. Human myeloma and mouse-human heteromyeloma cell lines also have been described for the production of human monoclonal antibodies.

The monoclonal antibody is secreted into the culture medium by the hybridoma cells. The culture medium is then assayed for the presence of monoclonal antibodies that recognize and bind the polysaccharide. The anti-polysaccharide binding specificity of particular monoclonal antibodies produced by the hybridoma cells is determined by one of numerous procedures that are well known in the art.

For example, antibody binding specificity may be determined by immunoprecipitation, radioimmunoassay (RIA), western blot, enzyme-linked immunoabsorbent assay (ELISA) or surface plasmon resonance (e.g., Biacore). The precise epitope recognized by the monoclonal antibody is determined by epitope mapping. Such techniques and assays are well known in the art.

After hybridoma cells producing antibodies with the desired specificity are identified, the clones are subcloned by limiting dilution and cultured using standard methods. Suitable culture media for this purpose include, for example, Dulbecco's Modified Eagle's Medium and RPMI-1640 medium. Alternatively, the hybridoma cells are grown in vivo as ascites in a mammal. The monoclonal antibodies secreted by the subclones are isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, antibodies having the desired specificity and from the desired species of origin can be obtained through the use of phage display libraries. Additionally, examples of methods and reagents particularly amenable for use in generating and screening antibody display library can be found in the art.

Uses of Antibodies

In one aspect, the invention relates to use of an immunogenic composition described herein for producing a GBS antibody and/or antibody fragment. The polysaccharide-protein conjugates described herein and/or antibodies generated therefrom may be used in a variety of immunodiagnostic techniques known to those of skill in the art, including ELISA- and microarray-related technologies. In addition, these reagents may be used to evaluate antibody responses, including serum antibody levels, for example, to immunogenic polysaccharide conjugates. The assay methodologies of the invention may involve the use of labels such as fluorescent, chemiluminescent, radioactive, enzymatic labels or dye molecules, and/or secondary immunologic reagents for direct or indirect detection of a complex between an antigen or antibody in a biological sample and a corresponding antibody or antigen bound to a solid support.

The antibody or antibody fragment produced may also be useful in passive immunotherapy or for prophylaxis against a streptococcal infection.

Method of Producing a Polysaccharide

In yet another aspect, the invention relates to a method for producing the polysaccharides described herein. The method includes culturing a GBS and collecting the polysaccharide produced by the bacterium. In one embodiment, the GBS includes *S. agalactiae*. The bacterium may be any strain of *S. agalactiae*. In a preferred embodiment, the bacterium is an encapsulated strain of *S. agalactiae*. *S. agalactiae* strains for use in the present invention include 090, A909 (ATCC Accession No. BAA-1138), 515 (ATCC Accession No. BAA-1177), B523, CJB524, MB 4052 (ATCC Accession No. 31574), H36B (ATCC Accession No. 12401), S40, S42, MB 4053 (ATCC Accession No. 31575), M709, 133, 7357, PFEGBST0267, MB 4055 (ATCC Accession No. 31576), 18RS21 (ATCC Accession No. BAA-1175), S16, S20, V8 (ATCC Accession No. 12973), DK21, DK23, UAB, 5401, PFEGBST0708, MB 4082 (ATCC Accession No. 31577), M132, 110, M781 (ATCC Accession No. BAA-22), D136C (3) (ATCC Accession No. 12403), M782, S23, 120, MB 4316 (M-732; ATCC Accession No. 31475), M132, K79, COH1 (ATCC Accession No. BAA-1176), PFEGBST0563, 3139 (ATCC Accession No. 49446), CZ-NI-016, PFEGBST0961, 1169-NT1, CJB111 (ATCC Accession No. BAA-23), CJB112, 2603 V/R (ATCC Accession No. BAA-611), NCTC 10/81, CJ11, PFEGBST0837, 118754, 114852, 114862, 114866, 118775, B 4589, B 4645, SS1214, CZ-PW-119, 7271, CZ-PW-045, JM9130013, JM9130672, IT-NI-016, IT-PW-62, and IT-PW-64.

A polysaccharide described herein may be produced by culturing the GBS in an appropriate medium. An appropriate medium may include Columbia broth. The medium may include dextrose, hemin, and/or glucose. Preferably, the medium includes Columbia broth and dextrose. If *S. agalactiae* is cultured using Columbia broth and dextrose, preferably the temperature for culture is 20 to 40° C., preferably 37° C. In a preferred embodiment, the bacterium is cultured under aerobic conditions. In another preferred embodiment, the bacterium is cultured for 12 to 60 hours.

A polysaccharide may be collected from the obtained culture by using a method known in the art to collect a target substance from a culture, such as, for example, heating, enzyme treatment, centrifugation, precipitation, treatment with activated carbon, and/or filtration. (See, for example, U.S. Patent Appl. Pub. Nos. 2006/0228380, 2006/0228381, 2007/0184071, 2007/0184072, 2007/0231340, and 2008/0102498; Int'l Patent Appl. Pub. No. WO 2008/118752). In one embodiment, the culture containing the bacterium and polysaccharide is centrifuged and treated with an enzyme, such as, for example, lysozyme, RNase, DNase, Pronase, mutanolysin, and combinations thereof. For example, in one embodiment, an appropriate organic solvent is added to the obtained supernatant to precipitate proteins, and the precipitate is removed by centrifugation. Then a polysaccharide may be precipitated by further adding an appropriate organic solvent to the supernatant, and the polysaccharide may be collected by centrifugation. More specifically, a polysaccharide described herein may be obtained by adding ethanol at a final concentration of about 25 volume % to the supernatant from which the bacterium has been removed, removing a precipitation that contains protein by centrifugation, further adding ethanol to a final concentration of about 75 volume % thereto, and then collecting a precipitate by centrifugation. The resulting precipitate may be dried with nitrogen. The resulting precipitate may be resuspended in Tris and 0.05% Na Azide.

A further aspect of the invention provides a novel method, using organic reagents such as derivatized hydroxyl amine compounds, for the isolation of largely intact high molecular weight CPs while preserving N- and O-acetyl groups. Since this method does not lyse the cells, the CPs isolated by centrifugation is minimally contaminated with intracellular components and may lead to higher overall yield. Moreover, these reagents cleave the group B antigen impurity to very small fragments due to its multiple phospodiester linkages, which can be easily removed by diafiltration.

In one embodiment, the CP is isolated by reacting a hydroxyl amine with a cell paste comprising a capsular polysaccharide producing bacterium. In a particular embodiment, the method further comprises the step of centrifuging. In another embodiment, the method further comprises the step of filtering. In yet another embodiment, the capsular polysaccharide producing bacterium is selected from the group consisting of *Streptococcus agalactiae, Streptococcus pneumoniae, Staphylococcus aureus, Neisseria meningitidis, Escherichia coli, Salmonella typhi, Haemophilus influenzae, Klebsiella pneumoniae, Enterococcus faecium*, and *Enterococcus faecalis*.

In an aspect of the invention, the hydroxyl amine may be those listed in Table 2 in Example 2. In a preferred embodiment, the hydroxyl amine is selected from the group consisting of dibenzyl hydroxylamine; diethyl hydroxylamine; hydroxylamine; ethylenediamine; triethylenetetramine; 1,1,4,7,10,10 hexamethyl triethylene tetramine; and 2,6,10, Trimethyl 2,6,10 triazaundecane.

In one aspect of the invention, the concentration of hydroxyl amine is about 5 mM to about 200 mM, such as about 5 mM to about 150 mM, about 5 mM to about 100 mM, about 5 mM to about 75 mM, about 5 mM to about 50 mM, about 5 mM to about 25 mM, about 5 mM to about 10 mM, 10 mM to about 200 mM, such as about 10 mM to about 150 mM, about 10 mM to about 100 mM, about 10 mM to about 75 mM, about 10 mM to about 50 mM, about 10 mM to about 25 mM, about 25 mM to about 200 mM, about 25 mM to about 150 mM, about 25 mM to about 100 mM, about 25 mM to about 75 mM, about 25 mM to about 50 mM, about 50 mM to about 200 mM, about 50 mM to about 150 mM, 50 mM to about 100 mM, and about 50 mM to about 75 mM.

In another aspect, the pH of the reaction is maintained at about 5.5 to about 9.5, such as about 5.5 to about 9.0, about 5.5 to about 8.5, about 5.5 to about 8.0, about 5.5 to about 7.5, about 5.5 to about 7.0, about 5.5 to about 6.5, about 6.0 to about 9.5, about 6.0 to about 9.0, about 6.0 to about 8.5, about 6.0 to about 8.0, about 6.0 to about 7.5, about 6.0 to about 7.0, about 6.5 to about 9.5, about 6.5 to about 8.5, about 6.5 to about 8.0, about 6.5 to about 7.5, about 7.0 to about 9.5, about 7.0 to about 9.0, 7.0 to about 8.5, and about 7.0 to about 8.0.

In a further aspect of the invention, the reaction takes place at a temperature of about 20° C. to about 85° C., such as about 20° C. to about 80° C., about 20° C. to about 75° C., about 20° C. to about 70° C., about 20° C. to about 65° C., about 20° C. to about 60° C., about 20° C. to about 55° C., about 20° C. to about 50° C., about 25° C. to about 85° C., about 25° C. to about 80° C., about 25° C. to about 75° C., about 25° C. to about 70° C., about 25° C. to about 65° C., about 25° C. to about 60° C., about 25° C. to about 55° C., about 25° C. to about 50° C., about 30° C. to about 85° C., about 30° C. to about 80° C., about 30° C. to about 75° C., about 30° C. to about 70° C., about 30° C. to about 65° C., about 30° C. to about 60° C., about 30° C. to about 55° C., about 30° C. to about 50° C., about 35° C. to about 85° C., about 35° C. to about 80° C., about 35° C. to about 75° C., about 35° C. to about 70° C., about 35° C. to about 65° C., about 35° C. to about 60° C., about 35° C. to about 55° C., about 40° C. to about 85° C., about 40° C. to about 80° C., about 40° C. to about 75° C., about 40° C. to about 70° C., about 40° C. to about 65° C., about 40° C. to about 60° C., about 45° C. to about 85° C., about 45° C. to about 80° C., about 45° C. to about 75° C., about 45° C. to about 70° C., about 45° C. to about 65° C., about 50° C. to about 85° C., about 50° C. to about 80° C., about 50° C. to about 75° C., about 50° C. to about 70° C., about 55° C. to about 85° C., about 55° C. to about 80° C., about 55° C. to about 75° C., about 60° C. to about 85° C., and about 65° C. to about 85° C.

In yet another aspect, the reaction time is about 10 hours to about 90 hours, such as about 10 hours to about 85 hours, about 10 hours to about 80 hours, about 10 hours to about 75 hours, about 10 hours to about 70 hours, about 10 hours to about 60 hours, about 10 hours to about 50 hours, about 10 hours to about 40 hours, about 10 hours to about 30 hours, about 10 hours to about 25 hours, about 10 hours to about 20 hours, about 10 hours to about 15 hours, about 15 hours to about 90 hours, about 15 hours to about 85 hours, about 15 hours to about 80 hours, about 15 hours to about 75 hours, about 15 hours to about 70 hours, about 15 hours to about 60 hours, about 15 hours to about 50 hours, about 15 hours to about 40 hours, about 15 hours to about 30 hours, 15 hours to about 20 hours, such as about 20 hours to about 90 hours, about 20 hours to about 85 hours, about 20 hours to about 80 hours, about 20 hours to about 75 hours, about 20 hours to about 70 hours, about 20 hours to about 60 hours, about 20 hours to about 50 hours, about 20 hours to about 40 hours, about 20 hours to about 30 hours, and about 20 hours to about 25 hours.

Alternatively, in another embodiment of the invention, the polysaccharide is chemically synthesized. The polysaccharide may be chemically synthesized according to conventional methods.

In yet another embodiment of the invention the polysaccharide is prepared by expression in a surrogate host after cloning and expressing a biosynthetic pathway to produce the polysaccharide. For example, a host cell may be modified to produce a polysaccharide having structural similarity to a polysaccharide described herein, wherein a repeating unit of the polysaccharide produced in the host cell is partially identical to a repeating unit of a polysaccharide described herein. A polysaccharide is structurally similar to a polysaccharide described herein if, for example, a repeating unit of the polysaccharide has a missing branch, is heterogeneous in size and/or is heterogeneous in branching arrangement, as compared to a repeating unit of a polysaccharide described herein. Preferably, the host cell is a bacterial host cell.

EXAMPLES

The following examples demonstrate some embodiments of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. All parts and percents referred to herein are on a weight basis and all temperatures are expressed in degrees centigrade unless otherwise specified.

Furthermore, the following examples were carried out using standard techniques, which are well known and routine to those of skill in the art, except where otherwise described in detail. As noted above, the following examples are presented for illustrative purpose, and should not be construed in any way limiting the scope of this invention.

Example 1

Preparation of Polysaccharide-Protein Conjugates with De-O-Acetylated Polysaccharides

*S. agalactiae* strains for respective serotypes were fermented in submerged culture with pH-control in a defined medium. The procedures and media used were optimized through experimentation and were extensions of basic techniques previously described in von Hunolstein, C. et al., Appl. Micro. Biotech. 38(4):458-462 (1993). The capsular polysaccharide was removed from the cells by NaOH treatment. After clarification, a series of UF/DF, precipitation, and carbon filtration steps afforded the purified polysaccharide. See, e.g., U.S. Pat. No. 8,652,480 Reductive amination chemistry was used to conjugate the activated polysaccharide to $CRM_{197}$. See, e.g., U.S. Pat. No. 5,360,897.

Example 2

Isolation of O-Acetylated Polysaccharides

The cell paste from GBS capsular polysaccharide (CP) serotype Ia obtained after heat killing and centrifugation of the fermentation broth (1.2 L) was resuspended in 175 mL of 25 mM potassium phosphate buffer (25 mM, pH 6.9). The suspension was mixed with an aqueous hydroxyl amine O-sulfonic acid solution to a final concentration of 10 mM. The pH of the suspension was determined to be about 5.8. The suspension was stirred at 55° C. for 72 hours. Afterward, the suspension was centrifuged at around 10,000 rpm and the supernatant was collected. The supernatant containing the crude cleaved CPs was analyzed for molecular weight and yield. The remaining portion was subjected to purification by diafiltration using 30 kDa MWCO membrane using water for injection (WFI). The purified polysaccharide was further analyzed for molecular weight by size exclusion chromatography combined with multiangle light scattering detector (SEC-MALS) (Table 1).

TABLE 1

Purification of GBS Serotype Ia by Diafiltration

| Sample | Mw (kDa) | Poly Dispersity (PD) |
|---|---|---|
| Crude | 340 | 1.2 |
| Purified poly | 320 | 1.3 |

Several hydroxyl amines, both nitrogen- and oxygen-substituted compounds, were screened for their activity using the method described above. The yields were calculated by gel permeation chromatography combined with multi-angle light scattering detection (GPC-MALS) of crude supernatants using the refractive index (RI) response and the square of specific refractive index increment (dn/dc) value of 0.135. The yield depended on the type of hydroxyl amines and optimization of conditions such as the concentration, temperature and reaction time (see Table 2). In general, increased hydroxyl amine concentration, higher temperature and longer reaction time lead to higher yield.

TABLE 2

Screening of Various Hydroxyl Amines and Optimization of Conditions of GBS Capsular Polysaccharide Serotype Ia

| Expt. No | Reagent | Conc. (Mm) | Temp (° C.) | Time (hr) | Yield/1 L fermentation | Polysaccharide Mw (kDa) | Poly Dispersity (PD) |
|---|---|---|---|---|---|---|---|
| 1 | O-benzylhydroxylamine hydrochloride | 10 | 55 | 72 | 42 | 2240 | 1.2 |
| 2 | Benzaldehyde oxime | 10 | 55 | 72 | 68 | 1400 | 1.2 |
| 3 | N,N-dibenzylhydroxylamine | 10 | 55 | 72 | 101 | 980 | 1.3 |
| 4 | N,N-dibenzylhydroxylamine | 50 | 55 | 17 | 320 | 590 | 1.3 |
| 5 | O-phenylhydroxylamine hydrochloride | 10 | 55 | 72 | 109 | 850 | 1.3 |

TABLE 2-continued

Screening of Various Hydroxyl Amines and Optimization of Conditions of GBS Capsular Polysaccharide Serotype Ia

| Expt. No | Reagent | Conc. (Mm) | Temp (° C.) | Time (hr) | Yield/1 L fermentation | Poly-saccharide Mw (kDa) | Poly Dispersity (PD) |
|---|---|---|---|---|---|---|---|
| 6 | 4-(dimethylamino)benzaldehyde oxime | 10 | 55 | 72 | 90 | 1400 | 1.2 |
| 7 | Benzyl hydroxylcarbamate | 10 | 55 | 84 | 323 | 1835 | 1.5 |
| 8 | O-(tetrahydro-2H-pyran-2-yl)hydroxylamine | 10 | 55 | 84 | 304 | 1270 | 1.4 |
| 9 | O-((perfluorophenyl)methyl)hydroxylamine | 10 | 55 | 84 | 185 | 1330 | 1.6 |
| 10 | O-tritylhydroxylamine | 10 | 55 | 84 | 371 | 1275 | 1.7 |
| 11 | O-(4-nitrobenzyl)hydroxylamine hydrochloride | 10 | 55 | 84 | 190 | 3500 | 1.3 |

TABLE 2-continued

Screening of Various Hydroxyl Amines and Optimization of Conditions of GBS Capsular Polysaccharide Serotype Ia

| Expt. No | Reagent | Conc. (Mm) | Temp (° C.) | Time (hr) | Yield/1 L fermentation | Polysaccharide Mw (kDa) | Poly Dispersity (PD) |
|---|---|---|---|---|---|---|---|
| 12 | 2-(aminooxy)acetic acid hydrochloride · ½HCl | 10 | 55 | 84 | 252 | 2600 | 1.2 |
| 13 | (aminooxy)sulfonic acid | 10 | 55 | 84 | 463 | 490 | 1.4 |
| 14 | (aminooxy)sulfonic acid | 50 | 55 | 17 | 460 | 270 | 1.2 |
| 15 | (aminooxy)sulfonic acid | 100 | 23 | 21 | 240 | 500 | 1.2 |
| 16 | N,N-dioctadecylhydroxylamine | 10 | 55 | 84 | 380 | 4700 | 1.7 |

Substituted and unsubstituted hydroxyl amines were found to be very effective in releasing the GBS capsular polysaccharide from the cell wall. This approach results in the isolation of high molecular weight CPS with preservation of N- and O-acetyl groups. Among the several compounds screened, dibenzyl hydroxyl amine was found to be most effective. Data are shown in Table 3 ([dibenzyl hydroxylamine]—50 mM; ph—7-8; temp—50° C.; time—24 hrs).

TABLE 3

GBS CPs Release Data Using Dibenzyl Hydroxylamine

| GBS Type | Ia | Ib | III |
|---|---|---|---|
| Polysaccharide release yield | 86% | 81% | 46% |
| Overall purification yield | 63% | 54% | 30% |
| Molecular weight (Mw) | 330 kDa | 212 kDa | 171 kDa |
| O-acetylation (NMR) | NA | 31% | 37% |
| N-acetylation (NMR) | 106% | 104% | 87% |

NA - Serotype Ia is not O-acetylated

Since the dibenzyl hydroxyl amine has poor solubility in water, an alternative derivative of hydroxyl amine that is freely water soluble and has similar or higher activity than dibenzyl hydroxylamine is desired. After screening a few compounds, diethyl hydroxyl amine was found to be a good alternative. Data are shown in Table 4 ([diethyl hydroxylamine]—100 mM; pH—7-8; temp—60° C.; time—19 hrs).

TABLE 4

GBS CPs Release Data Using Diethyl Hydroxylamine

| GBS Type | Ia | Ib | III |
|---|---|---|---|
| Poly release yield % | 100 | 94 | 59 |
| Molecular weight (Mw) | 890 kDa | 560 kDa | 309 kDa |

Hydroxyl amine ($NH_2$—OH) was also found to be effective in CPS cleavage from the cell wall. The data is shown is in Table 5 ([hydroxylamine]—100 mM; pH—7-7.5; temp—65° C.; time—17 hrs). For serotype III, the yield was 54% after 17 hours; however, the yield increased up to 70% after 3 and half days.

TABLE 5

GBS CPs Release Data Using Hydroxylamine

| GBS Type | Ia | III |
|---|---|---|
| Poly release yield % | 100 | 54 |
| Molecular weight (Mw) | 1160 kDa | 500 kDa |

Screening of Oligoamines for the Release of GBS Capsular Polysaccharide from Cells Hydroxyl amine and its substituted compounds were found to be very efficient for the cleavage of capsular polysaccharides from GBS cell wall. However, they were found to be less efficient for serotypes II and V. Therefore, oligoamines were tested due to the belief that they could be more active due to multiple amine functionality.

Ethylene diamine was found to be effective in releasing capsular polysaccharides from all the serotypes. The data is shown in Table 6 ([ethylenediamine]—50 or 100 mM; pH 8.0; 16 hr; 80° C.; 25 mM EDTA).

TABLE 6

GBS CPs Release Data Using Ethylenediamine

| GBS Serotype | Recovery (%) | Mw (kDa) |
|---|---|---|
| Ia | 96% | 242 |
| Ib | 83% | 225 |
| II | 30% | 76 |
| III | 68% | 94 |
| V | 30% | 235 |

Other representative oligoamines were tested for their activity using serotyps Ia and V cell pastes but were also found to be less efficient for serotype V. The data are shown in Tables 7 ([triethylenetetramine]—100 mM; pH—8.9; temp—60° C.; time—15 hrs), 8 ([1,1,4,7,10,10 hexamethyl triethylene tetramine]—10 mM; pH—6.3; temp—60° C.; time—20 hrs), and 9 ([2,6,10, Trimethyl 2,6,10 triazaundecane]—10 mM; pH—7-8; temp—60° C.; time—19 hrs).

TABLE 7

GBS CPs Release Data Using Triethylenetetramine triethylenetetramine

| GBS Type | Ia | V |
|---|---|---|
| Poly release yield % | 100 | ~10 after 2.5 days |
| Molecular weight (Mw) | 1280 | nd | nd—not determined

TABLE 8

GBS CPs Release Data Using 1,1,4,7,10,10 Hexamethyl Triethylene Tetramine 1,1,4,7,10,10 hexamethyl triethylene tetramine

| GBS Type | Ia | V |
|---|---|---|
| Poly release yield % | 100 | ~1% |
| Molecular weight (Mw) | 980 | nd | nd—not determined

TABLE 9

GBS CPs Release Data Using 2,6,10,Trimethyl 2,6,10 Triazaundecane 2,6,10,Trimethyl 2,6,10 triazaundecane

| GBS Type | Ia | V |
|---|---|---|
| Poly release yield % | 100 | ~1% |
| Molecular weight (Mw) | 1100 | nd | nd = not determined

Example 3

Conjugation of GBS Capsular Polysaccharides by Reductive Amination

Activating Polysaccharide

Polysaccharide oxidation was carried out in 100 mM potassium phosphate buffer (pH 6.0±0.5) by sequential addition of calculated amount of 500 mM potassium phosphate buffer (pH 6.0) and water for injection (WFI) to give final polysaccharide concentration of 2.0 g/L. If required, the reaction pH was adjusted to pH 6.0, approximately. After pH adjustment, the reaction temperature was adjusted to 23° C. Oxidation was initiated by the addition of approximately 0.25 molar equivalents of sodium periodate. The oxidation reaction was performed at 5±3° C. during 16 hrs, approximately.

Concentration and diafiltration of the activated polysaccharide was carried out using 5K MWCO ultrafiltration cassettes. Diafiltration was performed against 20-fold diavolumes of WFI. The purified activated polysaccharide was then stored at 5±3° C. The purified activated saccharide is characterized, inter alia, by (i) saccharide concentration by colorimetric assay; (ii) aldehyde concentration by colorimetric assay; (iii) degree of oxidation; and (iv) molecular weight by SEC-MALLS.

The degree of oxidation (DO=moles of sugar repeat unit/moles of aldehyde) of the activated polysaccharide was determined as follows:

The moles of sugar repeat unit are determined by various colorimetric methods, for example, by using the Anthrone method. By the Anthrone method, the polysaccharide is first broken down to monosaccharides by the action of sulfuric acid and heat. The Anthrone reagent reacts with the hexoses to form a yellow-green colored complex whose absorbance is read spectrophotometrically at 625 nm. Within the range of the assay, the absorbance is directly proportional to the amount of hexose present.

The moles of aldehyde are also determined simultaneously, using the MBTH colorimetric method. The MBTH assay involves the formation of an azine compound by reacting aldehyde groups (from a given sample) with a 3-methyl-2-benzothiazolone hydrazone (MBTH assay reagent). The excess 3-methyl-2-benzothiazolone hydrazone oxidizes to form a reactive cation. The reactive cation and the azine react to form a blue chromophore. The formed chromophore is then read spectroscopically at 650 nm.

Compounding Activated Polysaccharide with Sucrose Excipient, and Lyophilizing

The activated polysaccharide was compounded with sucrose to a ratio of 25 grams of sucrose per gram of activated polysaccharide. The bottle of compounded mixture was then lyophilized. Following lyophilization, bottles containing lyophilized activated polysaccharide were stored at −20±5° C. Calculated amount of CRM$_{197}$ protein was shell-frozen and lyophilized separately. Lyophilized CRM$_{197}$ was stored at −20±5° C.

Reconstituting Lyophilized Activated Polysaccharide and Carrier Protein

Lyophilized activated polysaccharide was reconstituted in anhydrous dimethyl sulfoxide (DMSO). Upon complete dissolution of polysaccharide, an equal amount of anhydrous DMSO was added to lyophilized CRM$_{197}$ for reconstitution.

Conjugating and Capping

Reconstituted activated polysaccharide was combined with reconstituted CRM$_{197}$ in the reaction vessel, followed by mixing thoroughly to obtain a clear solution before initiating the conjugation with sodium cyanoborohydride. The final polysaccharide concentration in reaction solution was approximately 1 g/L. Conjugation was initiated by adding 1.0-1.5 MEq of sodium cyanoborohydride to the reaction mixture and incubating at 23±2° C. for 20-48 hrs. The conjugation reaction was terminated by adding 2 MEq of sodium borohydride (NaBH$_4$) to cap unreacted aldehydes. This capping reaction continued at 23±2° C. for 3±1 hrs.

Purifying the Conjugate

The conjugate solution was diluted 1:10 with chilled 5 mM succinate-0.9% saline (pH 6.0) in preparation for purification by tangential flow filtration using 100-300K MWCO membranes.

The diluted conjugate solution was passed through a 5 μm filter, and diafiltration was performed using 5 mM succinate/0.9% saline (pH 6.0) as the medium. After the diafiltration was completed, the conjugate retentate was transferred through a 0.22 μm filter. The conjugate was diluted further with 5 mM succinate/0.9% saline (pH 6), to a target saccharide concentration of approximately 0.5 mg/mL. Alternatively, the conjugate is purified using 20 mM Histidine-0.9% saline (pH 6.5) by tangential flow filtration using 100-300K MWCO membranes. Final 0.22 μm filtration step was completed to obtain the immunogenic conjugate.

Example 4

Effects of Varying Conjugation Conditions on GBS Polysaccharide-CRM$_{197}$ Conjugates GBS serotypes Ia, Ib, II, III, IV and V conjugates were generated by deliberately varying periodate oxidation/reductive amination chemistry (PO/RAC) conditions, including the solvent for the reagent (aqueous medium versus DMSO), varying levels of sialic acid in the initial polysaccharide, and degree of oxidation/saccharide epitope modification. In general, the conjugates produced using DMSO as the solvent were found to have lower levels of unreacted (free) polysaccharide, higher conjugate molecular weight, and higher saccharide/protein ratios than conjugates produced using aqueous medium.

A conjugation process that produces conjugates with lower levels of unreacted (free) polysaccharide is advantageous and preferable. It is well known that high levels of unreacted (free) polysaccharide may cause an excessive T-cell independent immune response, which has the potential to dilute the T-cell dependent response generated by the polysaccharide-protein conjugate, thereby lowering the immunogenic response generated by the conjugate.

Selected GBS polysaccharides were chemically desialylated by methods known in the art (see Chaffin, D. O, et al., J Bacteriol 187(13):4615-4626 (2005)) to generate conjugate variants to determine the impact of % desialylation on immunogenicity. Desialylation of more than about 40% (i.e. sialic acid levels less than about 60%) had a negative impact on immunogenicity.

Similarly in most cases, a degree of oxidation of less than about 5, or saccharide epitope modification greater than about 20%, had a negative impact on immunogenicity. Since oxidation occurs through the sialic acid on the capsular polysaccharide, the results appear to indicate that saccharide epitope modification greater than about 20% reduces the sialic acid content, which results in reduced immunogenicity.

Conversely, conjugates having a variety of saccharide/protein ratio or polysaccharide molecular weight produced an immunogenic response in mice, indicating a relatively broad range of acceptance criteria with regard to these attributes.

Additional conjugate variants were also generated using alternative chemistry routes. One alternative chemistry included generating conjugates by reacting the polysaccharide with carbonylditriazole (CDT), and carrying out the conjugation reaction in DMSO. In another alternative chemistry, conjugates were generated by oxidation of the polysaccharide using TEMPO [(2,2,6,6-Tetramethylpiperidin-1-yl)oxyl] reagent (instead of sodium periodate) followed by conjugation using reductive amination chemistry (TEMPO/RAC) in DMSO, as detailed in Example 3 above. All conjugates generated by these alternative chemistries were demonstrated to be immunogenic in mice, indicating the suitability of alternative chemistry routes besides PO/RAC. However, some conjugation chemistries performed better with some serotypes than others.

OPAs were performed as per Nanra, J. S., et al., Hum. Vaccin. Immunother., 9(3):480-487 (2013), with the substitution of group B streptococcal isolates for *Staphylococcus aureus* isolates and omission of the preopsonization step. Post dose three (PD3) OPA titers are provided as a geomean from a group of 10-20 mice immunized with 1 mcg/ml in each dose of the respective conjugate.

GBS Serotype Ia Polysaccharide-CRM$_{197}$ Conjugates

Conjugates generated using PO/RAC and activated polysaccharides having a DO of 16-17 (approximately 6% saccharide epitope modification) were demonstrated to be immunogenic (Conjugates 1 and 3). However, using activated polysaccharides having a DO of 5.4 (approximately 19% saccharide epitope modification) had a negative impact on immunogenicity (Conjugate 2). Similarly, a sialic acid level of 50% produced almost no immunogenic response (Conjugate 4). Results are shown in Table 10.

TABLE 10

Effects of Varying Process Conditions of Periodate Oxidation/Reductive Amination Chemistry on GBS Serotype Ia-CRM$_{197}$ Conjugates

| Conjugate | 1 | 2 | 3 | 4 |
|---|---|---|---|---|
| Solvent | DMSO | DMSO | Aqueous | DMSO |
| Poly MW (kDa) | 190 | 190 | 190 | 190 |
| % Sialic Acid in initial polysaccharide | >95 | >95 | >95 | 50 |
| % Modification | 6 | 19 | 6 | 6 |
| Degree of Oxidation (DO) | 16.8 | 5.4 | 16.2 | 16.4 |
| Saccharide/Protein Ratio | 0.8 | 0.8 | 2.0 | 1.1 |
| % Free Saccharide | <5 | <5 | 26 | <5 |

TABLE 10-continued

Effects of Varying Process Conditions of Periodate Oxidation/Reductive Amination Chemistry on GBS Serotype Ia-CRM$_{197}$ Conjugates

| Conjugate | 1 | 2 | 3 | 4 |
|---|---|---|---|---|
| Conjugate MW by SEC-MALLS, kDa | 6040 | 15390 | 806 | 3763 |
| OPA Titer | 300 | 172 | 406 | 68 |

Additional conjugate variants were generated using alternative conjugation chemistries and conjugate molecular attributes (results are shown in Table 11). Conjugate 5 was generated by reacting the polysaccharide with carbonylditriazole (CDT), and the conjugation reaction was carried out in DMSO. Conjugate 6 was generated by oxidation of the polysaccharide using TEMPO reagent (instead of sodium periodate) followed by conjugation using reductive amination chemistry in DMSO, as detailed in Example 3 above. Conjugate 7 was generated by PO/RAC and deliberately varying the conjugation parameters to produce a conjugate with high saccharide/protein ratio (SPR). Conjugate 8 was generated by PO/RAC using a polysaccharide having a low MW (40 kDa). All these conjugates were demonstrated to be immunogenic in mice, indicating the suitability of alternative conjugation chemistries, besides periodate oxidation/reductive amination chemistry, as well as alternative conjugate attributes, such as SPR and low MW of the initial polysaccharide.

TABLE 11

Effects of Varying Process Conditions of Periodate Oxidation/Reductive Amination Chemistry and Alternative Chemistry Options on GBS Serotype Ia-CRM$_{197}$ Conjugates

| Conjugate | 5 | 6 | 7 | 8 |
|---|---|---|---|---|
| Conjugation Chemistry | CDT | TEMPO/RAC | PO/RAC | PO/RAC |
| Poly MW (kDa) | 383 | 220 | 383 | 40 |
| % Sialic Acid in initial polysaccharide | >95 | >95 | >95 | >95 |
| % Modification | N/A | 11 | 6 | 8 |
| Degree of Oxidation (DO) | N/A | 9.2 | 17.5 | 12 |
| Saccharide/Protein Ratio | 1.2 | 0.9 | 2.5 | 1 |
| % Free Saccharide | 12.5 | 11.2 | 13.3 | 24.3 |
| MW by SEC-MALLS, kDa | 7128 | 1678 | 4347 | 2000 |
| OPA Titer | 1028 | 371 | 303 | 1484 |

GBS Serotype Ib Polysaccharide-CRM$_{197}$ Conjugates

Conjugates generated using PO/RAC and activated polysaccharides having a DO of 15.8 (approximately 6% saccharide epitope modification) in DMSO was demonstrated to be immunogenic in mice (Conjugates 9 and 11). The conjugates generated by PO/RAC in DMSO was slightly more immunogenic than the conjugate generated by PO/RAC in the aqueous medium when all other conjugate molecular attributes were similar (Conjugates 9 and 11, respectively). However, using activated polysaccharides having a DO of 4.7 (approximately 21% saccharide epitope modification) had a negative impact on immunogenicity (Conjugate 10). Immunogenicity was almost completely abolished, with very few responders, in the conjugate generated using PO/RAC and a 95% desialylated (5% sialic acid level) polysaccharide (Conjugate 12). Results are shown in Table 12.

TABLE 12

Effects of Varying Process Conditions of Periodate oxidation/reductive Amination Chemistry on GBS Serotype Ib-CRM$_{197}$ Conjugates

| Conjugate | 9 | 10 | 11 | 12 |
|---|---|---|---|---|
| Solvent | DMSO | DMSO | Aqueous | DMSO |
| Poly MW (kDa) | 120 | 120 | 120 | 120 |
| % Sialic Acid in initial polysaccharide | >95 | >95 | >95 | 5 |
| % Modification | 6 | 21 | 6 | 9 |
| Degree of Oxidation (DO) | 15.8 | 4.7 | 15.8 | 11.7 |
| Saccharide/Protein Ratio | 1.1 | 1 | 2 | 1.1 |
| % Free Saccharide | 11 | <5 | 33 | 7 |
| MW by SEC-MALLS, kDa | 2608 | 7302 | 381 | 8418 |
| OPA Titer | 417 | 159 | 278 | 62 |

Additional conjugate variants were generated using alternative conjugation chemistries and conjugate molecular attributes (results are shown in Table 13). Conjugate 13 was generated by PO/RAC using a polysaccharide having a low sialylation (65%) in the initial polysaccharide. Conjugate 14 was generated by PO/RAC and deliberately varying the conjugation parameters to produce a conjugate with high saccharide/protein ratio (SPR). Conjugate 15 was generated by reacting the polysaccharide with carbonylditriazole (CDT), and the conjugation reaction was carried out in DMSO. Conjugate 16 was generated by oxidation of the polysaccharide using TEMPO reagent (instead of sodium periodate) followed by conjugation using reductive amination chemistry in DMSO, as detailed in Example 3 above. All these conjugates were demonstrated to be immunogenic in mice indicating the suitability of alternative conjugation chemistries, besides periodate oxidation/reductive amination chemistry, as well as alternative conjugate attributes such as SPR and low MW of the initial polysaccharide.

TABLE 13

Effects of Varying Process Conditions of Periodate Oxidation/Reductive Amination Chemistry and Alternative Chemistry Options for GBS Serotype Ib-CRM$_{197}$ Conjugates

| Conjugate | 13 | 14 | 15 | 16 |
|---|---|---|---|---|
| Conjugation Chemistry | PO/RAC | PO/RAC | CDT | TEMPO/RAC |
| Poly MW (kDa) | 141 | 141 | 141 | 150 |
| % Sialic Acid in initial polysaccharide | 65 | >95 | >95 | >95 |
| % Modification | 8 | 7 | N/A | 13 |
| Degree of Oxidation (DO) | 12 | 14.7 | N/A | 7.8 |
| Saccharide/Protein Ratio | 1.06 | 2.1 | 1.29 | 0.85 |
| % Free Saccharide | <5% | 16% | 21 | 7 |
| MW by SEC-MALLS, kDa | 5345 | 1594 | 2760 | 1400 |
| OPA Titer | 246 | 118 | 287 | 548 |

GBS Serotype II Polysaccharide-CRM$_{197}$ Conjugates

Conjugates generated using PO/RAC and activated polysaccharides having a DO of 4-15 (approximately 7-23% saccharide epitope modification) were demonstrated to be immunogenic in mice (Conjugates 17-20). The conjugate generated using PO/RAC and a polysaccharide with 74% sialylation level (26% desialylated) was also demonstrated to be immunogenic (Conjugate 20). Results are shown in Table 14.

TABLE 14

Effects of Varying Process Conditions of Periodate oxidation/reductive Amination Chemistry on GBS Serotype II-CRM$_{197}$ Conjugates

| Conjugate | 17 | 18 | 19 | 20 |
|---|---|---|---|---|
| Solvent | DMSO | DMSO | Aqueous | DMSO |
| Poly MW (kDa) | 95 | 95 | 109 | 109 |
| % Sialic Acid in initial polysaccharide | >95 | >95 | >95 | 74 |
| % Modification | 8 | 23 | 10 | 7 |
| Degree of Oxidation (DO) | 12.6 | 4.3 | 9.8 | 15.2 |
| Saccharide/Protein Ratio | 0.84 | 0.90 | 1.13 | 0.63 |
| % Free Saccharide | 16 | <5 | 6 | <5 |
| MW by SEC-MALLS, kDa | 3600 | 4650 | 1611 | 6140 |
| OPA Titer | 610 | 967 | 2149 | 684 |

Additional conjugate variants were generated using alternative conjugation chemistries and conjugate molecular attributes (results are shown in Table 15). Conjugates 21 and 22 were generated by PO/RAC and deliberately varying the conjugation parameters to produce conjugates with low and high saccharide/protein ratios (SPR), respectively. Conjugate 23 was generated by oxidation of the polysaccharide using TEMPO reagent (instead of sodium periodate) followed by conjugation using reductive amination chemistry in DMSO, as detailed in Example 3 above. Conjugate 24 was generated by reacting the polysaccharide with carbonyldiimidazole (CDT), and the conjugation reaction was carried out in DMSO. All these conjugates were demonstrated to be immunogenic in mice indicating the suitability of alternative conjugation chemistries, besides periodate oxidation/reductive amination chemistry, as well as alternative conjugate attributes such as SPR.

TABLE 15

Effects of Varying Process Conditions of Periodate Oxidation/Reductive Amination Chemistry and Alternative Chemistry Options for GBS Serotype II-CRM$_{197}$ Conjugates

| Conjugate | 21 | 22 | 23 | 24 |
|---|---|---|---|---|
| Conjugation Chemistry | PO/RAC | PO/RAC | TEMPO/RAC | CDT |
| Poly MW (kDa) | 109 | 109 | 109 | 109 |
| % Sialic Acid in initial polysaccharide | >95 | >95 | >95 | >95 |
| % Modification | 10 | 10 | 11 | N/A |
| Degree of Oxidation (DO) | 10 | 10 | 8.8 | N/A |
| Saccharide/Protein Ratio | 0.61 | 2.03 | 0.66 | 0.87 |
| % Free Saccharide | <5 | 25 | <5% | 12 |
| MW by SEC-MALLS, kDa | 8850 | 1480 | 5270 | 603 |
| OPA Titer | 3117 | 891 | 2167 | 631 |

GBS Serotype III Polysaccharide-CRM$_{197}$ Conjugates

Conjugates generated using PO/RAC and activated polysaccharides having a DO of 10-17 (approximately 6-10% saccharide epitope modification) in DMSO were demonstrated to be immunogenic in mice (Conjugates 25 and 30). The conjugates having a DO of 2.9 (approximately 34% saccharide epitope modification) or a high saccharide/protein ratio (2.1) (Conjugates 26 and 27, respectively) were demonstrated to be relatively less immunogenic. The conjugate generated using PO/RAC and a polysaccharide with 81% sialylation level (19% desialylated) was demonstrated to be immunogenic (Conjugate 30). However, the conjugate generated using polysaccharide with 58% sialylation level (42% desialylated) was demonstrated to be poorly immunogenic (Conjugate 29). The conjugate generated by PO/RAC in DMSO was slightly more immunogenic than the conjugate generated by PO/RAC in the aqueous medium when all other conjugate molecular attributes were similar (Conjugates 25 and 28, respectively). Results are shown in Table 16.

TABLE 16

Effects of Varying Process Conditions of Periodate Oxidation/Reductive Amination Chemistry on GBS Serotype III-CRM$_{197}$ Conjugates

| Conjugate | 25 | 26 | 27 | 28 | 29 | 30 |
|---|---|---|---|---|---|---|
| Solvent | DMSO | DMSO | DMSO | Aqueous | DMSO | DMSO |
| Poly MW (kDa) | 263 | 358 | 358 | 358 | 355 | 358 |
| % Sialic Acid in initial polysaccharide | >95 | >95 | >95 | >95 | 58 | 81 |
| % Modification | 10 | 34 | 6 | 8 | 6 | 6 |
| Degree of Oxidation (DO) | 10 | 2.9 | 17 | 13 | 16 | 17 |
| Saccharide/Protein Ratio | 1.1 | 1.2 | 2.1 | 1.7 | 1.15 | 1.19 |
| % Free Saccharide | 10 | 7 | 24 | 19 | <5 | <5 |
| MW by SEC-MALLS, kDa | 2396 | 14340 | 3066 | 1885 | 5110 | 4643 |
| OPA Titer | 701 | 57 | 252 | 248 | 137 | 505 |

Additional conjugate variants were generated using alternative conjugation chemistries and conjugate molecular attributes (results are shown in Table 17). Conjugates 31-35 were generated by PO/RAC and deliberately varying the conjugation parameters to produce conjugates with varying MW. Conjugate 36 was generated by reacting the polysaccharide with carbonylditriazole (CDT) and the conjugation reaction was carried out in DMSO. Conjugate 37 was generated by oxidation of the polysaccharide using TEMPO reagent (instead of sodium periodate) followed by conjugation using reductive amination chemistry in DMSO, as detailed in Example 3 above. All these conjugates were demonstrated to be immunogenic in mice indicating the suitability of alternative conjugation chemistries, besides periodate oxidation/reductive amination chemistry, as well as alternative conjugate attributes such as MW. Conjugates generated with a DO as low as 5 (approximately 20% saccharide epitope modification) were still immunogenic in mice (Conjugate 32 in Table 17) compared to the conjugates generated with a DO of 2.9 (approximately 34% saccharide epitope modification) (Conjugate 26 in Table 16 above).

TABLE 17

Effects of Varying Process Conditions of Periodate Oxidation/Reductive Amination Chemistry and Alternative Chemistry Options for GBS Serotype III-CRM$_{197}$ Conjugates

| Conjugate | 31 | 32 | 33 | 34 | 35 | 36 | 37 |
|---|---|---|---|---|---|---|---|
| Conjugation Chemistry | PO/RAC | PO/RAC | PO/RAC | PO/RAC | PO/RAC | CDT | TEMPO/RAC |
| Poly MW (kDa) | 353 | 350 | 355 | 50 | 349 | 355 | 355 |
| % Sialic Acid in initial polysaccharide | >95 | >95 | >95 | >95 | >95 | >95 | >95 |
| % Modification | 6 | 5 | 6 | 8 | 20 | N/A | 10 |
| Degree of Oxidation (DO) | 17 | 19 | 17 | 12 | 5 | N/A | 10 |
| Saccharide/Protein Ratio | 0.8 | 1.1 | 1.2 | 0.9 | 1.0 | 1.16 | 0.96 |
| % Free Saccharide | <5 | <5 | <5 | 20 | <5 | <5 | <5 |
| MW by SEC-MALLS. kDa | 9278 | 5291 | 4982 | 1201 | 8024 | 10740 | 3415 |
| OPA Titer | 646 | 204 | 176 | 441 | 1116 | 448 | 336 |

GBS Serotype IV Polysaccharide-CRM$_{197}$ Conjugates

Conjugates generated using PO/RAC and activated polysaccharides having a DO of 6.9-14.2 (approximately 7-14% saccharide epitope modification) were demonstrated to be immunogenic in mice (Conjugates 38-41). The conjugate generated using PO/RAC and a polysaccharide with 60% sialylation level (40% desialylated) was also demonstrated to be immunogenic (Conjugate 41). Results are shown in Table 18.

TABLE 18

Effects of Varying Process Conditions of Periodate Oxidation/Reductive Amination Chemistry on GBS Serotype IV-CRM$_{197}$ Conjugates

| Conjugate | 38 | 39 | 40 | 41 |
|---|---|---|---|---|
| Solvent | DMSO | DMSO | Aqueous | DMSO |
| Poly MW (kDa) | 143 | 143 | 133 | 121 |
| % Sialic Acid in initial polysaccharide | >95 | >95 | >95 | 60 |
| % Modification | 7 | 14 | 7 | 8 |
| Degree of Oxidation (DO) | 14.2 | 6.9 | 13.6 | 13.2 |

TABLE 18-continued

Effects of Varying Process Conditions of Periodate Oxidation/Reductive Amination Chemistry on GBS Serotype IV-CRM$_{197}$ Conjugates

| Conjugate | 38 | 39 | 40 | 41 |
|---|---|---|---|---|
| Saccharide/Protein Ratio | 0.80 | 0.91 | 1.92 | 1.0 |
| % Free Saccharide | <5 | <5 | 33.4 | <5 |
| MW by SEC-MALLS. kDa | 8268 | 10210 | 657 | 5691 |
| OPA Titer | 3140 | 2379 | 3080 | 6708 |

Additional conjugate variants were generated using alternative conjugation chemistries and conjugate molecular attributes. Results are shown in Table 19. Conjugates 42 and 45 were generated by PO/RAC and deliberately varying the conjugation parameters to produce conjugates with high DO (lower oxidation level) and high SPR respectively. Conjugate 43 was generated by reacting the polysaccharide with carbonylditriazole (CDT), and the conjugation reaction was carried out in DMSO. Conjugate 44 was generated by oxidation of the polysaccharide using TEMPO reagent (instead of sodium periodate) followed by conjugation using reductive amination chemistry in DMSO, as detailed in Example 3 above. All the Serotype IV conjugates were demonstrated to be immunogenic in mice, indicating the suitability of alternative conjugation chemistries, besides periodate oxidation/reductive amination chemistry, as well as conjugate attributes such as SPR. Conjugates generated with a DO (lower oxidation) up to at least 20 (approximately 5% saccharide epitope modification) were still immunogenic in mice.

TABLE 19

Effects of Varying Process Conditions of Periodate Oxidation/Reductive Amination Chemistry and Alternative Chemistry Options on GBS Serotype IV-CRM$_{197}$ Conjugates

| Conjugate | 42 | 43 | 44 | 45 |
|---|---|---|---|---|
| Conjugation Chemistry | PO/RAC | CDT | TEMPO | PO/RAC |
| Poly MW (kDa) | 143 | 133 | 133 | 140 |

TABLE 19-continued

Effects of Varying Process Conditions of Periodate Oxidation/Reductive Amination Chemistry and Alternative Chemistry Options on GBS Serotype IV-CRM$_{197}$ Conjugates

| Conjugate | 42 | 43 | 44 | 45 |
|---|---|---|---|---|
| % Sialic Acid in initial polysaccharide | >95 | >95 | >95 | >95 |
| % Modification | 5 | N/A | 7 | 7 |
| Degree of Oxidation (DO) | 20 | N/A | 13.7 | 14.6 |
| Saccharide/Protein Ratio | 1.0 | 0.9 | 0.52 | 1.96 |
| % Free Saccharide | <5 | <5 | 6 | <5 |
| MW by SEC-MALLS. kDa | 3580 | 12390 | 4580 | 2710 |
| OPA Titer | 8614 | 1989 | 7567 | 3695 |

GBS Serotype V Polysaccharide-CRM$_{197}$ Conjugates

Conjugates generated using PO/RAC and activated polysaccharides having a DO of 4.4-14.6 (approximately 7-23% saccharide epitope modification) were demonstrated to be immunogenic in mice (Conjugates 46 and 47). The desialylated (5% sialylation level) conjugate was not immunogenic (Conjugate 49), and the conjugate generated using a PO/RAC process using an aqueous solvent produced a low immune response (Conjugate 48). Results are shown in Table 20.

TABLE 20

Effects of Varying Process Conditions of Periodate Oxidation/Reductive Amination Chemistry on GBS Serotype V-CRM$_{197}$ Conjugates

| Conjugate | 46 | 47 | 48 | 49 |
|---|---|---|---|---|
| Solvent | DMSO | DMSO | Aqueous | DMSO |
| Poly MW (kDa) | 132 | 132 | 132 | 132 |
| % Sialic Acid in initial polysaccharide | >95% | >95% | >95% | 5% |
| % Modification | 7 | 23 | 8 | 6 |
| Degree of Oxidation (DO) | 14.6 | 4.4 | 12.1 | 18 |
| Saccharide/Protein Ratio | 1.32 | 1.43 | 1.27 | 0.94 |
| % Free Saccharide | 11 | <5 | 25.4 | <5 |
| MW by SEC-MALLS. kDa | 4304 | 14510 | 573 | 4847 |
| OPA Titer | 335 | 181 | 93 | 60 |

Additional conjugate variants were generated using alternative conjugation chemistries and conjugate molecular attributes. Results are shown in Table 21. Conjugates 50 and 53 were generated by PO/RAC and deliberately varying the conjugation parameters to produce conjugates with lower sialylation level 81% sialylation) and low MW respectively. Conjugate 51 was generated by reacting the polysaccharide with carbonylditriazole (CDT), and the conjugation reaction was carried out in DMSO. Conjugate 52 was generated by oxidation of the polysaccharide using TEMPO reagent (instead of sodium periodate) followed by conjugation using reductive amination chemistry in DMSO, as detailed in Example 3 above. All the Serotype V conjugates, except the conjugate generated using CDT chemistry, were demonstrated to be immunogenic in mice, indicating the suitability of alternative conjugation chemistries, besides periodate oxidation/reductive amination chemistry, as well as conjugate attributes, such as MW. The conjugate generated using the CDT chemistry was shown be significantly less immunogenic compared to other conjugates generated by RAC. The conjugate with 81% sialylation (Conjugate 50) provided a lower immune response compared to the conjugate with >95% sialylation (Conjugate 53), but higher than the conjugate with 5% sialylation (Conjugate 49 in Table 20 above).

TABLE 21

Effects of Varying Process Conditions of Periodate Oxidation/Reductive Amination Chemistry and Alternative Chemistry Options on GBS Serotype V-CRM$_{197}$ Conjugates

| Conjugate | 50 | 51 | 52 | 53 |
|---|---|---|---|---|
| Conjugation Chemistry | PO/RAC | CDT | TEMPO | PO/RAC |
| Poly MW (kDa) | 159 | 193 | 193 | 37 |
| % Sialic Acid in initial polysaccharide | >81% | >95% | >95% | >95% |
| % Modification | 7 | N/A | 5 | 10 |
| Degree of Oxidation (DO) | 13.5 | N/A | 18.2 | 10.3 |
| Saccharide/Protein Ratio | 1.2 | 1.14 | 0.71 | 0.53 |
| % Free Saccharide | <5 | <5 | 22.3 | 7.3 |
| MW by SEC-MALLS. kDa | 3037 | 4756 | 3501 | 3044 |
| OPA Titer | 160.3 | 101 | 320 | 279 |

Example 5

GBS III-CRM$_{197}$ and GBS V-CRM$_{197}$ Monovalent Conjugate Vaccines Produced OPA Response in Mice Female CD-1 mice were immunized with 1 mcg, 0.1 mcg or 0.01 mcg of group B streptococcus (GBS) serotype III conjugated to CRM$_{197}$ (GBS III-CRM$_{197}$) or GBS serotype V conjugated to CRM$_{197}$ (GBS V-CRM$_{197}$) three times subcutaneously on weeks 0, 3, and 6. Post dose three (PD3) sera were evaluated by opsonophagocytic assay (OPA). OPAs were performed as described in Example 4. Both conjugates induced OPA responses in mice (Table 22). Samples without a detectable OPA response were assigned a value of 50.

TABLE 22

GBS III and GBS V Conjugates Induce OPA Responses in Mice

| Conjugate type | Dose (mcg) | Geomean OPA Titer |
|---|---|---|
| III | 1 | 701 |
|  | 0.1 | 103 |
|  | 0.01 | 50 |
| V | 1 | 378 |
|  | 0.1 | 204 |

Example 6

GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$ Monovalent Conjugate Vaccines Produced OPA Response in Mice Six sets of female CD-1 mice were immunized three times subcutaneously with a vaccine containing 1 mcg of an individual GBS capsular polysaccharide (CP) conjugated to CRM$_{197}$ on weeks 0, 3 and 6. Initial studies had shown that mice do not have pre-existing OPA titers to any of the six serotypes tested. Sera from PD3 were analyzed by OPA against the cognate GBS serotype contained in the vaccine. OPAs were performed as described in Example 4. Results are shown in Tables 23 and 24 below.

TABLE 23

Geomean OPA Titers of Mice After Immunization with Individual GBS CPS-CRM$_{197}$ Conjugates

| Serotype | Geomean OPA Titer |
|---|---|
| Ia | 300 |
| Ib | 417 |
| II | 610 |
| III | 188 |
| IV | 3140 |
| V | 378 |

TABLE 24

Fold Rise OPA Titers of Mice After Immunization with Individual GBS CPS-CRM$_{197}$ Conjugates

| Serotype | Geomean OPA Titer |
|---|---|
| Ia | 6 |
| Ib | 8 |
| II | 12 |
| III | 4 |
| IV | 63 |
| V | 8 |

NB: Fold rise is calculated assuming mice did not have pre-existing titer.

Example 7

Opsonic Activity of Sera Compared to Isolated IgG from Mice Immunized with GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$ Monovalent Conjugate Vaccines Female CD-1 or BALB/c mice were immunized with 1 mcg of an individual GBS CPs conjugated to CRM$_{197}$ three times subcutaneously on weeks 0, 3 and 6. Either AlPO$_4$ or QS-21 was used as an adjuvant. PD3 sera were tested by serotype-specific OPA and then the immunoglobulin G fraction was isolated and tested for OPA activity. Purified IgG OPA activity was normalized to 5 mg/ml (in the range of the amount of IgG in normal mouse serum). All six GBS CPS conjugates induced IgG antibodies with opsonic activity (FIG. 1).

Example 8

GBS Ia-TT, GBS Ib-TT, GBS II-TT, GBS III-TT, GBS IV-TT and GBS V-TT, Monovalent Conjugate Vaccines Produced OPA Response in Rabbits Rabbits were immunized three times with 50 mcg/ml GBS serotype Ia polysaccharide conjugated to tetanus toxoid, 10 mcg/ml GBS serotype Ib polysaccharide conjugated to tetanus toxoid, 50 mcg/ml GBS serotype II polysaccharide conjugates to tetanus toxoid, 50 mcg/ml GBS serotype III polysaccharide conjugated to tetanus toxoid, 50 mcg/ml GBS serotype IV polysaccharide conjugated to tetanus toxoid, or 50 mcg/ml GBS serotype V polysaccharide conjugated to tetanus toxoid adjuvanted with Complete Freund's Adjuvant in the first dose and Incomplete Freund's Adjuvant in the second and third doses. The conjugates were produced using polysaccharides having a sialic acid level of >95% and CDAP (1-cyano-4-dimethylamino pyridinium tetrafluoroborate) chemistry. PD3 immune responses were measured by OPA as described in Example 4. Sera titers are shown in Table 25 while purified IgG titers are shown in Table 26 below. GBS serotype Ia, Ib, II, III, IV, and V polysaccharides conjugated to TT were highly immunogenic in rabbits.

TABLE 25

Geomean OPA Titers of Rabbit Sera After Immunization with Individual GBS CPS-TT Conjugates

| GBS Serotype | Geomean OPA Titer |
|---|---|
| Ib | 11550 |
| II | 36753 |
| IV | 34345 |

TABLE 26

Geomean OPA Titers of Purified Rabbit IgG After Immunization with Individual GBS CPS-TT Conjugates

| GBS Serotype | Geomean OPA Titer (1 mg/ml pAb) |
|---|---|
| Ia | 7190 |
| Ib | 2817 |
| II | 41870 |
| III | 40146 |
| IV | 15565 |
| V | 12124 |

Example 9

Hexavalent GBS Conjugate Vaccine Produced OPA Response in Nonhuman Primates

Three groups of rhesus macaques were immunized with a hexavalent group B streptococcus (GBS6) vaccine three times intramuscularly on weeks 0, 4 and 8. The GBS6 vaccine comprised GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$. Two groups included aluminum phosphate (AlPO$_4$) as an adjuvant and were dosed with either 5 mcg of each conjugate or 50 mcg of each conjugate. The third group was dosed with 5 mcg of each conjugate and did not contain and adjuvant. Table 27 below describes the immunization schedule.

TABLE 27

Immunization schedule of rhesus macaques

| Group | No. of NHP | Vaccine Dose (Each Conjugate) | Alum as AlPO4 (mg/mL) | Vaccination volume | Delivery | Immunization Schedule (Weeks) |
|---|---|---|---|---|---|---|
| 1 | 10 | 5 µg | 0.5 | 1.0 mL | IM | 0, 4, 8 |
| 2 | 10 | 50 µg | 0.5 | 1.0 mL | IM | 0, 4, 8 |
| 3 | 10 | 5 µg | None | 1.0 mL | IM | 0, 4, 8 |

Preimmune serum and serum from PD3 were analyzed by OPA for all six GBS serotypes contained in the vaccine.

OPAs were performed as described in Example 4. Results are shown in Tables 28 and 29 below. For all six serotypes, AlPO$_4$ adjuvanted formulas elicited a detectable OPA response (increase in titer from pre to PD3, or fold rise pre/PD3>1). The non-adjuvanted 5 mcg/conjugate dose elicited detectable OPA responses for five of six serotypes.

TABLE 28

Geomean OPA titers of rhesus macaques before and after immunization with GBS6

| Serotype | 5 mcg + AlPO$_4$ | | 50 mcg + AlPO$_4$ | | 5 mcg No adjuvant | |
|---|---|---|---|---|---|---|
| | Pre | PD3 | Pre | PD3 | Pre | PD3 |
| Ia | 97 | 2907 | 118 | 8106 | 166 | 69 |
| Ib | 53 | 3821 | 53 | 2957 | 50 | 313 |
| II | 54 | 980 | 62 | 764 | 61 | 362 |
| III | 105 | 7759 | 204 | 8448 | 762 | 4515 |
| IV | 78 | 2350 | 89 | 3331 | 309 | 899 |
| V | 233 | 5556 | 442 | 16476 | 6192 | 4226 |

TABLE 29

OPA titer fold rise of rhesus macaques after immunization with GBS6

| Serotype | 5 mcg + AlPO$_4$ | 50 mcg + AlPO$_4$ | 5 mcg No adjuvant |
|---|---|---|---|
| Ia | 30 | 69 | 4 |
| Ib | 72 | 56 | 6 |
| II | 18 | 12 | 6 |
| III | 74 | 41 | 6 |
| IV | 30 | 37 | 3 |
| V | 24 | 37 | 1 |

Example 10

Hexavalent GBS Conjugate Vaccine Produced OPA Response in Rats

Female Sprague-Dawley rats were immunized twice subcutaneously with 5 mcg/ml of each conjugate in the GBS6 polysaccharide conjugate vaccine as described in Example 9 formulated either with or without aluminum phosphate (AlPO$_4$). Preimmune (baseline) and post-dose two sera was evaluated for OPA assay titer against all six cognate GBS serotypes. OPA titers were measured for each serotype in the GBS 384 well assay format and fold rises were calculated. Rats administered the GBS6 vaccine had a robust functional antibody response against each serotype after the second dose; in the absence of AlPO$_4$, a 7 to 205-fold increase among the serotypes was seen, whereas in its presence this ranged from 11 to 294-fold (Table 30).

TABLE 30

Post-Dose 2 (PD2) Fold Rise in Opsonophagocytic Activity (OPA) Assay Titers in Rats Immunized with a Hexavalent GBS Conjugate Vaccine

| GBS Serotype | Fold Rise in Geomean OPA Titer from Preimmune to PD2 | |
|---|---|---|
| | Without AlPO$_4$ | With AlPO$_4$ |
| Ia | 36 | 11 |
| Ib | 7 | 39 |
| II | 205 | 294 |
| III | 107 | 141 |

TABLE 30-continued

Post-Dose 2 (PD2) Fold Rise in Opsonophagocytic Activity (OPA) Assay Titers in Rats Immunized with a Hexavalent GBS Conjugate Vaccine

| GBS Serotype | Fold Rise in Geomean OPA Titer from Preimmune to PD2 | |
|---|---|---|
| | Without AlPO$_4$ | With AlPO$_4$ |
| IV | 45 | 33 |
| V | 185 | 195 |

Example 11

Immunization of Pregnant Dams with a Monovalent or Hexavalent GBS Glycoconjugate Vaccine Showed Protective Effect from GBS III or V Infection in their Offspring after Birth Female CD-1 mice were immunized three times subcutaneously with the GBS6 vaccine as described in Example 9 containing 5 mcg/ml of each conjugate and 100 mcg/ml AlPO$_4$, a GBS III or V monovalent glycoconjugate vaccine (each containing 10 mcg/ml of the conjugate and 100 mcg/ml AlPO$_4$), or vehicle control alone. Mice were bred prior to the third immunization. Offspring of immunized mice were challenged with a lethal dose of either GBS serotype III or GBS serotype V bacteria in accordance with the vaccine received, and survival was monitored for 90 hours. Immunization of dams with GBS6+AlPO$_4$ or GBS III-CRM197+AlPO$_4$ provided significant protection (p<0.0001) for their pups against lethal GBS serotype III challenge. Likewise, immunization of dams with GBS V-CRM197+AlPO4 provided significant protection (p<0.0001) for their pups against lethal GBS serotype V challenge. Results are shown in Table 31.

TABLE 31

Immunization with Monovalent and Hexavalent GBS Vaccine Increased Survival in Offspring

| | # Surviving Offspring/Total Offspring (% Survival) | | |
|---|---|---|---|
| Serotype Challenge | Offspring of GBS6 Immunized Dam | Offspring of Cognate Monovalent Immunized Dam | Offspring of Vehicle Immunized Dam |
| III | 20/22 (91%) | 28/28 (100%) | 9/29 (31%) |
| V | | 35/40 (85%) | 3/27 (11%) |

Example 12

Passive Immunization of GBS III Monoclonal Antibodies in Infant Rats Showed Protective Effect Group B streptococcus serotype III (GBS III) monoclonal antibodies (mAb) were generated by immunizing mice with a pentavalent vaccine comprising serotypes Ia, Ib, II, III, and V. The GBS III-specific mAb clones were selected, and mAb recognizing CPs of GBS III were generated using standard procedures. GBS serotype III mAb was passively administered to infant rats (n=10 per group; 2 independent experiments shown) 16 hours before challenge with a clinical GBS III isolate. Four hours after challenge blood was harvested and remaining CFU enumerated. Treatment with a GBS III mAb reduced recovered CFU in infant rats by 4 logs or greater (Table 32).

TABLE 32

GBS III mAb Reduced Recovered CFU in Infant Rats

| | Treatment | Recovered CFU (log) |
|---|---|---|
| Experiment 1 | GBS III mAb | 1.8 |
| | Control | 7.5 |
| Experiment 2 | GBS III mAb | 2.4 |
| | Control | 6.4 |

Example 13

Passive Immunization of GBS Ib, III, & V Monoclonal Antibodies in Pregnant Mice Showed Protective Effect in Their Offspring after Birth Monoclonal antibodies (mAb) were generated from mice immunized with a pentavalent vaccine (GBS Ia-CRM$_{197}$, GBS Ib-CRM$_{197}$, GBS II-CRM$_{197}$, GBS III-CRM$_{197}$, and GBS V-CRM$_{197}$) using standard procedures. The mAbs were then identified as specifically recognizing capsular polysaccharides of each of the five serotypes. 500 mcg/ml doses of the GBS serotype Ib (GBS Ib) mAb, the GBS serotype III (GBS III) mAb, the GBS serotype V (GBS V) mAb, or an isotype-matched control mAb was passively administered to pregnant mice approximately 24 to 48 hours before delivery. Twenty-four to 48 hours after birth, the offspring of the immunized murine dams were challenged with a lethal dose of GBS Ib, GBS III, or GBS V bacteria. Survival was monitored for 96 hours. Significantly higher survival was seen in pups born to dams immunized with the GBS Ib mAb, the GBS III mAb, or the GBS V mAb compared to the control mAb after GBS challenge (Table 33).

TABLE 33

GBS III & V mAb Increased Survival in Offspring

| | % Survival of Pups Born to Dams Passively Immunized with: | |
|---|---|---|
| GBS Challenge Serotype | Cognate mAb | Control mAb |
| Ib | 80 | 0 |
| III | 93 | 0 |
| V | 100 | 12 |

Example 14

Stability of GBS Conjugates

GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$ were individually formulated in 10 mM succinate-phosphate and 155 mM NaCl at varying pH levels to test the stability of the conjugates in accelerated storage conditions. Percent change in molecular weight, as determined by SEC MALLS, was measured after 4 weeks of storage at 50° C. Results are shown in FIGS. 2-7.

Figure 8:
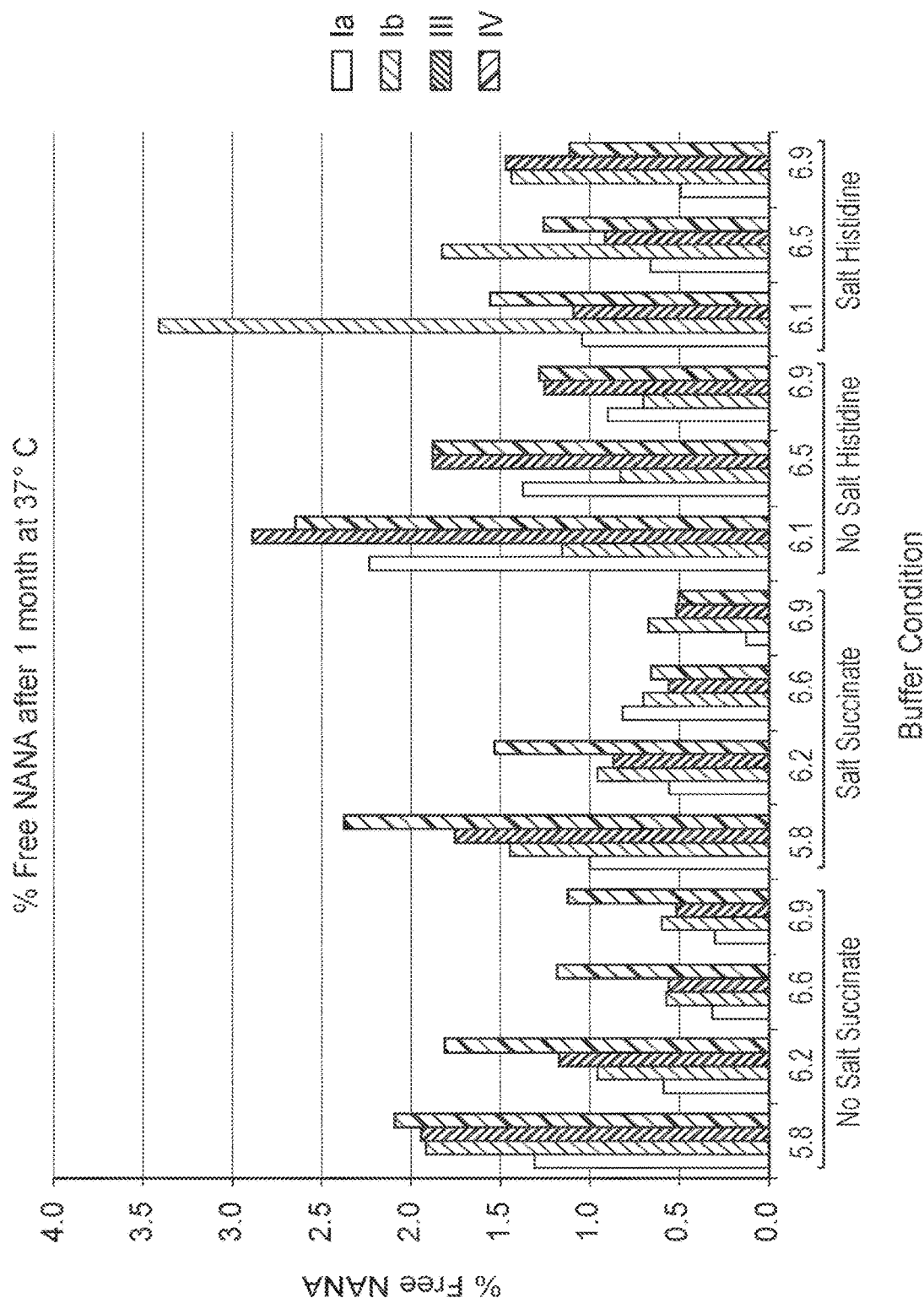
FIG. 8: Stability of GBS Ia-CRM$_{197}$, GBS Ib-CRM$_{197}$, GBS III-CRM$_{197}$, and GBS IV-CRM$_{197}$, (as shown by free sialic acid) following storage at 37° C.

The GBS Ia-CRM$_{197}$, GBS Ib-CRM$_{197}$, GBS III-CRM$_{197}$, and GBS IV-CRM$_{197}$ conjugates were tested for stability of sialylation under various buffer conditions shown in Table 34. Free sialic acid (N acetyl neuraminic acid; NANA) was measured using HPLC after 1 month of storage at 37° C. Results are shown in FIG. 8.

Both studies suggested that the conjugates performed better at a pH above 6.0, and optimally at about pH 6.5.

TABLE 34

Buffer Conditions for Sialylation Stability Testing

| pH | Salt | Salt Conc. (mM) | Buffer | Buffer Conc. (mM) |
|---|---|---|---|---|
| 5.8 | None | 0 | Succinate | 10 |
| 6.2 | None | 0 | Succinate | 10 |
| 6.6 | None | 0 | Succinate | 10 |
| 6.9 | None | 0 | Succinate | 10 |
| 5.8 | NaCl | 150 | Succinate | 10 |
| 6.3 | NaCl | 150 | Succinate | 10 |
| 6.6 | NaCl | 150 | Succinate | 10 |
| 6.9 | NaCl | 150 | Succinate | 10 |
| 6.1 | None | 0 | Histidine | 10 |
| 6.5 | None | 0 | Histidine | 10 |
| 6.9 | None | 0 | Histidine | 10 |
| 6.1 | NaCl | 150 | Histidine | 10 |
| 6.5 | NaCl | 150 | Histidine | 10 |
| 6.9 | NaCl | 150 | Histidine | 10 |

Example 15

GBS6 Formulation

Figure 9:
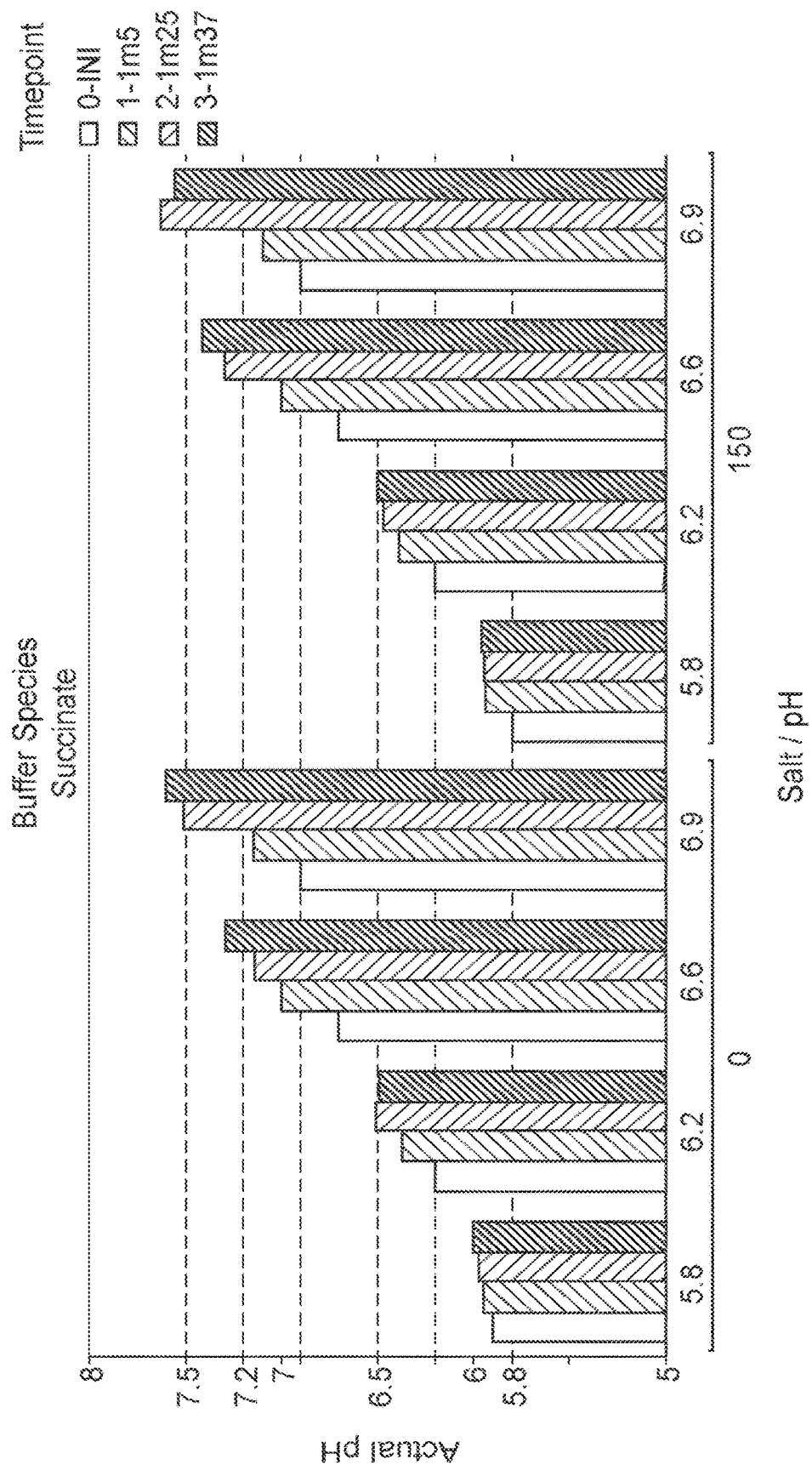
FIG. 9: Stability of pH in hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) using succinate as the buffer.
Figure 10:
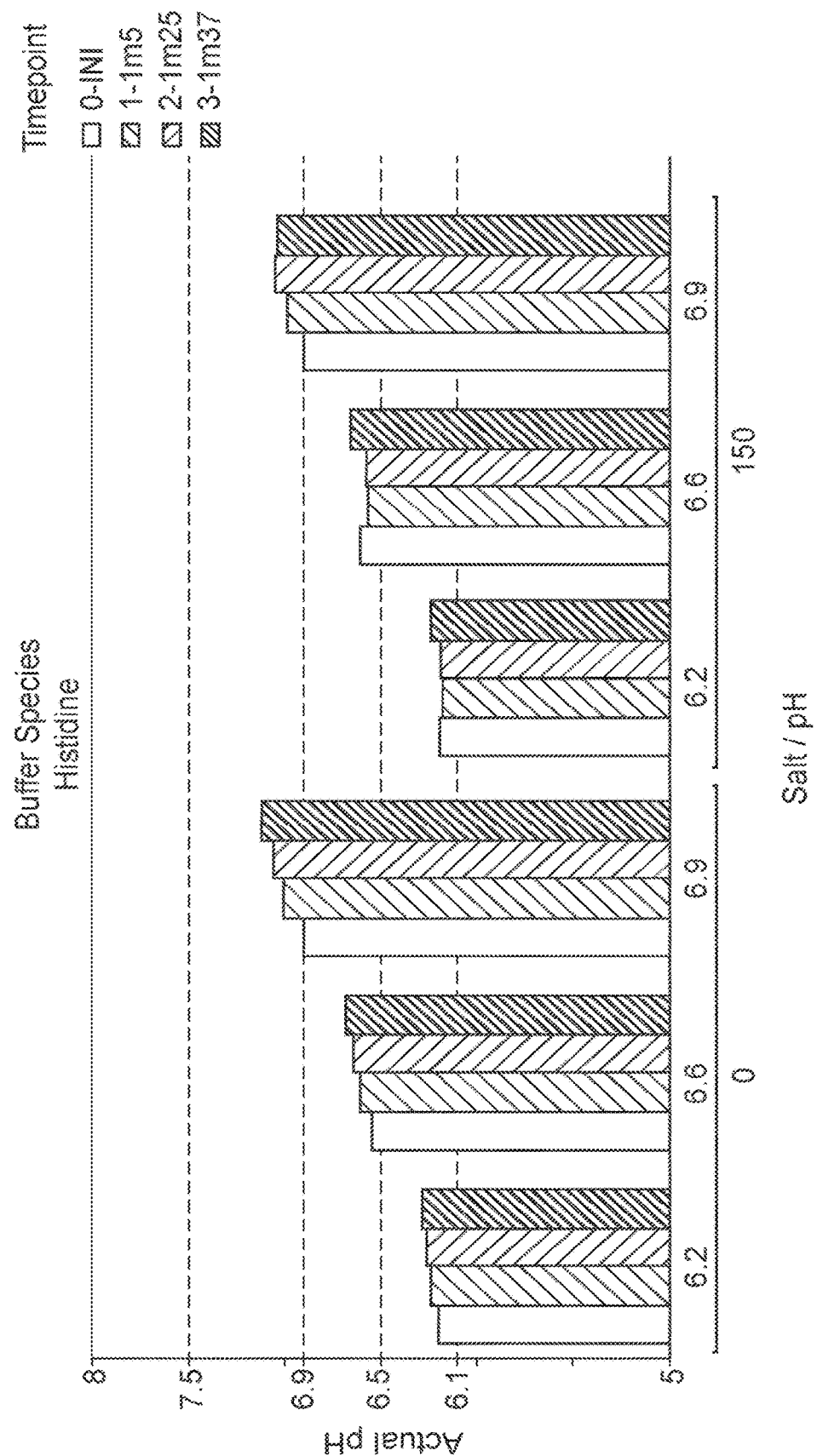
FIG. 10: Stability of pH in hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) using histidine as the buffer.

To determine the choice of buffer, GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$ (GBS6) were formulated together using the same buffer conditions as indicated in Table 33 above. The actual pH of the formulations was tested at the following timepoints: 0 (when the formulation was made), after 1 month at 5° C., after 1 month at 25° C., and after 1 month at 37° C. A shift in pH was seen in the formulations using succinate as the buffer, whereas no shift was seen in the formulations using histidine as the buffer. Results are shown in FIGS. 9-10.

Figure 11:
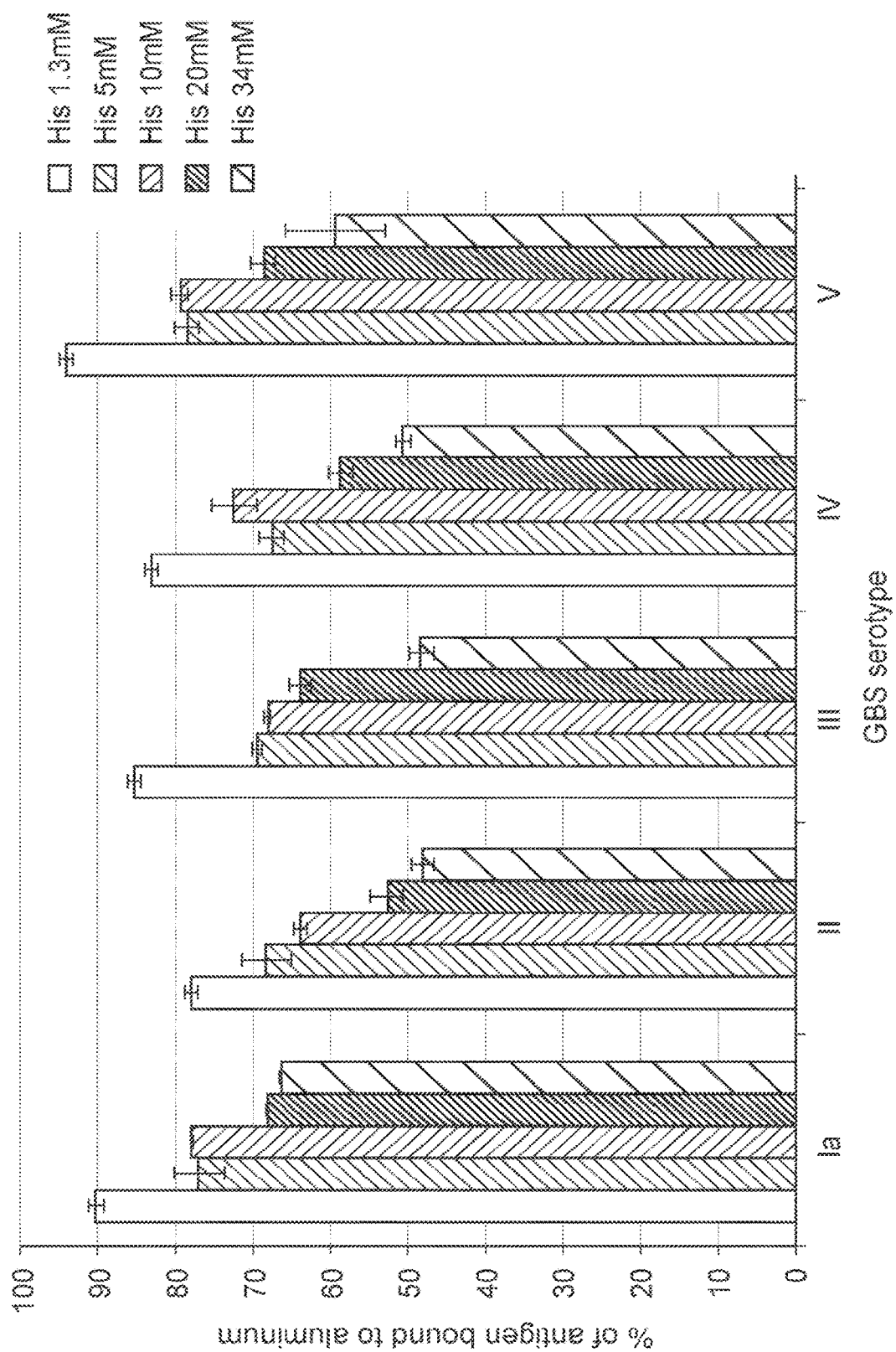
FIG. 11: Effect of histidine buffer concentration in a hexavalent GBS vaccine (GBS Ia-CRM$_{197}$, GBS Ib-CRM$_{197}$ (not shown), GBS II-CRM$_{197}$, GBS III-CRM$_{197}$, GBS IV-CRM$_{197}$, and GBS V-CRM$_{197}$) on binding of GBS conjugates to aluminum at a dose of 10 mcg/ml.
Figure 12:
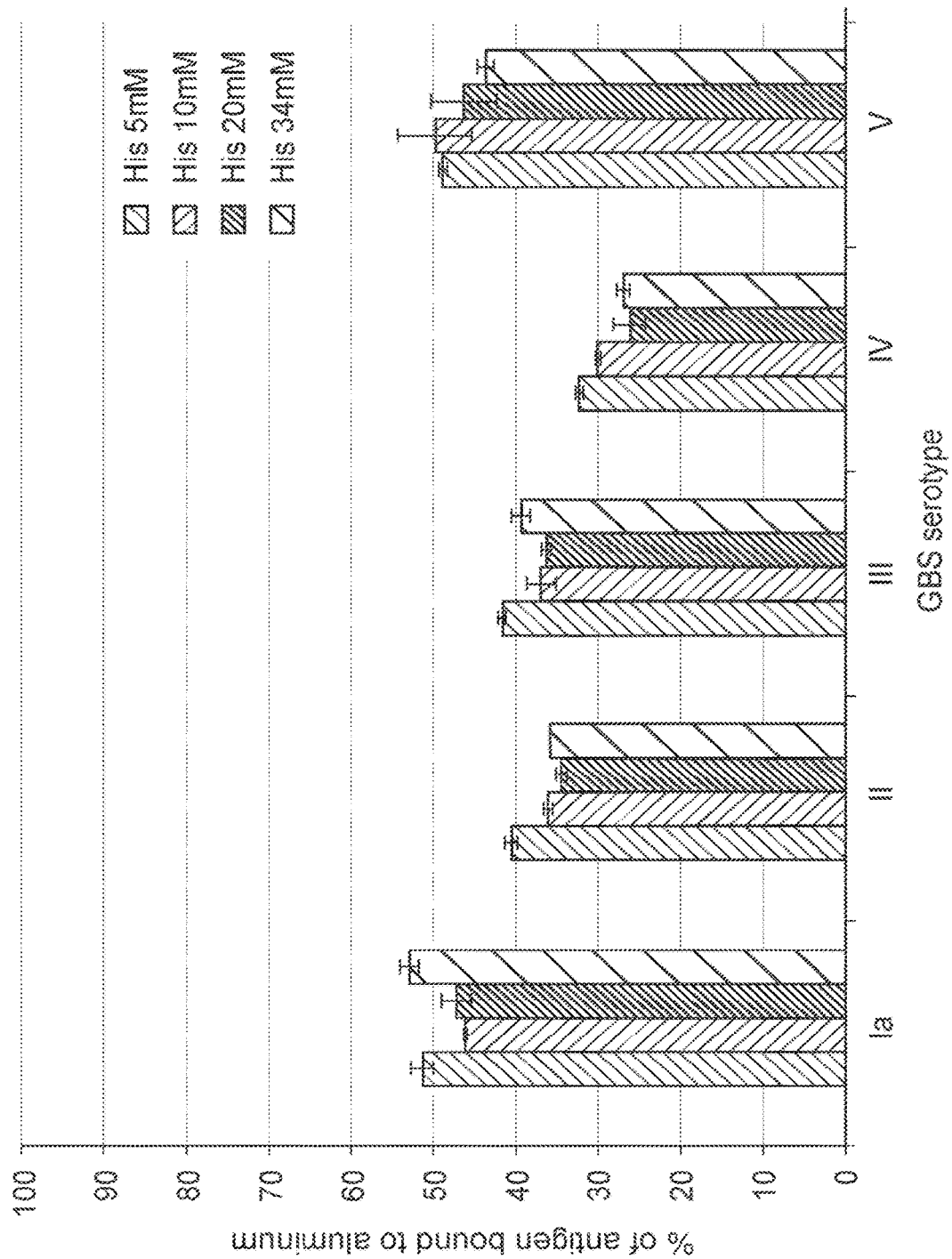
FIG. 12: Effect of histidine buffer concentration in a hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on binding of GBS conjugates to aluminum at a dose of 40 mcg/ml.

The effect of histidine buffer concentration on binding of GBS conjugates to aluminum was also tested. A formulation comprising 150 mM NaCl, 0.01% polysorbate-80 at pH 6.5, and 0.5 mg/ml of aluminum as AlPO$_4$ was tested with two different concentrations of conjugates (10 mcg/ml and 40 mg/ml of each serotype) and several different concentrations of histidine. The percent of conjugates bound to aluminum was determined by measuring the total amount of each of the conjugates in the vaccine and the amount of each of the conjugates bound to the aluminum. The bound conjugates were measured by centrifuging the vaccine formulation, resuspending the aluminum pellet, solubilizing the aluminum, and measuring the conjugates bound using nephelometry with serotype-specific polyclonal antibodies against each of the serotypes. Results are shown in FIGS. 11-12. It was found that the concentration of histidine buffer influenced the percent of each serotype bound to aluminum, and the influence was more pronounced at the lower dose than the higher dose.

Figure 13:
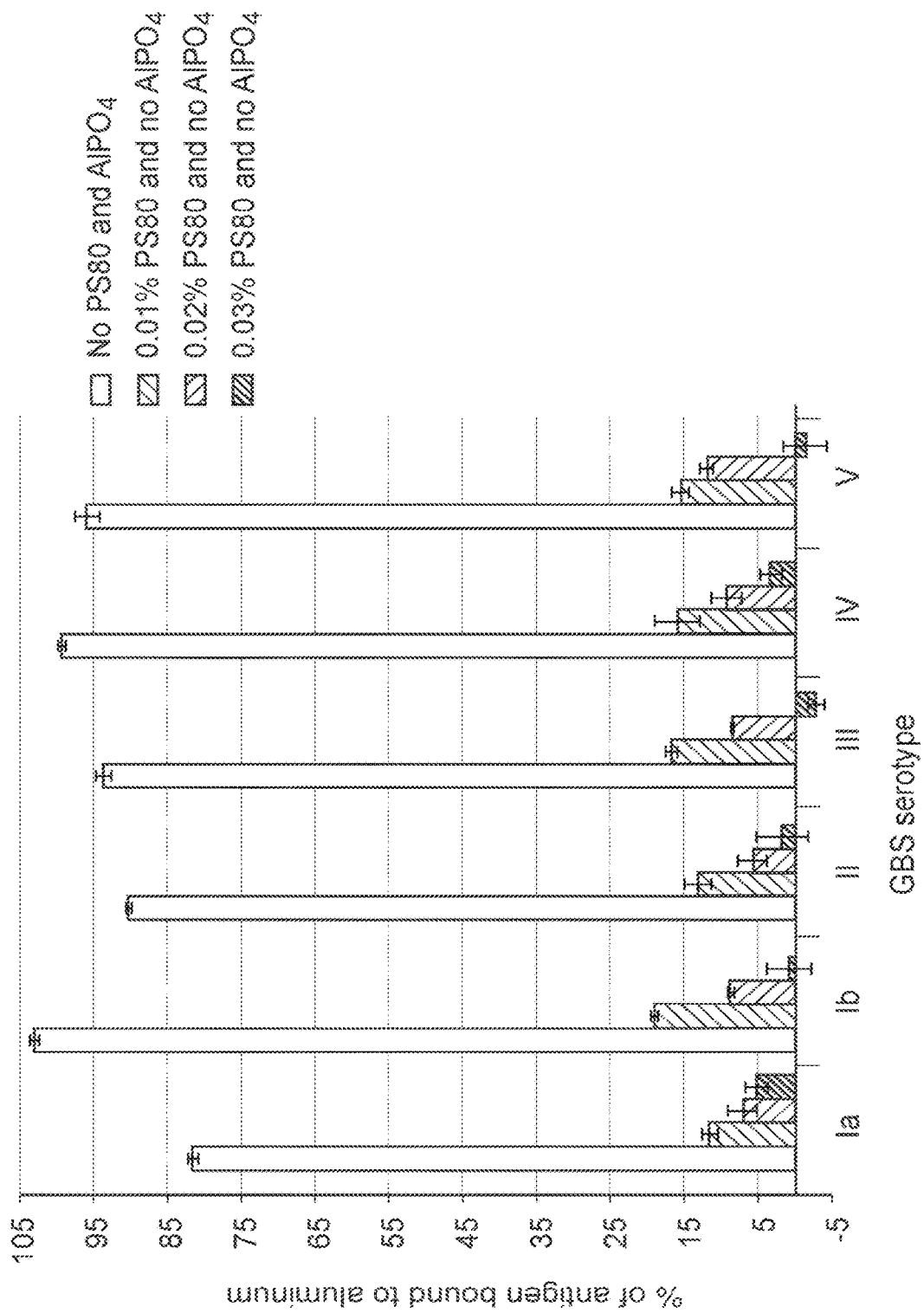
FIG. 13: Effect of polysorbate-80 concentration in a hexavalent GBS vaccine (GBS Ia-CRM$_{197}$, GBS Ib-CRM$_{197}$ (not shown), GBS II-CRM$_{197}$, GBS III-CRM$_{197}$, GBS IV-CRM$_{197}$, and GBS V-CRM$_{197}$) on percent loss of total antigenicity upon agitation stress.

An agitation study was conducted to determine the amount of polysorbate-80 (PS80) that would be desirable. GBS6 formulations comprising 20 mM Histidine, 150 mM NaCl, 0.5 mg/ml AlPO$_4$ (if present), and either no PS80, 0.01% PS80, 0.02% PS80, or 0.03% PS80 at pH 6.5 were tested for percentage of total antigenicity lost upon agitation stress. Syringes prefilled with the formulations were agitated at 500 RPM for 72 hours at room temperature. Control samples (unagitated) were stored at room temperature for 72 hours. Results are shown in FIG. 13.

Figure 14:
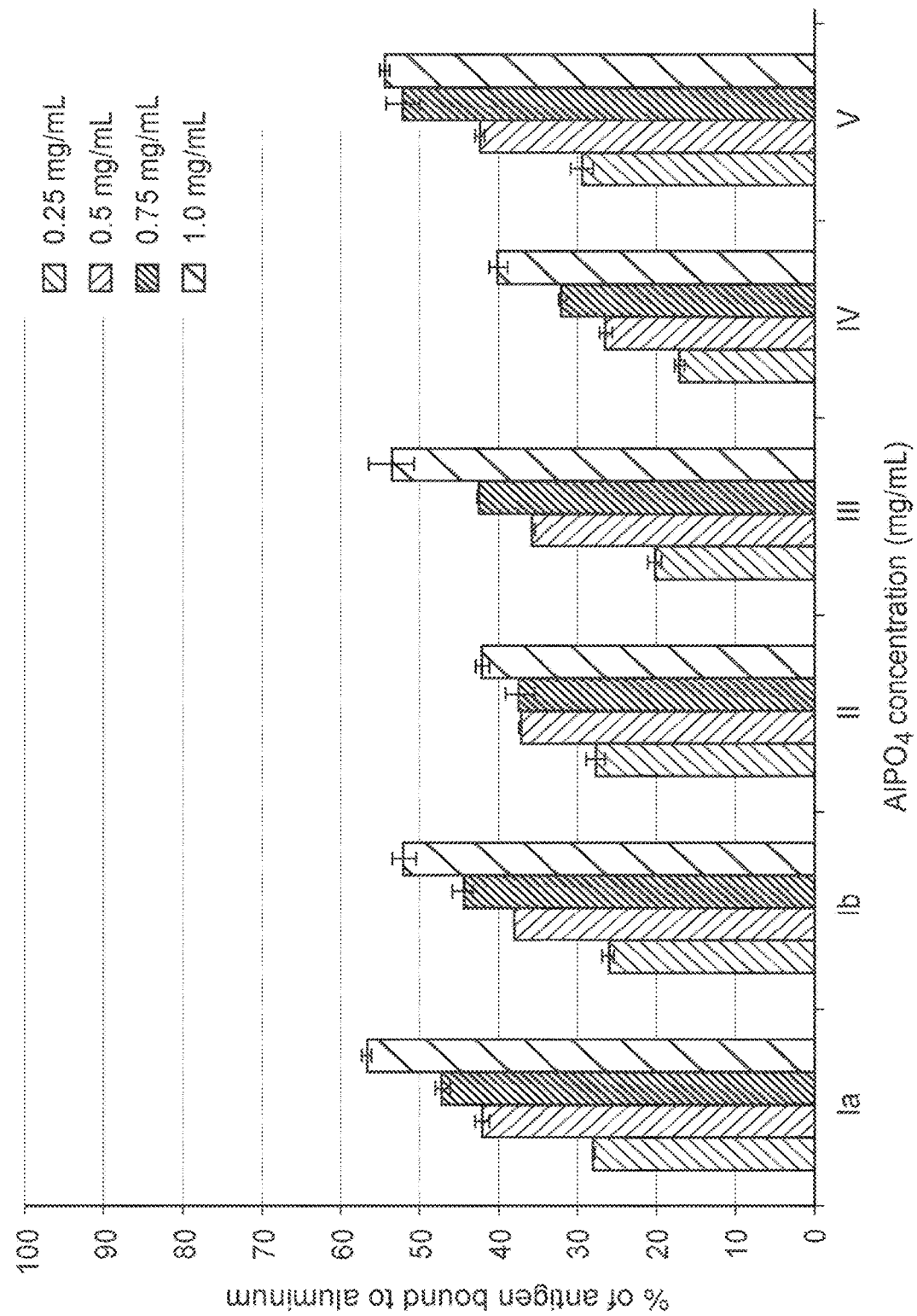
FIG. 14: Effect of aluminum concentration in a hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on GBS conjugates binding to aluminum.
Figure 15:
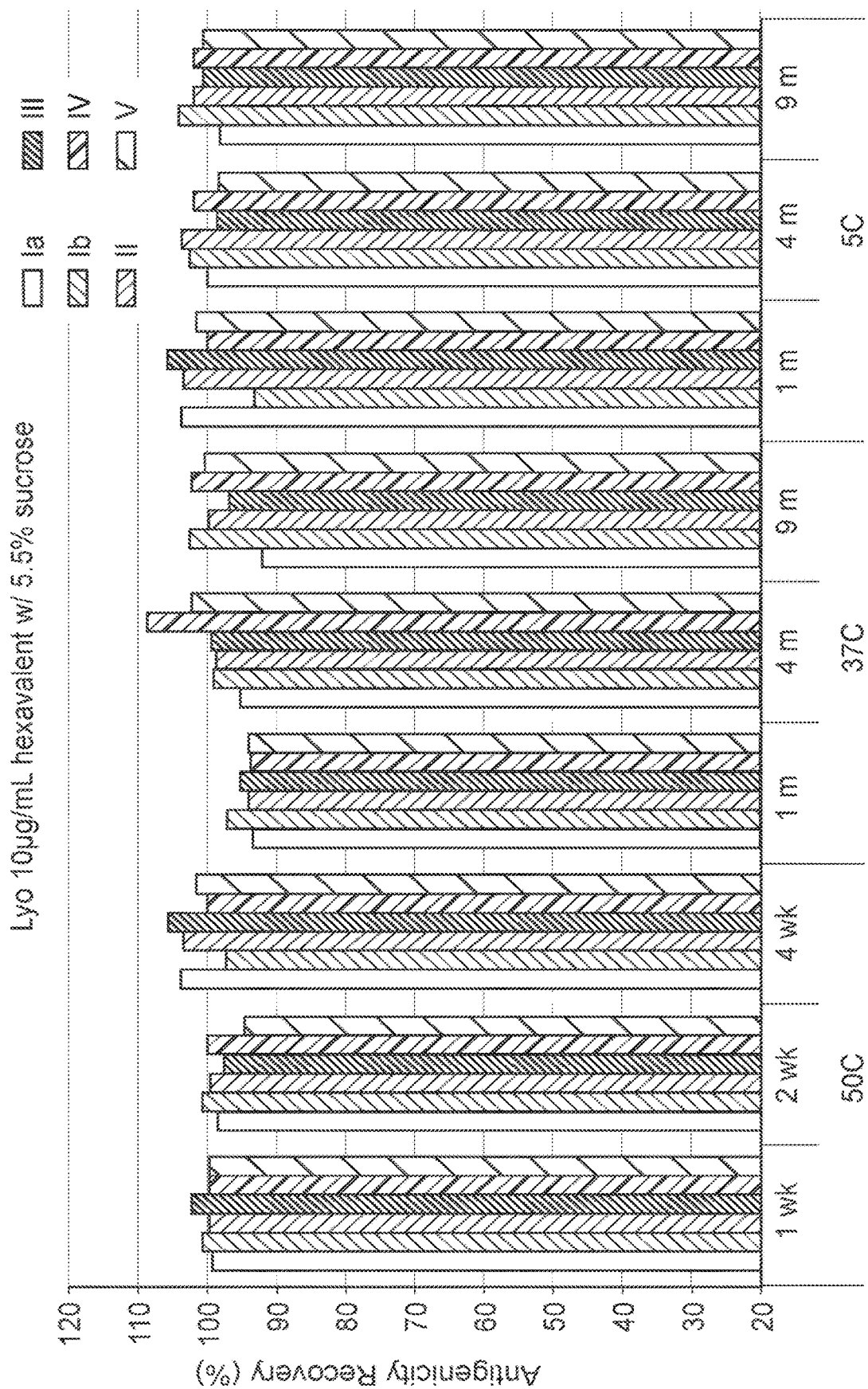
FIG. 15: Effect of 5.5% (w/v) sucrose in a 10 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 16:
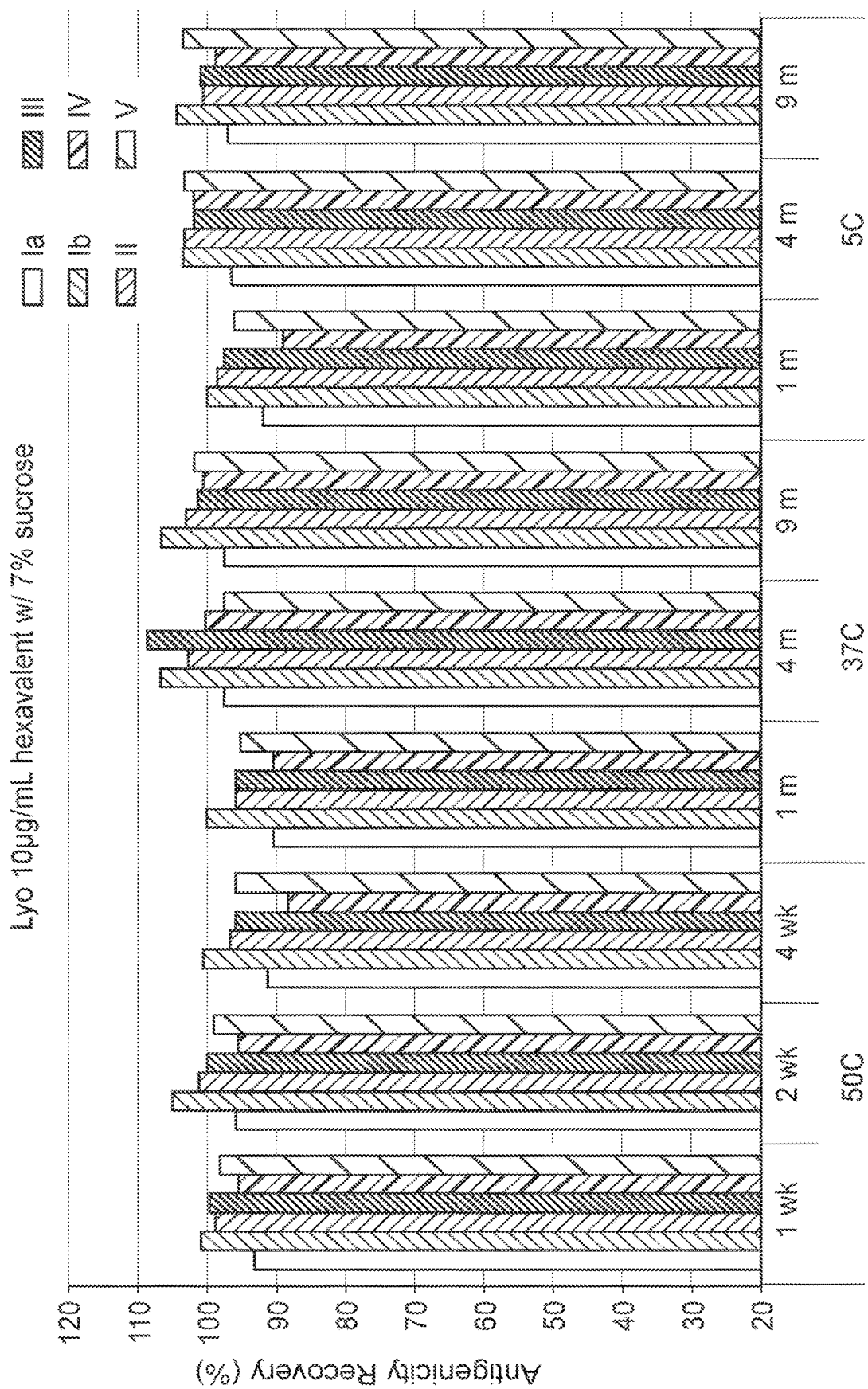
FIG. 16: Effect of 7.0% (w/v) sucrose in a 10 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 17:
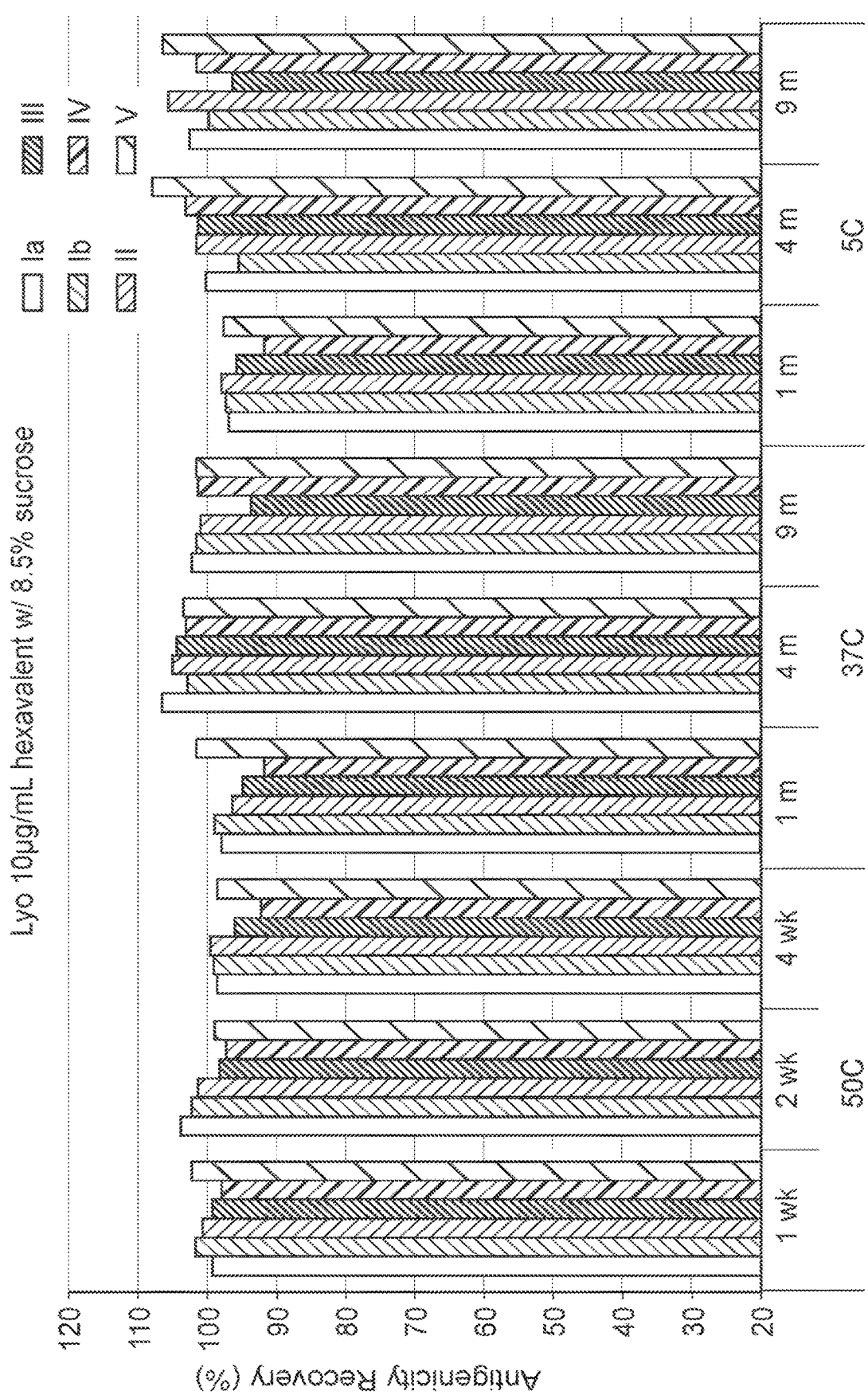
FIG. 17: Effect of 8.5% (w/v) sucrose in a 10 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$7, GBS IV-CRM$_{197}$, and GBS V-CRM$_{197}$) on antigenicity recovery for each serotype.
Figure 18:
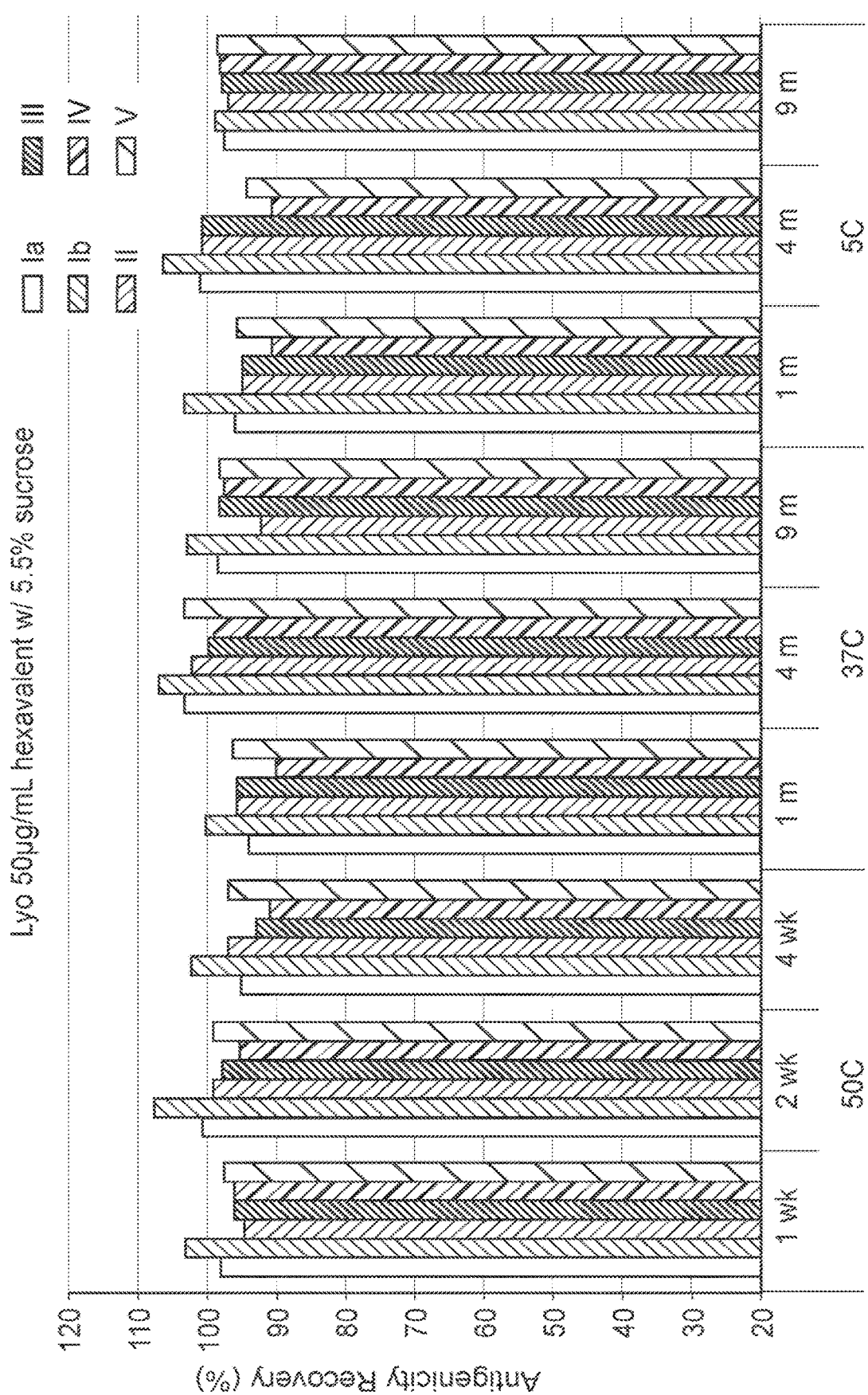
FIG. 18: Effect of 5.5% (w/v) sucrose in a 50 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 19:
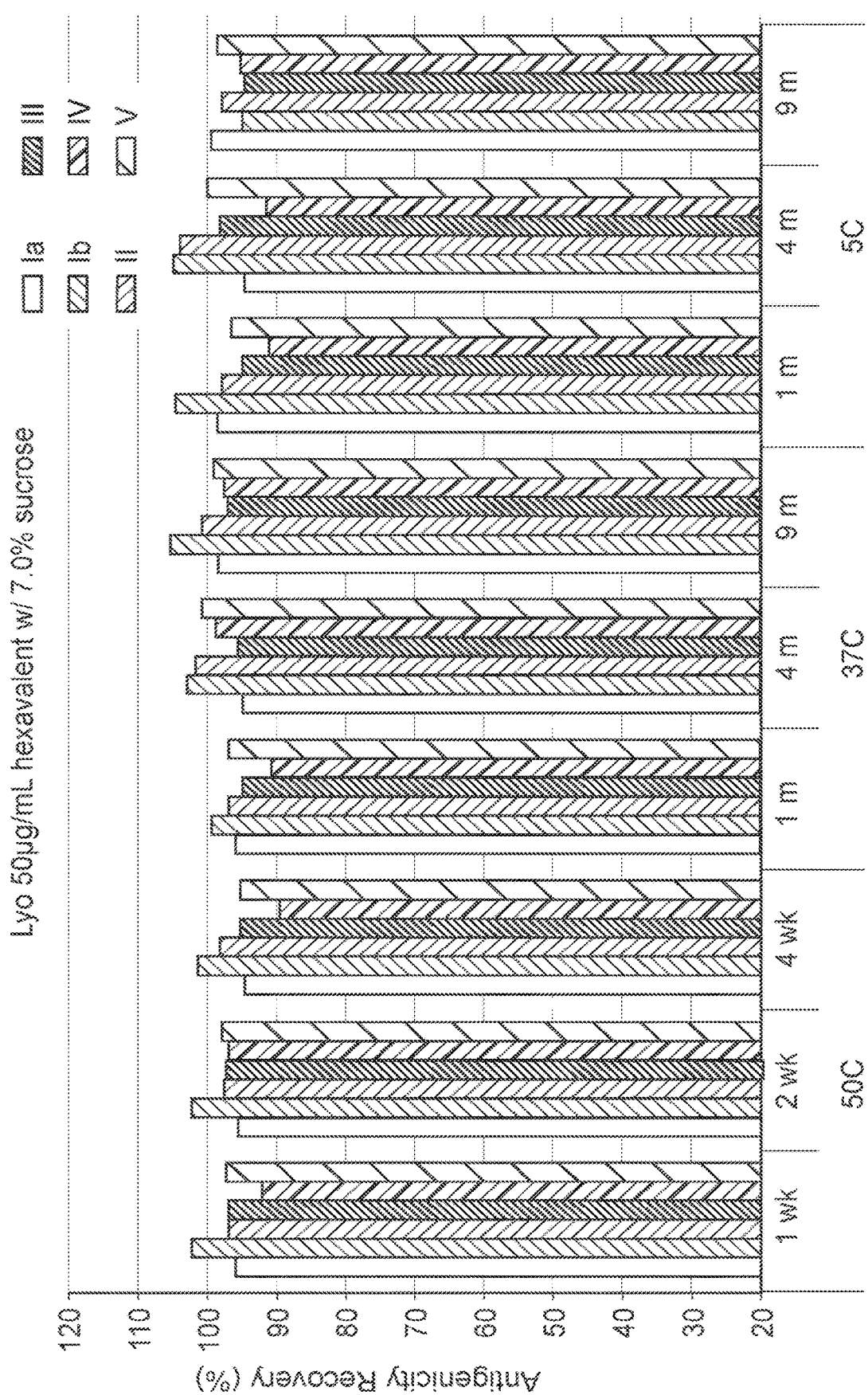
FIG. 19: Effect of 7.0% (w/v) sucrose in a 50 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 20:
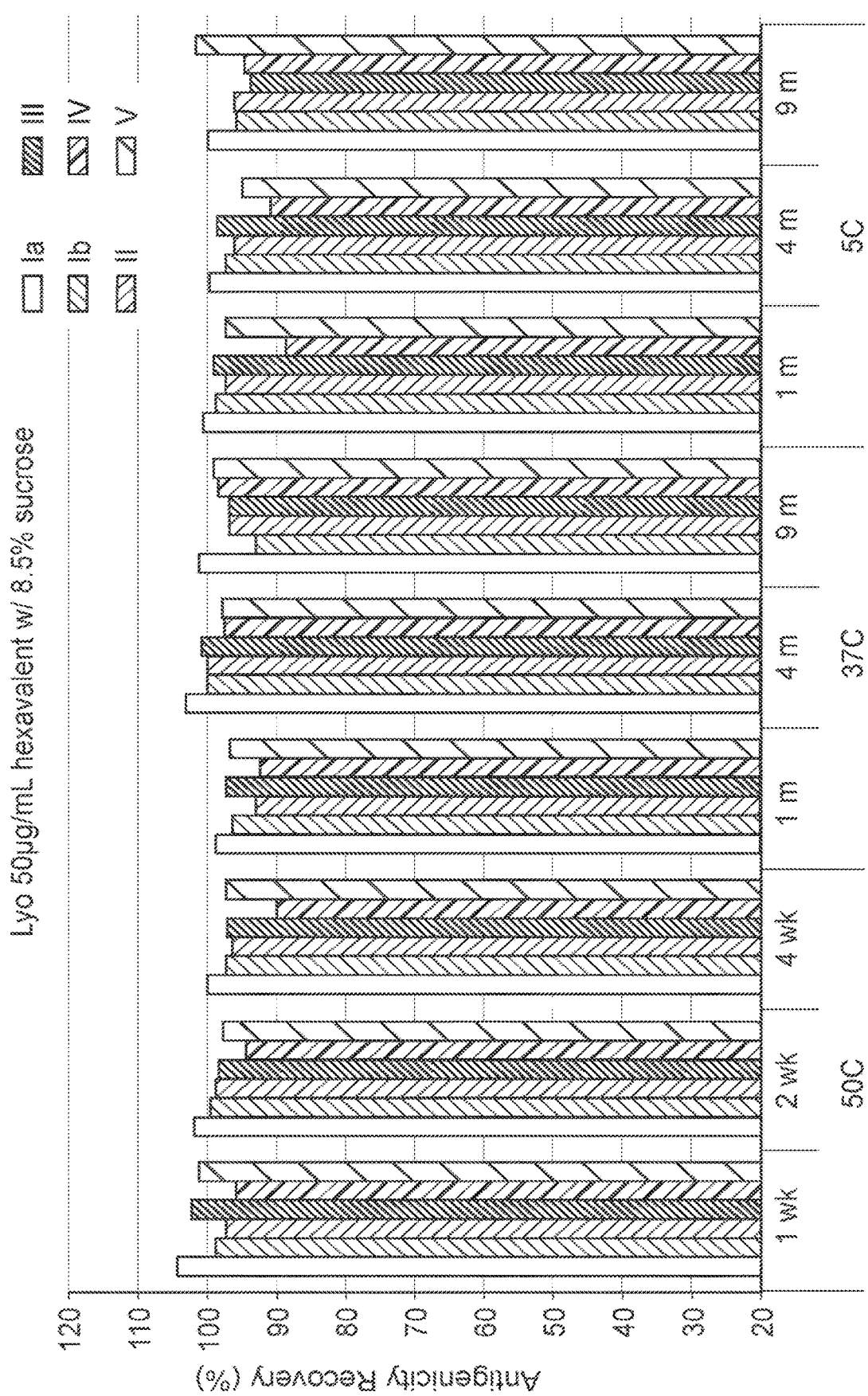
FIG. 20: Effect of 8.5% (w/v) sucrose in a 50 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 21:
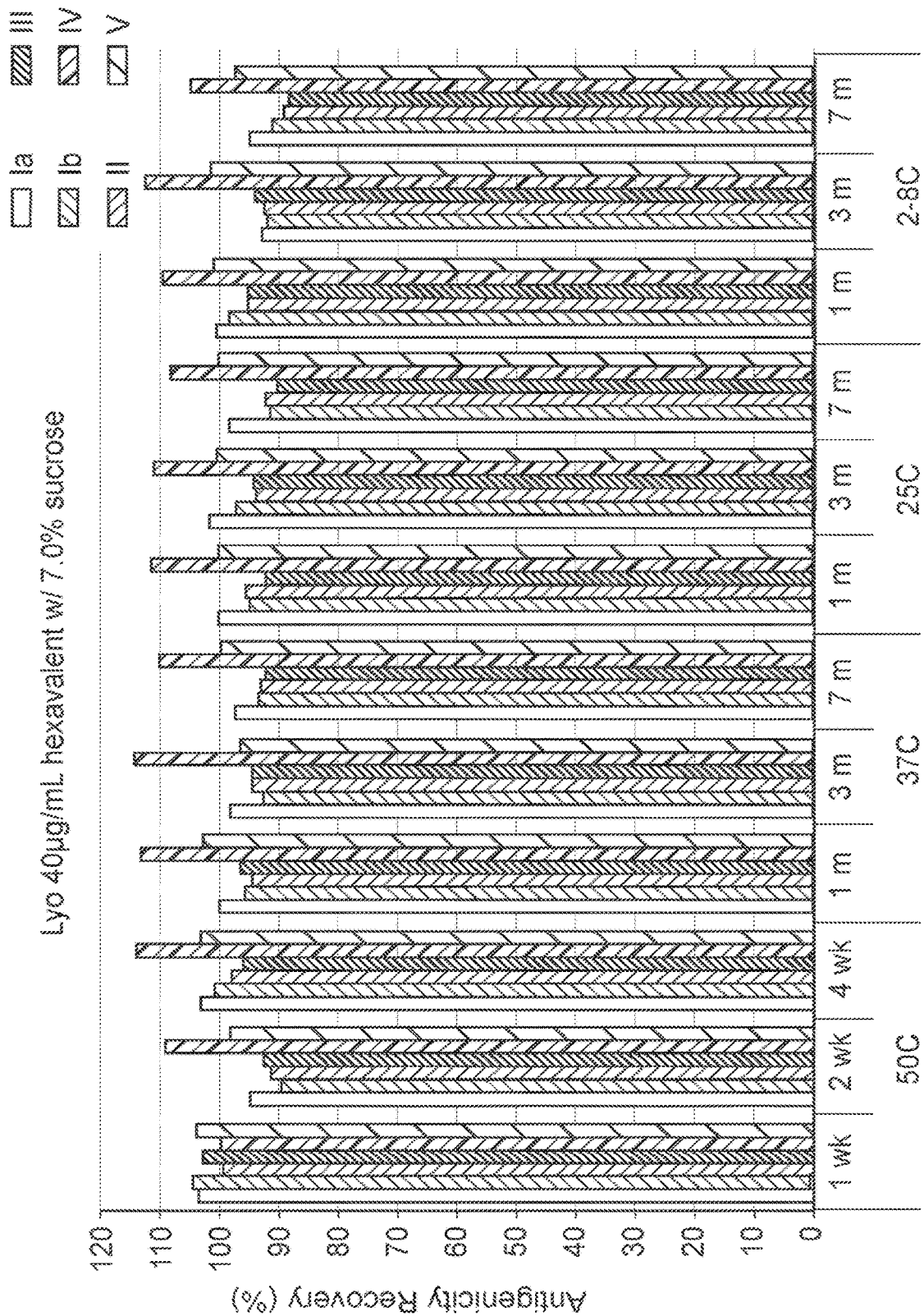
FIG. 21: Effect of 7.0% (w/v) sucrose in a 40 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 22:
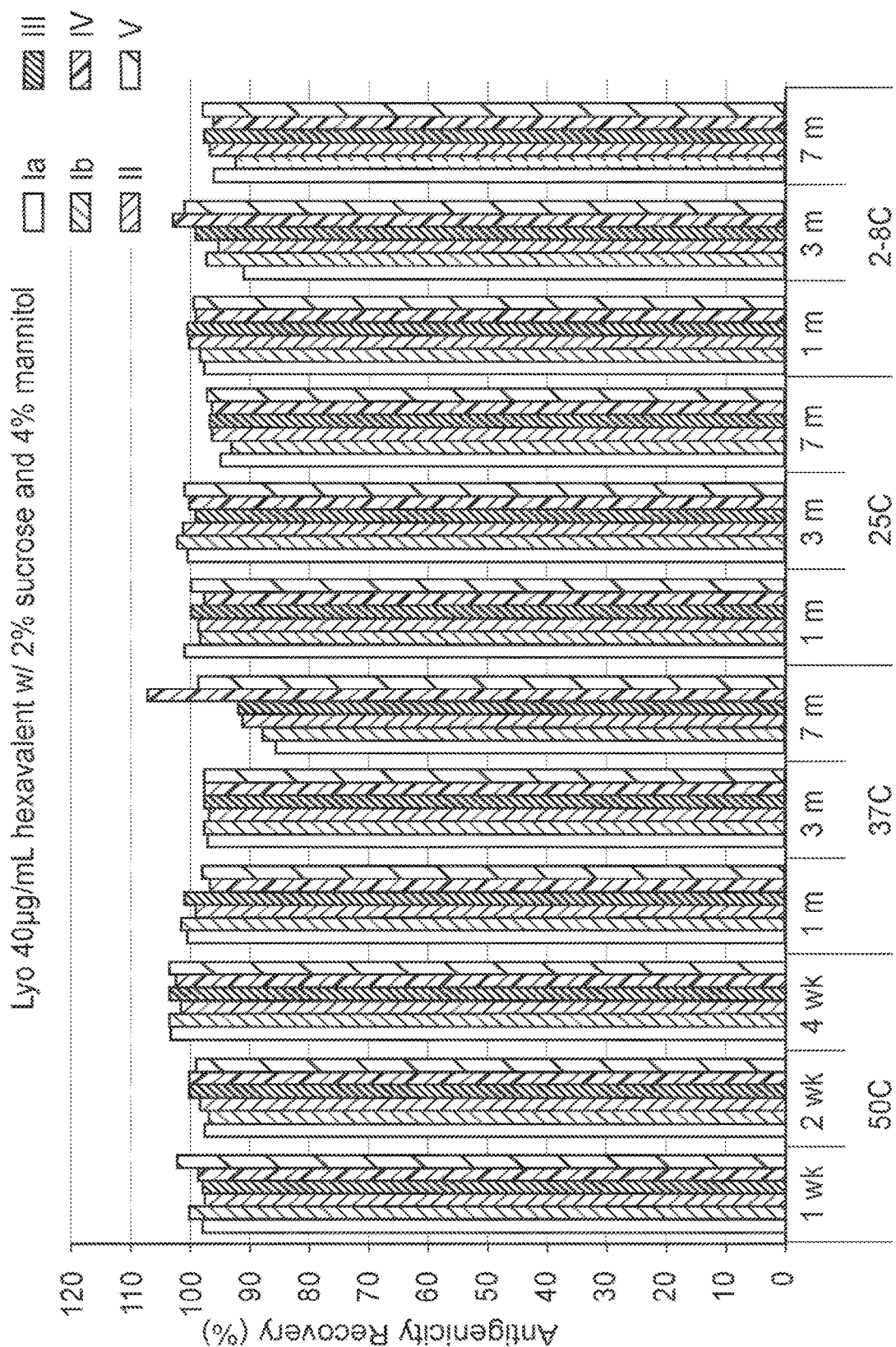
FIG. 22: Effect of 2.0% (w/v) sucrose and 4.0% (w/v) mannitol in a 40 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 23:
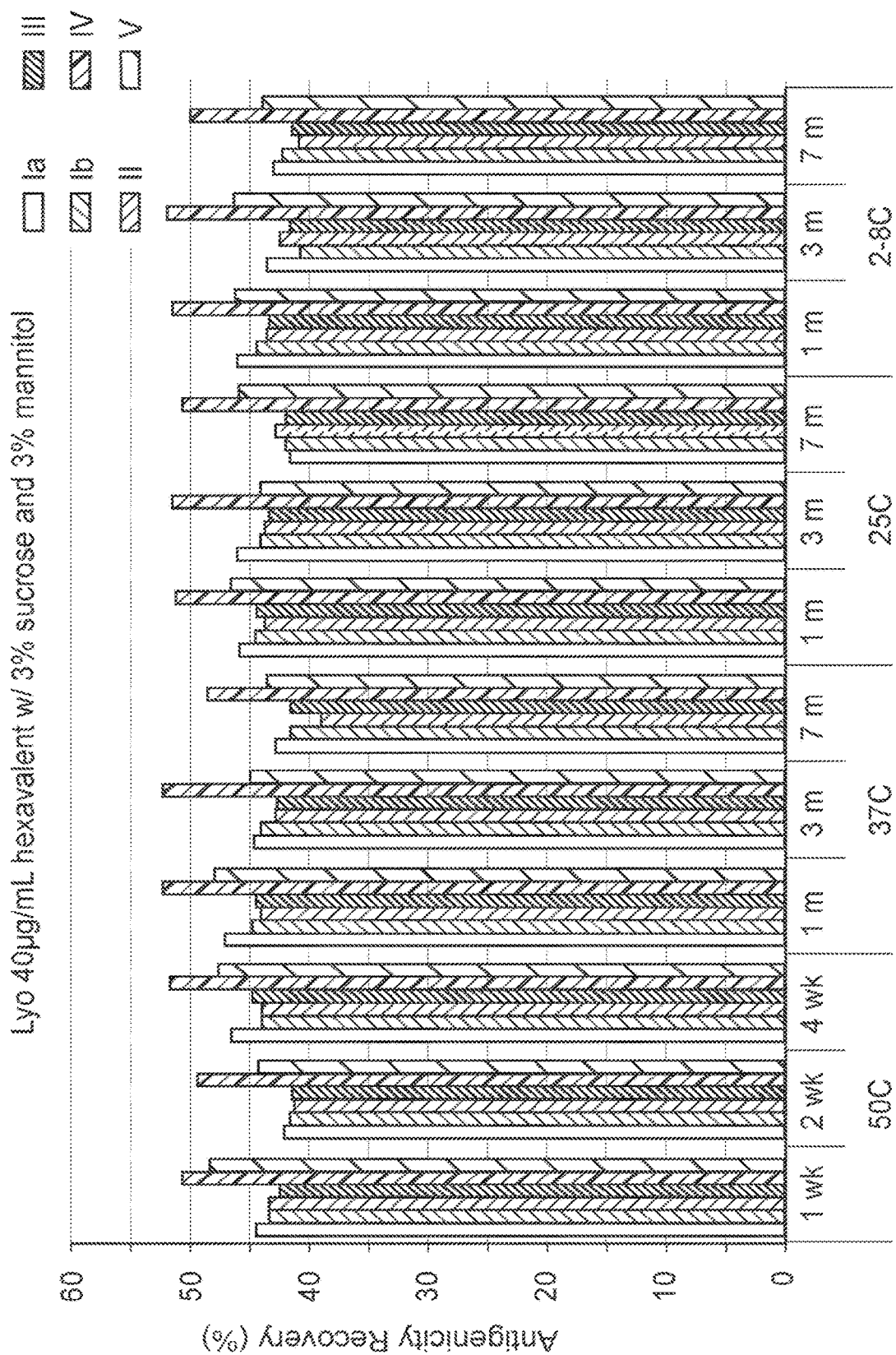
FIG. 23: Effect of 3.0% (w/v) sucrose and 3.0% (w/v) mannitol in a 40 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 24:
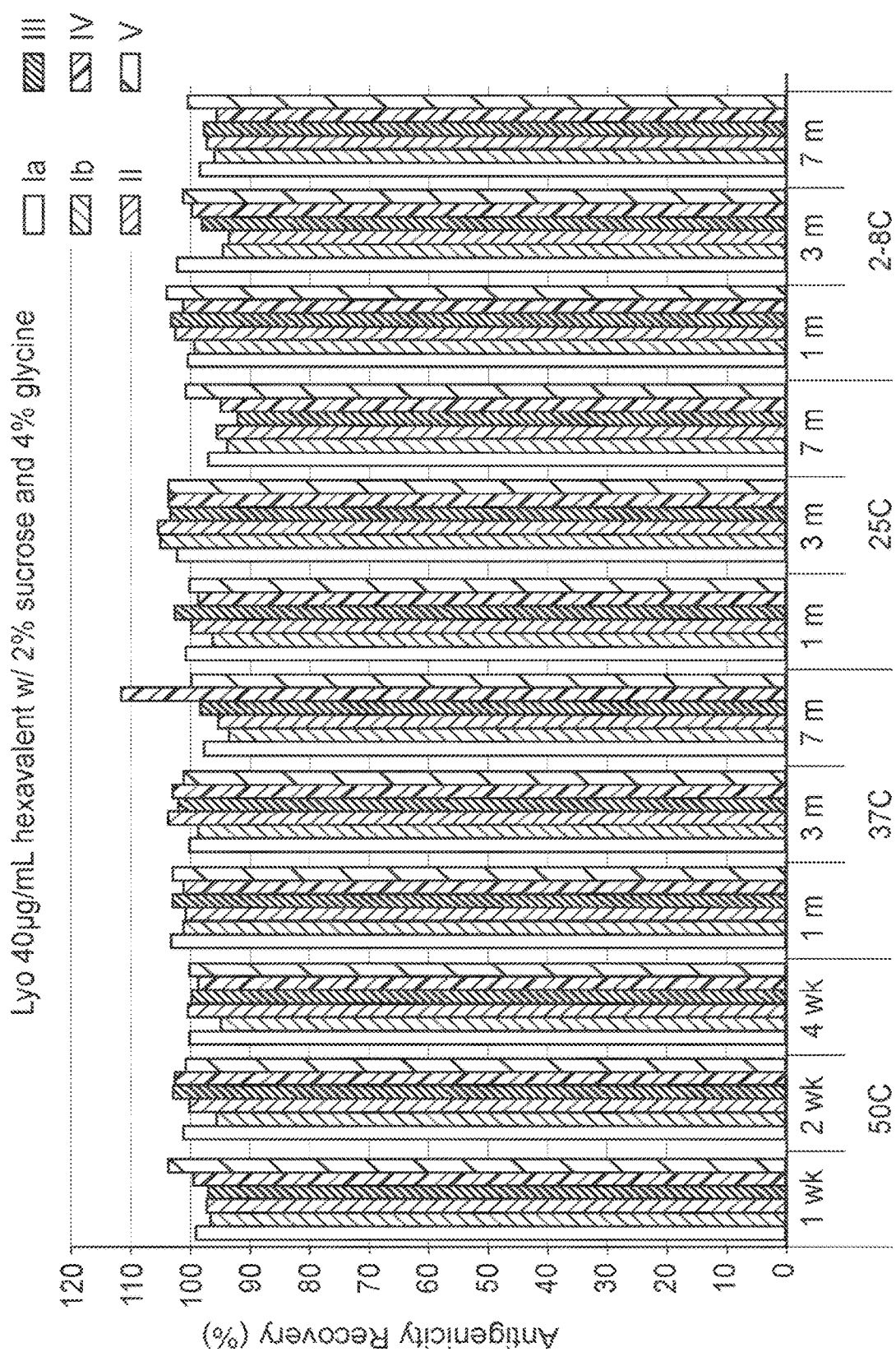
FIG. 24: Effect of 2.0% (w/v) sucrose and 4.0% (w/v) glycine in a 40 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.
Figure 25:
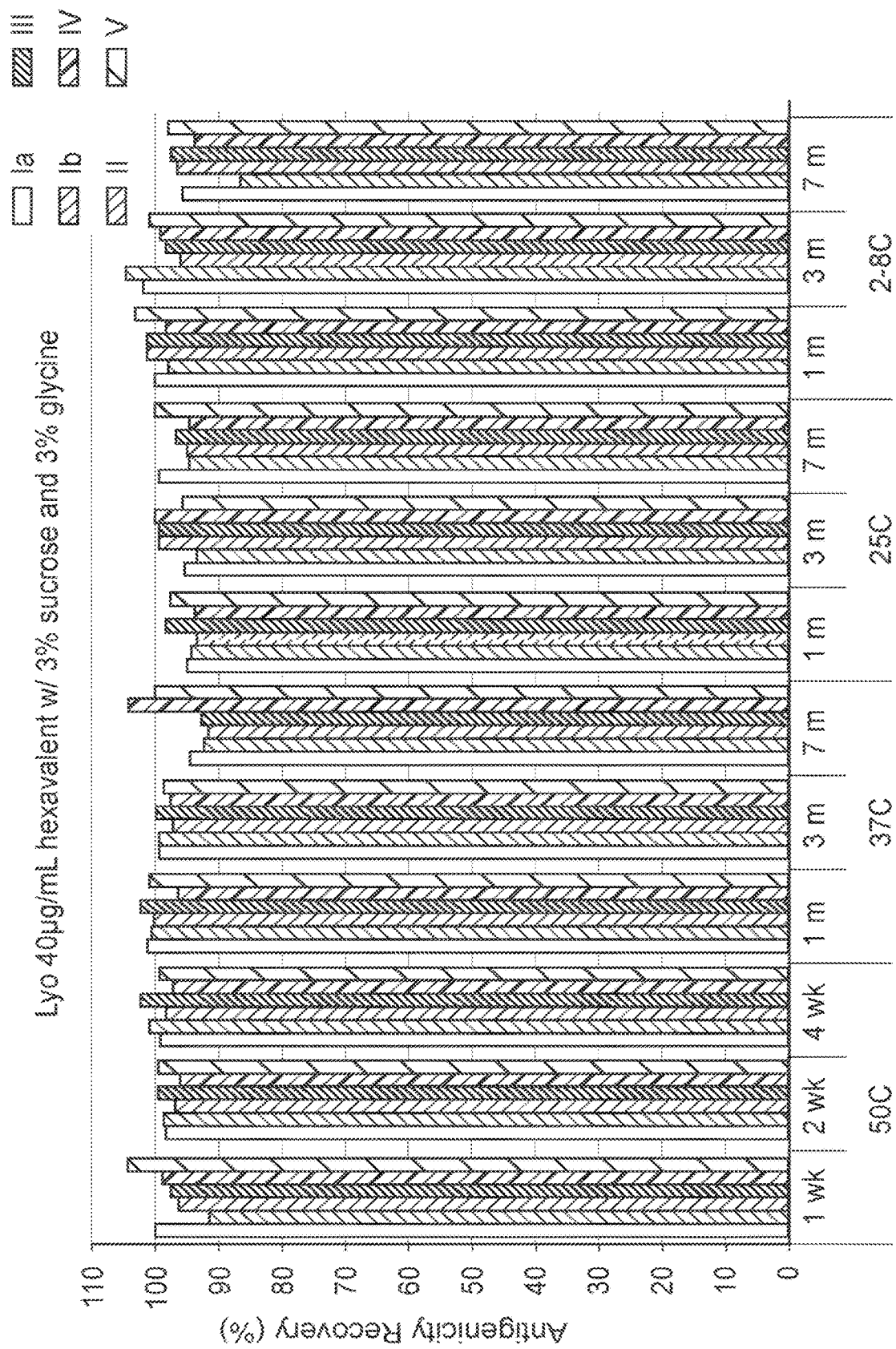
FIG. 25: Effect of 3.0% (w/v) sucrose and 3.0% (w/v) glycine in a 40 mcg/ml dose lyophilized hexavalent GBS vaccine (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) on antigenicity recovery for each serotype.

The concentration of aluminum in GBS6 formulations was also studied to determine the effect on GBS conjugates binding to aluminum. GBS6 formulations comprising 10 mM Histidine, 150 mM NaCl, 0.02% PS80, and either 0.25 mg/ml, 0.5 mg/ml, 0.75 mg/ml, or 1.0 mg/ml of aluminum as aluminum phosphate (AlPO$_4$) at pH 6.5 were tested for percent of conjugate bound to the aluminum. The percentage of binding to AlPO$_4$ increases with increasing AlPO$_4$ concentration. Results are shown in FIG. 14.

Example 16

GBS6 Lyophilized Formulation

A variety of lyophilized formulations of GBS6 (GBS Ia-CRM$_{197}$, GBS Ib-CRM$_{197}$, GBS II-CRM$_{197}$, GBS III-CRM$_{197}$, GBS IV-CRM$_{197}$, and GBS V-CRM$_{197}$) were tested for stability. Low (10 mcg/ml) and high (50 mcg/ml) dose formulations comprising 20 mM histidine at pH 6.5, 0.02% PS80, about 28 mM NaCl, and either 5.5%, 7.0%, or 8.5% (w/v) sucrose were lyophilized. Stability of the lyophilized formulations was tested by measuring pH and moisture after 4 months at 5° C., 4 months at 37° C., and 1 month at 50° C. All formulations were stable based on pH and moisture (data not shown). In addition, the percentage of antigenicity recovery for each serotype was tested for all the formulations after 1, 4, and 9 months at both 5° C. and 37° C. and after 1, 2, and 4 weeks at 50° C. Results are shown in FIGS. 15-20.

The following variations in excipients were also prepared and evaluated for a 40 mcg/ml dose of the GBS6 formulation: 1) 7% (w/v) sucrose, 2) 2% (w/v) sucrose and 4% (w/v) mannitol, 3) 3% (w/v) sucrose and 3% (w/v) mannitol, 4) 2% (w/v) sucrose and 4% (w/v) glycine, or 5) 3% (w/v) sucrose and 3% (w/v) glycine. The pH and moisture for all five formulations were stable after 3 months at 5° C., 3 months at 25° C., 3 months at 37° C., and 1 month at 50° C. (data not shown). In addition, the percentage of antigenicity recovery for each serotype was tested for all the formulations after 1, 3, and 7 months at 52-8° C., 25° C., and 37° C. and after 1, 2, and 4 weeks at 50° C. Results are shown in FIGS. 21-25.

The percent of antigen bound to aluminum phosphate adjuvant for the GBS6 vaccine in a reconstituted lyophilized formulation and a liquid formulation were tested using nephelometry. Both lyophilized and liquid formulations containing 20 mM histidine, 0.02% PS80, 7.0% (w/v) sucrose, and 500 mcg/ml aluminum as aluminum phosphate were prepared in low (10 mcg/ml) and high (50 mcg/ml) doses. Varying concentrations of sodium chloride (NaCl) were also tested to determine the effect on antigen binding. Results for the lyophilized formulations and liquid formulations are shown in Tables 35 and 36, respectively. The low dose formulations for both lyophilized and liquid compositions had comparable results when NaCl concentrations of about 150 mM and higher were used.

TABLE 35

Percent of Antigen Bound to Aluminum Phosphate in Reconstituted Lyophilized Formulations with varying levels of NaCl

|  | NaCl (mM) | Ia (%) | Ib (%) | II (%) | III (%) | IV (%) | V (%) |
|---|---|---|---|---|---|---|---|
| 10 mcg/ml of each conjugate | ~23 | 40 | 36 | 31 | 34 | 38 | 39 |
|  | ~80 | 46 | 45 | 37 | 40 | 44 | 44 |
|  | ~150 | 78 | 69 | 63 | 62 | 82 | 84 |

TABLE 35-continued

Percent of Antigen Bound to Aluminum Phosphate in Reconstituted Lyophilized Formulations with varying levels of NaCl

|  | NaCl (mM) | Ia (%) | Ib (%) | II (%) | III (%) | IV (%) | V (%) |
|---|---|---|---|---|---|---|---|
|  | ~300 | 77 | 64 | 63 | 60 | 79 | 86 |
| w/7.0% sucrose |  |  |  |  |  |  |  |
| 50 mcg/mL of each conjugate | ~23 | 21 | 23 | 24 | 18 | 27 | 24 |
|  | ~34 | 24 | 23 | 23 | 21 | 27 | 40 |
|  | ~150 | 66 | 58 | 52 | 46 | 65 | 67 |
|  | ~300 | 65 | 56 | 50 | 48 | 66 | 64 |
| w/7.0% sucrose |  |  |  |  |  |  |  |

TABLE 36

Percent of Antigen Bound to Aluminum Phosphate in Liquid Formulations with varying levels of NaCl

|  | NaCl (mM) | Ia (%) | Ib (%) | II (%) | III (%) | IV (%) | V (%) |
|---|---|---|---|---|---|---|---|
| 10 mcg/mL of each conjugate | 40 | 78.4 | 72.4 | 62.9 | 73.3 | 70.9 | 70.8 |
|  | 100 | 61.0 | 63.3 | 52.3 | 51.9 | 49.8 | 53.9 |
|  | 150 | 72.7 | 77.0 | 68.1 | 67.1 | 64.0 | 71.0 |
|  | 200 | 67.7 | 73.0 | 58.6 | 52.3 | 51.9 | 60.1 |
|  | 300 | 78.3 | 79.2 | 71.1 | 57.1 | 58.0 | 74.1 |
| 50 mcg/mL of each conjugate | 100 | 50.5 | 38.3 | 49.0 | 52.8 | 51.7 | 37.9 |
|  | 150 | 49.8 | 37.6 | 49.0 | 50.8 | 50.9 | 38.7 |
|  | 200 | 40.1 | 35.9 | 45.3 | 47.4 | 44.0 | 34.7 |
|  | 300 | 40.3 | 41.9 | 50.9 | 42.2 | 43.5 | 37.5 |

Example 17

Resuspension Properties of GBS6 Formulations

GBS6 formulations comprising 240 mcg/mL (high) or 60 mcg/mL (low) total dose of polysaccharide-protein conjugates, 20 mM histidine, 150 mM NaCl, 0.02% PS80, and 0.5 mg/mL of AlPO$_4$ at pH 6.5 were prepared. Similar monovalent formulations of each serotype were also prepared at 240 mcg/mL (high) or 60 mcg/mL (low) doses. Samples were filled into either 1) 2 mL glass vials at a fill volume of 0.73 mL per vial or 2) BD HYPAK SCF™ PRTC (Becton, Dickinson and Company) 1 mL short, glass prefilled syringes (PFS) with 0.58 mL fill volume and capped with 4432/50 stoppers (West Pharmaceutical Services, Inc.), keeping a headspace of about 5±1 mm. Formulations in vials were stored upright while those in PFS were held at two different orientations, namely tip down and horizontal, at 5° C.

Figure 26:
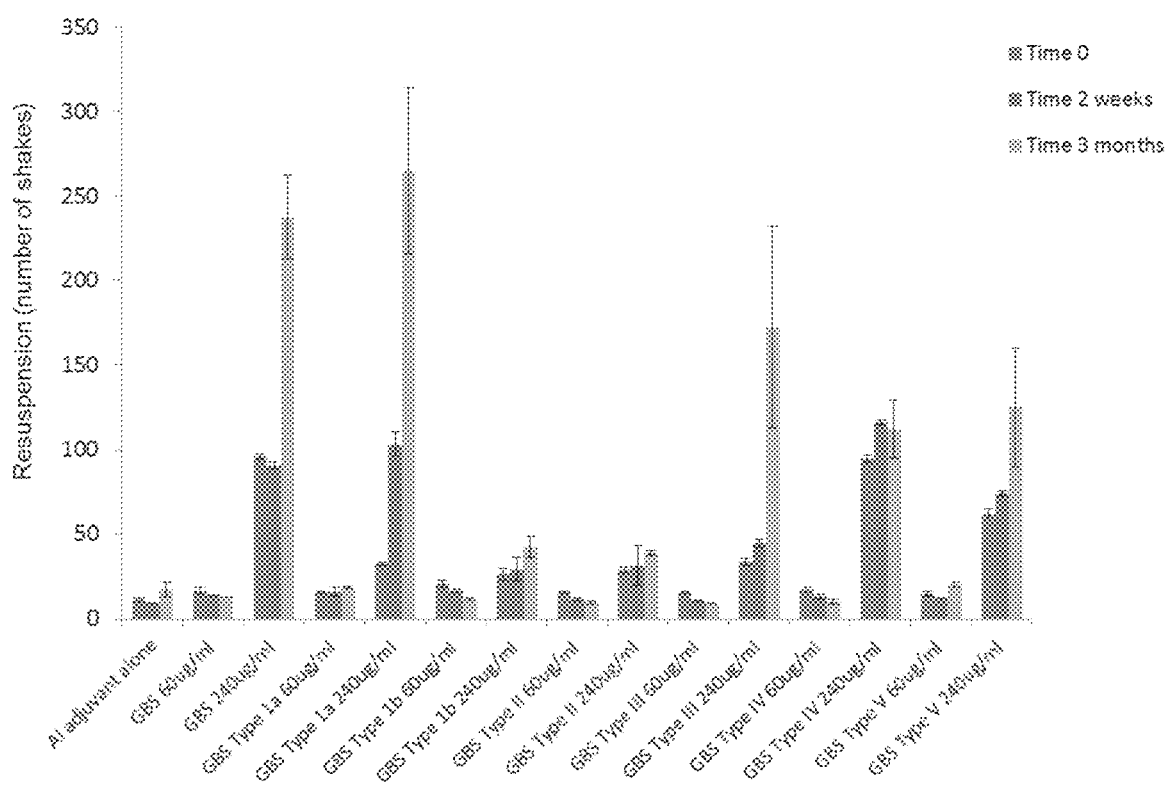
FIG. 26: Comparison of the resuspension of GBS6 and monovalent formulations in high and low doses stored in PFS in the tip down orientation at Time 0, 2 weeks and 3 months.
Figure 27:
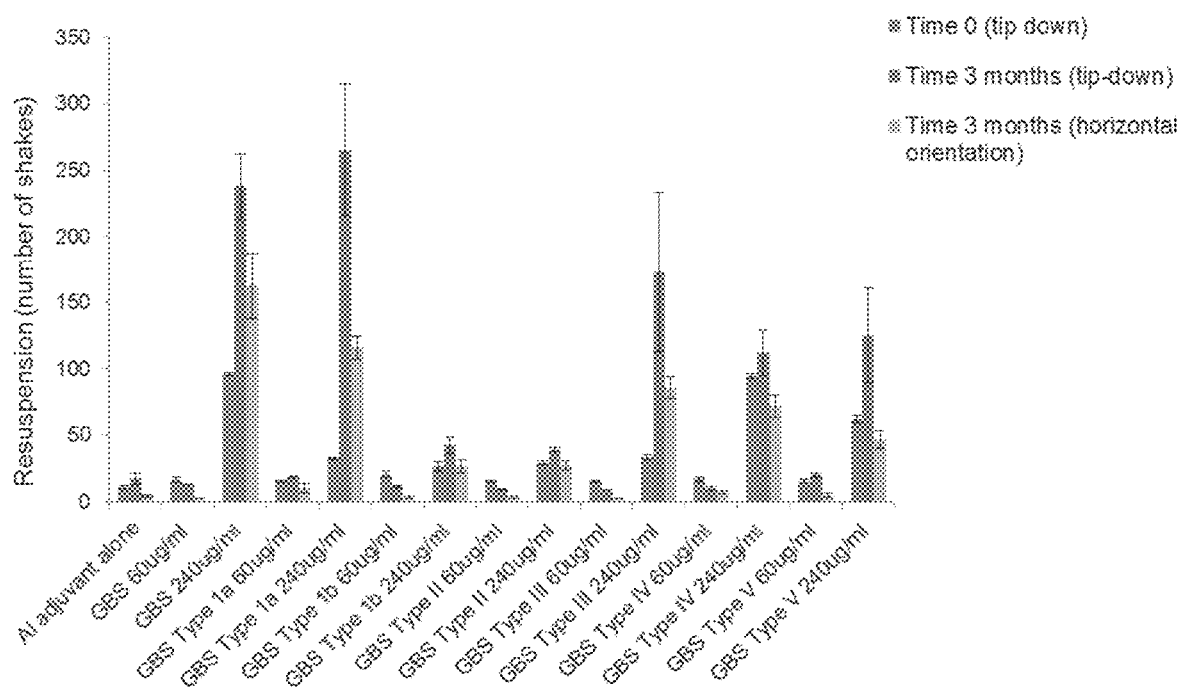
FIG. 27: Comparison of the resuspension of GBS6 and monovalent formulations in high and low doses stored in PFS in the tip down and horizontal orientations.

Resuspension was measured by number of shakes required to fully resuspend the formulations after 2 weeks and 3 months of storage. It took fewer than 5 shakes to resuspend all formulations filled in vials after 2 weeks and 3 months of storage. When stored horizontally, the GBS6 low dose formulation in PFS also only required 3 shakes after 3 months of storage. However, low dose formulations required about 15 shakes to resuspend in PFS stored tip down at either 2 weeks or 3 months of storage. By comparison, the high dose formulations in PFS were difficult to resuspend irrespective of the orientation for storage. The GBS6 high dose formulation required more than 50 shakes even with horizontal storage. In addition, the number of shakes required to resuspend the high dose formulation increased over time. Around 100 shakes were required to fully resuspend the GBS6 high dose formulations in PFS stored tip down for up to 16 hours post fill (T0) and increased to over 200 shakes with 3 months of storage. Finally, some monovalent formulations prepared using the polysaccharide conjugates from serotypes Ia, III, IV and V were difficult to resuspend in PFS stored at both orientations and required more shakes to resuspend over time, suggesting that the resuspension behavior of monovalent formulations was serotype-specific. Data comparing the resuspension of GBS6 and monovalent formulations in high and low doses stored in PFS in the tip down orientation at T0, 2 weeks and 3 months are shown in FIG. 26. Data comparing the resuspension of GBS6 and monovalent formulations in high and low doses stored in PFS in the tip down and horizontal orientations are shown in FIG. 27.

High and low doses of GBS6 formulations were further tested to determine whether resuspension would be affected by extended storage in vials, PFS in the tip down orientation, and PFS in the horizontal orientation. In addition, a mid dose (120 mcg/mL total dose of polysaccharide-protein conjugates) formulation was also tested to compare to the low and high dose formulations. It was discovered that the low dose formulation became more difficult to resuspend after 6 months of storage in PFS in the tip down orientation, requiring more than 50 shakes. The mid dose formulation was difficult to resuspend after only 1 month of storage in PFS in the tip down orientation and required 30 shakes to resuspend after 1 month in PFS in the horizontal orientation. Results are shown in Table 37.

TABLE 37

Comparison of Resuspension Behavior of GBS6 Formulations at Three Different Doses Stored in Vials and Prefilled Syringes

| Container | Storage Time at 2-8° C. (months) | Number of Shakes to Resuspend | | |
|---|---|---|---|---|
| | | Low Dose | Mid dose | High Dose |
| PFS (tip down) | 6 | >50 | >50* | >50 |
| PFS (horizontal) | 6 | <10 | 30* | >50 |
| Vial | 11 | <10 | NT | <10 |

*1 month storage time
NT—Not tested

From these studies it was determined that difficulties associated with resuspension can be mitigated by storing formulations comprising 20 mM histidine, 150 mM NaCl, 0.02% PS80, and 0.5 mg/mL of AlPO4 at pH 6.5 in vials or PFS in a horizontal manner. However, resuspension will only be within acceptable limits (i.e., fewer than 10 shakes) for formulations stored in PFS in a horizontal orientation if it has a total dose of polysaccharide-protein conjugates of 60 mcg/ml or less.

Figure 28:
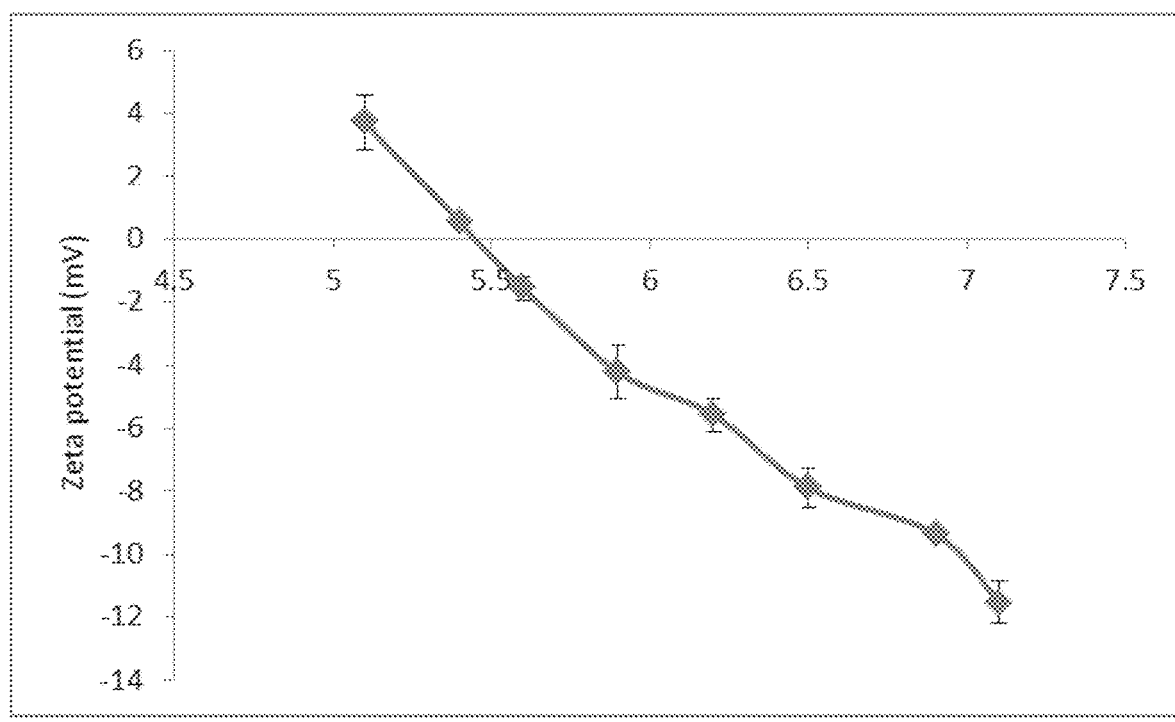
FIG. 28: Zeta potential of $AlPO_4$ as a function of pH.
Figure 29:
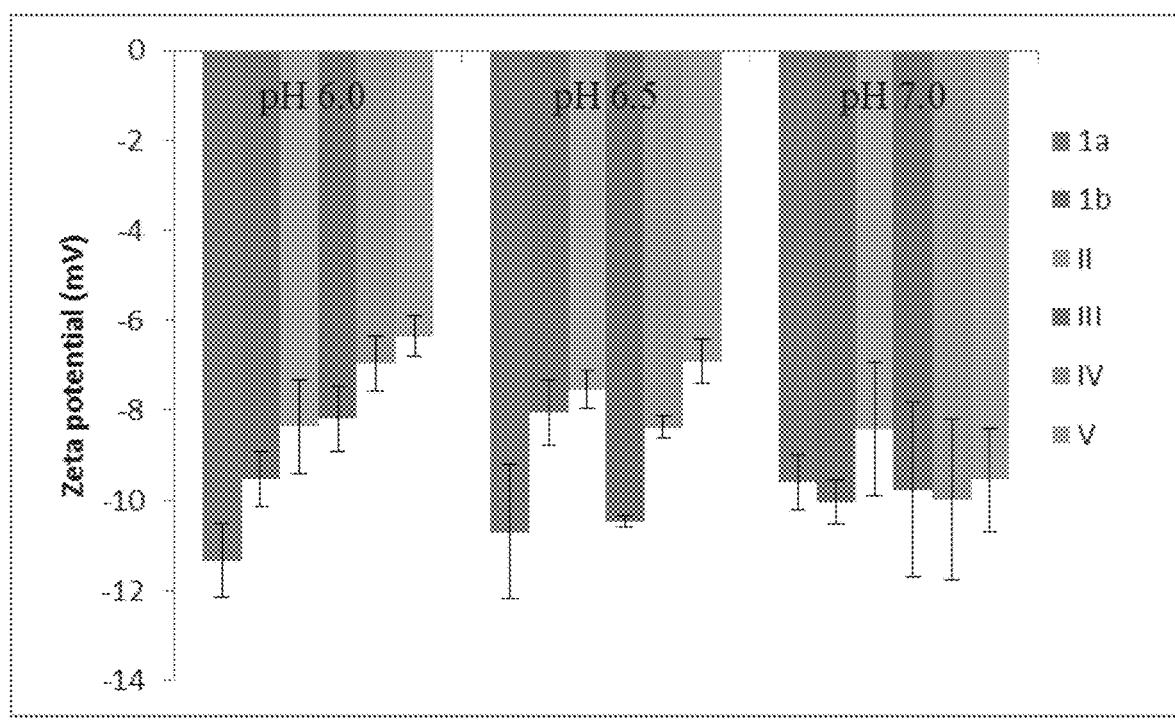
FIG. 29: Zeta potential of conjugates of GBS serotypes Ia, Ib, II, III, IV, and V as a function of pH.

Additional studies were performed to test the effect of three physical properties on resuspension: (1) surface charge or Zeta potential using a Zetasizer Nano ZS (Malvern Instruments Ltd.); (2) particle size using a Mastersizer 3000 laser diffraction particle size analyzer (Malvern Instruments Ltd.); and (3) sedimentation or settling rate using a LUMI-SIZER® Dispersion Analyzer (L.U.M. GmbH). The Zeta potential of AlPO$_4$ and conjugates of GBS serotypes Ia, Ib, II, III, IV, and V as a function of pH are shown in FIGS. 28 and 29, respectively. The Zeta potential and particle size of various GBS6 and monovalent GBS formulations are summarized in Table 38. The zeta potential values of 15 formulations were about −7 to −10 mV. There was no correlation observed between the surface charge and resuspension for these samples. On the other hand, resuspension was affected by particle size. Particle size for the low dose formulation was larger than that of the high dose formulation in GBS6 and monovalent preparations, and generally, the smaller the particle size, the more difficult it was to uniformly resuspend the formulation.

TABLE 38

Comparison of Zeta Potential and Particle Size of GBS6 and Monovalent Formulations in High and Low Doses

| | | Zeta | Particle Size | | | # |
|---|---|---|---|---|---|---|
| Formulation | Conc. (mcg/mL) | Potential (mV) | D10 (μm) | D50 (μm) | D90 (μm) | Shakes at T0 |
| 1 GBS | 60 | −7.1 | 6.3 | 11.6 | 24.5 | 17 |
| 2 Hexavalent | 240 | −8.5 | 4.2 | 7.1 | 12.6 | 96 |
| 3 Monovalent | 60 | −8.8 | 6.1 | 11.8 | 25.1 | 16 |
| 4 Type Ia | 240 | −10.0 | 4.3 | 7.2 | 14.3 | 33 |
| 5 Monovalent | 60 | −8.7 | 6.7 | 12.4 | 23.1 | 21 |
| 6 Type Ib | 240 | −10.2 | 4.0 | 7.2 | 14.1 | 27 |
| 7 Monovalent | 60 | −8.0 | 6.7 | 12.9 | 25.5 | 16 |
| 8 Type II | 240 | −7.1 | 3.9 | 7 | 15 | 29 |
| 9 Monovalent | 60 | −9.6 | 11 | 20.8 | 37.3 | 16 |
| 10 Type III | 240 | −9.6 | 4.8 | 9.1 | 32.6 | 34 |
| 11 Monovalent | 60 | −9.0 | 5.4 | 9.1 | 16.4 | 17 |
| 12 Type IV | 240 | −7.1 | 3.8 | 7.7 | 22.9 | 95 |
| 13 Monovalent | 60 | −7.7 | 5.3 | 9.1 | 17.0 | 15 |
| 14 Type V | 240 | −8.3 | 4.1 | 7.2 | 13.0 | 62 |
| 15 AlPO$_4$ placebo | 500 | −9.1 | 4.4 | 7.1 | 11.6 | 11 |

Figure 30:
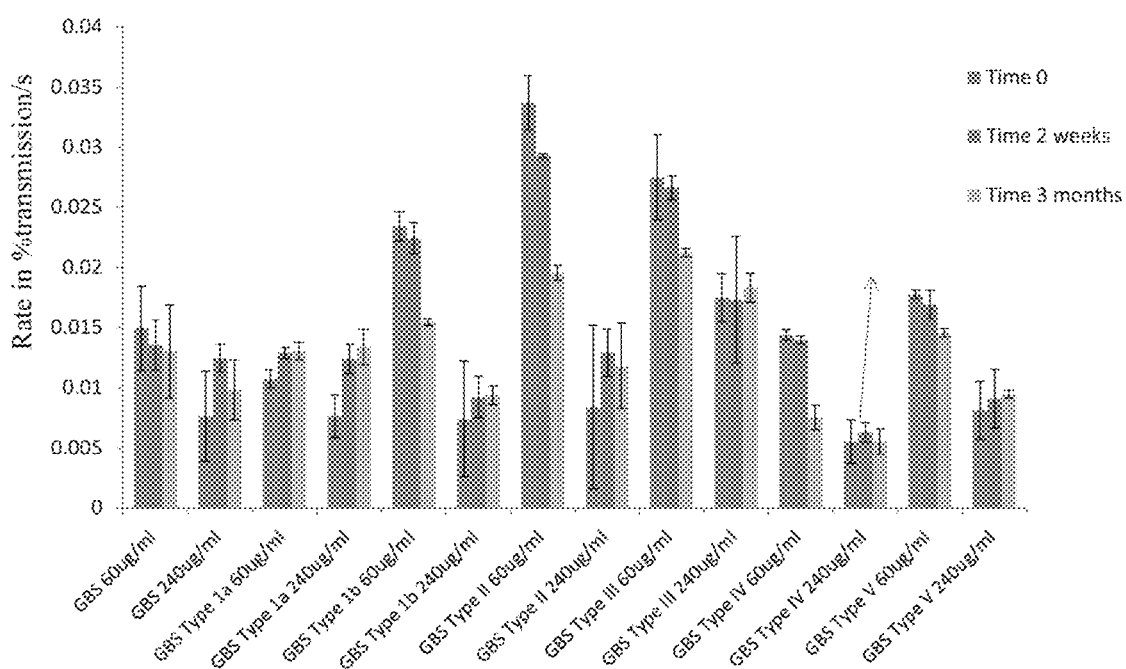
FIG. 30: Comparison of sedimentation rates of different GBS6 and monovalent formulations in high and low doses stored in pFS in the tip down orientation at Time 0, 2 weeks and 3 months.

The sedimentation rate was measured for the aluminum particles in the formulations at Time 0, 2 weeks, and 3 months. High dose formulations showed a lower sedimentation rate than low dose formulations. The sedimentation rate did not change following three months of storage at 5° C. A direct correlation was observed between resuspension and sedimentation rate: the faster the sedimentation rate, the easier the formulation was to resuspend. Moreover, low dose formulations, which had larger particle size than the high dose formulations, demonstrated faster sedimentation rate and easier resuspension. Data are shown in FIG. 30.

Example 18

Effect of GBS6 Formulation Factors on Sedimentation Rates

Figure 31:
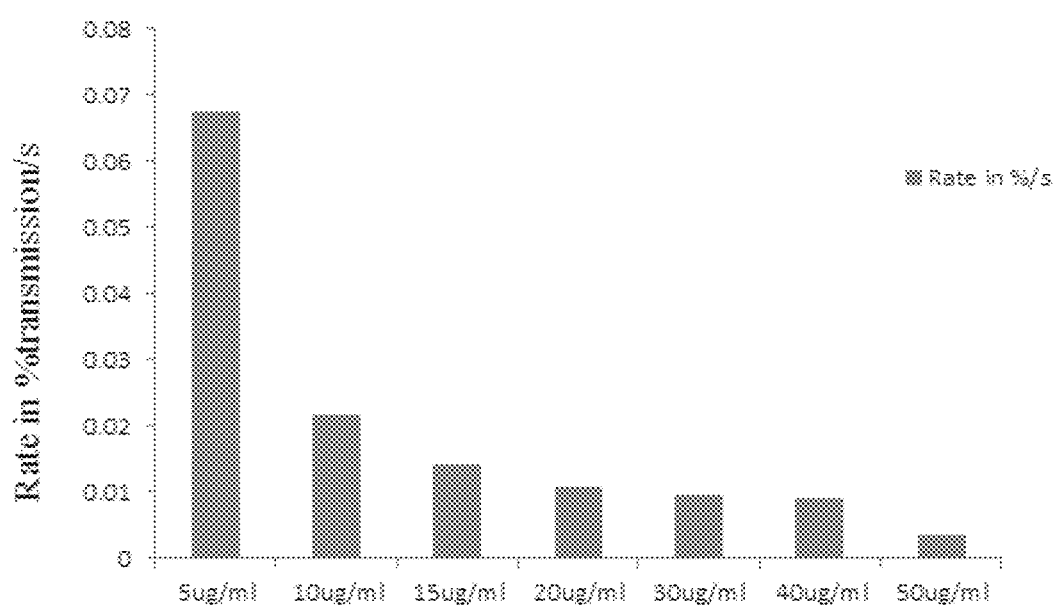
FIG. 31: Sedimentation rate of GBS6 formulations as a function of dose levels (concentration per serotype).

The impact of formulation factors such as antigen concentration, pH, and salt concentration on resuspension characteristics was studied. First, GBS6 formulations at various antigen concentrations in histidine buffers at pH 6.5 were investigated. Data from this study showed demonstrated that higher antigen concentration led to slower settling rate (see FIG. 31; dosage shown for each serotype), which would cause difficulty in resuspension. At low concentrations, particles can freely settle without interference from one another by way of collisions and/or Brownian motion.

Figure 32:
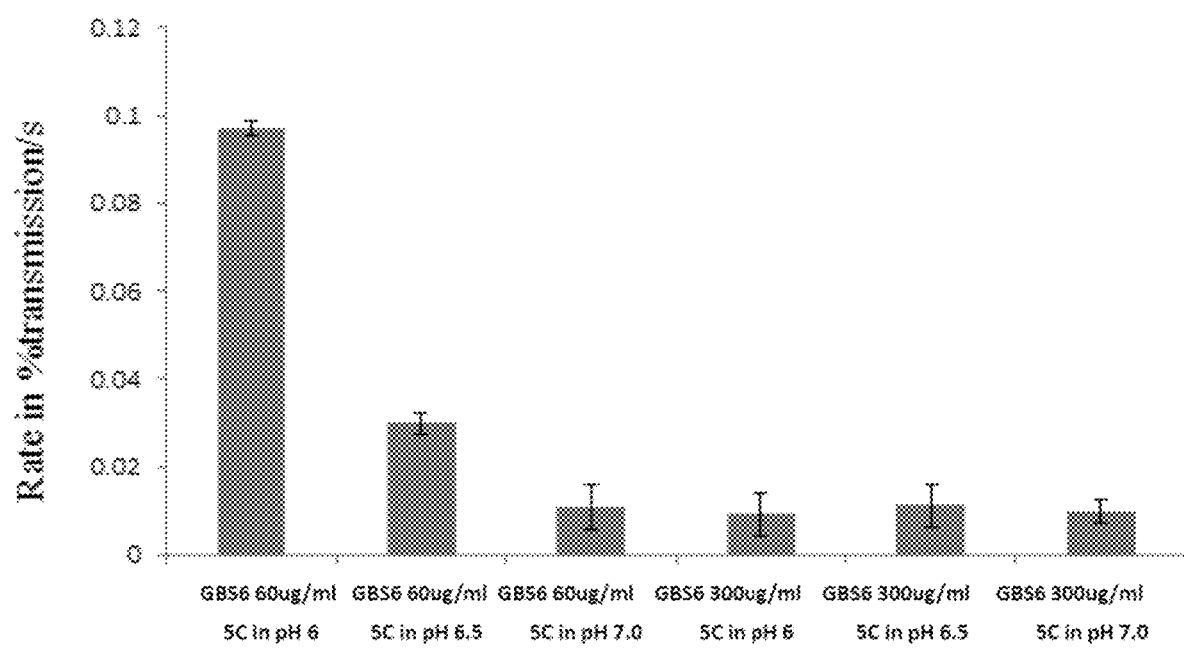
FIG. 32: Sedimentation rate of GBS6 formulations as a function of pH at low dose (60 mcg/mL) and high dose (240 mcg/mL).

Second, the sedimentation behavior of GBS6 formulations at total antigen concentrations of 60 mcg/mL and 300 mcg/mL in histidine buffers at pH 6.0, 6.5, and 7.0 were investigated. The sedimentation behavior of the 60 mcg/mL GBS6 formulations showed that the pH has a significant effect on the sedimentation rate. However, pH had no significant effect on sedimentation rate of the 300 mcg/mL GBS6 formulation. Data are shown in FIG. 32. The surface charge of AlPO$_4$ decreased from −10.3 mV to −7.9 mV when the pH was decreased from 7.0 to pH 6.0 (data not shown). Typically, a high zeta potential would indicate that the particles are fully dispersed in the medium because of the dominant repulsive forces that exist between the particles. In this case, the particles exist in suspension as separate entities, and the sedimentation rate is often slow because of the wide distribution of particle size, causing the particles to settle at different rates.

Figure 33:
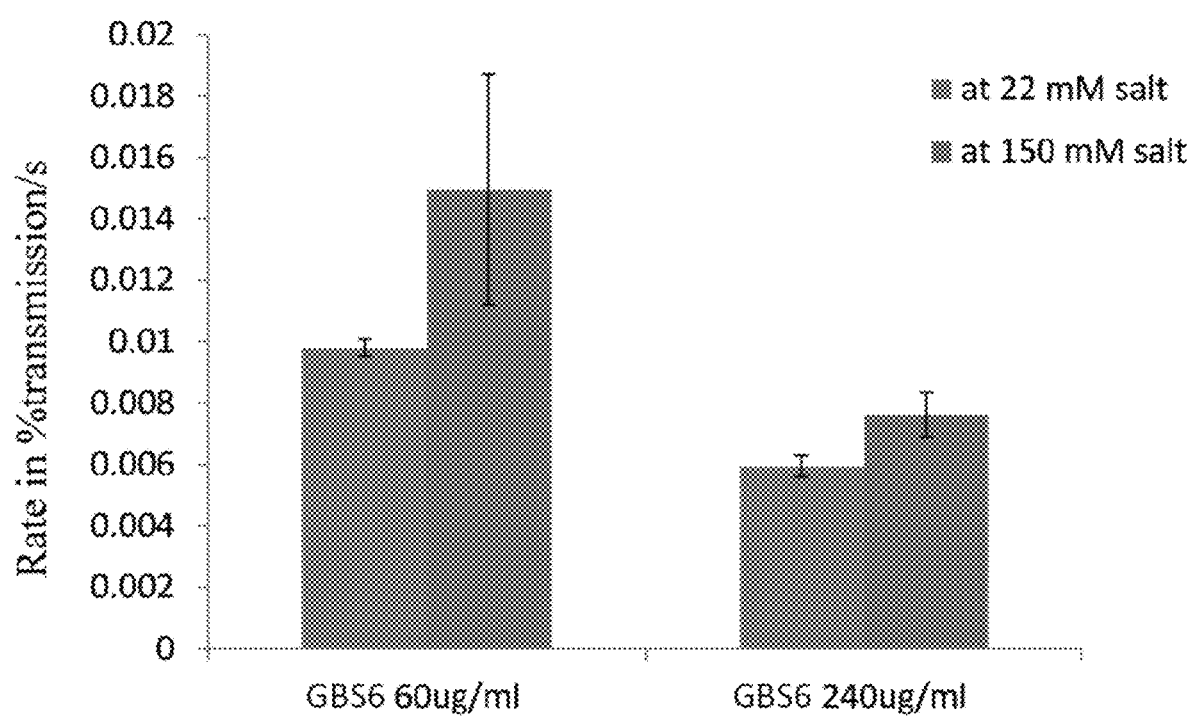
FIG. 33: Effect of dose and NaCl concentration on sedimentation rate.

Finally, the effect of ionic strength on the physicochemical properties of $AlPO_4$ and its subsequent impact on the suspension properties was also examined. The GBS6 formulations were prepared at three different dose levels (60 mcg/mL, 150 mcg/mL, and 20 mcg/mL total antigen) and two different NaCl concentrations (22 mM and 150 mM), The Zeta potential values become more negative when the salt concentrations were low. All three doses of the GBS6 formulations with minimal salt concentration (22 mM) were negatively charged. The Zeta potential values were about −16 to about −17 mV. By comparison, the high and low dose GBS6 formulations with 150 mM NaCl are about −8 mV. Higher salt concentration reduced the surface charge and accelerated the settling rate, which could improve resuspension. Data are shown in FIG. 33 and Table 39.

TABLE 39

Comparison of Zeta Potential and Particle Size of GBS6 Formulations with Different Doses and NaCl Concentration

| | | Zeta Potential (mV) | Particle Size | | |
|---|---|---|---|---|---|
| | Formulation | | D10 (μm) | D50 (μm) | D90 (μm) |
| 1 | GBS6 Low Dose and Low Salt (60 mcg/mL total antigen w/ 22 mM NaCl) | −15.9 | 5.4 | 10.0 | 20.2 |
| 2 | GBS6 Mid Dose and Low Salt (150 mcg/mL total antigen w/ 22 mM NaCl) | −17.0 | 3.8 | 7.8 | 19.7 |
| 3 | GBS6 High Dose and Low Salt (240 mcg/mL total antigen w/ 22 mM NaCl) | −17.0 | 3.9 | 7.0 | 14.3 |
| 4 | GBS6 Low Dose and High Salt (60 mcg/mL total antigen w/ 150 mM NaCl) | −7.1 | 6.3 | 11.6 | 24.5 |
| 5 | GBS6 High Dose and High Salt (240 mcg/mL total antigen w/ 150 mM NaCl) | −8.5 | 4.2 | 7.1 | 12.6 |

Example 19

Resuspension Behavior of Different Antigens and Aluminum Salts

A study was conducted to further investigate whether the correlation between antigen concentration and difficulty in resuspending the formulation was specific to GBS or a common attribute for other antigens, such as proteins, polysaccharides, and non-GBS polysaccharide-protein conjugates. Formulations comprising $CRM_{197}$; a combination of polysaccharides from GBS serotypes Ia, Ib, II, III, IV, and V; BSA; or a combination of 20 pneumococcal polysaccharide-protein conjugates (20vPnC) were formulated at the same high dose (240 mcg/mL total antigen) in the same buffer matrix and 0.5 mg/mL $AlPO_4$ adjuvant as the GBS formulations tested in Examples 17 and 18. GBS6 formulated with ALHYDROGEL® 85 (Brenntag Biosector A/S) was also included as a comparator. Samples were tested for the following attributes: 1) resuspension time (time required to resuspend the pellet in 1.5 mL centrifuge tubes using a hand motion shaker after 30-45 minutes centrifugation at 200 rpm), 2) settling in cylinders by visual observation (sedimentation bed height at different time intervals), 3) particle size, 4) surface charge, and 5) particle size distribution using a MICRO-FLOW IMAGING® (MFI) Flow DPA 4200 Microscope (Brightwell Technologies Inc.).

Figure 34:
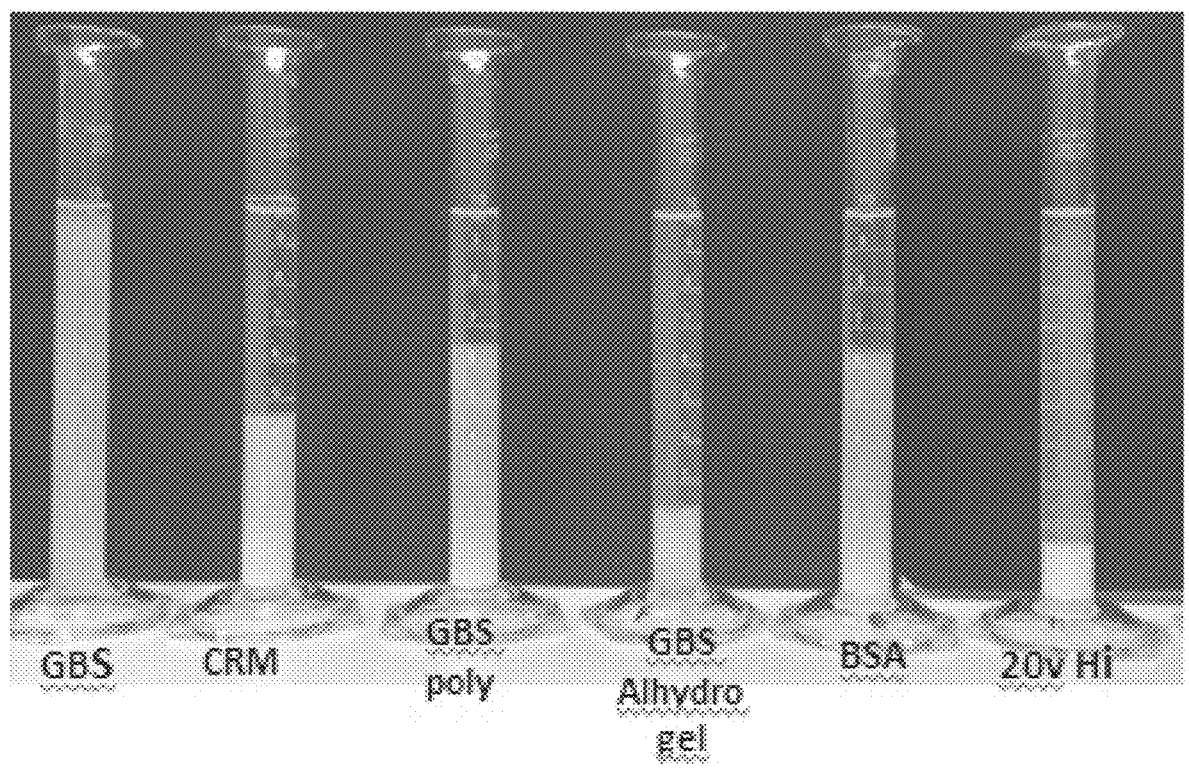
FIG. 34: Comparison for settling behavior of different antigen formulations after 45 minutes.
Figure 35A:
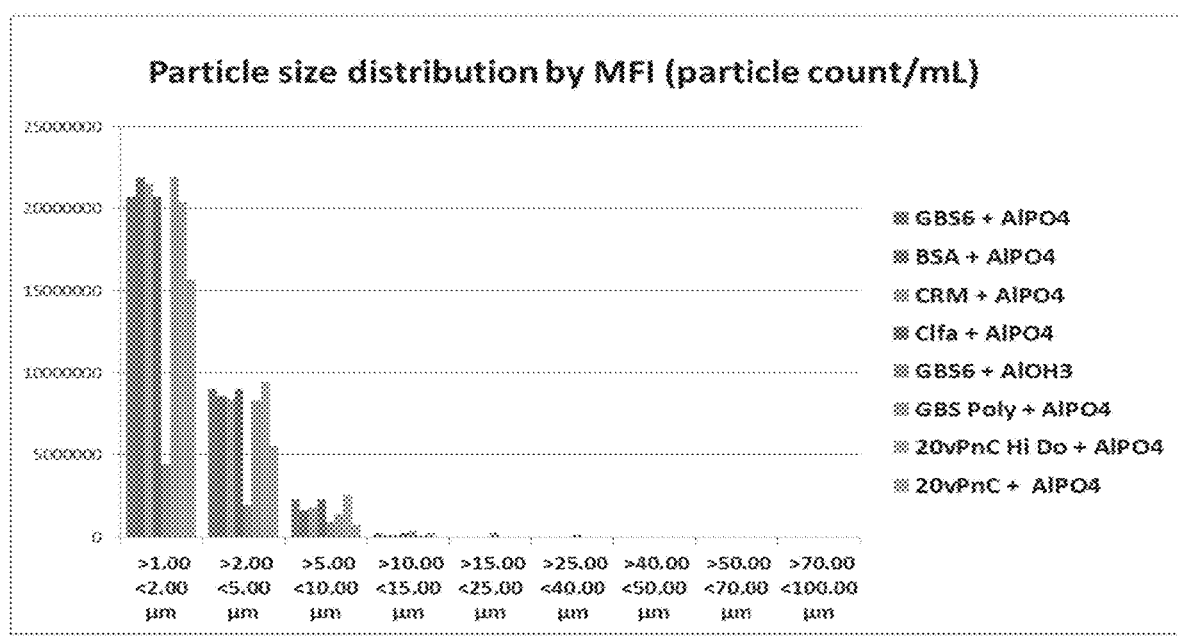
FIG. 35A: Detailed particle size distribution of different antigen formulations.
Figure 35B:
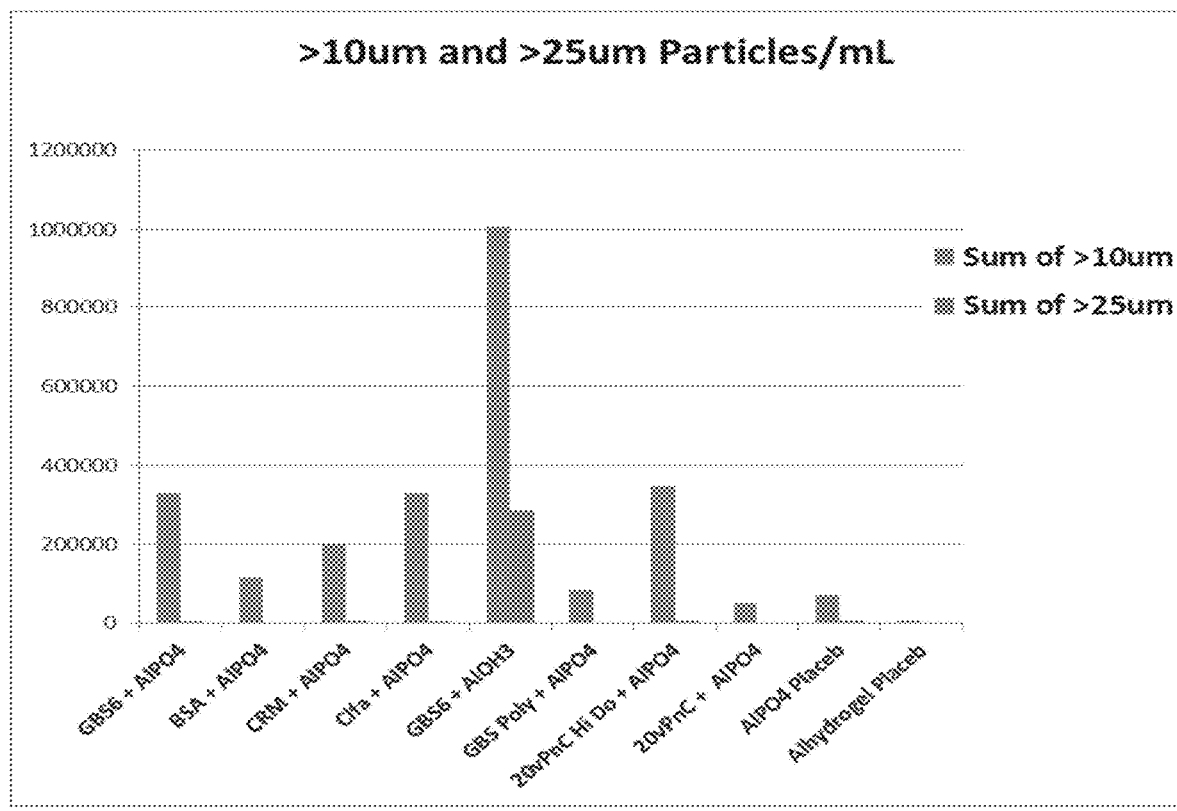
FIG. 35B: Particle size distribution of different antigen formulations categorized as either ≥0 μm or ≥25 μm.

The different antigens demonstrated varied settling and resuspension behaviors (data are shown in FIG. 34 and Table 40, respectively). The formulations that settled faster were easier to resuspend as observed earlier. There was no correlation observed between resuspension and average particle size or particle size distribution. Particle size distribution data are shown in FIGS. 35A and 35B. However GBS6 formulations comprising ALHYDROGEL® 85 were the easiest to resuspend and showed significantly larger particle size, faster rate of settling, and low surface charge, suggesting that particle size and surface charge correlate with resuspension. It should be noted that the aluminum hydroxide is positively charged at pH 6.5 while the conjugates are negatively charged, leading to a strong electrostatic interaction and higher neutralization of charges. By contrast, $AlPO_4$ is negatively charged at pH 6.5.

TABLE 40

Comparison of Particle Size, Resuspension Time, and Zeta Potential of Different Antigen Formulations

| Antigen | Particle Size | | | Resuspension Time (sec) | Zeta Potential (mV) |
|---|---|---|---|---|---|
| | D10 | D50 | D90 | | |
| GBS6 | 4.5 | 7.4 | 12.6 | 75 | −8.1 |
| $CRM_{197}$ | 5.1 | 7.4 | 11.1 | 20 | −6.4 |
| GBS Polysaccharides | 4.8 | 6.9 | 9.7 | 10 | −7.1 |
| BSA | 4.8 | 6.9 | 10.1 | 15 | −6.6 |
| 20vPnC | 7.7 | 14.8 | 28.9 | 25 | −6.9 |
| GBS6 + ALHYDROGEL ® 85 | 15.0 | 26.8 | 46.9 | 15 | −5 |

Example 20

Modification of Device Configuration

Figure 36:
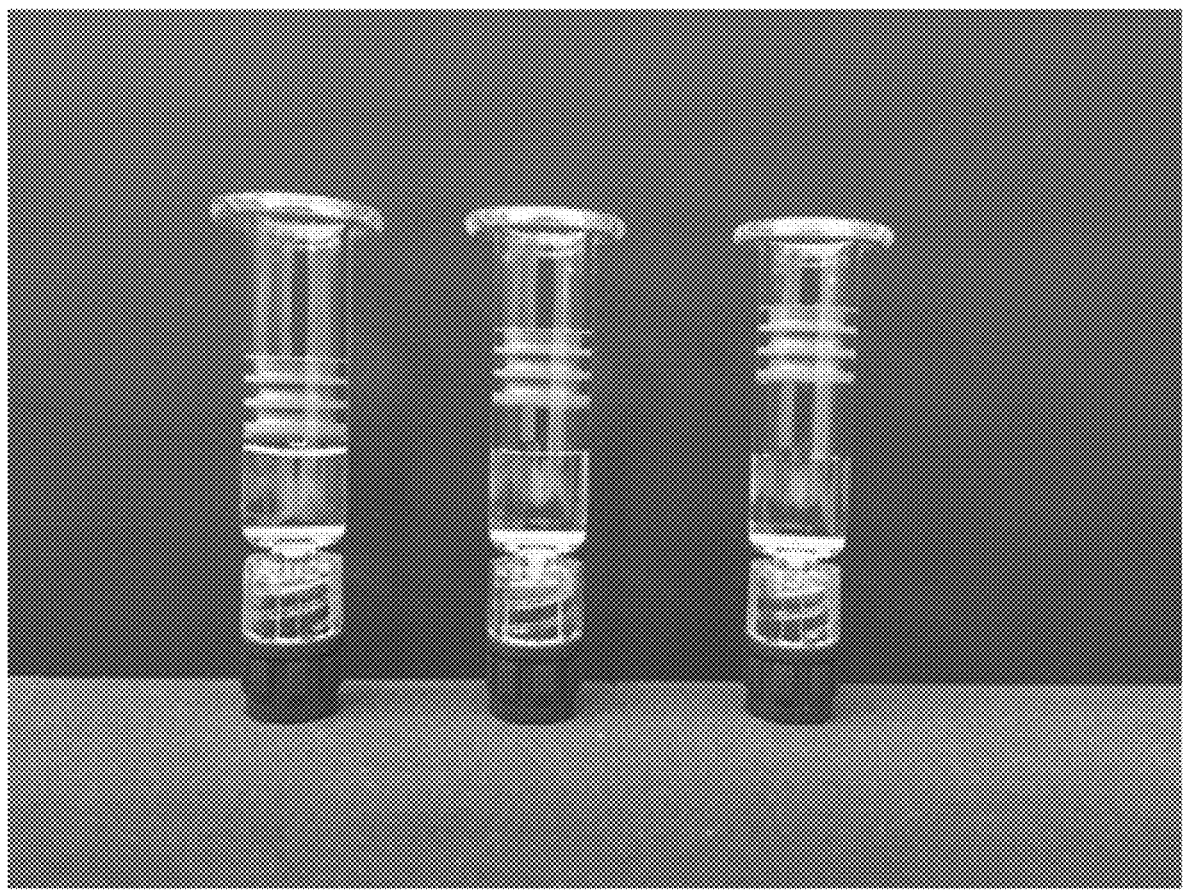
FIG. 36: GBS6 formulations in PFS with varying headspace.
Figure 37:
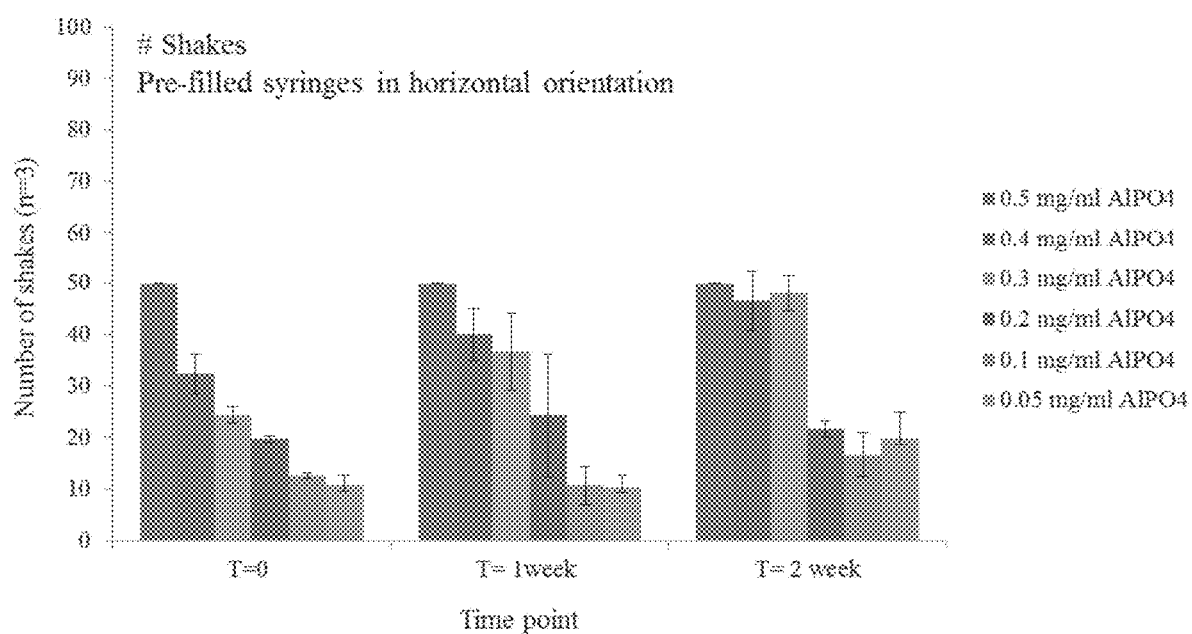
FIG. 37: Number of shakes required to resuspend high dose GBS6 formulations with varying concentrations of $AlPO_4$ after 2 weeks of storage in the horizontal position.
Figure 38:
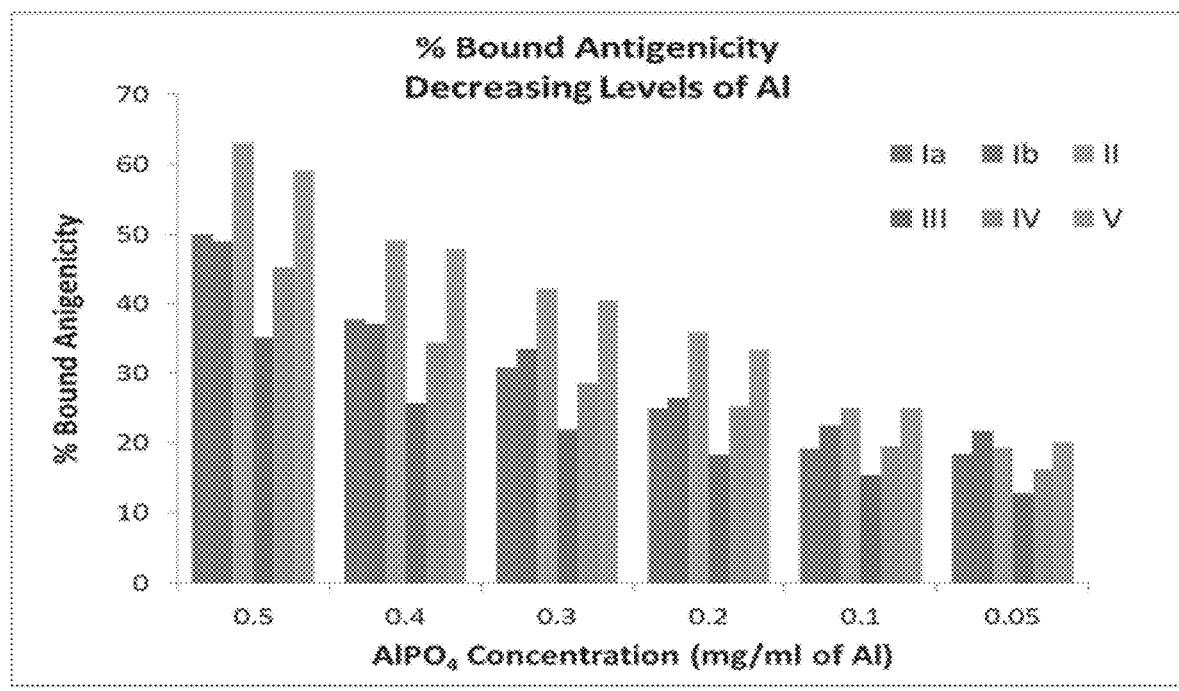
FIG. 38: Binding of conjugates of GBS serotypes Ia, Ib, II, III, IV, and V with varying concentrations of $AlPO_4$ after 2 weeks of storage in the horizontal position.
Figure 39:
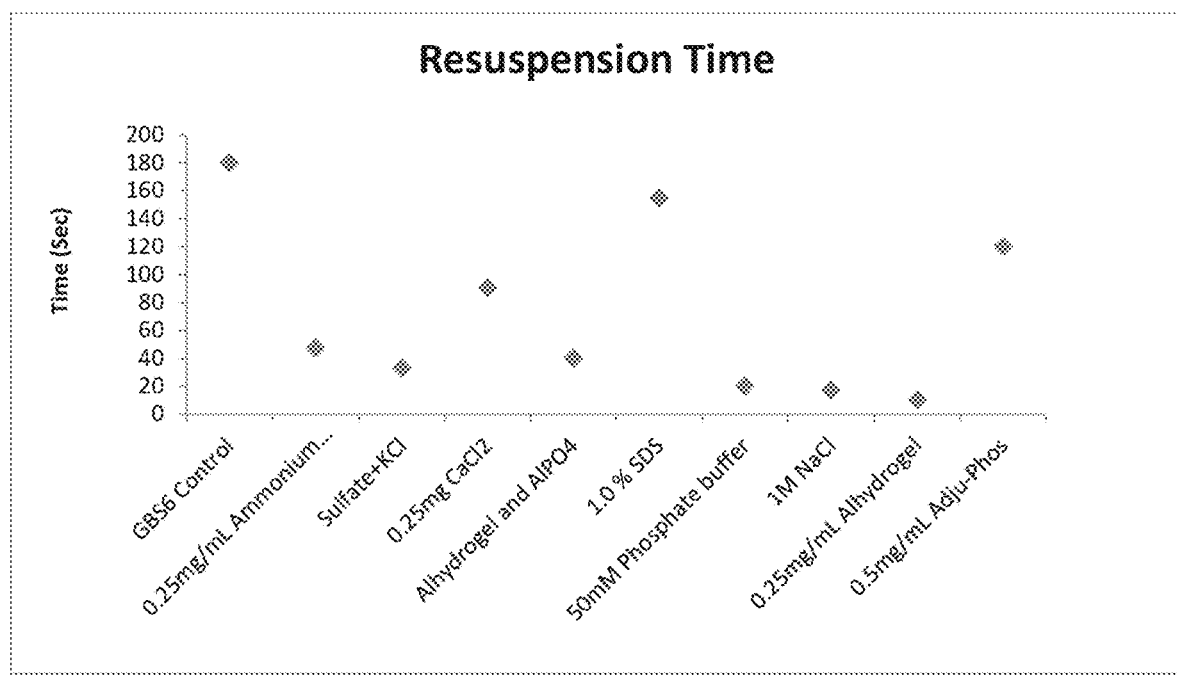
FIG. 39: Effect of different flocculating agents and aluminum salts on resuspension.
Figure 40:
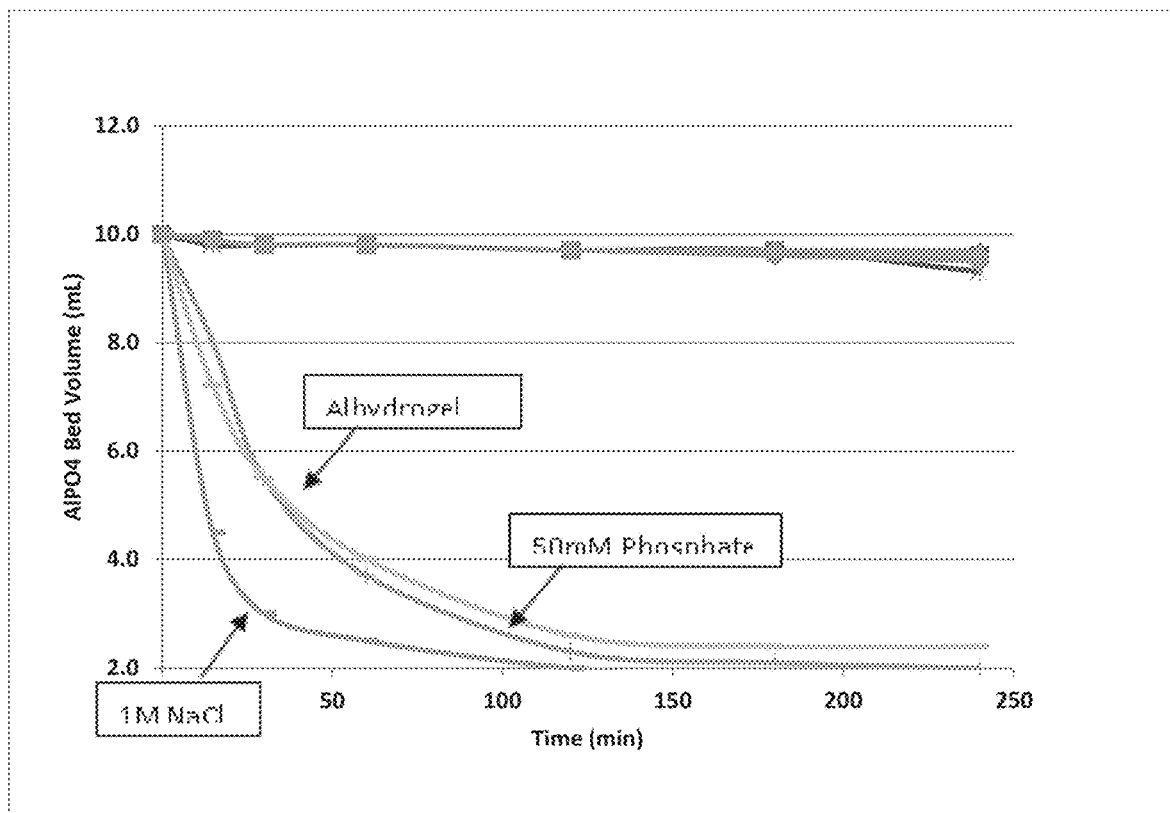
FIG. 40: Effect of different flocculating agents and aluminum salts on settling rate.
Figure 41:
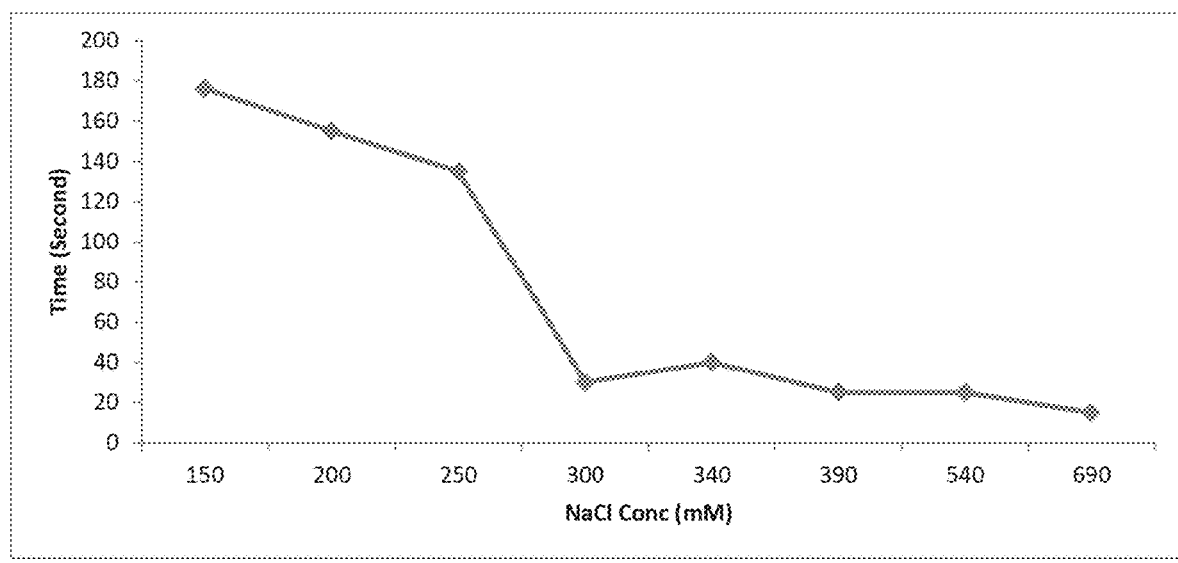
FIG. 41: Effect of NaCl concentrations on resuspension time of high dose GBS6 formulations.
Figure 42:
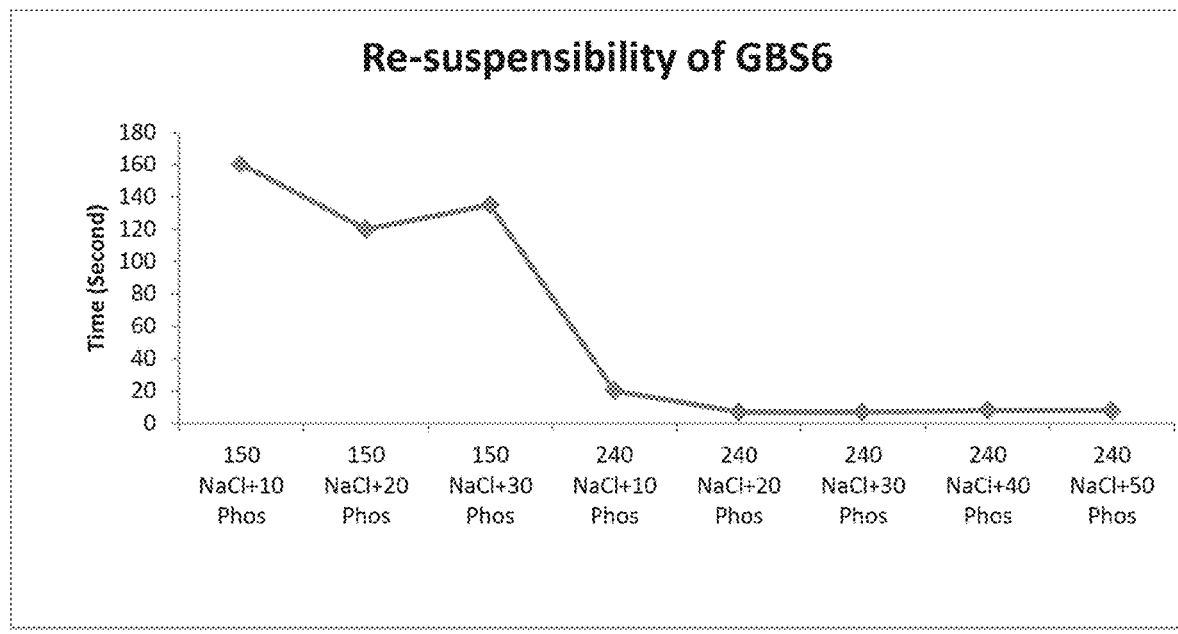
FIG. 42: Effect of combination of NaCl and phosphate ions on resuspension time.
Figure 43A:
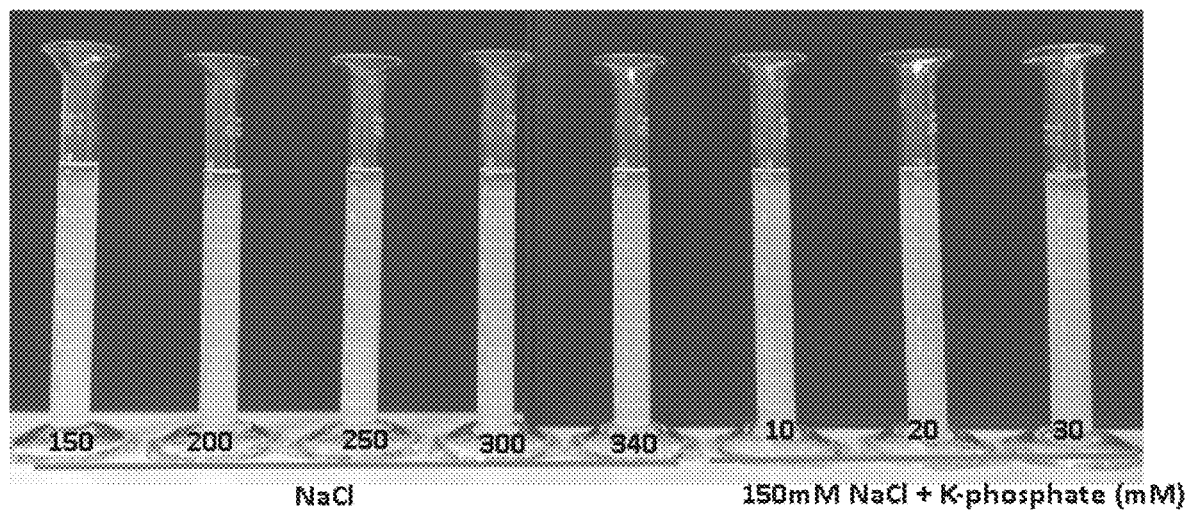
FIG. 43A: Effect of NaCl and potassium phosphate concentrations on settling after 2 hours.
Figure 43B:
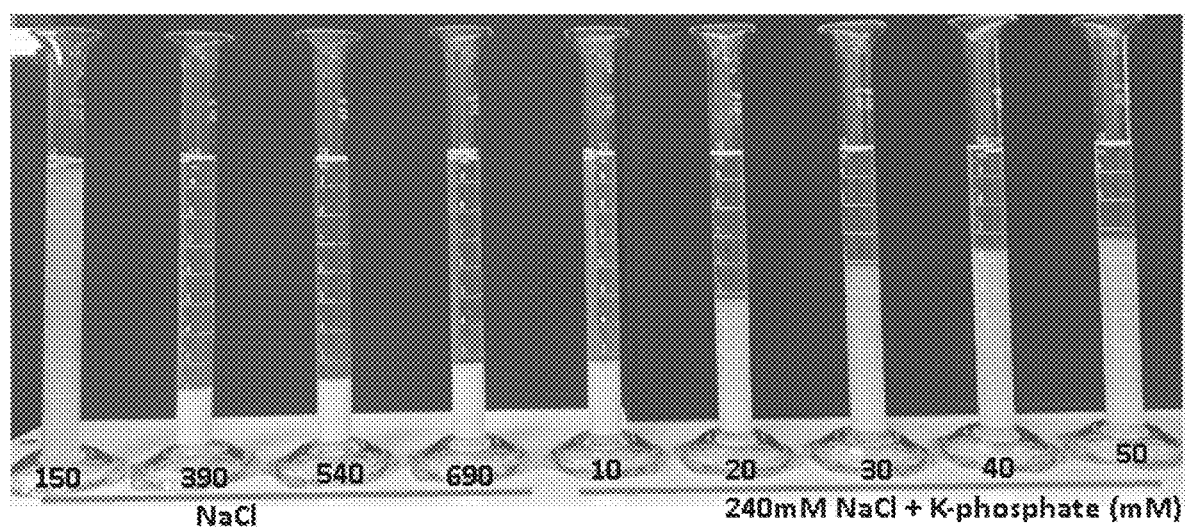
FIG. 43B: Effect of NaCl and potassium phosphate concentrations on settling after 30 minutes.
Figure 44:
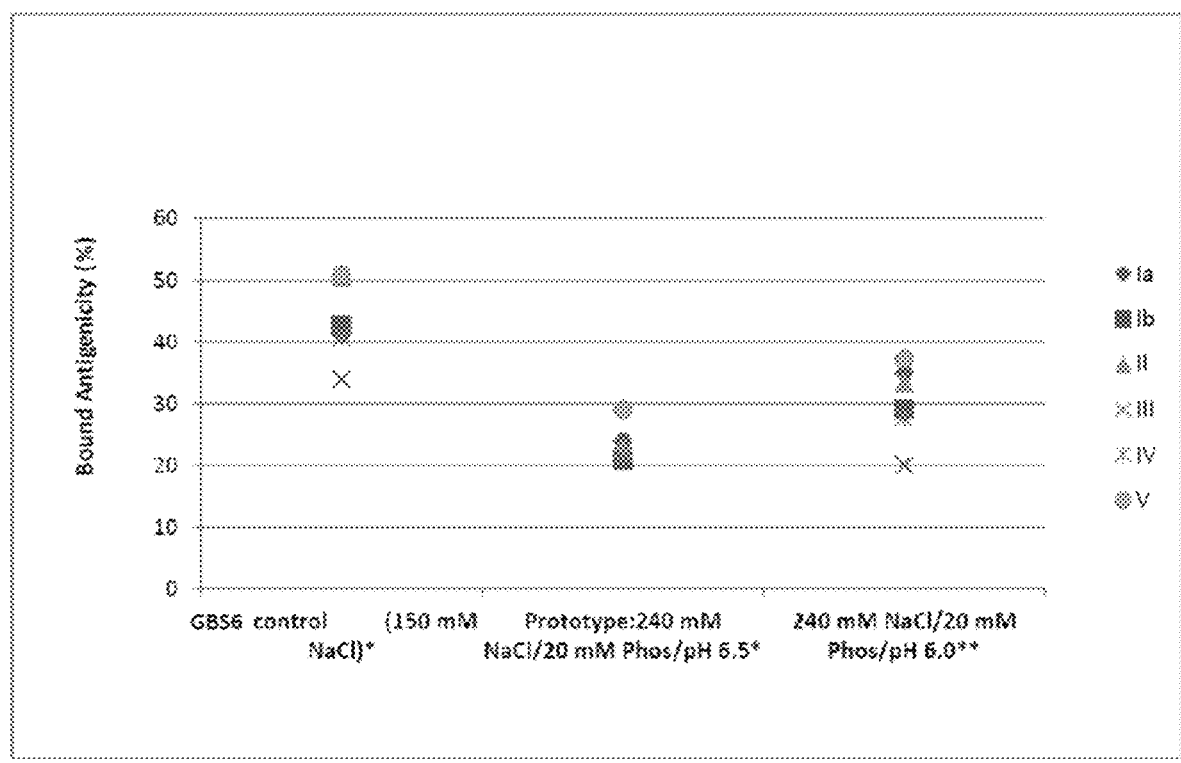
FIG. 44: Percent bound antigenicity of GBS6 formulation comprising 20 mM phosphate and 240 mM NaCl in comparison to the control GBS6 formulation.

The studies indicated that the formulations resuspended easily in a vial, but not in PFS, both of which are made from Type 1 glass and use rubber stoppers. The key difference between the two systems, however, is the available head space that allows for free mixing of the formulation, which leads to a more uniformly resuspended product. Therefore, the effect of headspace was investigated as a factor impacting resuspension in PFS to understand if a higher headspace in PFS would allow for more mixing. Syringes were filled with high dose GBS6 formulations (with $AlPO_4$), stoppered with varying headspace (2 mm, 6 mm, and 10 mm; shown in FIG. 36), and stored in an horizontal orientation at 2-8° C. Resuspension behavior (# shakes) was tested after of 2 weeks storage time. The data indicated that increasing headspace decreased the number of shakes required for resuspension. Data are shown in Table 41. The ease of resuspension was attributed to an increased turbulence due to higher headspace that allowed easier mixing. This behavior is evident in vials as well, which do not show any resuspension challenges (due to the larger headspace).

TABLE 41

| Effect of Increasing Headspace on Resuspension Characteristics of GBS6 Formulations | |
|---|---|
| Headspace (±1 mm) | # Shakes* |
| 2 | >50 |
| 6 | 17 |
| 10 | 10 |

Storage time: 2 weeks at 2-8° C.
*Average of 3 samples

Example 21

Impact of Aluminum Concentration

A study was conducted to determine the impact of aluminum concentration on the ability to resuspend the formulation. This was done by evaluating GBS6 formulations with decreasing $AlPO_4$ concentrations. GBS6 formulations were prepared at a high dose (240 mcg/mL total antigen) in the same buffer matrix with concentrations of aluminum levels ranging from 0.5-0.05 mg/mL. Samples were filled into BD HYPAK SCF™ PRTC (Becton, Dickinson and Company) 1 mL short, glass PFS with 0.58 mL fill volume; capped with 4432/50 stoppers (West Pharmaceutical Services, Inc.), keeping a headspace of about ~0.4 mm; and stored horizontally. Resuspension was tested at 0, 1, 2, and 4 weeks at 5° C. The total and bound antigenicity for each of the serotypes in the individual formulations was analyzed by nephelometry using serotype-specific polyclonal antibodies.

Although a decrease in aluminum levels had a positive effect on resuspension, formulations with 0.3 mg/mL aluminum still needed more than 20 shakes at T0 and more than 50 shakes at 2 weeks. Formulations containing 0.05 mg/mL aluminum required about 20 shakes after 2 weeks of horizontal storage. Data are shown in FIG. 37.

A decrease in the amount of antigen bound to aluminum was also observed. Data are shown in FIG. 38.

Example 22

Screening of Different Flocculating Agents

A suspension with fine particles shows a slow settling velocity and will result in a low-volume, high density settlement that would be difficult or impossible to resuspend. Resuspension properties can be controlled by pharmaceutical manipulation, such as adding flocculating agents to neutralize the surface charge on the suspended particles and allows the formation of bigger particle floccules, or clusters, hence increasing the sedimentation velocity and improving resuspension. The difference in sedimentation behavior between the non-flocculated and flocculated suspensions is illustrated in Table 42.

TABLE 42

| Comparison of Non-flocculated and Flocculated Suspensions | | |
|---|---|---|
| | Non-flocculated | Flocculated |
| 1 | Solids present as individual particles, low aggregation | Solids present as aggregates |
| 2 | Particles exhibit repulsive forces | Particles exhibit attractive or low repulsive forces |
| 3 | Rate of sedimentation is slow and particle size is small | Rate of sedimentation is high particles form loose aggregates |
| 4 | Particle settle as a cake | Particle settle as flocks |

Incorporation of flocculating agents into GBS6 formulations was taken as an approach to improve resuspension properties. The following flocculating agents and aluminum-based salt were evaluated for their effect on sedimentation rate and resuspension of a high dose GBS6 formulation:

Flocculating Agents:

1. GBS6 control (GBS6 comprising 20 mM His buffer, 150 mM NaCl, 0.02% PS80, and 0.5 mg/mL AlPO4 at pH 6.5)
2. Ammonium sulfate (0.25 mg/mL)
3. Ammonium sulfate and KCl (0.25 mg/mL and 20 mM)
4. $CaCl_2$ (0.25 mg/mL)
5. SDS (1%)
6. Potassium phosphate (50 mM)
7. NaCl (1M)

Aluminum-Based Salts:

1. ALHYDROGEL® 85 (Brenntag Biosector A/S) [Al $(OH)_3$; 0.25 mg/mL]
2. ADJU-PHOS® (Brenntag Biosector A/S) (0.5 mg/mL)
3. $AlPO_4$ and $Al(OH)_3$ (1:1 mix of 0.25 mg/mL each)

High dose (240 μg/mL) GBS6 formulations were prepared comprising 20 mM histidine, 150 mM NaCl, 0.02% PS80, and 0.5 mg/mL $AlPO_4$ at pH 6.5 with either one of the flocculating agents listed above or one of the aluminum-based salts listed above. Samples were tested for accelerated resuspension time (after spinning the samples for 45 minutes at 200 rpm in 1.5 mL centrifuge tubes), settling rate, particle size, surface charge, and total and bound conjugates.

Among all the flocculating agents tested, NaCl and potassium phosphate were able to greatly reduce the resuspension time to less than 20 seconds compared to 180 seconds for GBS6 control. Data are shown in FIG. 39 and Table 42. The settling rate of these two samples was also faster than the other formulations with calcium or ammonium salts or SDS. Data are shown in FIG. 40. The formulation containing 1M NaCl had large particle size and low surface charge as expected based on the theory of flocculation. However, the same was not observed with samples containing 50 mM phosphate, suggesting that phosphate facilitated the resuspension through a different mechanism than NaCl. Data are shown in Table 42.

Among the two aluminum salts tested, ALHYDROGEL® 85 demonstrated superior resuspension behavior than ADJU-PHOS®. A major concern for a formulation containing ALHYDROGEL® 85 is that it binds to antigens tightly, as shown by the higher binding strength to antigens compared to $AlPO_4$. Data are shown in Table 43. This phenomenon has been reported to have adverse impact on the immune response of the vaccine. Egan, P. M., et al., Vaccine, 27:3175-3180 (2009).

TABLE 43

Resuspension Characteristics of GBS6 Formulations with a Flocculating Agent or Aluminum Salt

| | Particle Size (μm) | | | Resus-pension Time | Zeta Poten-tial | Bind-ing |
|---|---|---|---|---|---|---|
| Batch 00708311-114 | D10 | D50 | D90 | (sec) | (mOsm) | (%) |
| 1 GBS6 Control | 4.46 | 7.25 | 12.27 | 180 | −7.9 | 40.8 |
| 2 0.25 mg/mL Ammonium sulfate | 4.40 | 7.23 | 11.90 | 47 | −7.2 | 36.8 |
| 3 Sulfate + KCl | 4.62 | 7.81 | 15.83 | 33 | −7.8 | 37.1 |
| 4 0.25 mg CaCl2 | 4.47 | 7.34 | 13.27 | 90 | −6.9 | 40.5 |
| 5 ALHYDRO-GEL ®85 and $AlPO_4$ | 4.96 | 6.95 | 9.76 | 40 | −9.2 | 68.2 |
| 6 1.0% SDS | 5.13 | 6.94 | 9.52 | 155 | −20.0 | 17.6 |
| 7 50 mM Phosphate buffer | 4.53 | 7.27 | 12.33 | 20 | −12.5 | 10.8 |
| 8 1M NaCl | 7.10 | 13.10 | 25.13 | 17 | −1.5 | 11.2 |
| 9 0.25 mg/mL ALHYDROGEL ® 85 | 12.80 | 23.20 | 42.10 | 10 | −5.3 | 93.1 |
| 10 0.25 mg/mL ADJU-PHOS ® | 2.37 | 5.27 | 18.87 | 120 | −8.5 | 16.2 |

Example 23

Optimization of NaCl and Phosphate Levels

A study was conducted to optimize the concentrations of NaCl and potassium phosphate to levels that would not only meet the desired resuspension characteristics, but also other attributes such as osmolality and antigen binding to aluminum, which are two important aspects associated with reactogenicity and the potency of a vaccine.

High dose (240 mcg/mL total antigen) GBS6 formulations were prepared comprising varying concentrations of NaCl (150-690 mM), 20 mM histidine, 0.02% PS80, and 0.5 mg/mL $AlPO_4$ at pH 6.5. Formulations were also prepared comprising varying potassium phosphate concentrations (10-50 mM) and two different NaCl concentrations (150 mM and 240 mM) to investigate the combination effect of the two salts. Formulated bulk samples were tested for settling rate, resuspension time after centrifugation, particle size, and surface charge.

Increasing NaCl concentration significantly reduced the resuspension time. Data are shown in FIG. 41. There was a sharp decrease of resuspension time at 300 mM NaCl, suggesting the formulation turned from deflocculated to flocculated state, and 300 mM NaCl concentration was the critical coagulation concentration (CCC) for this transition. The CCC was reduced to 240 mM in presence of 10 mM or more phosphate, suggesting that there was a synergistic effect with NaCl and phosphate. Data are shown in FIG. 42. Fast settling and flocculated sediments were observed with samples containing 10-30 mM phosphate with 240 mM NaCl, as shown in FIGS. 43A and 43B. Zeta potential and particle size data revealed that increase in NaCl concentration lead to reduction of surface charge and increase in particle size, which supported the flocculation theory. This trend was not clear with phosphate. Data are shown in Table 44. Based on the results from this study, 240 mM NaCl and 20 mM phosphate were considered optimal target concentrations.

TABLE 44

Effect of NaCl and Phosphate on Zeta Potential and Particle Size

| | Zeta Potential | | Particle Size | | |
|---|---|---|---|---|---|
| | ZP (mV) | Stdv | D10 | D50 | D90 |
| 150 mM NaCl | −9.1 | 0.5 | 2.6 | 5.5 | 16.3 |
| 200 mM NaCl | −7.6 | 0.8 | 3.3 | 6.3 | 12.4 |
| 250 mM NaCl | −8.2 | 0.9 | 3.5 | 6.6 | 15.4 |
| 300 mM NaCl | −5.5 | 0.5 | 4.3 | 7.1 | 11.9 |
| 390 mM NaCl | −6.8 | 0.9 | 4.6 | 7.2 | 11.5 |
| 540 mM NaCl | −5.1 | 0.5 | 5.3 | 9.3 | 19.9 |
| 690 mM NaCl | −3.4 | 0.5 | 5.9 | 10.8 | 22.9 |
| 150 mM NaCl + 10 mM Phos | −8.9 | 0.4 | 3.4 | 6.3 | 11.1 |
| 150 mM NaCl + 20 mM Phos | −8.3 | 0.8 | 3.2 | 6.2 | 12.6 |
| 150 mM NaCl + 30 mM Phos | −9.9 | 0.9 | 3.2 | 6.2 | 12.2 |
| 240 mM NaCl + 10 mM Phos | −6.0 | 0.4 | 5.3 | 6.5 | 7.9 |
| 240 mM NaCl + 20 mM Phos | −10.5 | 0.9 | 4.3 | 7.1 | 11.6 |
| 240 mM NaCl + 30 mM Phos | −5.5 | 2.1 | 4.5 | 7.4 | 13.4 |

Three batches of a GBS6 formulation comprising a polysaccharide concentration of 40 mcg/mL of each serotype (240 mcg/mL total antigen), 20 mM phosphate, 240 mM NaCl, 0.02% PS80, and 0.5 mg/mL $AlPO_4$ at pH 6.5 was further characterized. A formulation of GBS6 comprising 20 mM His buffer, 150 mM NaCl, 0.02% PS80, and 0.5 mg/mL $AlPO_4$ at pH 6.5 was included as a control. All 3 formulations with the additional NaCl and phosphate at pH6.5 demonstrated easy resuspension with an average resuspension time of 16 seconds (compared to 120 seconds of the control) and osmolality above 500 mOsm. Bound antigenicity was about 20% lower than the control for each of the serotypes. Data are shown in Table 45.

TABLE 45

Characterization of GBS6 Formulations with Additional NaCl and Phosphate

| | Resuspension | Osmo | Zeta Potential | Antigen Binding to AlPO4 (%) | | | | | | Particle size (μm) | | |
|---|---|---|---|---|---|---|---|---|---|---|---|---|
| | (sec) | (mOsm) | (mV) | Ia | Ib | II | III | IV | V | D10 | D50 | D90 |
| GBS6 Control | 120 | 316 | −9.1 | 41 | 43 | 51 | 34 | 41 | 51 | 2.6 | 5.5 | 16.3 |
| GBS6 with 20 mM phosphate & 240 mM NaCl at pH 6.5* | 16 | 519 | −6.0 | 24 | 21 | 23 | 21 | 22 | 29 | 5.3 | 6.5 | 7.9 |

*Average of 3 batches.

Example 24

Short-term Stability of GBS6 Formulations Containing 240 mM NaCl and 20 mM Phosphate Three doses (60 mcg/mL, 120 mcg/mL, and 240 mcg/mL of total antigen) of GBS6 formulations comprising 20 mM phosphate, 240 mM NaCl, 0.02% polysorbate 80, and 0.5 mg/mL AlPO$_4$ at pH 6.5 were filled into BD HYPAK SCF™ PRTC (Becton, Dickinson and Company) 1 mL short, glass PFS with 0.58 mL fill volume and capped with 4432/50 stoppers (West Pharmaceutical Services, Inc.), keeping a headspace of about ~0.4 mm. Resuspension at both tip down and horizontal orientations were monitored for stability for 1 month at RT and 3 months at 5° C.

One month data showed that PFS stored horizontally could be resuspended with 10 or fewer shakes for all three dose levels. PFS stored tip down, however, still required 40 or more shakes. Data are shown in Table 46. Total antigenicity and binding to AlPO$_4$ of each serotype was stable for 1 month at RT. Data are shown in Table 47.

TABLE 46

Comparison of Resuspension Behavior of PFS Stored Horizontally Versus Tip Down

| Dose | pH | Storage time at 2-8° C. (months) | Horizontal (# Shakes) | Tip Down (# Shake) |
|---|---|---|---|---|
| Low | 6.5 | 1 month | 3 | 40 |
| Mid | 6.5 | | 8 | >45 |
| High | 6.5 | | 7 | >50 |
| High | 6.0 | | 10 | 50 |

TABLE 47

Total Antigenicity of GBS Formulations

| Dose | Time point | Total Antigenicity (µg/mL) | | | | | |
|---|---|---|---|---|---|---|---|
| | | Ia | Ib | II | III | IV | V |
| High | 0 | 40 | 41.2 | 41.1 | 42.0 | 40.4 | 39.1 |
| | 1 m RT | 44.8 | 43.1 | 44.6 | 44.3 | 43.7 | 44.6 |
| Mid | 0 | 18.3 | 17.9 | 19.0 | 18.2 | 18.4 | 17.9 |
| | 1 m RT | 19.5 | 19.3 | 21.7 | 20.4 | 20.0 | 20.6 |
| Low | 0 | 10.4 | 11.6 | 9.5 | 8.6 | 9.2 | 9.9 |
| | 1 m RT | 9.0 | 9.1 | 9.5 | 9.2 | 9.0 | 9.3 |
| % Binding to AlPO$_4$ | | | | | | | |
| High | 0 | 30.8 | 24.6 | 26.2 | 18.7 | 22.3 | 31.2 |
| | 1 m RT | 33.3 | 29.7 | 33.3 | 19.9 | 25.9 | 35.0 |
| Mid | 0 | 39.9 | 40.0 | 29.1 | 20.0 | 25.5 | 37.9 |
| | 1 m RT | 45.0 | 40.5 | 39.9 | 33.6 | 34.0 | 40.8 |
| Low | 0 | 49.3 | 52.5 | 38.0 | 25.3 | 31.2 | 45.2 |
| | 1 m RT | 51.5 | 42.8 | 41.4 | 30.1 | 37.6 | 45.3 |

Example 25

Application of Design of Experiment (DoE) and Quality by Design (QbD) Concepts for GBS Formulations with Flocculating Agents in PFS A design of experiment (DoE) was executed to determine the optimal GBS6 formulation for PFS. Three factors were evaluated using the response surface methodology (Box-Behnken design): 1) pH (6.0, 6.5, and 7.0); 2) NaCl concentration (220 mM, 240 mM, and 260 mM); and 3) phosphate concentration (15 mM, 20 mM, and 25 mM). All formulations otherwise comprised a 240 mg/mL dose (60 ug/mL of each serotype, 0.02% PS80, about 10 mM histidine carried over from drug substance, and 0.5 mg/mL AlPO$_4$. A total of 15 formulations were investigated for ease of resuspension (see Table 48).

TABLE 48

DoE Study Formulations

| Formulation | NaCl (mM) | Na-phosphate (mM) | pH |
|---|---|---|---|
| 1 | 240 | 20 | 6.5 |
| 2 | 260 | 15 | 6.5 |
| 3 | 240 | 15 | 7.0 |
| 4 | 220 | 25 | 6.5 |
| 5 | 260 | 25 | 6.5 |
| 6 | 240 | 25 | 6.0 |
| 7 | 240 | 20 | 6.5 |
| 8 | 240 | 15 | 6.0 |
| 9 | 220 | 20 | 7.0 |
| 10 | 240 | 20 | 6.5 |
| 11 | 260 | 20 | 6.0 |
| 12 | 240 | 25 | 7.0 |
| 13 | 220 | 15 | 6.5 |
| 14 | 220 | 20 | 6.0 |
| 15 | 260 | 20 | 7.0 |

To account for any associated variability, the studies were performed in triplicate and by two operators. Samples were filled into BD HYPAK SCF™ PRTC (Becton, Dickinson and Company) 1 mL short, glass PFS with 0.58 mL fill volume and capped with 4432/50 stoppers (West Pharmaceutical Services, Inc.), keeping a headspace of about ~0.4 mm. Filled syringes were stored horizontally at 2-8° C. and 25° C. for 3 months. Resuspension was monitored at 5° C. only, and strength by nephelometry was monitored at 5° C. and 25° C. Resuspension results are shown in Table 49.

TABLE 49

Number of Shakes Required for Resuspension at 3 Months

| Formulation | Operator 1* | Operator 2* |
|---|---|---|
| 1 | 11 | 8 |
| 2 | 8 | 6 |
| 3 | 7 | 4 |
| 4 | 11 | 8 |
| 5 | 8 | 8 |
| 6 | 19 | 12 |
| 7 | 7 | 7 |
| 8 | 19 | 14 |
| 9 | 10 | 6 |
| 10 | 8 | 6 |
| 11 | 11 | 13 |
| 12 | 8 | 4 |
| 13 | 11 | 11 |
| 14 | 28 | 17 |
| 15 | 5 | 5 |

*Average of 3 samples

JMP statistical software (SAS Institute) was used to analyze the data and predict the optimal and most robust formulation that would require 10 shakes to resuspend.

Figure 45:
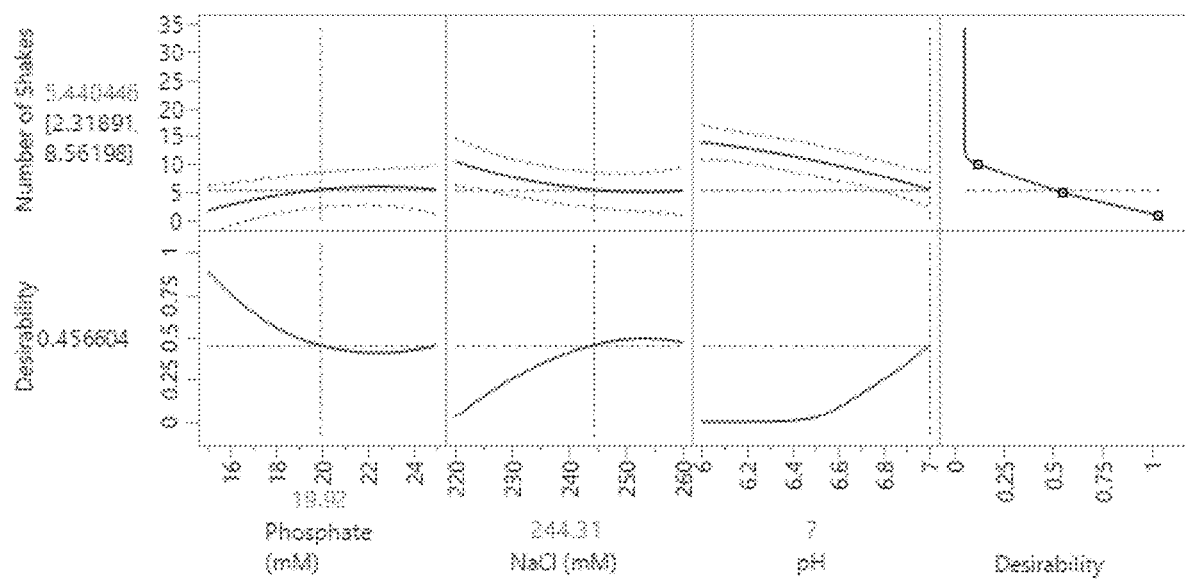
FIG. 45: Prediction profiler recommendations for optimal and robust formulation conditions that facilitate easier resuspension (≤10 shakes).

The prediction profiler from JMP based on the resuspension data for one of the operators is shown in FIG. 45. pH and salt were significant individual factors that impacted the number of shakes. In addition, the interaction between phosphate and pH was significant. Based on the desirability index, the following conditions allowed for easier resuspension (# shakes ≥10): pH 7.0±0.5, 245±20 mM NaCl, and 20±5 mM phosphate. Similar results were obtained when data from the second operator was analyzed.

Figure 46:
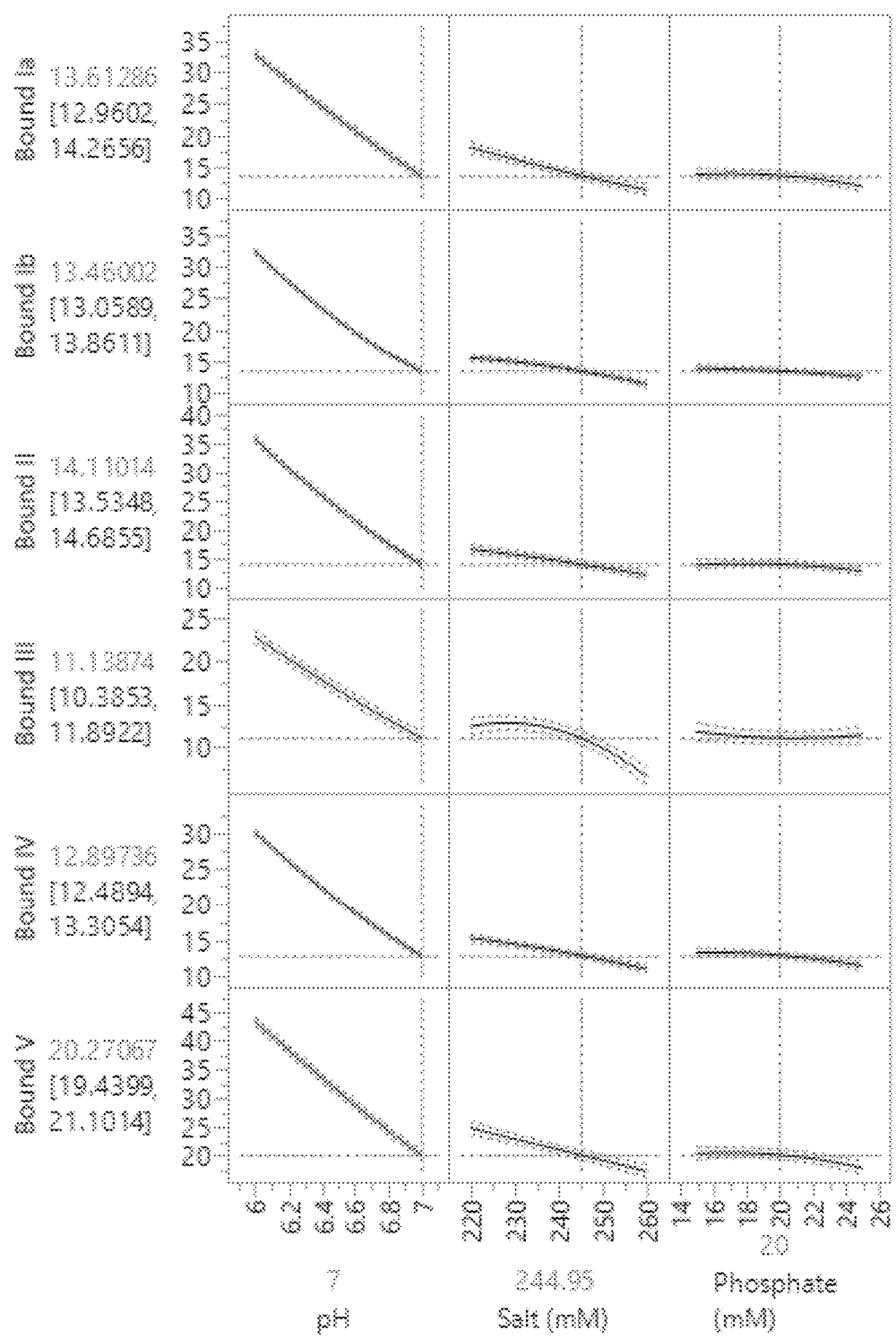
FIG. 46: Percent bound antigenicity for GBS6 formulations based on prediction profiler recommendations.

With the recommended formulation parameters, however, the extent of binding was lower. As shown in FIG. 46, the binding of the conjugates for each of the GBS serotypes varied between 10-20%. Additionally, the recommended formulation had a higher osmolality (about 500 mOsm/kg) but was still well within the range for vaccines.

Example 26

Al(OH)$_3$-Based GBS6 Formulations

As described in Example 22, GBS6 formulations with Al(OH)$_3$ had superior resuspension behavior but had a higher binding strength with the antigens, which could have an adverse impact on immune response. Accordingly, experiments were conducted to characterize the binding of Al(OH)$_3$ to GBS conjugates and modulate adsorption strength of Al(OH)$_3$.

Figure 47:
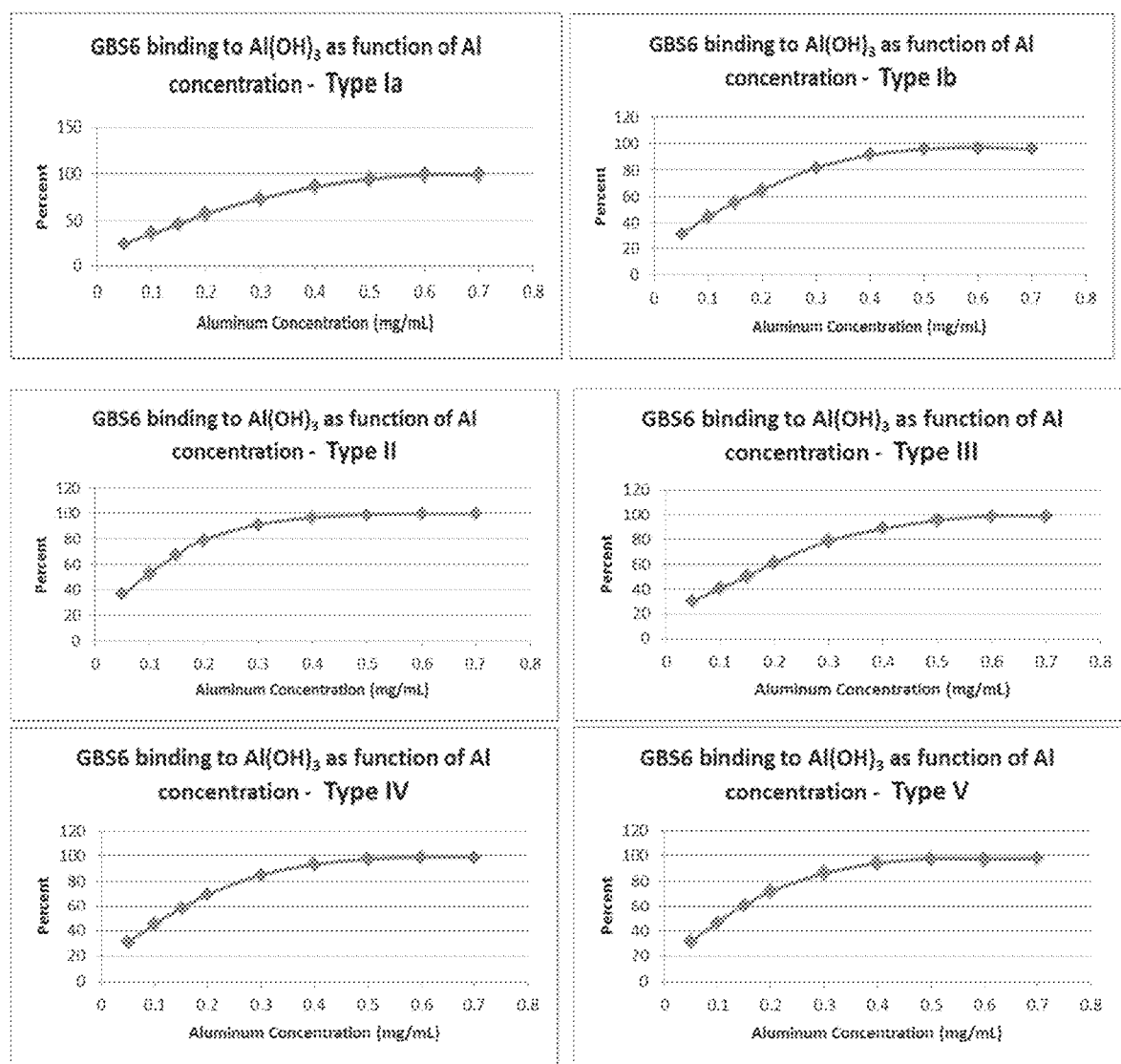
FIG. 47: Binding of GBS serotypes Ia, Ib, II, III, IV, and V with varying concentrations of $Al(OH)_3$.

High dose (240 mcg/mL of total conjugates) GBS6 formulations comprising 20 mM histidine, 150 mM NaCl, and 0.02% PS80 at pH 6.5 were prepared with varying concentrations of Al(OH)$_3$ (0.7 mg/mL, 0.6 mg/mL, 0.5 mg/mL, 0.4 mg/mL, 0.3 mg/mL, 0.2 mg/mL, 0.15 mg/mL, 0.1 mg/mL, and 0.05 mg/mL). Binding was determined by measuring the total and supernatant antigenicity by nephelometry. As shown in FIG. 47, binding to Al(OH)$_3$ plateaued at 0.5 mg/mL Al(OH)$_3$ for all six serotypes. Adsorption capacity and adsorption coefficient was determined by Langmuir equation. Data are shown in Table 50 with data for AlPO$_4$ as a comparator.

TABLE 50

Characteristics of GBS Conjugate Binding to AlPO$_4$ and Al(OH)$_3$

| GBS Serotype | Adsorbtive Capacity mcg serotype/mg Al | Adsorption Coefficient mL/mg protein |
|---|---|---|
| With AlPO$_4$ | | |
| Ia | 39.5 | 1488.2 |
| Ib | 38.6 | 1786.2 |
| II | 41.8 | 377.6 |
| III | 25.6 | 1649.8 |
| IV | 29.8 | 1407.6 |
| V | 41.7 | 1403.5 |
| With Al(OH)$_3$ | | |
| Ia | 109.9 | 5352.9 |
| Ib | 117.6 | 3400.0 |
| II | 161.3 | 3263.2 |
| III | 122.0 | 2411.8 |
| IV | 138.9 | 3428.6 |
| V | 147.1 | 2956.5 |

To modulate the binding strength of Al(OH)$_3$, the buffer in the formulation was changed to sodium phosphate in order to replace surface hydroxyls on aluminum hydroxide with phosphate and reduce ligand exchange. GBS6 formulations comprising 150 mM NaCl, 0.02% PS80, and 0.15 mg/ML Al(OH)$_3$ at pH 6.5, were prepared at 3 different phosphate concentrations (10 mM, 20 mM, and 30 mM) and various doses (15 mcg/mL, 30 mcg/mL, 60 mcg/mL, 90 mcg/mL, 120 mcg/mL, 150 mcg/mL, and 210 mcg/mL total conjugate). Binding was determined by total and supernatant antigenicity. Adsorption capacity and coefficient was determined by Langmuir equation. Data are shown in Table 51 with data for an AlPO$_4$ formulation as a comparator.

TABLE 51

Effect of Phosphate Concentration on GBS Conjugate Binding to Al(OH)$_3$

| GBS Serotype | Na-Phosphate Conc (mM)* | Adsorptive coefficient (ml/mg) | Adsorptive capacity (µg serotype/mg Al) | Binding to Al (%)** | % Extraction*** |
|---|---|---|---|---|---|
| Ia | 0 | 5353 | 110 | >95 | 14 |
| | 10 | 890 | 32 | 66 | 103 |
| | 20 | 665 | 26 | 52 | 101 |
| | 30 | 429 | 19 | 45 | 109 |
| | AlPO$_4$ formulation | 40 | 1488 | 46 | NA |
| Ib | 0 | 3400 | 118 | >95 | 6 |
| | 10 | 1622 | 56 | 66 | 93 |
| | 20 | 520 | 21 | 63 | 105 |
| | 30 | 338 | 15 | 44 | 103 |
| | AlPO$_4$ formulation | 39 | 1786 | 50 | NA |
| II | 0 | 3263 | 161 | >95 | 2 |
| | 10 | 1333 | 86 | 80 | 99 |
| | 20 | 852 | 79 | 75 | 105 |
| | 30 | 711 | 67 | 66 | 103 |
| | AlPO$_4$ formulation | 42 | 378 | 57 | NA |
| III | 0 | 2412 | 122 | >95 | 10 |
| | 10 | 878 | 37 | 66 | 104 |
| | 20 | 478 | 23 | 47 | 107 |
| | 30 | 207 | 7 | 30 | 109 |
| | AlPO$_4$ formulation | 26 | 1650 | 37 | NA |
| IV | 0 | 3429 | 139 | >95 | 4 |
| | 10 | 2571 | 62 | 73 | 102 |
| | 20 | 1509 | 39 | 63 | 104 |
| | 30 | 1114 | 29 | 47 | 95 |
| | AlPO$_4$ formulation | 30 | 1408 | 44 | NA |

TABLE 51-continued

Effect of Phosphate Concentration on GBS Conjugate Binding to Al(OH)₃

| GBS Serotype | Na-Phosphate Conc (mM)* | Adsorptive coefficient (ml/mg) | Adsorptive capacity (μg serotype/mg Al) | Binding to Al (%)** | % Extraction*** |
|---|---|---|---|---|---|
| V | 0 | 4957 | 147 | >95 | 3 |
|  | 10 | 2040 | 65 | 77 | 104 |
|  | 20 | 1982 | 45 | 64 | 106 |
|  | 30 | 1758 | 47 | 58 | 95 |
|  | AlPO₄ formulation | 42 | 1404 | 53 | NA |

*AlPO₄ formulation contains ~10 mM Histidine carried over from drug substance.
**Binding of AlPO₄ formulation is averaged from 3 batches.
***Extraction condition: 0.1N NaOH RT rotating for 24 hrs.

Binding capacity and coefficient of GBS6 to Al(OH)₃ were 3-4 times higher than to AlPO₄. However, adsorptive strength of aluminum hydroxide to GBS6 was modulated by introducing phosphate into the formulation. Phosphate concentration adversely affected the adsorptive strength and capacity. Phosphate also impacted the percent antigen binding, but was still above the level of AlPO₄. In addition, GBS was able to be fully extracted from aluminum in presence of phosphate. Based on the results, it was determined that 20 mM phosphate, 150 mM NaCl, and 0.2% PS80 at pH6.5 was optimal with aluminum hydroxide.

Aspects of the Invention

The following clauses describe additional embodiments of the invention.

C1. An immunogenic polysaccharide-protein conjugate comprising a group B streptococcus (GBS) capsular polysaccharide and a carrier protein, wherein the capsular polysaccharide has a sialic acid level of greater than about 60%.
C2. The immunogenic conjugate of C1, wherein the capsular polysaccharide is selected from the group consisting of serotypes Ia, Ib, II, III, IV, V, VI, VII, VIII, and IX.
C3. The immunogenic conjugate of C2, wherein the capsular polysaccharide is serotype Ia.
C4. The immunogenic conjugate of C2, wherein the capsular polysaccharide is serotype Ib.
C5. The immunogenic conjugate of C2, wherein the capsular polysaccharide is serotype II.
C6. The immunogenic conjugate of C2, wherein the capsular polysaccharide is serotype III.
C7. The immunogenic conjugate of C2, wherein the capsular polysaccharide is serotype IV.
C8. The immunogenic conjugate of C2, wherein the capsular polysaccharide is serotype V.
C9. The immunogenic conjugate of C2, wherein the capsular polysaccharide is serotype VI.
C10. The immunogenic conjugate of C2, wherein the capsular polysaccharide is serotype VII.
C11. The immunogenic conjugate of C2, wherein the capsular polysaccharide is serotype VIII.
C12. The immunogenic conjugate of C2, wherein the capsular polysaccharide is serotype IX.
C13. The immunogenic conjugate of any one of C1-C12, wherein the capsular polysaccharide has a sialic acid level of greater than about 95%.
C14. The immunogenic conjugate of any one of C1-C13, wherein the capsular polysaccharide has a sialic acid level of about 100%.
C15. The immunogenic conjugate of any one of C1-C14, wherein the capsular polysaccharides has at least about 0.6 mM sialic acid per mM of polysaccharide.
C16. The immunogenic conjugate of any one of C1-C15, wherein the capsular polysaccharides has at least about 0.65 mM sialic acid per mM of polysaccharide.
C17. The immunogenic conjugate of any one of C1-C16, wherein the capsular polysaccharides has at least about 0.7 mM sialic acid per mM of polysaccharide.
C18. The immunogenic conjugate of any one of C1-C17, wherein the capsular polysaccharides has at least about 0.75 mM sialic acid per mM of polysaccharide.
C19. The immunogenic conjugate of any one of C1-C18, wherein the capsular polysaccharides has at least about 0.8 mM sialic acid per mM of polysaccharide
C20. The immunogenic conjugate of any one of C1-C19, wherein the capsular polysaccharides has at least about 0.85 mM sialic acid per mM of polysaccharide.
C21. The immunogenic conjugate of any one of C1-C20, wherein the capsular polysaccharides has at least about 0.9 mM sialic acid per mM of polysaccharide.
C22. The immunogenic conjugate of any one of C1-C21, wherein the capsular polysaccharides has at least about 0.95 mM sialic acid per mM of polysaccharide.
C23. The immunogenic conjugate of any one of C1-C22, wherein the capsular polysaccharide has a molecular weight of between about 5 kDa and about 1,000 kDa.
C24. The immunogenic conjugate of any one of C1-C23, wherein the capsular polysaccharide has a molecular weight of between about 25 kDa and about 750 kDa.
C25. The immunogenic conjugate of any one of C1-C24, wherein the capsular polysaccharide has a molecular weight of between about 25 kDa and about 400 kDa.
C26. The immunogenic conjugate of any one of C1-C25, wherein the capsular polysaccharide has a molecular weight of between about 25 kDa and about 200 kDa.
C27. The immunogenic conjugate of any one of C1-C25, wherein the capsular polysaccharide has a molecular weight of between about 100 kDa and about 400 kDa.
C28. The immunogenic conjugate of any one of C1-C27, wherein the molecular weight of the conjugate is between about 300 kDa and about 20,000 kDa.
C29. The immunogenic conjugate of any one of C1-C28, wherein the molecular weight of the conjugate is between about 1,000 kDa and about 15,000 kDa.
C30. The immunogenic conjugate of any one of C1-C29, wherein the molecular weight of the conjugate is between about 1,000 kDa and about 10,000 kDa.
C31. The immunogenic conjugate of any one of C1-C30, wherein the capsular polysaccharide is between about 0% and about 40% O-acetylated.
C32. The immunogenic conjugate of any one of C1-C31, wherein the capsular polysaccharide less than about 5% O-acetylated.

C33. The immunogenic conjugate of any one of C1-C32, wherein the capsular polysaccharide less than about 4% O-acetylated.

C34. The immunogenic conjugate of any one of C1-C33, wherein the capsular polysaccharide less than about 3% O-acetylated.

C35. The immunogenic conjugate of any one of C1-C34, wherein the capsular polysaccharide less than about 2% O-acetylated.

C36. The immunogenic conjugate of any one of C1-C35, wherein the capsular polysaccharide less than about 1% O-acetylated.

C37. The immunogenic conjugate of any one of C1-C36, wherein the capsular polysaccharide comprises at least about 0.1 mM O-acetate per mM saccharide repeating unit.

C38. The immunogenic conjugate of any one of C1-C37, wherein the capsular polysaccharide comprises at least about 0.2 mM O-acetate per mM saccharide repeating unit.

C39. The immunogenic conjugate of any one of C1-C38, wherein the capsular polysaccharide comprises at least about 0.3 mM O-acetate per mM saccharide repeating unit.

C40. The immunogenic conjugate of any one of C1-C39, wherein the capsular polysaccharide comprises at least about 0.35 mM O-acetate per mM saccharide repeating unit.

C41. The immunogenic conjugate of any one of C1-C40, wherein the capsular polysaccharide comprises about 0.4 mM O-acetate per mM saccharide repeating unit.

C42. The immunogenic conjugate of any one of C1-C41, wherein the capsular polysaccharide comprises less than about 0.01 mM O-acetate per mM saccharide repeating unit.

C43. The immunogenic conjugate of any one of C1-C42, wherein the capsular polysaccharide comprises less than about 0.05 mM O-acetate per mM saccharide repeating unit.

C44. The immunogenic conjugate of any one of C1-C43, wherein the capsular polysaccharide comprises less than about 0.04 mM O-acetate per mM saccharide repeating unit.

C45. The immunogenic conjugate of any one of C1-C44, wherein the capsular polysaccharide comprises less than about 0.03 mM O-acetate per mM saccharide repeating unit.

C46. The immunogenic conjugate of any one of C1-C45, wherein the capsular polysaccharide comprises less than about 0.02 mM O-acetate per mM saccharide repeating unit.

C47. The immunogenic conjugate of any one of C1-C46, wherein the polysaccharides are each individually conjugated to the carrier protein.

C48. The immunogenic conjugate of any one of C1-C47, wherein the carrier protein is $CRM_{197}$ or tetanus toxoid.

C49. The immunogenic conjugate of any one of C1-C48, wherein the carrier protein is $CRM_{197}$.

C50. A method of isolating a capsular polysaccharide comprising reacting an organic reagent with a cell broth comprising a capsular polysaccharide producing bacterium.

C51. The method of C50, wherein the bacterium is not lysed.

C52. The method of C50 or C51, wherein the bacterium is heat killed.

C53. The method of any one of C50-C52, wherein the method further comprises the step of centrifuging to provide a cell paste.

C54. The method of any one of C50-C53, wherein the method further comprises the step of filtering.

C55. The method of C54, wherein said filtering step is a diafiltration.

C56. The method of any one of C50-C56, wherein the capsular polysaccharide producing bacterium is selected from the group consisting of *Streptococcus agalactiae, Streptococcus pneumoniae, Staphylococcus aureus, Neisseria meningitidis, Escherichia coli, Salmonella typhi, Haemophilus influenzae, Klebsiella pneumoniae, Enterococcus faecium*, and *Enterococcus faecalis*.

C57. The method of C56, wherein the bacteria is *Streptococcus agalactiae*.

C58. The method of any one of C50-C57, wherein said organic reagents is a derivatized hydroxyl amine compounds.

C59. The method of any one of C50-58, wherein the hydroxyl amine is any hydroxyl amine listed in Table 2 of Example 2.

C60. The method of any one of C50-C59, wherein the hydroxyl amine is selected from the group consisting of dibenzyl hydroxylamine; diethyl hydroxylamine; hydroxylamine; ethylenediamine; triethylenetetramine; 1,1,4,7,10,10 hexamethyl triethylene tetramine; and 2,6,10, Trimethyl 2,6,10 triazaundecane.

C61. The method of any one of C50-C60, wherein the concentration of hydroxyl amine is about 5 mM to about 200 mM.

C62. The method of any one of C50-C61, wherein the pH of the reaction is about 5.5 to about 9.5.

C63. The method of any one of C50-C62, wherein the reaction takes place at a temperature of about 20° C. to about 85° C.

C64. The method of any one of C50-C63, wherein the reaction time is about 10 hours to about 90 hours.

C65. A method of making the immunogenic polysaccharide-protein conjugate of any one of C1-C49, wherein the capsular polysaccharide is isolated according to the method of any one of C50-C64.

C66 An immunogenic polysaccharide-protein conjugate comprising a capsular polysaccharide prepared by the method any one of C50-C64.

C67. An immunogenic composition comprising the immunogenic polysaccharide-protein conjugate of any one of C1-C49 or C66.

C68. An immunogenic composition comprising polysaccharide-protein conjugates, wherein the conjugates comprise capsular polysaccharides from group B streptococcus (GBS) serotype IV and at least one additional serotype selected from the group consisting of Ia, Ib, II, III, V, VI, VII, VIII, and IX.

C69. The immunogenic composition of C68, wherein the at least one additional serotype is Ia.

C70. The immunogenic composition of C69, wherein the composition further comprises a conjugate comprising a capsular polysaccharide from GBS serotype Ib.

C71. The immunogenic composition of C69 or C70, wherein the composition further comprises a conjugate comprising a capsular polysaccharide from GBS serotype II.

C72. The immunogenic composition of any one of C69-C71, wherein the composition further comprises a conjugate comprising a capsular polysaccharide from GBS serotype III.

C73. The immunogenic composition of any one of C69-C72, wherein the composition further comprises a conjugate comprising a capsular polysaccharide from GBS serotype V.

C74. The immunogenic composition of any one of C69-C73, wherein the composition further comprises a conjugate comprising a capsular polysaccharide from GBS serotype VI.

C75. The immunogenic composition of any one of C69-C74, wherein the composition further comprises a conjugate comprising a capsular polysaccharide from GBS serotype VII.

C76. The immunogenic composition of any one of C69-C75, wherein the composition further comprises a conjugate comprising a capsular polysaccharide from GBS serotype VIII.

C77. The immunogenic composition of any one of C69-C76, wherein the composition further comprises a conjugate comprising a capsular polysaccharide from GBS serotype IX.

C78. The immunogenic composition of C68, wherein the at least one additional serotype is Ib.

C79. The immunogenic composition of C78, wherein the composition further comprises a conjugate comprising a capsular polysaccharide from GBS serotype II.

C80. The immunogenic composition of C78 or C79, wherein the composition further comprises a conjugate comprising a capsular polysaccharide from GBS serotype III.

C81. The immunogenic composition of any one of C78-C80, wherein the composition further comprises a conjugate comprising a capsular polysaccharide from GBS serotype V.

C82. The immunogenic composition of any one of C78-C81, wherein the composition further comprises a conjugate comprising a capsular polysaccharide from GBS serotype VI.

C83. The immunogenic composition of any one of C78-C82, wherein the composition further comprises a conjugate comprising a capsular polysaccharide from GBS serotype VII.

C84. The immunogenic composition of any one of 8-C83, wherein the composition further comprises a conjugate comprising a capsular polysaccharide from GBS serotype VIII.

C85. The immunogenic composition of any one of C78-C84, wherein the composition further comprises a conjugate comprising capsular polysaccharide from GBS serotype IX.

C86. The immunogenic composition of C68, wherein the at least one additional serotype is II.

C87. The immunogenic composition of C86, wherein the composition further comprises a conjugate comprising a capsular polysaccharide from GBS serotype III.

C88. The immunogenic composition of C86 or C87, wherein the composition further comprises a conjugate comprising a capsular polysaccharide from GBS serotype V.

C89. The immunogenic composition of any one of C86-C88, wherein the composition further comprises a conjugate comprising a capsular polysaccharide from GBS serotype VI.

C90. The immunogenic composition of any one of C86-C89, wherein the composition further comprises a conjugate comprising a capsular polysaccharide from GBS serotype VII.

C91. The immunogenic composition of any one of C86-C90, wherein the composition further comprises a conjugate comprising a capsular polysaccharide from GBS serotype VIII.

C92. The immunogenic composition of any one of C86-C91, wherein the composition further comprises a conjugate comprising a capsular polysaccharide from GBS serotype IX.

C93. The immunogenic composition of C68, wherein the at least one additional serotype is III.

C94. The immunogenic composition of C93, wherein the composition further comprises a conjugate comprising a capsular polysaccharide from GBS serotype V.

C95. The immunogenic composition of C93 or C94, wherein the composition further comprises a conjugate comprising a capsular polysaccharide from GBS serotype VI.

C96. The immunogenic composition of any one of C93-C95, wherein the composition further comprises a conjugate comprising a capsular polysaccharide from GBS serotype VII.

C97. The immunogenic composition of any one of C93-C96, wherein the composition further comprises a conjugate comprising a capsular polysaccharide from GBS serotype VIII.

C98. The immunogenic composition of any one of C93-C97, wherein the composition further comprises a conjugate comprising a capsular polysaccharide from GBS serotype IX.

C99. The immunogenic composition of C68, wherein the at least one additional serotype is V.

C100. The immunogenic composition of C99, wherein the composition further comprises a conjugate comprising a capsular polysaccharide from GBS serotype VI.

C101. The immunogenic composition of any one of C99 or C100, wherein the composition further comprises a conjugate comprising a capsular polysaccharide from GBS serotype VII.

C102. The immunogenic composition of any one of C99-C101, wherein the composition further comprises a conjugate comprising a capsular polysaccharide from GBS serotype VIII.

C103. The immunogenic composition of any one of C99-C102, wherein the composition further comprises a conjugate comprising a capsular polysaccharide from GBS serotype IX.

C104. The immunogenic composition of C68, wherein the at least one additional serotype is VI.

C105. The immunogenic composition of C104, wherein the composition further comprises a conjugate comprising a capsular polysaccharide from GBS serotype VII.

C106. The immunogenic composition of any one of C104 or C105, wherein the composition further comprises a conjugate comprising a capsular polysaccharide from GBS serotype VIII.

C107. The immunogenic composition of any one of C104-C106, wherein the composition further comprises a conjugate comprising a capsular polysaccharide from GBS serotype IX.

C108. The immunogenic composition of C68, wherein the at least one additional serotype is VII.

C109. The immunogenic composition of C108, wherein the composition further comprises a conjugate comprising a capsular polysaccharide from GBS serotype VIII.

C110. The immunogenic composition of any one of C108 or C109, wherein the composition further comprises a conjugate comprising a capsular polysaccharide from GBS serotype IX.

C111. The immunogenic composition of C68, wherein the at least one additional serotype is VIII.

C112. The immunogenic composition of C111, wherein the composition further comprises a conjugate comprising a capsular polysaccharide from GBS serotype IX.

C113. The immunogenic composition of C112, wherein the at least one additional serotype is IX.

C114. An immunogenic composition comprising polysaccharide-protein conjugates, wherein the conjugates comprise capsular polysaccharides from GBS serotypes Ia, Ib, II, III, and IV.

C115. An immunogenic composition comprising polysaccharide-protein conjugates, wherein the conjugates comprise capsular polysaccharides from GBS serotypes Ia, Ib, II, III, and V.

C116. An immunogenic composition comprising polysaccharide-protein conjugates, wherein the conjugates comprise capsular polysaccharides from GBS serotypes Ia, Ib, II, III, IV, and V.

C117. An immunogenic composition comprising polysaccharide-protein conjugates comprising at least four GBS capsular polysaccharide serotypes selected from the group consisting of Ia, Ib, II, III, IV, V, VI, VII, VIII, and IX.

C118. The immunogenic composition of C117, wherein the composition comprises at least five GBS capsular polysaccharide serotypes.

C119. The immunogenic composition of C117 or C118, wherein the composition comprises at least six GBS capsular polysaccharide serotypes.

C120. The immunogenic composition of any one of C117-C119, wherein the composition comprises at least seven GBS capsular polysaccharide serotypes.

C121. The immunogenic composition of any one of C117-C120, wherein the composition comprises at least eight GBS capsular polysaccharide serotypes.

C122. The immunogenic composition of any one of C117-C121, wherein the composition comprises at least nine GBS capsular polysaccharide serotypes.

C123. The immunogenic composition of any one of C117-C122, wherein the composition comprises GBS capsular polysaccharide serotype V.

C124. The immunogenic composition of any one of C117-C123, wherein the composition does not have immune interference.

C125. The immunogenic composition of any one of C67-C124, wherein the composition further comprises a pharmaceutically acceptable excipient, buffer, stabilizer, adjuvant, a cryoprotectant, a salt, a divalent cation, a non-ionic detergent, an inhibitor of free radical oxidation, a carrier, or a mixture thereof.

C126. The immunogenic composition of any one of C67-C125, wherein the composition further comprises a buffer.

C127. The immunogenic composition of C126, wherein the buffer is selected from the group consisting of HEPES, PIPES, MES, Tris (trimethamine), phosphate, acetate, borate, citrate, glycine, histidine and succinate.

C128. The immunogenic composition of C127, wherein the buffer is histidine.

C129. The immunogenic composition of any one of C67-C128, wherein the composition further comprises a surfactant.

C130. The immunogenic composition of C129, wherein the surfactant is selected from the group consisting of polyoxyethylene sorbitan fatty acid esters, polysorbate-80, polysorbate-60, polysorbate-40, polysorbate-20, and polyoxyethylene alkyl ethers.

C131. The immunogenic composition of C130, wherein the surfactant is polysorbate-80.

C132. The immunogenic composition of any one of C67-C131, wherein the composition further comprises an excipient.

C133. The immunogenic composition of C132, wherein the excipient is selected from the group consisting of starch, glucose, lactose, sucrose, trehalose, raffinose, stachyose, melezitose, dextran, mannitol, lactitol, palatinit, gelatin, malt, rice, flour, chalk, silica gel, sodium stearate, glycerol monostearate, talc, glycine, arginine, lysine, sodium chloride (NaCl), dried skim milk, glycerol, propylene glycol, water, and ethanol.

C134. The immunogenic composition of C133, wherein the excipient is sodium chloride.

C135. The immunogenic composition of any one of C67-C134, wherein the composition further comprises an adjuvant.

C136. The immunogenic composition of any one of C135, wherein the adjuvant is an aluminum-based adjuvant or QS-21.

C137. The immunogenic composition of any one of C136, wherein the aluminum-based adjuvant is selected from the group consisting of aluminum phosphate, aluminum hydroxyl phosphate, and aluminum hydroxide.

C138. The immunogenic composition of any one of C137, wherein the adjuvant is aluminum phosphate.

C139. The immunogenic composition of any one of C138, wherein the adjuvant is aluminum hydroxyl phosphate.

C140. The immunogenic composition of any one of C67-C139, wherein the composition comprises a buffer, a surfactant, an excipient, and optionally an adjuvant, wherein the composition is buffered to a pH of about 6.0 to about 7.0.

C141. The immunogenic composition of any one of C67-C140, wherein the composition comprises histidine, polysorbate-80, sodium chloride, and optionally aluminum phosphate, wherein the composition is buffered to a pH of about 6.0 to about 7.0.

C142. The immunogenic composition of any one of C67-C141, wherein the composition comprises about 10 mM to about 25 mM of histidine, about 0.01% to about 0.03% (v/w) of polysorbate-80, about 10 mM to about 250 mM of sodium chloride, and optionally about 0.25 mg/ml to about 0.75 mg/ml of aluminum as aluminum phosphate.

C143. The immunogenic composition of any one of C67-C142, wherein the composition comprises a dose of about 5 mcg/ml to about 50 mcg/ml.

C144. The immunogenic composition of any one of C67-C143, wherein the composition is lyophilized, optionally in the presence of at least one excipient.

C145. The immunogenic composition of C144, wherein the at least one excipient is selected from the group consisting of starch, glucose, lactose, sucrose, trehalose, raffinose, stachyose, melezitose, dextran, mannitol, lactitol, palatinit, gelatin, malt, rice, flour, chalk, silica gel, sodium stearate, glycerol monostearate, talc, glycine, arginine, lysine, sodium chloride (NaCl), dried skim milk, glycerol, propylene glycol, water, and ethanol.

C146. The immunogenic composition of C145, wherein the at least one excipient is sucrose.

C147. The immunogenic composition of any one of C144-C146, wherein the composition comprises about 1% (w/v) to about 10% (w/v) of the at least one excipient.

C148. The immunogenic composition of any one of C144-C147, wherein the composition comprises an additional excipient.

C149. The immunogenic composition of C148, wherein the additional excipient is mannitol or glycine.

C150. The immunogenic composition of C148 or C149, wherein the composition comprises about 1% (w/v) to about 10% (w/v) of the additional excipient.

C151. The immunogenic composition of any one of C143-C150, wherein the composition is reconstituted with water, water for injection (WFI), an adjuvant suspension, or saline.

C152. An immunogenic composition of any one of C67-C151 for use as a medicament.

C153. An immunogenic composition of any one of C67-C152 for use in a method of inducing an immune response against GBS in a subject.

C154. The immunogenic composition of C153, wherein the subject is a female planning to become pregnant or a pregnant female.

C155. The immunogenic composition of C154, wherein the female is in her second half of pregnancy.

C156. The immunogenic composition of C155, wherein the pregnant female is at least at 20 weeks gestation.

C157. The immunogenic composition of C156, wherein the pregnant female is at 27 weeks to 36 weeks gestation.

C158. The immunogenic composition of C157, wherein the subject is an adult 50 years of age or older.

C159. The immunogenic composition of C158, wherein the subject is an adult 65 years of age or older.

C160. The immunogenic composition of C159, wherein the subject is an adult 85 years of age or older.

C161. The immunogenic composition of any one of C153-C160, wherein the subject is immunocompromised.

C162. The immunogenic composition of C161, wherein the subject has a medical condition selected from the group consisting of obesity, diabetes, HIV infection, cancer, cardiovascular disease, or liver disease.

C163. The immunogenic composition of any one of C153-162, wherein the group B streptococcus is *Streptococcus agalactiae*.

C164. A method of inducing an immune response against group B streptococcus comprising administering to a subject an effective amount of the immunogenic composition of any one of C67-C150.

C165. A method of preventing or reducing a disease or condition associated with group B streptococcus in a subject comprising administering to a subject an effective amount of the immunogenic composition of any one of C67-C151.

C166. The method of C164 or C165, wherein the subject is a female planning to become pregnant or a pregnant female.

C167. The method of C166, wherein the female is in her second half of pregnancy.

C168. The method of C166 or C167, wherein the pregnant female is at least at 20 weeks gestation.

C169. The method of any one of C166-C168, wherein the pregnant female is at 27 weeks to 36 weeks gestation.

C170. The method of C164 or C165, wherein the subject is an adult 50 years of age or older.

C171. The method of C170, wherein the subject is an adult 65 years of age or older.

C172. The method of C170 or C171, wherein the subject is an adult 85 years of age or older.

C173. The method of any one of C164-C172, wherein the subject is immunocompromised.

C174. The method of C173, wherein the subject has a medical condition selected from the group consisting of obesity, diabetes, HIV infection, cancer, cardiovascular disease, or liver disease.

C175. The method of any one of C164-C174, wherein the group B streptococcus is *Streptococcus agalactiae*.

C176. An antibody that binds to a capsular polysaccharide in the immunogenic conjugate of any one of C1-C49 or C66.

C177. A composition comprising the antibody of C176.

C178. A method of producing an antibody comprising administering the immunogenic composition of any one of C67-C151 to a subject.

C179. An antibody produced by the method of C178.

C180. A method of conferring passive immunity to a subject comprising the steps of:
(a) generating an antibody preparation using the immunogenic composition of any one of C67-C151; and
(b) administering the antibody preparation to the subject to confer passive immunity.

C181. A method of making an immunogenic polysaccharide-protein conjugate of any one of C1-C49 or C66 comprising the steps of:
(a) reacting the GBS capsular polysaccharide with an oxidizing agent resulting in an activated polysaccharide; and
(b) reacting the activated polysaccharide with the carrier protein resulting in a polysaccharide-protein conjugate.

C182. The method of C181, wherein step (b) is carried out in a polar aprotic solvent.

C183. The method of C182, wherein the solvent is selected from the group consisting of dimethylsulfoxide (DMSO), sulfolane, dimethylformamide (DMF), and hexamethylphosporamide (HMPA).

C184. The method of C183, wherein the solvent is dimethylsulfoxide (DMSO).

C185. The method of any one of C181-C184, wherein the polysaccharide is reacted with 0.01 to 10.0 molar equivalents of the oxidizing agent.

C186. The method of any one of C181-C185, wherein the oxidizing agent is a periodate.

C187. The method of C186, wherein the periodate is sodium periodate.

C188. The method of any one of C181-C187, wherein the oxidation reaction of step (a) is between 1 hour and 50 hours.

C189. The method of any one of C181-C188, wherein the temperature of the oxidation reaction is maintained between about 2° C. and about 25° C.

C190. The method of any one of C181-C189, wherein the oxidation reaction is carried out in a buffer selected from the group consisting of sodium phosphate, potassium phosphate, 2-(N-morpholino)ethanesulfonic acid (MES), and Bis-Tris.

C191. The method of C190, wherein the buffer has a concentration of between about 1 mM and about 500 mM.

C192. The method of any one of C181-C191, wherein the oxidation reaction is carried out at a pH between about 4.0 and about 8.0.

C193. The method of C181, wherein the oxidizing agent is 2,2,6,6-tetramethyl-1-piperidinyloxy (TEMPO).

C194. The method of C193, wherein N-chlorosuccinimide (NCS) is a cooxidant.

C195. The method of any one of C181-C194, wherein step (a) further comprises quenching the oxidation reaction by addition of a quenching agent.

C196. The method of any one of C182-C195, wherein the concentration of polysaccharide is between about 0.1 mg/mL and about 10.0 mg/mL.

C197. The method of any one of C181-C196, wherein the degree of oxidation of the activated polysaccharide is between 5 and 25.

C198. The method of any one of C181-C197, wherein the method further comprises the step of lyophilizing the activated polysaccharide.

C199. The method of C188, wherein the activated polysaccharide is lyophilized in the presence of a saccharide selected from the group consisting of sucrose, trehalose, raffinose, stachyose, melezitose, dextran, mannitol, lactitol and palatinit.

C200. The method of any one of C181-C199, wherein step (b) comprises:
(1) compounding the activated polysaccharide with a carrier protein, and
(2) reacting the compounded activated polysaccharide and carrier protein with a reducing agent to form a GBS capsular polysaccharide-carrier protein conjugate.

C201. The method of C200, wherein the concentration of activated polysaccharide in step (2) is between about 0.1 mg/mL and about 10.0 mg/mL.

C202. The method of C200 or C201, wherein the initial ratio (weight by weight) of activated polysaccharide to carrier protein is between 5:1 and 0.1:1.

C203. The method of any one of C200-C202, wherein the reducing agent is selected from the group consisting of sodium cyanoborohydride, sodium triacetoxyborohydride, sodium or zinc borohydride in the presence of Bronsted or Lewis acids, pyridine borane, 2-picoline borane, 2,6-diborane-methanol, dimethylamine-borane, t-BuMe$^i$PrN—BH$_3$, benzylamine-BH$_3$ or 5-ethyl-2-methylpyridine borane (PEMB).

C204. The method of C203, wherein the reducing agent is sodium cyanoborohydride.

C205. The method of any one of C200-C204, wherein the quantity of reducing agent is between about 0.1 and about 10.0 molar equivalents.

C206. The method of any one of C200-C205, wherein the duration of reduction reaction of step (2) is between 1 hour and 60 hours.

C207. The method of any one of C200-C206, wherein the temperature of the reduction reaction is maintained between 10° C. and 40° C.

C208. The method of any one of C181-C207, wherein the method further comprises a step (step (c)) of capping unreacted aldehyde by addition of a borohydride.

C209. The method of C208, wherein the quantity of borohydride is between about 0.1 and about 10.0 molar equivalents.

C210. The method of C208, wherein the borohydride is selected from the group consisting of sodium borohydride (NaBH$_4$), sodium cyanoborohydride, lithium borohydride, potassium borohydride, tetrabutylammonium borohydride, calcium borohydride, and magnesium borohydride.

C211. The method of C292, wherein the borohydride is sodium borohydride (NaBH$_4$).

C212. The method of any one of C207-C211, wherein the duration of capping step is between 0.1 hours and 10 hours.

C213. The method of any one of C207-C212, wherein the temperature of the capping step is maintained between about 15° C. and about 45° C.

C214. The method of any one of C181-C213, wherein the method further comprises the step of purifying the polysaccharide-protein conjugate.

C215. The method of any one of C181-C214, wherein the polysaccharide-protein conjugate comprises less than about 40% of free polysaccharide compared to the total amount of polysaccharide.

C216. The method of any one of C181-C215, wherein the ratio (weight by weight) of polysaccharide to carrier protein in the conjugate is between about 0.5 and about 3.0.

C217. The method of any one of C181-C216, wherein the degree of conjugation of the conjugate is between 2 and 15.

C218. A method of making a polysaccharide-protein conjugate comprising the steps of:
(a) reacting isolated GBS capsular polysaccharide with an oxidizing agent;
(b) quenching the oxidation reaction of step (a) by addition of a quenching agent resulting in an activated GBS capsular polysaccharide;
(c) compounding the activated GBS capsular polysaccharide with a carrier protein,
(d) reacting the compounded activated GBS capsular polysaccharide and carrier protein with a reducing agent to form a GBS capsular polysaccharide-carrier protein conjugate, and
(e) capping unreacted aldehyde by addition of sodium borohydride (NaBH$_4$),
wherein steps (c) and (d) are carried out in DMSO.

C219. An immunogenic composition comprising a capsular polysaccharide from a group B streptococcus (GBS) conjugated to a carrier protein and an aluminum-based adjuvant.

C220. The immunogenic composition of C219, wherein the aluminum-based adjuvant is selected from the group consisting of aluminum phosphate, aluminum hydroxyl phosphate, and aluminum hydroxide.

C221. The immunogenic composition of C219 or C220, wherein the adjuvant is aluminum phosphate.

C222. The immunogenic composition of C219 or C220, wherein the adjuvant is aluminum hydroxide.

C223. The immunogenic composition of any one of C219-C222, wherein the aluminum-based adjuvant is in a concentration of about 0.25 mg/ml to about 0.75 mg/ml.

C224. The immunogenic composition of C223, wherein the aluminum-based adjuvant is in a concentration of about 0.5 mg/ml.

C225. The immunogenic composition of any one of C219-C224, wherein the capsular polysaccharide is selected from the group consisting of serotypes Ia, Ib, II, III, IV, V, VI, VII, VIII, and IX.

C226. The immunogenic composition of any one of C219-C225, wherein the immunogenic composition is a hexavalent GBS conjugate composition.

C227. The immunogenic composition of C225, wherein the immunogenic composition comprises the capsular polysaccharides from GBS serotypes Ia, Ib, II, III, IV, and V.

C228. The immunogenic composition of any one of C219-C227, wherein the immunogenic composition is filled in a syringe.

C229. The immunogenic composition of C228, wherein the syringe is glass.

C230. The immunogenic composition of any one of C219-C229, wherein the immunogenic composition is filled in the syringe with a headspace of about 1 mm to about 15 mm.

C231. The immunogenic composition of C230, wherein the immunogenic composition is filled in the syringe with a headspace of about 2 mm to about 6 mm.

C232. The immunogenic composition of any one of C219-C231, wherein the immunogenic composition is resuspended in about 50 or fewer shakes.

C233. The immunogenic composition of C232, wherein the immunogenic composition is resuspended in about 10 or fewer shakes.

C234. The immunogenic composition of any one of C219-C233, wherein the immunogenic composition further comprises phosphate.

C235. The immunogenic composition of C234, wherein the phosphate is in a concentration of about 15 mM to about 25 mM.

C236. The immunogenic composition of C235, wherein the phosphate is in a concentration of about 20 mM.

C237. The immunogenic composition of any one of C219-C236, wherein the composition further comprises sodium chloride.

C238. The immunogenic composition of C219-C237, wherein the sodium chloride is in a concentration of about 10 mM to about 350 mM.

C239. The immunogenic composition of C238, wherein the sodium chloride is in a concentration of about 225 mM to about 265 mM.

C240. The immunogenic composition of C239, wherein the sodium chloride is in a concentration of about 240 mM.

C241. The immunogenic composition of C219-C238, wherein the sodium chloride is in a concentration of about 200 mM.

C242. The immunogenic composition of C241, wherein the sodium chloride is in a concentration of about 150 mM.

C243. The immunogenic composition of any one of C219-C242, wherein the immunogenic composition comprises a total conjugate dose of about 60 mcg/ml to about 360 mcg/ml C244. The immunogenic composition of C243, wherein the total conjugate dose is about 120 mg/ml to about 240 mcg/ml.

C245. The immunogenic composition of any one of C219-C244, wherein the immunogenic composition has a pH of about 6.5 to about 7.5.

C246. The immunogenic composition of C245, wherein the immunogenic composition has a pH of about 7.0.

C247. An immunogenic composition comprising about 0.25 mg/ml to about 0.75 mg/ml of aluminum phosphate, about 15 mM to about 25 mM of phosphate, about 225 mM to about 265 mM of sodium chloride, and a total conjugate dose of about 60 mcg/ml to about 360 mcg/ml, wherein the immunogenic composition has a pH of about 6.5 to about 7.5.

C248. An immunogenic composition comprising about 0.25 mg/ml to about 0.75 mg/ml of aluminum hydroxide, about 15 mM to about 25 mM of phosphate, about 120 mM to about 170 mM of sodium chloride, and a total conjugate dose of about 60 mcg/ml to about 360 mcg/ml, wherein the immunogenic composition has a pH of about 6.5 to about 7.5.

C249. An immunogenic composition of any one of C219-248 for use as a medicament.

C250. An immunogenic composition of any one of C219-249 for use in a method of inducing an immune response against GBS in a subject.

C251. The immunogenic composition of C250, wherein the subject is a female planning to become pregnant or a pregnant female.

C252. The immunogenic composition of C251, wherein the female is in her second half of pregnancy.

C253. The immunogenic composition of C252, wherein the pregnant female is at least at 20 weeks gestation.

C254. The immunogenic composition of C253, wherein the pregnant female is at 27 weeks to 36 weeks gestation.

C255. The immunogenic composition of C250, wherein the subject is an adult 50 years of age or older.

C256. The immunogenic composition of C255, wherein the subject is an adult 65 years of age or older.

C257. The immunogenic composition of C256, wherein the subject is an adult 85 years of age or older.

C258. The immunogenic composition of any one of C250-C257, wherein the subject is immunocompromised.

C259. The immunogenic composition of C258, wherein the subject has a medical condition selected from the group consisting of obesity, diabetes, HIV infection, cancer, cardiovascular disease, or liver disease.

C260. The immunogenic composition of any one of C250-259, wherein the group B streptococcus is *Streptococcus agalactiae*.

C261. A method of inducing an immune response against group B streptococcus comprising administering to a subject an effective amount of the immunogenic composition of any one of C219-C248.

C262. A method of preventing or reducing a disease or condition associated with group B streptococcus in a subject comprising administering to a subject an effective amount of the immunogenic composition of any one of C219-C248.

C263. The method of C261 or C262, wherein the subject is a female planning to become pregnant or a pregnant female.

C264. The method of C263, wherein the female is in her second half of pregnancy.

C265. The method of C263 or C264, wherein the pregnant female is at least at 20 weeks gestation.

C266. The method of any one of C263-265, wherein the pregnant female is at 27 weeks to 36 weeks gestation.

C267. The method of C261 or C262, wherein the subject is an adult 50 years of age or older.

C268. The method of C267, wherein the subject is an adult 65 years of age or older.

C269. The method of C267 or C268, wherein the subject is an adult 85 years of age or older.

C270. The method of any one of C261-C269, wherein the subject is immunocompromised.

C271. The method of C270, wherein the subject has a medical condition selected from the group consisting of obesity, diabetes, HIV infection, cancer, cardiovascular disease, or liver disease.

C272. The method of any one of C261-C271, wherein the group B streptococcus is *Streptococcus agalactiae*.

C273. A method of producing an antibody comprising administering the immunogenic composition of any one of C219-C248 to a subject.

C274. An antibody produced by the method of C273.

C275. A method of conferring passive immunity to a subject comprising the steps of:
 (a) generating an antibody preparation using the immunogenic composition of any one of C219-C248; and
 (b) administering the antibody preparation to the subject to confer passive immunity.

The invention claimed is:

1. An immunogenic composition comprising polysaccharide-carrier protein conjugates, wherein:
 (i) each of the conjugates comprises a capsular polysaccharide from a different serotype of group B streptococcus (GBS) conjugated to a carrier protein, wherein the serotypes comprise serotypes Ia, Ib, II, III, IV, and V, wherein each conjugate has a sialic acid level of greater than 60%, and wherein the carrier protein comprises a diphtheria toxoid or $CRM_{197}$; and (ii) the immunogenic composition further comprises one or more of a pharmaceutically acceptable excipient, buffer, stabilizer, adjuvant, a cryoprotectant, a salt, a divalent cation, a non-ionic detergent, an inhibitor of free radical oxidation, a carrier, or a mixture thereof;

wherein the immunogenic composition does not yield a reduced immune response to serotype III.

2. The immunogenic composition of claim 1, wherein the carrier protein is $CRM_{197}$.

3. The immunogenic composition of claim 1, wherein the immunogenic composition is a hexavalent GBS conjugate composition.

4. The immunogenic composition of claim 1, further comprising an aluminum-based adjuvant.

5. The immunogenic composition of claim 4, wherein the aluminum-based adjuvant is selected from the group consisting of aluminum phosphate, aluminum hydroxyl phosphate, and aluminum hydroxide.

6. The immunogenic composition of claim 5, wherein the adjuvant is aluminum phosphate.

7. The immunogenic composition of claim 5, wherein the adjuvant is aluminum hydroxide.

8. The immunogenic composition of claim 4, wherein the aluminum-based adjuvant is present at a concentration of 0.25 mg/ml to 0.75 mg/ml.

9. The immunogenic composition of claim 4, wherein the aluminum-based adjuvant is present at a concentration of 0.5 mg/ml.

10. The immunogenic composition of claim 1, wherein the immunogenic composition is filled in a syringe.

11. The immunogenic composition of claim 1, wherein the immunogenic composition further comprises phosphate.

12. The immunogenic composition of claim 11, wherein the phosphate is present at a concentration of 15 mM to 25 mM.

13. The immunogenic composition of claim 11, wherein the phosphate is present at a concentration of 20 mM.

14. The immunogenic composition of claim 1, wherein the composition further comprises sodium chloride.

15. The immunogenic composition of claim 14, wherein the sodium chloride is present at a concentration of 10 mM to 350 mM.

16. The immunogenic composition of claim 14, wherein the sodium chloride is in a concentration of 225 mM to 265 mM.

17. The immunogenic composition of claim 14, wherein the sodium chloride is present at a concentration of 240 mM.

18. The immunogenic composition of claim 14, wherein the sodium chloride is present at a concentration of 200 mM.

19. The immunogenic composition of claim 14, wherein the sodium chloride is present at a concentration of 150 mM.

20. The immunogenic composition of claim 1, wherein the immunogenic composition comprises a total conjugate dose of 60 mcg/ml to 360 mcg/ml.

21. The immunogenic composition of claim 20, wherein the total conjugate dose is 120 mcg/ml to 240 mcg/ml.

22. The immunogenic composition of claim 1, wherein the immunogenic composition has a pH of 6.5 to 7.5, and wherein the buffer is histidine.

23. The immunogenic composition of claim 1, wherein the immunogenic composition has a pH of 7.0.

24. The immunogenic composition of claim 1, wherein the group B streptococcus is *Streptococcus agalactiae*.

* * * * *